US009206184B2

(12) United States Patent
Brohm et al.

(10) Patent No.: US 9,206,184 B2
(45) Date of Patent: Dec. 8, 2015

(54) DISUBSTITUTED BENZOTHIENYL-PYRROLOTRIAZINES AND USES THEREOF

(71) Applicant: BAYER INTELLECTUAL PROPERTY GmbH, Monheim (DE)

(72) Inventors: Dirk Brohm, Mettmann (DE); Melanie Heroult, Berlin (DE); Marie-Pierre Collin, Wuppertal (DE); Walter Hübsch, Wuppertal (DE); Mario Lobell, Wuppertal (DE); Klemens Lustig, Wuppertal (DE); Sylvia Grünewald, Berlin (DE); Ulf Bömer, Glienicke (DE)

(73) Assignee: BAYER INTELLECTUAL PROPERTY GmbH, Monheim (DE)

( * ) Notice: Subject to any disclaimer, the term of this patent is extended or adjusted under 35 U.S.C. 154(b) by 120 days.

(21) Appl. No.: 13/715,553

(22) Filed: Dec. 14, 2012

(65) Prior Publication Data

US 2013/0158000 A1 Jun. 20, 2013

(30) Foreign Application Priority Data

Dec. 15, 2011 (EP) .................................... 11193841

(51) Int. Cl.
*C07D 487/04* (2006.01)
*A61K 31/53* (2006.01)
*A61K 31/5355* (2006.01)
*A61K 31/5377* (2006.01)
*A61K 31/541* (2006.01)
*A61P 35/00* (2006.01)

(52) U.S. Cl.
CPC .............. *C07D 487/04* (2013.01); *A61K 31/53* (2013.01); *A61K 31/5355* (2013.01); *A61K 31/5377* (2013.01); *A61K 31/541* (2013.01)

(58) Field of Classification Search
CPC .... C07D 487/04; C07D 409/14; A61K 31/53; A61K 45/06
USPC .......................................... 544/183; 514/243
See application file for complete search history.

(56) References Cited

FOREIGN PATENT DOCUMENTS

| WO | 0071129 A1 | 11/2000 |
|---|---|---|
| WO | 0119828 A2 | 3/2001 |
| WO | 2005121147 A1 | 12/2005 |
| WO | 2007056170 A2 | 5/2007 |
| WO | 2007061737 A2 | 5/2007 |
| WO | 2007061882 A2 | 5/2007 |
| WO | 2007064883 A2 | 6/2007 |
| WO | 2007064931 A2 | 6/2007 |
| WO | 2007064932 A2 | 6/2007 |
| WO | 2007079164 A2 | 7/2007 |
| WO | 2009136966 A1 | 11/2009 |
| WO | 2010051043 A1 | 5/2010 |
| WO | 2010126960 A1 | 11/2010 |

OTHER PUBLICATIONS

Hynes et al., Cancer Res. Jul. 1, 2010;70(13):5199-202.*
Greulich et al.,Trends Mol Med. May 2011;17(5):283-92.*
Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Raach et al., "Sodium Chlorite-Hydrogen Peroxide—A Mild and Selective Reagent for the Oxidation of Aldehydes to Carboxylic Acids," J. Prakt. Chem., 2000, 342(6):605-608.
Venturelli et al., "Optimizing Cell Permeation of an Antibiotic Resistance Inhibitor for Improved Efficacy," 2007, 50:5644-5654.
Bergers et al., "Modes of resistance to antiangiogenic therapy," Nature Reviews Cancer, Aug. 2008, 8:592-603.
Knapp et al., "A General Solution for Unstable Boronic Acids: Slow-Release Cross-Coupling from Air-Stable MIDA Boronates," J.Am. Chem.Soc.2009, 131, 6961-6963.
Yoshida et al., "Studies on Quinolone Antibacterials. V.1) Synthesis and Antibacterial Activity of Chiral 5-Amino-7-(4-substituted-3-amino-1-pyrrolidinyl)-6-fluoro-1,4-dihydro-8-methyl-4-oxoquinoline-3-carboxylic Acids and Derivatives," Chem. Pharm. Bull., 1996, 44(7):1376-1386.
Pinnick et al., "Oxidation of α, β-Unsaturated Aldehydes," Tetrahedron, 1981, 37:2091-2096.
Haugsten et al., "Roles of Fibroblast Growth Factor Receptors in Carcinogenesis," Mol. Cancer Research, 2010, 8(11):1439-1452.
Heinzle et al., "Targeting fibroblast-growthfactor-receptor-dependent signaling for cancer therapy," Ther. Targets, 2011, 15(7):829-846.
Itoh et al., "Fibroblast growth factors: from molecular evolution to roles in development, metabolism and disease," 2011, 149(2):121-130.
Korc et al., "The Role of Fibroblast Growth Factors in Tumor Growth," Current Cancer Drug Targets, 2009, 9:639-651.
Plé et al., "Synthesis of Substituted Benzo[b]thiophenes by Acid-Catalyzed Cyclization of Thiophenylacetals and Ketones," J. Heterocyclic Chem., 1988, 25(4):1271-1272.
Polanska et al., "Extracellular Interactome of the FGF Receptor-Ligand System: Complexities and the Relative Simplicity of the Worm," Developmental Dynamics, 2009, 238:277-293.
Kotha et al., "Recent applications of the Suzuki-Miyaura cross-coupling reaction in organic synthesis," Tetrahedron, 2002, 58:9633-9695.
Buchwald et al., "A New Palladium Precatalyst Allows for the Fast Suzuki-Miyaura Coupling Reactions of Unstable Polyfluorophenyl and 2-Heteroaryl Boronic Acids," J. Am. Chem. Soc., 2010, 132(40):14073-14075.
Berge et al., "Pharmaceutical Salts," J. Pharm. Sci., Jan. 1977, 66(1):1-19.
Swinney et al., "How were new medicines discovered?," Nature Rev. Drug Disc. Jul. 2011, 10:507-519.
Barder et al., "Catalysts for Suzuki-Miyaura Coupling Processes: Scope and Studies of the Effect of Ligand Structure," J. Am. Chem. Soc., 2005, 127(13):4685-4696.
Wesche et al., "Fibroblast growth factors and their receptors in cancer," Biochem. J., 437(2):199-213.
International Search Report, PCT/EP2012/074977, Feb. 13, 2013.
Copending U.S. Appl. No. 14/365,424, filed Jun. 13, 2014.

* cited by examiner

*Primary Examiner* — Venkataraman Balasubramanian

(57) ABSTRACT

This invention relates to novel substituted 5-(1-benzothiophen-2-yl)pyrrolo[2,1-f][1,2,4]triazin-4-amine derivatives having protein tyrosine kinase inhibitory activities, to processes for the preparation of such compounds, to pharmaceutical compositions containing such compounds, and to the use of such compounds or compositions for treating proliferative disorders, in particular cancer and tumor diseases.

4 Claims, No Drawings

DISUBSTITUTED BENZOTHIENYL-PYRROLOTRIAZINES AND USES THEREOF

This invention relates to novel substituted 5-(1-benzothiophen-2-yl)pyrrolo[2,1-f][1,2,4]triazin-4-amine derivatives having protein tyrosine kinase inhibitory activities, to processes for the preparation of such compounds, to pharmaceutical compositions containing such compounds, and to the use of such compounds or compositions for treating proliferative disorders, in particular cancer and tumor diseases.

Cancer is a leading cause of death worldwide and accounted for 7.6 million deaths (around 13% of all deaths) in 2008. Deaths from cancer are projected to continue to rise worldwide to over 11 million in 2030 (WHO source, Fact Sheet No. 297, February 2011).

There are many ways how cancers can arise which is one of the reasons why their therapy is difficult. One way that transformation of cells can occur is following a genetic alteration. The completion of the human genome project showed genomic instability and heterogeneity of human cancer genes. Recent strategies to identify these genetic alterations sped up the process of cancer-gene discovery. Gene abnormality can, for instance, lead to the overexpression of proteins, and hence to a non-physiological activation of these proteins. One family of proteins from which a number of oncoproteins derive are tyrosine kinases and in particular receptor tyrosine kinases (RTKs). In the past two decades, numerous avenues of research have demonstrated the importance of RTK-mediated signalling in adverse cell growth leading to cancer. In recent years, promising results have been achieved in the clinic with selective small-molecule inhibitors of tyrosine kinases as a new class of anti-tumorigenic agents [Swinney and Anthony, *Nature Rev. Drug Disc.* 10 (7), 507-519 (2011)].

Fibroblast growth factors (FGFs) and their receptors (FGFRs) form part of a unique and diverse signalling system which plays a key role in a variety of biological processes which encompass various aspects of embryonic development and adult pathophysiology [Itoh and Ornitz, *J. Biochem.* 149 (2), 121-130 (2011)]. In a spatio-temporal manner, FGFs stimulate through FGFR binding a wide range of cellular functions including migration, proliferation, differentiation, and survival.

The FGF family comprises 18 secreted polypeptidic growth factors that bind to four highly conserved receptor tyrosine kinases (FGFR-1 to -4) expressed at the cell surface. In addition, FGFR-5 can bind to FGFs but does not have a kinase domain, and therefore is devoid of intracellular signalling. The specificity of the ligand/receptor interaction is enhanced by a number of transcriptional and translational processes which give rise to multiple isoforms by alternative transcriptional initiation, alternative splicing, and C-terminal truncations. Various heparan sulfate proteoglycans (e.g. syndecans) can be part of the FGF/FGFR complex and strongly influence the ability of FGFs to induce signalling responses [Polanska et al., *Developmental Dynamics* 238 (2), 277-293 (2009)]. FGFRs are cell surface receptors consisting of three extracellular immunoglobulin-like domains, a single-pass transmembrane domain, and an intracellular dimerized tyrosine kinase domain. Binding of FGF bring the intracellular kinases into close proximity, enabling them to transphosphorylate each other. Seven phosphorylation sites have been identified (e.g., in FGFR-1 Tyr463, Tyr583, Tyr585, Tyr653, Tyr654, Tyr730, and Tyr766).

Some of these phosphotyrosine groups act as docking sites for downstream signalling molecules which themselves may also be directly phosphorylated by FGFR, leading to the activation of multiple signal transduction pathways. Thus, the MAPK signalling cascade is implicated in cell growth and differentiation, the PI3K/Akt signalling cascade is involved in cell survival and cell fate determination, while the PI3K and PKC signalling cascades have a function in the control of cell polarity. Several feedback inhibitors of FGF signalling have now been identified and include members of the Spry (Sprouty) and Sef (similar expression to FGF) families. Additionally, in certain conditions, FGFR is released from pre-Golgi membranes into the cytosol. The receptor and its ligand, FGF-2, are co-transported into the nucleus by a mechanism that involves importin, and are engaged in the CREB-binding protein (CBP) complex, a common and essential transcriptional co-activator that acts as a gene activation gating factor. Multiple correlations between the immunohistochemical expression of FGF-2, FGFR-1 and FGFR-2 and their cytoplasmic and nuclear tumor cell localizations have been observed. For instance, in lung adenocarcinomas this association is also found at the nuclear level, emphasizing an active role of the complex at the nucleus [Korc and Friesel, *Curr. Cancer Drugs Targets* 5, 639-651 (2009)].

FGFs are widely expressed in both developing and adult tissues and play important roles in a variety of normal and pathological processes, including tissue development, tissue regeneration, angiogenesis, neoplastic transformation, cell migration, cellular differentiation, and cell survival. Additionally, FGFs as pro-angiogenic factors have also been implicated in the emerging phenomenon of resistance to vascular endothelial growth factor receptor-2 (VEGFR-2) inhibition [Bergers and Hanahan, *Nat. Rev. Cancer* 8, 592-603 (2008)].

Recent oncogenomic profiles of signalling networks demonstrated an important role for aberrant FGF signalling in the emergence of some common human cancers [Wesche et al., *Biochem. J.* 437 (2), 199-213 (2011)]. Ligand-independent FGFR constitutive signalling has been described in many human cancers, such as brain cancer, head and neck cancer, gastric cancer and ovarian cancer. FGFR-mutated forms as well as FGFR-intragenic translocations have been identified in malignancies such as myeloproliferative diseases. Interestingly, the same mutations discovered to be the cause of many developmental disorders are also found in tumor cells (e.g., the mutations found in achondroplasia and thanatophoric dysplasia, which cause dimerization and thus constitutive activation of FGFR-3, are also frequently found in bladder cancer). A mutation that promotes dimerization is just one mechanism that can increase ligand-independent signalling from FGFRs. Other mutations located inside or outside of the kinase domain of FGFRs can change the conformation of the domain giving rise to permanently active kinases.

Amplification of the chromosomal region 8p11-12, the genomic location of FGFR-1, is a common focal amplification in breast cancer and occurs in approximately 10% of breast cancers, predominantly in oestrogen receptor-positive cancers. FGFR-1 amplifications have also been reported in non-small cell lung squamous carcinoma and are found at a low incidence in ovarian cancer, bladder cancer and rhabdomyosarcoma. Similarly, approximately 10% of gastric cancers show FGFR-2 amplification, which is associated with poor prognosis, diffuse-type cancers. Moreover, multiple single nucleotide polymorphisms (SNPs) located in FGFR-1 to -4 were found to correlate with an increased risk of developing selective cancers, or were reported to be associated with poor prognosis (e.g., FGFR-4 G388R allele in breast cancer, colon cancer and lung adenocarcinoma). The direct role of these SNPs to promote cancer is still controversial.

In summary, a great number of in vitro and in vivo studies have been performed that validate FGFR-1 to -4 as important cancer targets, and comprehensive reviews have summarized these findings [see, for example, Heinzle et al., *Expert Opin. Ther. Targets* 15 (7), 829-846 (2011); Wesche et al., *Biochem. J.* 437 (2), 199-213 (2011); Greulich and Pollock, *Trends in Molecular Medicine* 17 (5), 283-292 (2011); Haugsten et al., *Mol. Cancer. Res.* 8 (11), 1439-1452 (2010)]. Several strategies have been followed to attenuate aberrant FGFR-1 to -4 signalling in human tumors including blocking antibodies and small-molecule inhibitors, amongst others. A number of selective small-molecule FGFR inhibitors are currently in clinical development, such as AZD-4547 (AstraZeneca) and BJG-398 (Novartis).

Notwithstanding the significant advancements that have generally been achieved in cancer therapy in recent years, there is a continuing need to identify new anti-cancer compounds with improved properties, such as higher potency, greater selectivity, reduced toxicity and/or better tolerability. Therefore, the technical problem to be solved according to the present invention may be seen in providing alternative compounds having inhibitory activity on the FGFR kinases, thus offering new therapeutic options for the treatment of FGFR-mediated diseases, in particular cancer and other proliferative disorders.

Fused hetero-5,6-bicyclic kinase inhibitors bearing a 9- or a 10-membered bicyclic heteroaryl substituent have been disclosed in WO 2007/061737-A2 and WO 2005/097800-A1, respectively. These compounds were stated to be useful for the treatment of cancer and other diseases owing to their inhibitory action on the mTOR (mammalian target of Rapamycin) and/or IGF-1R (type 1 insulin-like growth factor receptor) kinases. Further hetero-5,6-bicyclic template structures associated with the inhibition of kinases have been described in, inter alia, WO 01/19828-A2, WO 2007/079164-A2 and WO 2010/051043-A1.

4-Aminopyrrolo[2,1-f][1,2,4]triazine derivatives with differing inhibition profiles against a number of protein kinases have been disclosed in, inter alia, WO 00/71129-A1, WO 2007/056170-A2, WO 2007/061882-A2, WO 2007/064932-A2, WO 2009/136966-A1, and WO 2010/126960-A1.

In WO 2005/121147-A1, WO 2007/064883-A2 and WO 2007/064931-A2, 4-aminopyrrolo[2,1-f]-[1,2,4]triazine derivatives containing a substituted diarylurea group in 5-position were described as having FGFR-1 inhibiting activity. However, other receptor tyrosine kinases, notably the VEGFR, PDGFR and Tie-2 kinases, are also significantly inhibited by this particular class of compounds. As it was hypothesized that such multi-kinase activity might lead to an augmentation of potential side effects during treatment, it was the aim of the present invention to identify new agents having an improved selectivity for the FGFR kinases, thus providing new options for a more tolerable cancer therapy.

Surprisingly, it has now been found that certain 4-aminopyrrolo[2,1-f][1,2,4]triazine derivatives bearing a specifically substituted benzothiophen-2-yl residue in 5-position exhibit potent and selective inhibition of FGFR kinases, notably of the FGFR-1 and FGFR-3 kinases, which renders these compounds particularly useful for the treatment of proliferative disorders, such as cancer and tumor diseases.

Thus, in one aspect, the present invention relates to 6,7-disubstituted 5-(1-benzothiophen-2-yl)pyrrolo[2,1-f][1,2,4]triazin-4-amine derivatives of the general formula (I)

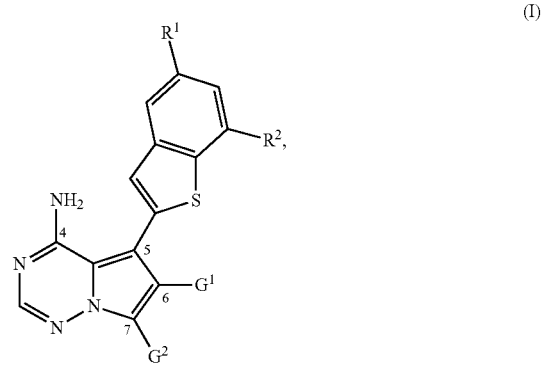

wherein
$R^1$ is hydrogen, chloro, methyl or methoxy,
$R^2$ is hydrogen or methoxy,
 with the proviso that at least one of $R^1$ and $R^2$ is other than hydrogen,
$G^1$ represents chloro, $(C_1-C_4)$-alkyl, $(C_1-C_4)$-alkoxycarbonyl, 5-membered aza-heteroaryl, or the group —$CH_2$—$OR^3$, —$CH_2$—$NR^4R^5$ or —C(=O)—$NR^4R^6$, wherein
 $R^3$ is hydrogen, $(C_1-C_4)$-alkyl, $(C_3-C_6)$-cycloalkyl or phenyl, wherein
  (i) said $(C_1-C_4)$-alkyl is optionally substituted with hydroxy, $(C_1-C_4)$-alkoxy, hydroxycarbonyl, $(C_1-C_4)$-alkoxycarbonyl, amino, aminocarbonyl, mono($C_1$-$C_4$)-alkylaminocarbonyl, di-$(C_1-C_4)$-alkylaminocarbonyl, $(C_3-C_6)$-cycloalkyl or up to three fluoro atoms, and
  (ii) said $(C_3-C_6)$-cycloalkyl is optionally substituted with one or two substituents independently selected from the group consisting of $(C_1-C_4)$-alkyl, hydroxy and amino, and
  (iii) said phenyl is optionally substituted with one or two substituents independently selected from the group consisting of fluoro, chloro, bromo, cyano, trifluoromethyl, trifluoromethoxy, $(C_1-C_4)$-alkyl and $(C_1-C_4)$-alkoxy,
 $R^4$ is hydrogen or $(C_1-C_4)$-alkyl,
 $R^5$ is hydrogen, $(C_1-C_4)$-alkyl, $(C_1-C_4)$-alkylcarbonyl, $(C_3-C_6)$-cycloalkyl or 4- to 6-membered heterocycloalkyl, wherein
  (i) said $(C_1-C_4)$-alkyl is optionally substituted with hydroxy, $(C_1-C_4)$-alkoxy, hydroxycarbonyl, $(C_1-C_4)$-alkoxycarbonyl, aminocarbonyl, mono-$(C_1-C_4)$alkylaminocarbonyl, di-$(C_1-C_4)$-alkylaminocarbonyl or $(C_3-C_6)$-cycloalkyl, and
  (ii) said $(C_3-C_6)$-cycloalkyl is optionally substituted with one or two substituents independently selected from the group consisting of $(C_1-C_4)$-alkyl, hydroxy and amino, and
  (iii) said 4- to 6-membered heterocycloalkyl is optionally substituted with one or two substituents independently selected from the group consisting of $(C_1-C_4)$ alkyl, hydroxy, oxo and amino,
 $R^6$ is hydrogen, $(C_1-C_4)$-alkyl, $(C_3-C_6)$-cycloalkyl or 4- to 6-membered heterocycloalkyl, wherein
  (i) said $(C_1-C_4)$-alkyl is optionally substituted with hydroxy, $(C_1-C_4)$-alkoxy, hydroxycarbonyl, $(C_1-C_4)$-alkoxycarbonyl, amino, aminocarbonyl, mono($C_1$-

$C_4$)-alkylaminocarbonyl, di-($C_1$-$C_4$)-alkylaminocarbonyl or ($C_3$-$C_6$)-cycloalkyl,
and
(ii) said ($C_3$-$C_6$)-cycloalkyl is optionally substituted with one or two substituents independently selected from the group consisting of ($C_1$-$C_4$)-alkyl, hydroxy and amino,
and
(iii) said 4- to 6-membered heterocycloalkyl is optionally substituted with one or two substituents independently selected from the group consisting of ($C_1$-$C_4$) alkyl, hydroxy, oxo and amino,
or
$R^4$ and $R^5$, or $R^4$ and $R^6$, respectively, are joined and, taken together with the nitrogen atom to which they are attached, form a monocyclic, saturated 4- to 7-membered heterocycloalkyl ring which may contain a second ring heteroatom selected from N($R^7$) and O, and which may be substituted on ring carbon atoms with one or two substituents independently selected from the group consisting of ($C_1$-$C_4$)-alkyl, oxo, hydroxy, amino and aminocarbonyl, and wherein
$R^7$ is hydrogen, ($C_1$-$C_4$)-alkyl, formyl or ($C_1$-$C_4$)-alkylcarbonyl,
and
$G^2$ represents chloro, cyano, ($C_1$-$C_4$)-alkyl, or the group —$CR^{8A}R^{8B}$—OH, —$CH_2$—$NR^9R^{10}$, —C(=O)—$NR^{11}R^{12}$ or —$CH_2$—$OR^{15}$, wherein
$R^{8A}$ and $R^{8B}$ are independently selected from the group consisting of hydrogen, ($C_1$-$C_4$)alkyl, cyclopropyl and cyclobutyl,
$R^9$ is hydrogen or ($C_1$-$C_4$)-alkyl,
$R^{10}$ is hydrogen, ($C_1$-$C_4$)-alkyl, ($C_1$-$C_4$)-alkylcarbonyl, ($C_3$-$C_6$)-cycloalkyl or 4- to 6-membered heterocycloalkyl, wherein
(i) said ($C_1$-$C_4$)-alkyl is optionally substituted with hydroxy, amino, aminocarbonyl, mono-($C_1$-$C_4$)-alkylaminocarbonyl or di-($C_1$-$C_4$)-alkylaminocarbonyl,
and
(ii) said ($C_3$-$C_6$)-cycloalkyl is optionally substituted with one or two substituents independently selected from the group consisting of ($C_1$-$C_4$)-alkyl, hydroxy and amino,
and
(iii) said 4- to 6-membered heterocycloalkyl is optionally substituted with one or two substituents independently selected from the group consisting of ($C_1$-$C_4$) alkyl, hydroxy, oxo and amino,
$R^{11}$ is hydrogen or ($C_1$-$C_4$)-alkyl,
$R^{12}$ is hydrogen, ($C_1$-$C_4$)-alkyl, ($C_3$-$C_6$)-cycloalkyl or 4- to 6-membered heterocycloalkyl, wherein
(i) said ($C_1$-$C_4$)-alkyl is optionally substituted with hydroxy, amino, aminocarbonyl, mono-($C_1$-$C_4$)-alkylaminocarbonyl or di-($C_1$-$C_4$)-alkylaminocarbonyl,
and
(ii) said ($C_3$-$C_6$)-cycloalkyl is optionally substituted with one or two substituents independently selected from the group consisting of ($C_1$-$C_4$)-alkyl, hydroxy and amino,
and
(iii) said 4- to 6-membered heterocycloalkyl is optionally substituted with one or two substituents independently selected from the group consisting of ($C_1$-$C_4$) alkyl, hydroxy, oxo and amino,
or
$R^9$ and $R^{10}$, or $R^{11}$ and $R^{12}$, respectively, are joined and, taken together with the nitrogen atom to which they are attached, form a monocyclic, saturated 4- to 7-membered heterocycloalkyl ring which may contain a second ring heteroatom selected from N($R^{13}$), O, S and S(O)$_2$, and which may be substituted on ring carbon atoms with up to three substituents independently selected from the group consisting of fluoro, ($C_1$-$C_4$)-alkyl, oxo, hydroxy, amino and aminocarbonyl, and wherein
$R^{13}$ is hydrogen, ($C_1$-$C_4$)-alkyl, ($C_3$-$C_6$)-cycloalkyl, formyl or ($C_1$-$C_4$)-alkylcarbonyl,
and
$R^{15}$ is ($C_1$-$C_4$)-alkyl,
with the proviso that $G^1$ is not chloro when $G^2$ is chloro or cyano.

The compounds according to this invention can also be present in the form of their salts, solvates and/or solvates of the salts.

Compounds according to the invention are the compounds of the formula (I) and their salts, solvates and solvates of the salts, the compounds included in the formula (I) of the formulae (I-A), (I-B), (I-C), (I-D) and (I-E) mentioned in the following and their salts, solvates and solvates of the salts, and the compounds included in the formula (I) and mentioned in the following as process products and/or embodiment examples and their salts, solvates and solvates of the salts, where the compounds included in the formula (I) and mentioned in the following are not already salts, solvates and solvates of the salts.

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19). Salts which are not themselves suitable for pharmaceutical uses but can be used, for example, for isolation or purification of the compounds according to the invention are also included.

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, lactic acid, tartaric acid, malic acid, citric acid, fumaric acid, maleic acid, and benzoic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, N,N-diisopropylethylamine, monoethanolamine, diethanolamine, triethanolamine, dimethylaminoethanol, diethylaminoethanol, procaine, dicyclohexylamine, dibenzylamine, N-methylmorpholine, N-methylpiperidine, arginine, lysine, and 1,2-ethylenediamine.

Solvates in the context of the invention are designated as those forms of the compounds according to the invention which form a complex in the solid or liquid state by stoichiometric coordination with solvent molecules. Hydrates are a specific form of solvates, in which the coordination takes place with water. Hydrates are preferred solvates in the context of the present invention.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S)-configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Geometric isomers by nature of substituents about a double bond or a ring may be present in cis (=Z-) or trans (=E-) form, and both isomeric forms are encompassed within the scope of this invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

The present invention also encompasses all suitable isotopic variants of the compounds according to the invention. An isotopic variant of a compound according to the invention is understood to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body. Due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. Such modifications of the compounds according to the invention may therefore in some cases also constitute a preferred embodiment of the present invention. Isotopic variants of the compounds according to the invention can be prepared by processes known to those skilled in the art, for example by the methods described below and the methods described in the working examples, by using corresponding isotopic modifications of the particular reagents and/or starting compounds therein.

In the context of the present invention, the substituents and residues have the following meaning, unless specified otherwise:

($C_1$-$C_4$)-Alkyl in the context of the invention represents a straight-chain or branched alkyl radical having 1 to 4 carbon atoms. There may be mentioned by way of example and preferably: methyl, ethyl, n-propyl, isopropyl, n-butyl, iso-butyl, sec-butyl, and tert-butyl.

($C_1$-$C_4$)-Alkoxy in the context of the invention represents a straight-chain or branched alkoxy radical having 1 to 4 carbon atoms. There may be mentioned by way of example and preferably: methoxy, ethoxy, n-propoxy, isopropoxy, n-butoxy, iso-butoxy, sec-butoxy, and tert-butoxy.

Mono-($C_1$-$C_4$)-alkylamino in the context of the invention represents an amino group with a straight-chain or branched alkyl substituent which contains 1 to 4 carbon atoms. There may be mentioned by way of example and preferably: methylamino, ethylamino, n-propylamino, isopropylamino, n-butylamino, and tert-butylamino.

Di-($C_1$-$C_4$)-alkylamino in the context of the invention represents an amino group with two identical or different straight-chain or branched alkyl substituents which each contain 1 to 4 carbon atoms. There may be mentioned by way of example and preferably: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, and N-tert-butyl-N-methylamino.

($C_1$-$C_4$)-Alkylcarbonyl in the context of the invention represents a straight-chain or branched alkyl radical having 1 to 4 carbon atoms which is bonded to the rest of the molecule via a carbonyl group [—C(=O)—]. There may be mentioned by way of example and preferably: acetyl, propionyl, n-butyryl, iso-butyryl, n-pentanoyl, and pivaloyl.

($C_1$-$C_4$)-Alkoxycarbonyl in the context of the invention represents a straight-chain or branched alkoxy radical having 1 to 4 carbon atoms which is bonded to the rest of the molecule via a carbonyl group [—C(=O)—]. There may be mentioned by way of example and preferably: methoxycarbonyl, ethoxycarbonyl, n-propoxycarbonyl, isopropoxycarbonyl, n-butoxycarbonyl, and tert-butoxycarbonyl.

Mono-($C_1$-$C_4$)-alkylaminocarbonyl in the context of the invention represents an amino group which is bonded to the rest of the molecule via a carbonyl group [—C(=O)—] and which has a straight-chain or branched alkyl substituent having 1 to 4 carbon atoms. There may be mentioned by way of example and preferably: methylaminocarbonyl, ethylaminocarbonyl, n-propylaminocarbonyl, isopropylaminocarbonyl, n-butylaminocarbonyl, and tert-butylaminocarbonyl.

Di-($C_1$-$C_4$)-alkylaminocarbonyl in the context of the invention represents an amino group which is bonded to the rest of the molecule via a carbonyl group [—C(=O)—] and which has two identical or different straight-chain or branched alkyl substituents having in each case 1 to 4 carbon atoms. There may be mentioned by way of example and preferably: N,N-dimethylaminocarbonyl, N,N-diethylaminocarbonyl, N-ethyl-N-methylaminocarbonyl, N-methyl-N-n-propylaminocarbonyl, N-isopropyl-N-methylaminocarbonyl, N,N-diisopropylaminocarbonyl, N-n-butyl-N-methylaminocarbonyl, and N-tert-butyl-N-methylaminocarbonyl.

($C_3$-$C_6$)-Cycloalkyl in the context of the invention represents a monocyclic, saturated carbocycle having 3 to 6 ring carbon atoms. There may be mentioned by way of example: cyclopropyl, cyclobutyl, cyclopentyl, and cyclohexyl. Preferred are cyclopropyl and cyclobutyl.

4- to 7-membered heterocycloalkyl and 4- to 6-membered heterocycloalkyl in the context of the invention represent a monocyclic, saturated heterocycle with 4 to 7 or, respectively, 4 to 6 ring atoms in total, which contains one or two identical or different ring heteroatoms from the series N, O, S and S(O)$_2$, and which can be bonded via a ring carbon atom or via a ring nitrogen atom (if present). 4- to 6-membered heterocycloalkyl containing one ring nitrogen atom and optionally one further ring heteroatom from the series N, O or S(O)$_2$ is preferred. 5- or 6-membered heterocycloalkyl containing one ring nitrogen atom and optionally one further ring heteroatom from the series N or O is particularly preferred. There may be mentioned by way of example: azetidinyl, oxetanyl, thietanyl, pyrrolidinyl, pyrazolidinyl, imidazolidinyl, tetrahydrofuranyl, thiolanyl, 1,1-dioxidothiolanyl, 1,2-oxazolidinyl, 1,3- oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl, thiomorpholinyl, 1,1-dioxidothiomorpholinyl, azepanyl, 1,4-diazepanyl, and 1,4-oxazepanyl. Preferred are azetidinyl, pyrrolidinyl, pyrazolidinyl, imidazolidinyl, 1,2-oxazolidinyl, 1,3-oxazolidinyl, piperidinyl, piperazinyl, 1,2-oxazinanyl, morpholinyl, and thiomorpholinyl. Particularly preferred are pyrrolidinyl, piperidinyl, piperazinyl, and morpholinyl.

5-membered aza-heteroaryl in the context of the invention represents an aromatic heterocyclic radical (heteroaromatic) having 5 ring atoms in total, which contains at least one ring nitrogen atom and optionally one or two further ring heteroatoms from the series N, O and/or S, and which is bonded via a ring carbon atom or optionally via a ring nitrogen atom (when allowed by valency). 5-membered aza-heteroaryl containing one ring nitrogen atom and one or two further ring heteroatoms from the series N and/or O is preferred. There may be mentioned by way of example: pyrrolyl, pyrazolyl, imidazolyl, oxazolyl, thiazolyl, isoxazolyl, isothiazolyl, triazolyl, oxadiazolyl, and thiadiazolyl. Preferred are pyrazolyl, imidazolyl, oxazolyl, isoxazolyl, and oxadiazolyl.

An oxo substituent in the context of the invention represents an oxygen atom, which is bonded to a carbon atom via a double bond.

In the context of the present invention, for all the radicals which occur several times, the meaning thereof is independent of each other. If radicals in the compounds according to the invention are substituted, the radicals can be mono- or polysubstituted, unless specified otherwise. Substitution by one or by two or three identical or different substituents is preferred. Substitution by one or by two identical or different substituents is particularly preferred.

In a preferred embodiment, the present invention relates to compounds of general formula (I), wherein
$R^1$ is chloro, methyl or methoxy,
$R^2$ is hydrogen or methoxy,
$G^1$ represents chloro, $(C_1-C_4)$-alkyl, $(C_1-C_4)$-alkoxycarbonyl or 5-membered aza-heteroaryl selected from the group consisting of pyrazolyl, imidazolyl, oxazolyl, isoxazolyl and oxadiazolyl, or represents the group —$CH_2$—$OR^3$ or —$CH_2$—$NR^4R^5$, wherein
  $R^3$ is hydrogen, $(C_1-C_4)$-alkyl or $(C_3-C_6)$-cycloalkyl,
    wherein said $(C_1-C_4)$-alkyl is optionally substituted with hydroxy, $(C_1-C_4)$-alkoxy, hydroxycarbonyl, $(C_1-C_4)$-alkoxycarbonyl, amino, aminocarbonyl, $(C_3-C_6)$-cycloalkyl or up to three fluoro atoms,
  $R^4$ is hydrogen or $(C_1-C_4)$-alkyl,
  $R^5$ is hydrogen, $(C_1-C_4)$-alkyl, $(C_1-C_4)$-alkylcarbonyl, $(C_3-C_6)$-cycloalkyl or 5- or 6-membered heterocycloalkyl, wherein
    (i) said $(C_1-C_4)$-alkyl is optionally substituted with hydroxy, hydroxycarbonyl or $(C_3-C_6)$-cycloalkyl, and
    (ii) said 5- or 6-membered heterocycloalkyl is optionally substituted with oxo,
  or
  $R^4$ and $R^5$ are joined and, taken together with the nitrogen atom to which they are attached, form a monocyclic, saturated 4- to 6-membered heterocycloalkyl ring which may contain a second ring heteroatom selected from $N(R^7)$ and O, and which may be substituted on a ring carbon atom with oxo or hydroxy, and wherein
    $R^7$ is hydrogen or $(C_1-C_4)$-alkyl,
and
$G^2$ represents chloro, cyano, $(C_1-C_4)$-alkyl, or the group —$CR^{8A}R^{8B}$—OH, —$CH_2$—$NR^9R^{10}$, —$C(=O)$—$NR^{11}R^{12}$ or —$CH_2$—$OR^{15}$, wherein
  $R^{8A}$ and $R^{8B}$ are independently selected from the group consisting of hydrogen, $(C_1-C_4)$alkyl and cyclopropyl, $R^9$ is hydrogen or methyl,
$R^{10}$ is hydrogen, $(C_1-C_4)$-alkyl, $(C_1-C_4)$-alkylcarbonyl, $(C_3-C_6)$-cycloalkyl or 5- or 6-membered heterocycloalkyl, wherein
  (i) said $(C_1-C_4)$-alkyl is optionally substituted with hydroxy or aminocarbonyl, and
  (ii) said 5- or 6-membered heterocycloalkyl is optionally substituted with oxo,
$R^{11}$ is hydrogen or methyl,
$R^{12}$ is hydrogen, $(C_1-C_4)$-alkyl, $(C_3-C_6)$-cycloalkyl or 5- or 6-membered heterocycloalkyl, wherein
  (i) said $(C_1-C_4)$-alkyl is optionally substituted with hydroxy, and
  (ii) said 5- or 6-membered heterocycloalkyl is optionally substituted with oxo,
or
$R^9$ and $R^{10}$, or $R^{11}$ and $R^{12}$, respectively, are joined and, taken together with the nitrogen atom to which they are attached, form a monocyclic, saturated 4- to 6-membered heterocycloalkyl ring which may contain a second ring heteroatom selected from $N(R^{13})$, O, S and $S(O)_2$, and which may be substituted on ring carbon atoms with up to three substituents independently selected from the group consisting of fluoro, $(C_1-C_4)$-alkyl, oxo, hydroxy, amino and aminocarbonyl, and wherein
  $R^{13}$ is hydrogen, $(C_1-C_4)$-alkyl, cyclopropyl, cyclobutyl, formyl or $(C_1-C_4)$alkylcarbonyl,
and
$R^{15}$ is methyl or ethyl,
with the proviso that $G^1$ is not chloro when $G^2$ is chloro or cyano.

In a particularly preferred embodiment, the present invention relates to compounds of general formula I), wherein
$R^1$ is methyl,
$R^2$ is methoxy,
$G^1$ represents methyl, oxazol-5-yl or the group —$CH_2$—$OR^3$ or —$CH_2$—$NR^4R^5$, wherein
  $R^3$ is hydrogen, $(C_1-C_4)$-alkyl, cyclopropyl or cyclobutyl, wherein said $(C_1-C_4)$-alkyl is optionally substituted with hydroxy, methoxy, ethoxy, hydroxycarbonyl, methoxycarbonyl, ethoxycarbonyl, amino, aminocarbonyl, cyclopropyl, cyclobutyl or up to three fluoro atoms,
  $R^4$ is hydrogen, methyl or ethyl,
  $R^5$ is hydrogen, $(C_1-C_4)$-alkyl, acetyl, cyclopropyl, cyclobutyl or 2-oxopyrrolidin-3-yl,
    wherein said $(C_1-C_4)$-alkyl is optionally substituted with hydroxy, hydroxycarbonyl, cyclopropyl or cyclobutyl,
  or
  $R^4$ and $R^5$ are joined and, taken together with the nitrogen atom to which they are attached, form a monocyclic, saturated 5- or 6-membered heterocycloalkyl ring which may contain a second ring heteroatom selected from NH and O, and which may be substituted on a ring carbon atom with oxo or hydroxy,
and
$G^2$ represents methyl or the group —$CR^{8A}R^{8B}$—OH, —$CH_2$—$NR^9R^{10}$ or —$C(=O)$—$NR^{11}R^{12}$, wherein
  $R^{8A}$ and $R^{8B}$ are independently hydrogen or methyl,
  $R^9$ is hydrogen,
  $R^{10}$ is hydrogen, $(C_1-C_4)$-alkyl, acetyl, cyclopropyl, cyclobutyl or 2-oxopyrrolidin-3-yl, wherein said $(C_1-C_4)$-alkyl is optionally substituted with hydroxy or aminocarbonyl,
  $R^{11}$ is hydrogen or methyl, $R^{12}$ is hydrogen, $(C_1-C_4)$-alkyl, cyclopropyl, cyclobutyl or 2-oxopyrrolidin-3-yl, wherein said $(C_1-C_4)$-alkyl is optionally substituted with hydroxy, or $R^9$ and $R^{10}$, or $R^{11}$ and $R^{12}$, respectively, are joined and, taken together with the nitrogen atom to which they are attached, form a monocyclic, saturated 4- to 6-membered heterocycloalkyl ring which may contain a second ring heteroatom selected from $N(R^{13})$, O and $S(O)_2$, and which may be substituted on ring carbon atoms with up to three substituents independently selected from the group consisting of fluoro, methyl, oxo, hydroxy, amino and aminocarbonyl, and wherein $R^{13}$ is hydrogen, formyl or acetyl.

In a distinct embodiment, the present invention relates to compounds of general formula (I), wherein
$R^1$ is methyl,
and
$R^2$ is methoxy.

In a further distinct embodiment, the present invention relates to compounds of general formula (I), wherein
$G^1$ represents the group —$CH_2$—$OR^3$, wherein
$R^3$ is hydrogen or $(C_1-C_4)$-alkyl optionally substituted with hydroxy, methoxy, amino, aminocarbonyl or up to three fluoro atoms.

In another distinct embodiment, the present invention relates to compounds of general formula (I), wherein
$G^1$ represents the group —$CH_2$—$NR^4R^5$, wherein
$R^4$ is hydrogen or methyl,
$R^5$ is $(C_1-C_4)$-alkyl, acetyl, cyclopropyl, cyclobutyl or 2-oxopyrrolidin-3-yl,
wherein said $(C_1-C_4)$-alkyl is optionally substituted with hydroxy, or $R^4$ and $R^5$ are joined and, taken together with the nitrogen atom to which they are attached, form a monocyclic, saturated 5- or 6-membered heterocycloalkyl ring which may contain a second ring heteroatom selected from NH and O, and which may be substituted on a ring carbon atom with oxo or hydroxy.

In another distinct embodiment, the present invention relates to compounds of general formula (I), wherein
$G^2$ represents the group —$CH_2$—$NR^9R^{10}$, wherein
$R^9$ is hydrogen, or $R^9$ and $R^{10}$ are joined and, taken together with the nitrogen atom to which they are attached, form a monocyclic, saturated 5- or 6-membered heterocycloalkyl ring which may contain a second ring heteroatom selected from $N(R^{13})$ and O, and which may be substituted on ring carbon atoms with up to two substituents independently selected from the group consisting of methyl, oxo, hydroxy and amino, and wherein
$R^{13}$ is hydrogen, formyl or acetyl.

In yet another distinct embodiment, the present invention relates to compounds of general formula (I), wherein
$G^2$ represents the group —$C(=O)$—$NR^{11}R^{12}$ wherein
$R^{11}$ is hydrogen,
$R^{12}$ is $(C_1-C_4)$-alkyl or 2-oxopyrrolidin-3-yl,
wherein said $(C_1-C_4)$-alkyl is optionally substituted with hydroxy, or $R^{11}$ and $R^{12}$ are joined and, taken together with the nitrogen atom to which they are attached, form a monocyclic, saturated 4- to 6-membered heterocycloalkyl ring which may contain a second ring heteroatom selected from NH and O, and which may be substituted on a ring carbon atom with oxo or hydroxy.

In an especially preferred embodiment, the present invention relates to compounds of general formula (I), wherein
$R^1$ is methyl,
$R^2$ is methoxy,
$G^1$ represents the group —$CH_2$—$OR^3$, wherein
$R^3$ is $(C_1-C_4)$-alkyl optionally substituted with hydroxy, amino or aminocarbonyl,
and
$G^2$ represents the group —$CH_2$—$NR^9R^{10}$ or —$C(=O)$—$NR^{11}R^{12}$, wherein
$R^9$ is hydrogen,
$R^{10}$ is 2-oxopyrrolidin-3-yl,
or
$R^9$ and $R^{10}$ are joined and, taken together with the nitrogen atom to which they are attached, form a piperazin-1-yl, 3-oxopiperazin-1-yl or 4-acetylpiperazin-1-yl ring,
$R^{11}$ is hydrogen,
$R^{12}$ is 2-oxopyrrolidin-3-yl,
or
$R^{11}$ and $R^{12}$ are joined and, taken together with the nitrogen atom to which they are attached, form a 3-hydroxyazetidin-1-yl, 4-hydroxypiperidin-1-yl or 3-oxopiperazin-1-yl ring.

The definitions of residues indicated specifically in the respective combinations or preferred combinations of residues are also replaced as desired by definitions of residues of other combinations, irrespective of the particular combinations indicated for the residues. Combinations of two or more of the abovementioned preferred ranges are particularly preferred.

The compounds of the general formula (I) can be prepared by various synthetic routes which are primarily governed by the nature of the particular $G^1$ and $G^2$ groups chosen (see definitions above).

Thus, in another embodiment, the present invention relates to a process for preparing the compounds of the general formula (I), characterized in that

[A] a 6-substituted 4-aminopyrrolo[2,1-f][1,2,4]triazine of formula (II)

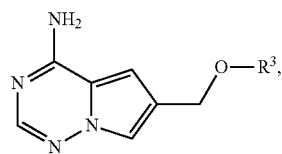

(II)

wherein $R^3$ has the meaning described above,
is at first reacted with formaldehyde and an amine of formula (III)

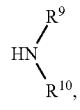

(III)

wherein $R^9$ and $R^{10}$ have the meanings described above,
in the presence of an acid to give a compound of formula (IV)

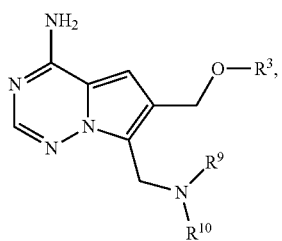
(IV)

wherein $R^3$, $R^9$ and $R^{10}$ have the meanings described above,
then brominated to a compound of formula (V)

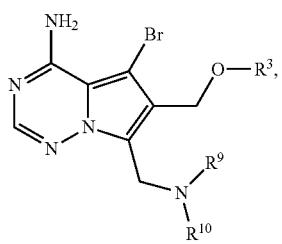
(V)

wherein $R^3$, $R^9$ and $R^{10}$ have the meanings described above,
and subsequently coupled with a benzothiophen-2-yl boronate of formula (VI)

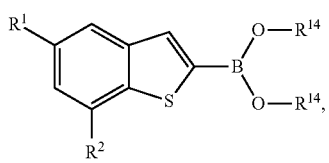
(VI)

wherein $R^1$ and $R^2$ have the meanings described above, and
$R^{14}$ represents hydrogen or $(C_1$-$C_4)$-alkyl, or both $R^{14}$ residues are linked together to form a —$(CH_2)_2$—, —$C(CH_3)_2$—$C(CH_3)_2$—, —$(CH_2)_3$—, —$CH_2$—$C(CH_3)_2$—$CH_2$— or —$C(=O)$—$CH_2$—$N(CH_3)$—$CH_2$—$C(=O)$— bridge,
in the presence of a palladium catalyst and a base to yield the target compound of formula (I-A)

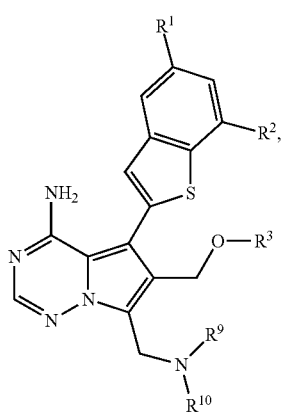
(I-A)

wherein $R^1$, $R^2$, $R^3$, $R^9$ and $R^{10}$ have the meanings described above,
or
[B] a 6-substituted 4-aminopyrrolo[2,1-f][1,2,4]triazine of formula (II)

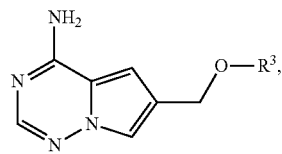
(II)

wherein $R^3$ has the meaning described above,
is at first formylated with N,N-dimethylformamide in the presence of phosphoryl chloride to an aldehyde of formula (VII)

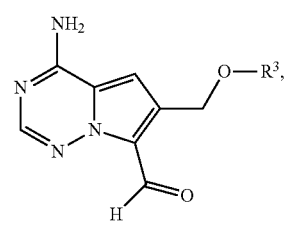
(VII)

wherein $R^3$ has the meaning described above,
then brominated to a compound of formula (VIII)

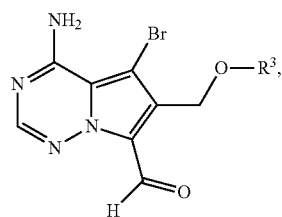
(VIII)

wherein $R^3$ has the meaning described above,
and subsequently coupled with a benzothiophen-2-yl boronate of formula (VI)

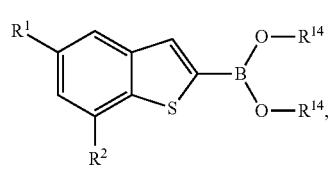
(VI)

wherein $R^1$, $R^2$ and $R^{14}$ have the meanings described above,
in the presence of a palladium catalyst and a base to give a compound of formula (IX)

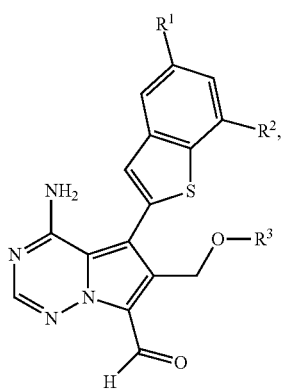

(IX)

wherein $R^1$, $R^2$ and $R^3$ have the meanings described above,
which then is either

[B-1] reacted with an amine of formula (III)

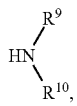

(III)

wherein $R^9$ and $R^{10}$ have the meanings described above,
in the presence of an acid and a reducing agent to yield the target compound of formula (I-A)

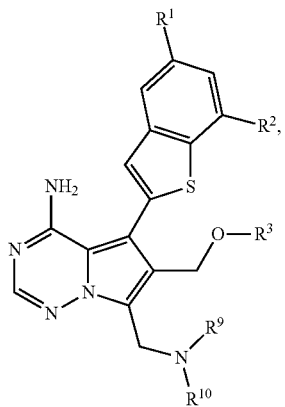

(I-A)

wherein $R^1$, $R^2$, $R^3$, $R^9$ and $R^{10}$ have the meanings described above,
or

[B-2] oxidized to a carboxylic acid of formula (X)

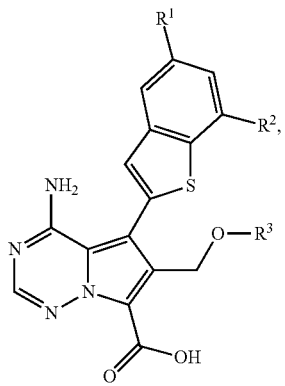

(X)

wherein $R^1$, $R^2$ and $R^3$ have the meanings described above, and finally coupled with an amine of formula (XI)

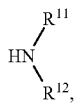

(XI)

wherein $R^{11}$ and $R^{12}$ have the meanings described above, in the presence of a condensing agent to yield the target compound of formula (I-B)

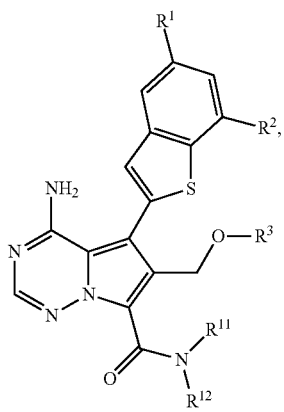

(I-B)

wherein $R^1$, $R^2$, $R^3$, $R^{11}$ and $R^{12}$ have the meanings described above, or

[C] a 6-substituted 4-amino-5-bromopyrrolo[2,1-f][1,2,4]triazine of formula (XII)

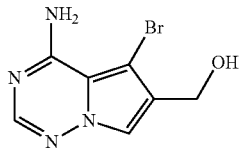

(XII)

is at first coupled with a benzothiophen-2-yl boronate of formula (VI)

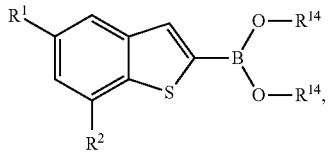

(VI)

wherein $R^1$, $R^2$ and $R^{14}$ have the meanings described above, in the presence of a palladium catalyst and a base to give a compound of formula (XIII)

(XIII)

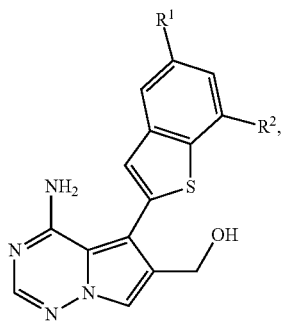

wherein $R^1$ and $R^2$ have the meanings described above, and then reacted with formaldehyde and an amine of formula (III)

(III)

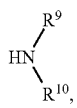

wherein $R^9$ and $R^{10}$ have the meanings described above, in the presence of an acid to yield the compound of formula (I-C)

(I-C)

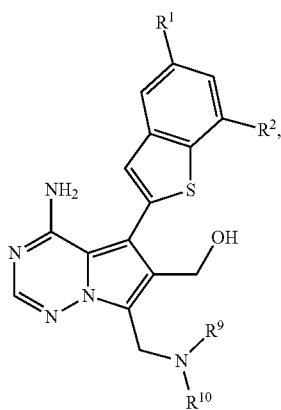

wherein $R^1$, $R^2$, $R^9$ and $R^{10}$ have the meanings described above,
which subsequently is either
[C-1] oxidized to an aldehyde of formula (XIV)

(XIV)

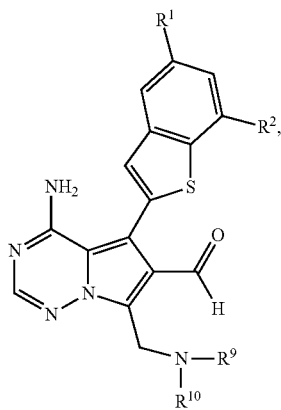

wherein $R^1$, $R^2$, $R^9$ and $R^{10}$ have the meanings described above, and treated with an amine of formula (XV)

(XV)

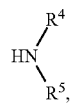

wherein $R^4$ and $R^5$ have the meanings described above, in the presence of an acid and a reducing agent to yield the target compound of formula (I-D)

(I-D)

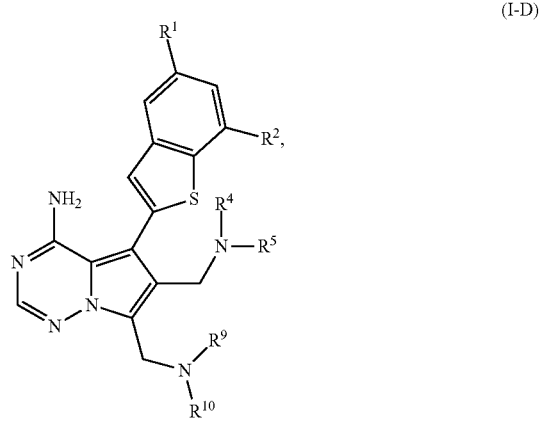

wherein $R^1$, $R^2$, $R^4$, $R^5$, $R^9$ and $R^{10}$ have the meanings described above,
or
[C-2] converted into the corresponding 6-(halomethyl) derivative of formula (XVI)

(XVI)

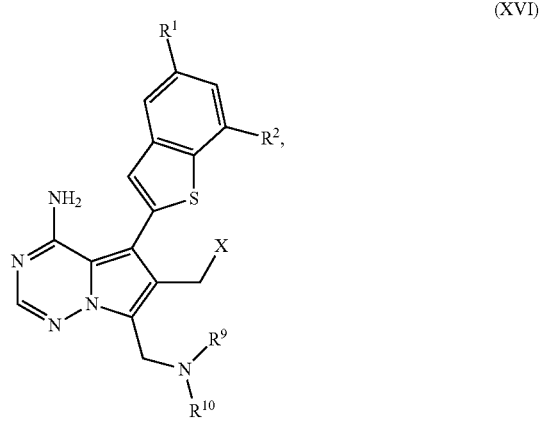

wherein $R^1$, $R^2$, $R^9$ and $R^{10}$ have the meanings described above,
and
X is chloro, bromo or iodo,
and treated with an alcohol of formula (XVII)

$R^{3A}$—OH  (XVII), wherein $R^{3A}$ has the meaning of $R^3$ as described above except for hydrogen,
in the presence of a base to yield the target compound of formula (I-E)

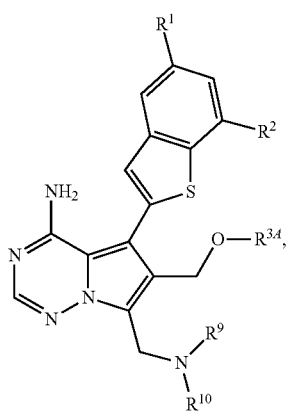

(I-E)

wherein $R^1$, $R^2$, $R^{3,4}$, $R^9$ and $R^{10}$ have the meanings described above, optionally followed, where appropriate, by (i) separating the compounds of formula (I) thus obtained into their respective enantiomers and/or diastereomers, preferably using chromatographic methods, and/or (ii) converting the compounds of formula (I) into their respective hydrates, solvates, salts and/or hydrates or solvates of the salts by treatment with the corresponding solvents and/or acids or bases.

The compounds of the formulae (I-A), (I-B), (I-C), (I-D) and (I-E), which can be prepared by the processes described above, each represent a particular subset of the compounds of the general formula (I).

Process steps [A] (II)→(IV) and [C] (XIII)→(I-C), representing Mannich-type aminomethylation reactions, are carried out in the usual way by treating the respective starting compound with a mixture of aqueous formaldehyde and amine component (III) in the presence of an acid catalyst such as formic acid or acetic acid. Preferably, acetic acid is used both as catalyst and solvent. The reaction is usually performed at a temperature ranging from +20° C. to +80° C.

As the brominating agent for process steps [A] (IV)→(V) and [B] (VII)→(VIII), preferably N-bromosuccinimide (NBS), 1,3-dibromo-5,5-dimethylhydantoin (DBDMH) or elemental bromine are used. The reactions are generally carried out in an inert solvent, such as dichloromethane, chloroform, tetrahydrofuran, acetonitrile or N,N-dimethylformamide (DMF), within a temperature range from −78° C. to +20° C.

The coupling reactions [A] (V)+(VI)→(I-A), [B] (VIII)+(VI)→(IX) and [C] (XII)+(VI)→(XIII) ["Suzuki-Miyaura coupling"] are generally carried out in an inert solvent with the aid of a palladium catalyst and an aqueous base. Palladium catalysts suitable for this purpose include, for example, palladium(II) acetate, palladium(II) chloride, bis(triphenylphosphine)palladium(II) chloride, bis(acetonitrile)palladium(II) chloride, [1,1'-bis(diphenylphosphino)ferrocene]palladium(II) chloride, tetrakis(triphenylphosphine)palladium(0), bis(dibenzylideneacetone)palladium(0), and tris(dibenzylideneacetone)dipalladium(0), optionally in combination with other phosphine ligands such as, for example, 2-dicyclohexylphosphino-2',4',6'-triisopropylbiphenyl (X-Phos), 2-dicyclohexylphosphino-2',6'-dimethoxybiphenyl (S-Phos), 4,5-bis(diphenylphosphino)-9,9-di-methylxanthene (Xantphos), or 4-(di-tert-butylphosphino)-N,N-dimethylaniline. Also, palladium pre-catalysts from which the catalytically active species is generated under the reaction conditions, such as (2'-aminobiphenyl-2-yl)(chloro)palladium-dicyclohexyl(2',4',6'-triisopropylbiphenyl-2-yl)phosphine, can be used [see, for example, S. Kotha et al., *Tetrahedron* 58, 9633-9695 (2002); T. E. Barder et al., *J. Am. Chem. Soc.* 127 (13), 4685-4696 (2005); S. L. Buchwald et al., *J. Am. Chem. Soc.* 132 (40), 14073-14075 (2010), and further references cited therein].

Suitable bases for these coupling reactions are in particular alkali carbonates, such as sodium, potassium or caesium carbonate, alkali phosphates, such as sodium or potassium phosphate, or alkali fluorides, such as potassium or caesium fluoride. Usually, these bases are employed as aqueous solutions. The reactions are carried out in organic solvents that are inert under the reaction conditions. Preferably, water-miscible organic solvents, such as 1,2-dimethoxyethane, tetrahydrofuran, 1,4-dioxane, acetonitrile, N,N-dimethylformamide (DMF) or dimethylsulfoxide (DMSO), are employed but other inert solvents, such as dichloromethane or toluene, may also be used.

Process step [B] (II)→VII) ["Vilsmeier-Haack formylation"] is carried out in the usual manner by treating the pyrrolotriazine (II) in N,N-dimethylformamide (DMF) solvent with phosphoryl chloride. The reaction is usually performed at a temperature from 0° C. to +80° C.

Reducing agents suitable for the reductive amination reactions [B-1] (IX)+(III)→(I-A) and [C-1] (XIV)+(XV)→(I-D) are customary alkali borohydrides, such as lithium borohydride, sodium borohydride, potassium borohydride, sodium cyanoborohydride or sodium triacetoxyborohydride. The transformations are generally carried out in the presence of an acid, preferably acetic acid, in an alcohol or ether solvent, such as methanol, ethanol, isopropanol, tetrahydrofuran or 1,4-dioxane, within a temperature range from 0° C. to +80° C., depending on the reactivity of the amine components (III) and (XV), respectively, and/or the particular borohydride used.

For the oxidation reaction in process step [B-2] (IX)→(X), oxidation with sodium chlorite in the presence of a hypochlorite scavenger such as 2-methyl-2-butene represents the method of choice [cf. H. W. Pinnick et al., *Tetrahedron* 37, 2091-2096 (1981); A. Raach and O. Reiser, *J. Prakt. Chem.* 342 (6), 605-608 (2000), and references cited therein]. The reaction is usually carried out in a tetrahydrofuran/water mixture at a temperature between 0° C. and ambient temperature.

Condensing agents suitable for process step [B-2] (X)+(XI)→(I-B) [amide formation] include, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide (EDC), phosgene derivatives such as N,N'-carbonyldiimidazole (CDI) or isobutyl chloroformate, α-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl)phosphoryl chloride, benzotriazol-1-yloxy-tris(dimethylamino)phosphonium hexafluorophosphate (BOP) or benzotriazol-1-yloxy-tris(pyrrolidino)phosphonium hexafluorophosphate (PyBOP), and uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with further auxiliaries, such as 1-hydroxybenzotriazole (HOBt) or N-hydroxysuccinimide (HOSu), and/or bases such as alkali carbonates, for example sodium or potassium carbonate, or organic amine bases, such as triethylamine, N-methylpiperidine, N-methylmorpholine (NMM), N,N-diisopropylethylamine (DIPEA), pyridine or 4-N,N-dimethylaminopyridine (DMAP). Preference is given to using O-(7-azabenzotriazol-1-yl)-N,N,N',N'-tetramethyluronium hexafluorophosphate (HATU) or O-(benzotriazol-1-yl)-N,N,N',N'-tetramethyluronium tetrafluoroborate (TBTU) in combination with N,N-diisopropylethylamine (DIPEA) and optionally 1-hydroxybenzotriazole (HOBt).

Inert solvents for process step [B-2] (X)+(XI)→(I-B) are, for example, ethers such as diethyl ether, tert-butyl methyl ether, tetrahydrofuran, 1,4-dioxane or 1,2-dimethoxyethane, hydrocarbons such as benzene, toluene, xylene, hexane or cyclohexane, halogenated hydrocarbons such as dichloromethane, trichloromethane, carbon tetrachloride, 1,2-dichloroethane, trichloroethylene or chlorobenzene, or other solvents such as acetone, acetonitrile, ethyl acetate, pyridine, dimethylsulfoxide (DMSO), N,N-dimethylformamide (DMF), N,N'-dimethylpropylene urea (DMPU) or N-methylpyrrolidinone (NMP). It is also possible to use mixtures of these solvents. Preference is given to using dichloromethane, tetrahydrofuran, N,N-dimethylformamide or mixtures thereof. The reactions are generally carried out at a temperature ranging from 0° C. to +60° C., preferably at +10° C. to +40° C.

Oxidizing agents that are capable of converting the primary alcohol (1-C) into the aldehyde (XIV) (process [C-1]) under mild conditions include 1,1,1-triacetoxy-1,1-dihydro-1,2-benziodoxol-3 (1H)-one ("Dess-Martin periodinane"), 2,2,6,6-tetramethylpiperidin-1-oxyl (TEMPO) in combination with secondary oxidants such as iodosobenzene-I,I-diacetate or sodium hypochlorite, and dimethylsulfoxide (DMSO)-based oxidation systems such as DMSO/trifluoroacetic anhydride or DMSO/N,N'-dicyclohexylcarbodiimide (DCC). Preference is given to 1,1,1-triacetoxy-1,1-dihydro-1,2-benziodoxol-3(1H)-one. The reaction is generally carried out in an inert solvent, preferably using dichloromethane.

For the hydroxy-to-halogen transformation in process step [C-2] (I-C)→(XVI), various standard methods and reagents that are well known in the art may be employed. Reagents of choice are thionyl chloride [for X=Cl], tetrabromomethane/triphenylphosphine [for X=Br], and iodine/triphenylphosphine [for X=I]. The preparation of 6-(chloromethyl) derivatives (XVI) [X=Cl] is preferred for reasons of convenience of work-up and compound stability.

Bases suitable for the process step [C-2] (XVI)+(XVII)→(1-E) [ether formation] are in particular alkali carbonates such as lithium, sodium, potassium or caesium carbonate, alkali acetates such as sodium or potassium acetate, or customary tertiary amine bases such as triethylamine, N-methylmorpholine, N-methylpiperidine, N,N-diisopropylethylamine or pyridine. Preference is given to N,N-diisopropylethylamine (DIPEA). The reaction (XVI)+(XVII)→(I-E) is performed in an inert solvent, such as tetrahydrofuran, or without solvent, using an excess of alcohol (XVII), at a temperature ranging from +20° C. to +200° C., preferably at +50° C. to +150° C. Advantageously, the conversion is carried out by means of a microwave reactor device.

The reaction sequence (I-C)→(XVI)→(I-E) may be carried out in two separate steps, i.e. with isolation and purification of the intermediate compound (XVI), or it may be performed using a one-pot procedure, i.e. employing the crude intermediate (XVI) as obtained in the preparation reaction.

In cases where a primary or secondary amine moiety forms part of the $G^1$ or $G^2$ group in the target compounds of formula (I), it may sometimes be appropriate in the preparation reactions described above to use a protected derivative of this amine as reaction component instead of the free amine. For this purpose, conventional temporary amino-protecting groups, such as acyl groups (e.g., acetyl or trifluoroacetyl) or carbamate-type protecting groups (e.g., a Boc-, Cbz- or Fmoc-group), may be employed. A Boc (tert-butoxycarbonyl) group is preferably used. Similarly, a hydroxy function being part of the $G^1$ or $G^2$ group may temporarily be blocked in precursor compounds and process intermediates, for example as a tetrahydropyranyl (THP) ether or as a silyl ether derivative, such as a trimethylsilyl or tert-butyldimethylsilyl ether.

These protecting groups may then be cleaved off concomitantly during aqueous work-up and purification procedures, or they are removed in a subsequent, separate reaction step using standard methods well known in the art. The preparation of such protected intermediates from the corresponding free amines or alcohols is likewise readily accomplished following general procedures described in the literature [see, for example, T. W. Greene and P. Wuts, *Protective Groups in Organic Synthesis*, Wiley, New York, 1999].

Certain types of protected (i.e. acylated) amine derivatives exert significant FGFR-inhibiting activity by their own. Accordingly, such compounds are also encompassed by the general formula (I) as defined above.

The preparation of the compounds of the invention may be illustrated by means of the following reaction schemes:

Scheme 1

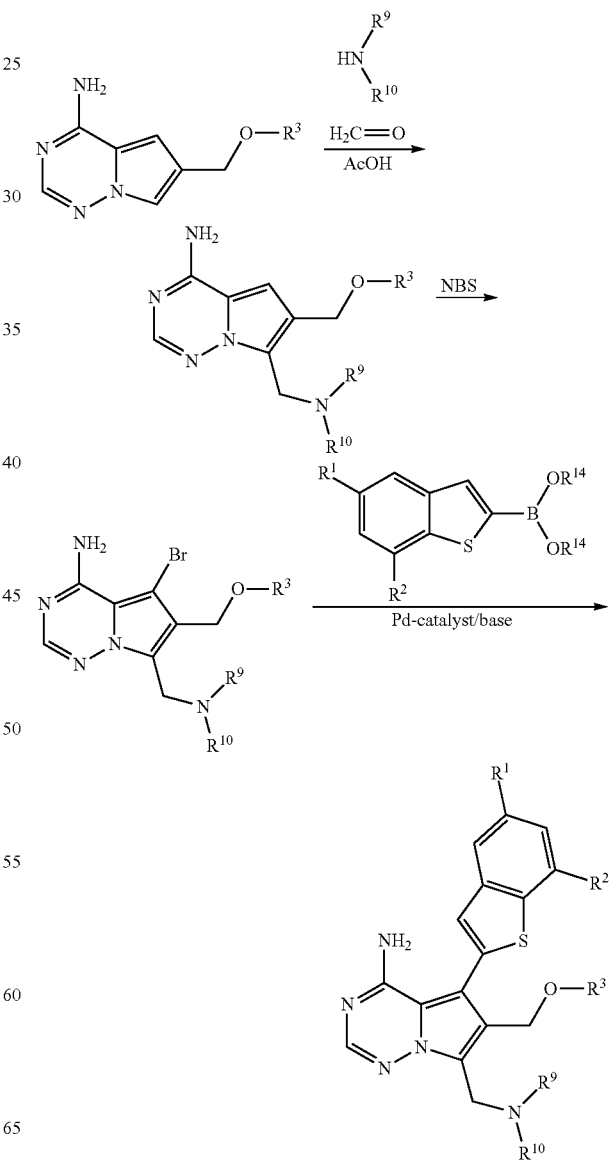

Scheme 2
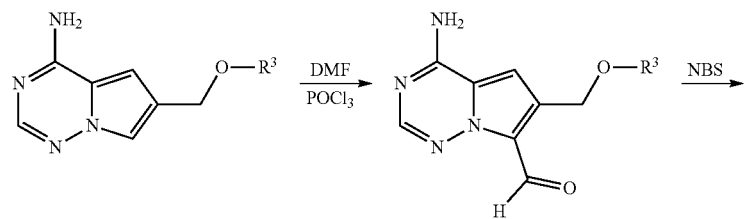
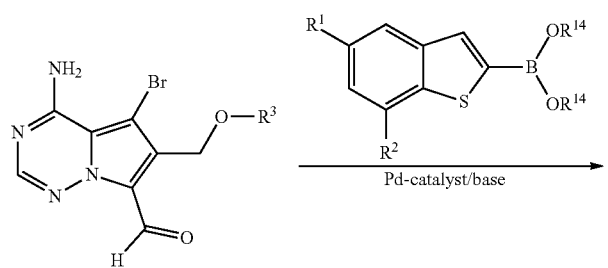
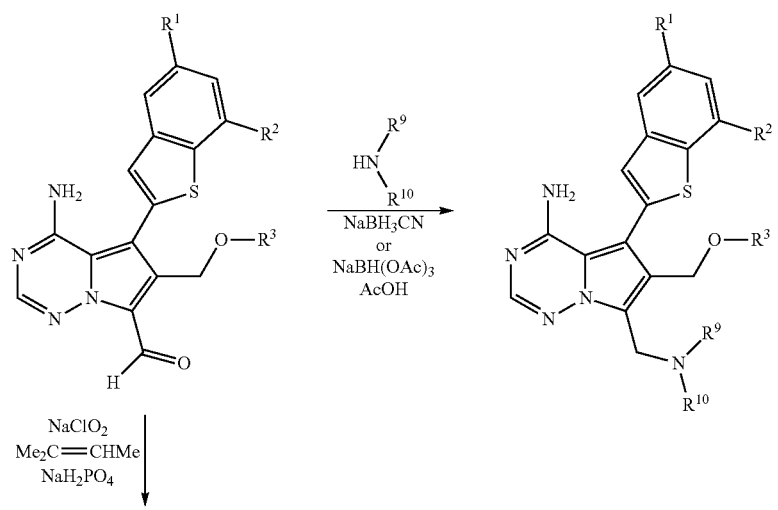
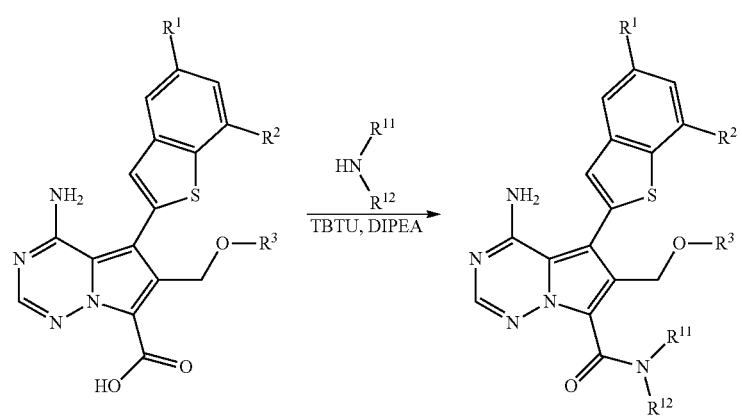

Scheme 3
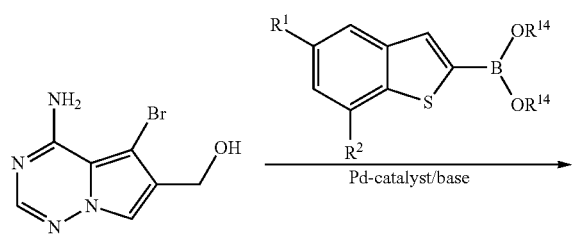
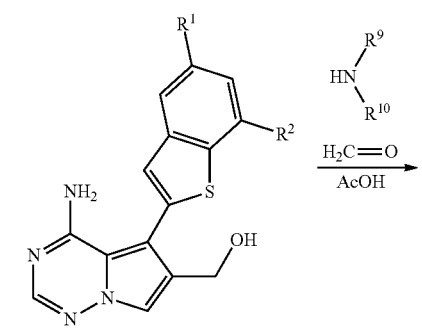
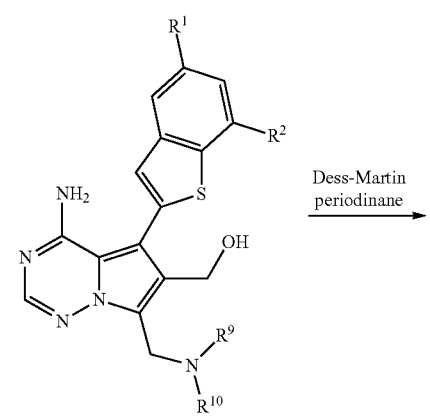
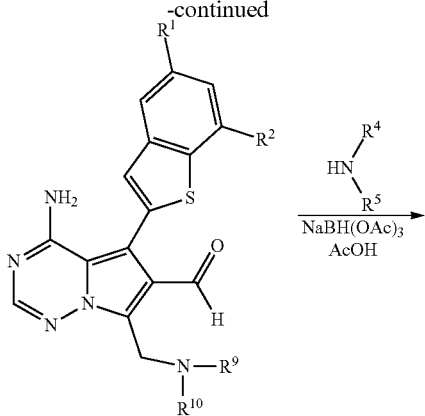
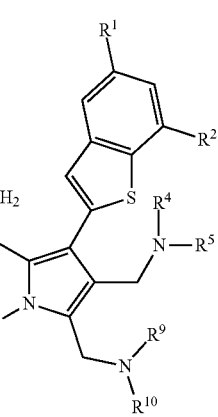
Scheme 4
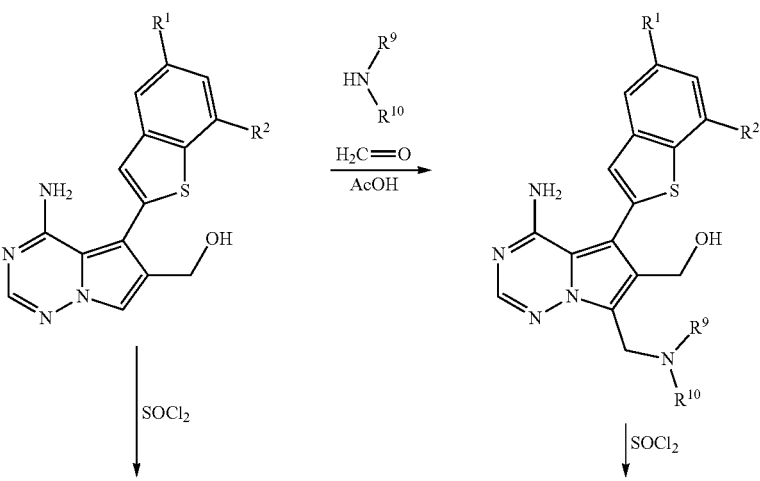

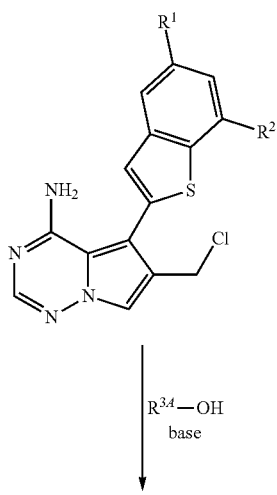

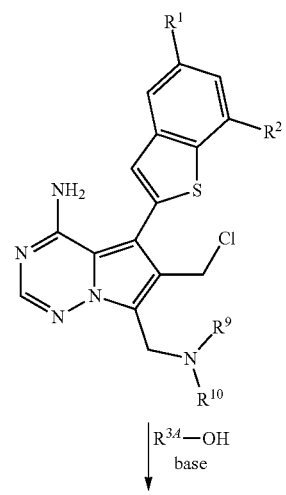

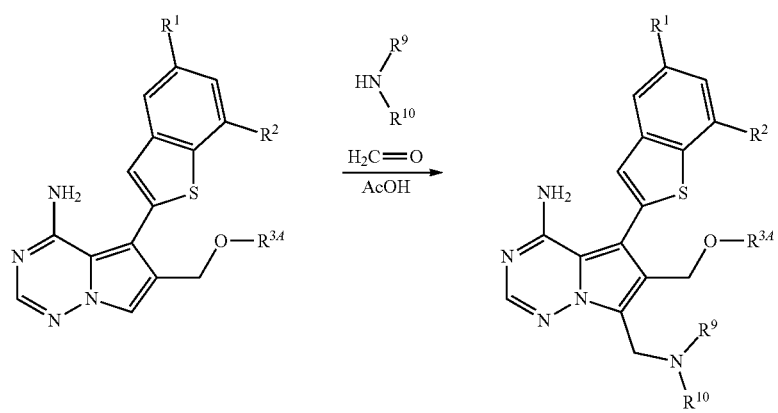

The 6-substituted 4-aminopyrrolo[2,1-f][1,2,4]triazines of formula (II) can, for example, be prepared by two different routes which are depicted in Scheme 5 below. In the first route, 4-amino-6-cyanopyrrolo[2,1-f][1,2,4]triazine (XVIII) is converted into the ester (XIX) by acid-mediated alcoholysis and then reduced to the 6-(hydroxymethyl) compound (IIa) [$R^3$ in (II)=H] using lithium triethylborohydride. Standard transformation into the corresponding 6-(halomethyl) pyrrolotriazine, such as the chloro compound (XX), followed by treatment with an alcohol of formula (XVII) in the presence of a base readily provides the ether derivatives of formula (IIb) [$R^3$ in (II)≠H]. The preparation of the starting compound (XVIII) has been described previously [see Int. Pat. Appl. WO 2007/064883 (Intermediate AX/Step 3)].

The second route starts from the protected 1-amino-4-bromo-2-cyanopyrrole (XXI) [preparation given in Int. Pat. Appl. WO 2007/064883 (Intermediate AAE, Step 3)]. Deprotonation of the urethane nitrogen, subsequent metalation in 4-position and reaction with formaldehyde affords the 4-(hydroxymethyl) derivative (XXII). Treatment with hydrogen chloride followed by addition of alcohol (XVII) and condensation with formamidine using a one-pot procedure then provides the target compound of formula (IIb). This route is especially suited for the preparation of alkyl ether derivatives [$R^{3A}$ in (IIb)=($C_1$-$C_4$)-alkyl] in that the alcohol reactant (XVII) may also serve as the reaction solvent in these cases.

Scheme 5

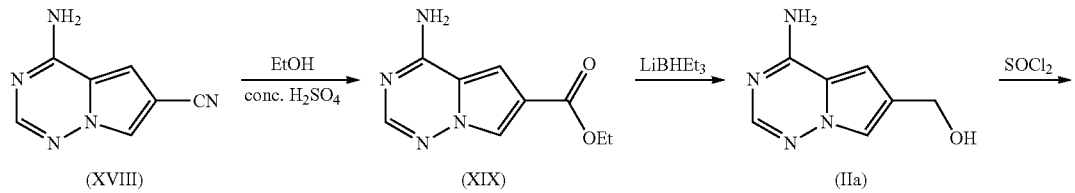

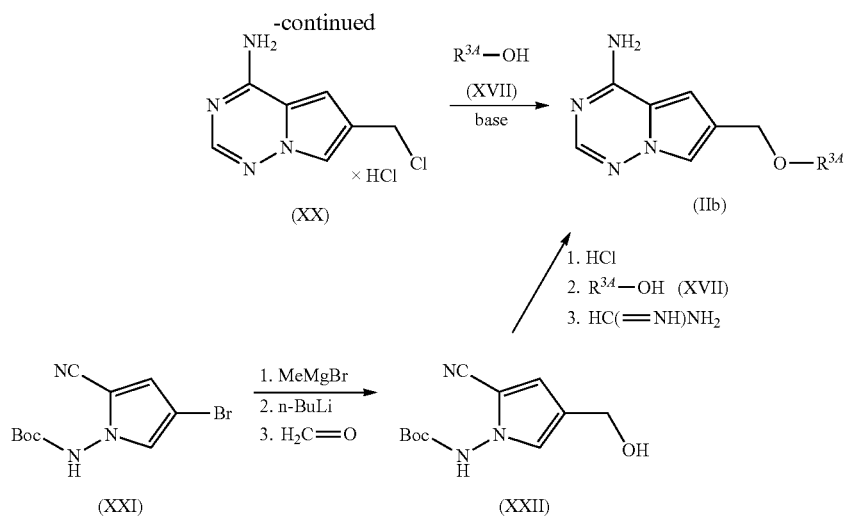

The 4-amino-5-bromopyrrolo[2,1-f][1,2,4]triazine derivative of formula (XII) is readily available from 4-amino-6-(hydroxymethyl)pyrrolo[2,1-f][1,2,4]triazine (IIa) (cf. Scheme 5) by initial 5,7-dibromination using 1,3-dibromo-5,5-dimethylhydantoin and subsequent selective 7-debromination via a halogen-metal exchange with n-butyllithium followed by methanol quenching (see Scheme 6 below).

Alkaline work-up affords the free (benzothiophen-2-yl)boronic acids of formula (VIa) which may be transformed, if desired, into cyclic boronates, e.g. so-called MIDA boronates of formula (VIb), by standard procedures known in the art [see, for example, D. M. Knapp et al., J. Am. Chem. Soc. 131 (20), 6961-6963 (2009)].

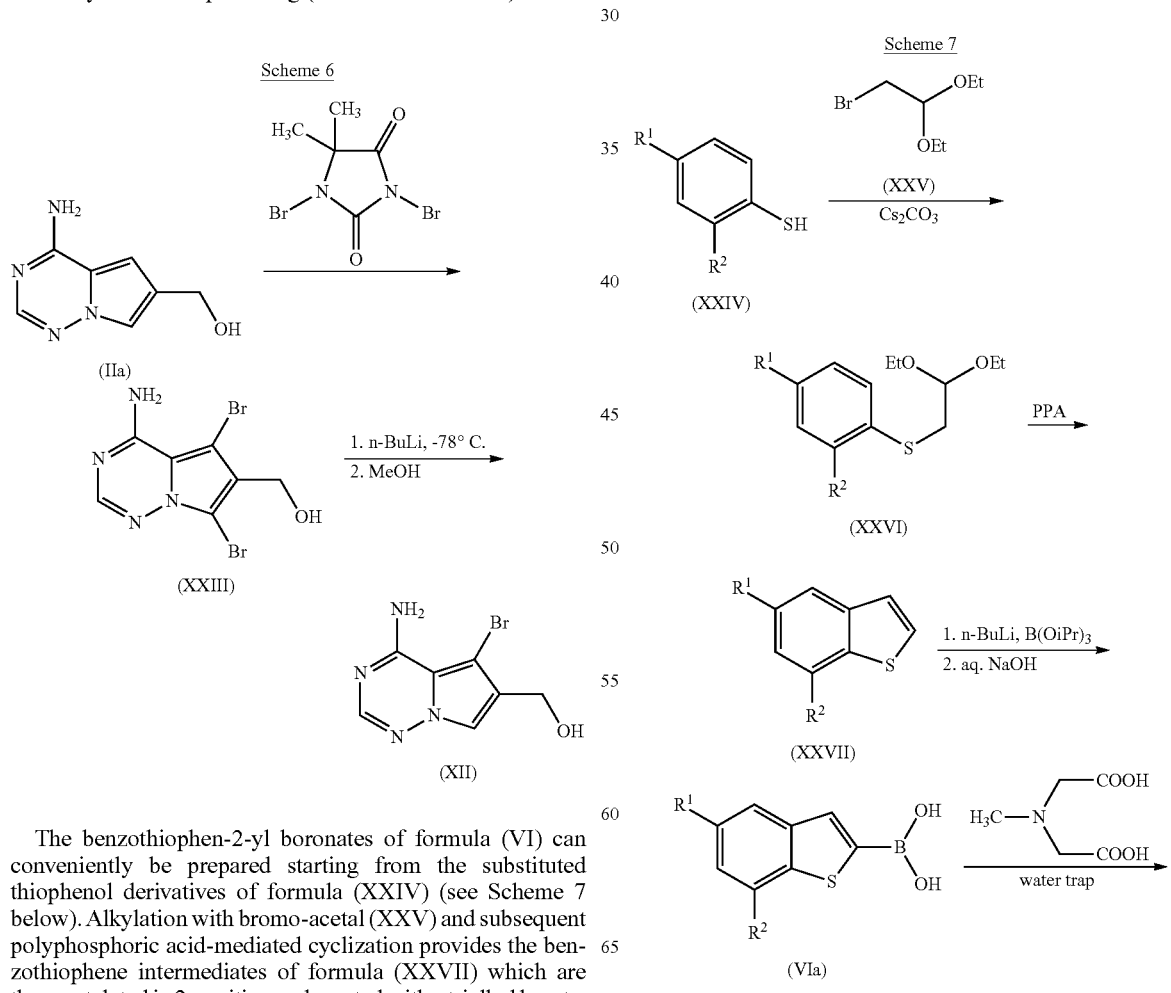

The benzothiophen-2-yl boronates of formula (VI) can conveniently be prepared starting from the substituted thiophenol derivatives of formula (XXIV) (see Scheme 7 below). Alkylation with bromo-acetal (XXV) and subsequent polyphosphoric acid-mediated cyclization provides the benzothiophene intermediates of formula (XXVII) which are then metalated in 2-position and reacted with a trialkyl borate.

-continued

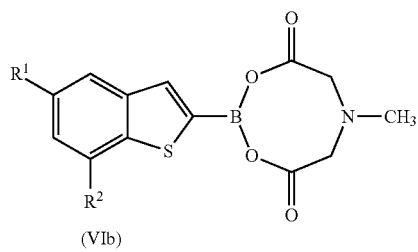

(VIb)

[cf. P. A. Plé and L. J. Marnett, *J. Heterocyclic Chem.* 25 (4), 1271-1272 (1988); A. Venturelli et al., *J. Med. Chem.* 50 (23), 5644-5654 (2007)].

The compounds of the formulae (III), (XI), (XV), (XVII), (XXIV) and (XXV) are either commercially available, known from the literature, or can be prepared from readily available starting materials by adaptation of standard methods described in the literature. Detailed procedures and literature references for preparing the starting materials can also be found in the Experimental Part in the section on the preparation of the starting materials and intermediates.

The preparation of further subgroups of the compounds of general formula (I) is illustrated in the following reaction schemes 8-14. The required pyrrolotriazine precursors can be readily synthesized by customary methods well known in the art, and further synthetic transformations, in most instances, follow the preparation routes that have been outlined in the process section above, using similar types of reactions, such as, for example, bromination, boronate coupling, aminomethylation, reductive amination, oxidation and/or ether or amide forming reactions. Further details are provided in the Experimental Part on the preparation of the exemplary embodiments and their respective precursor compounds.

Scheme 8

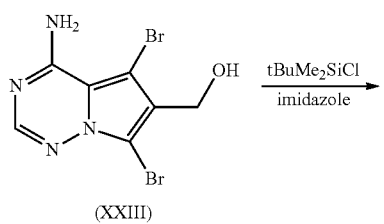

(XXIII)

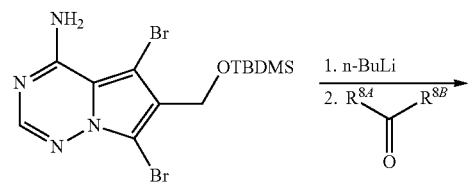

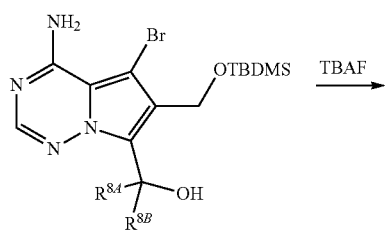

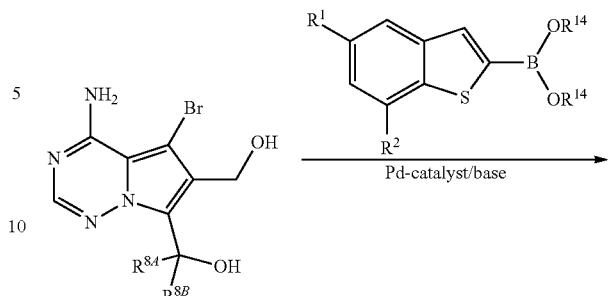

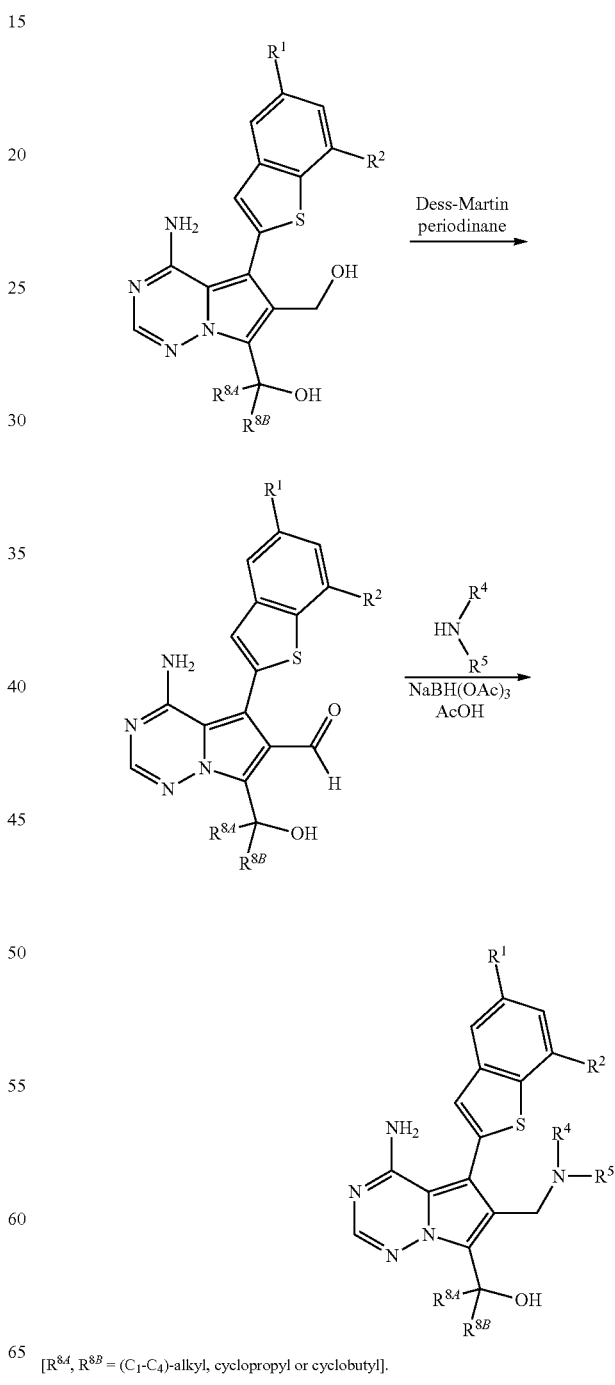

[$R^{8A}$, $R^{8B}$ = ($C_1$-$C_4$)-alkyl, cyclopropyl or cyclobutyl].

Scheme 9
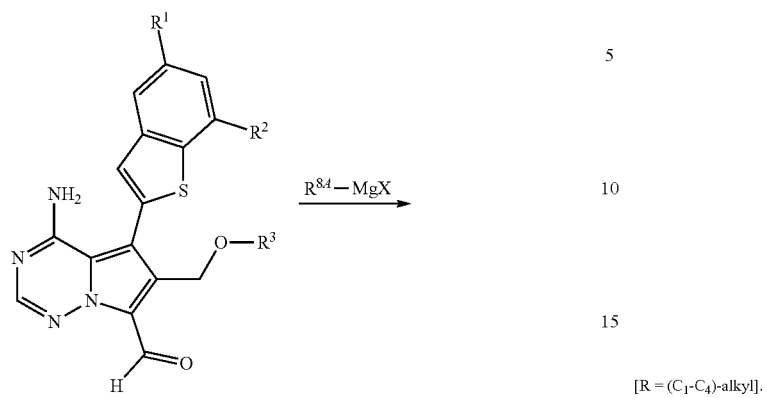
[$R^{84}$ = ($C_1$-$C_4$)-alkyl, cyclopropyl or cyclobutyl; X = Cl, Br or I].
Scheme 10
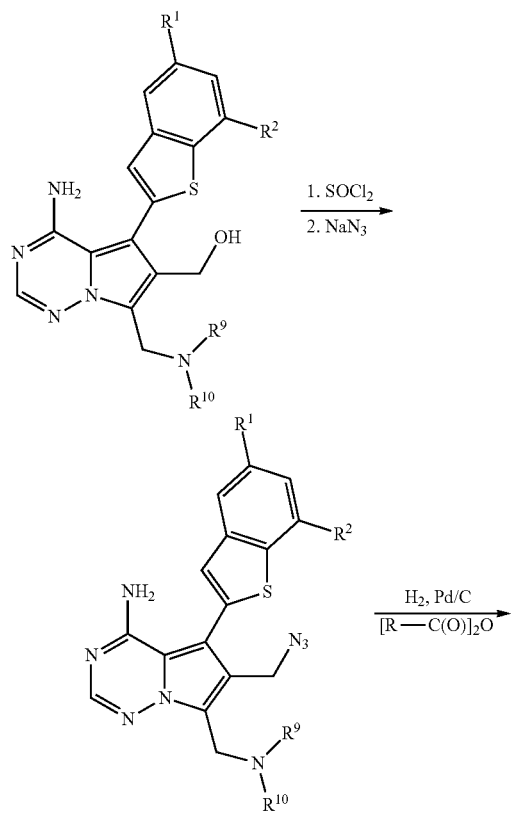
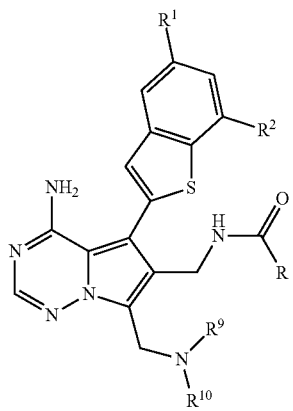
[R = ($C_1$-$C_4$)-alkyl].
Scheme 11
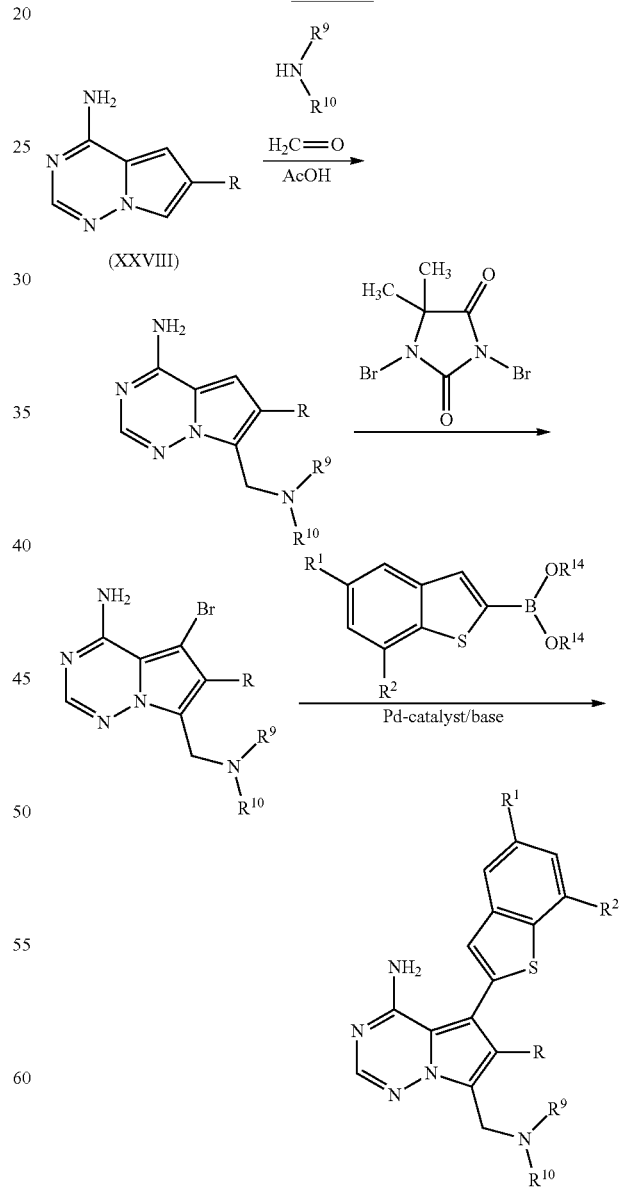
[R = chloro or ($C_1$-$C_4$)-alkyl; for the preparation of the starting material (XXVIII), see Int. Pat. Appl. WO 2007/064883 and WO 2007/056170, respectively].

Scheme 12
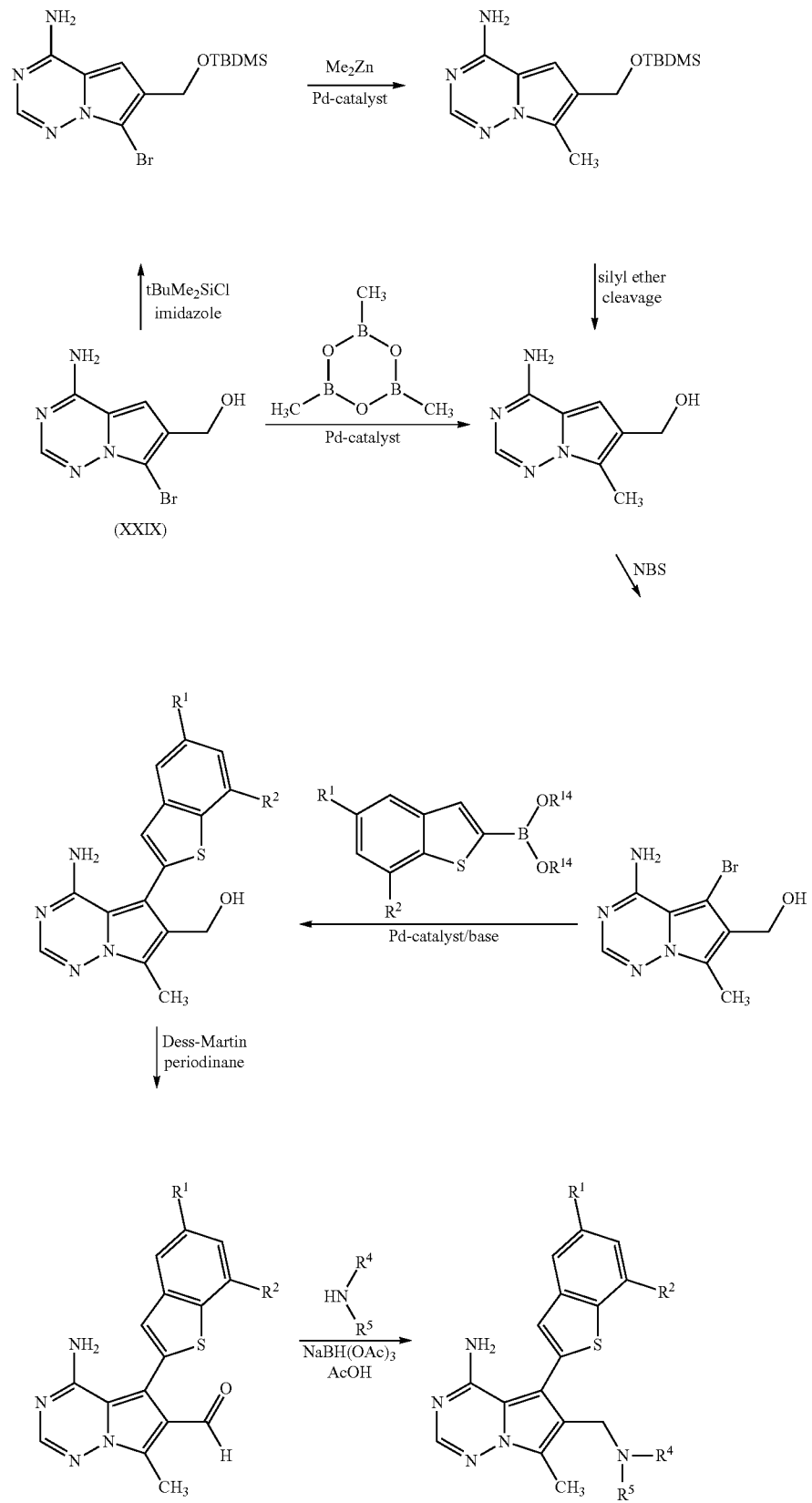
[for the preparation of the starting compound (XXIX), see Scheme 14 below].

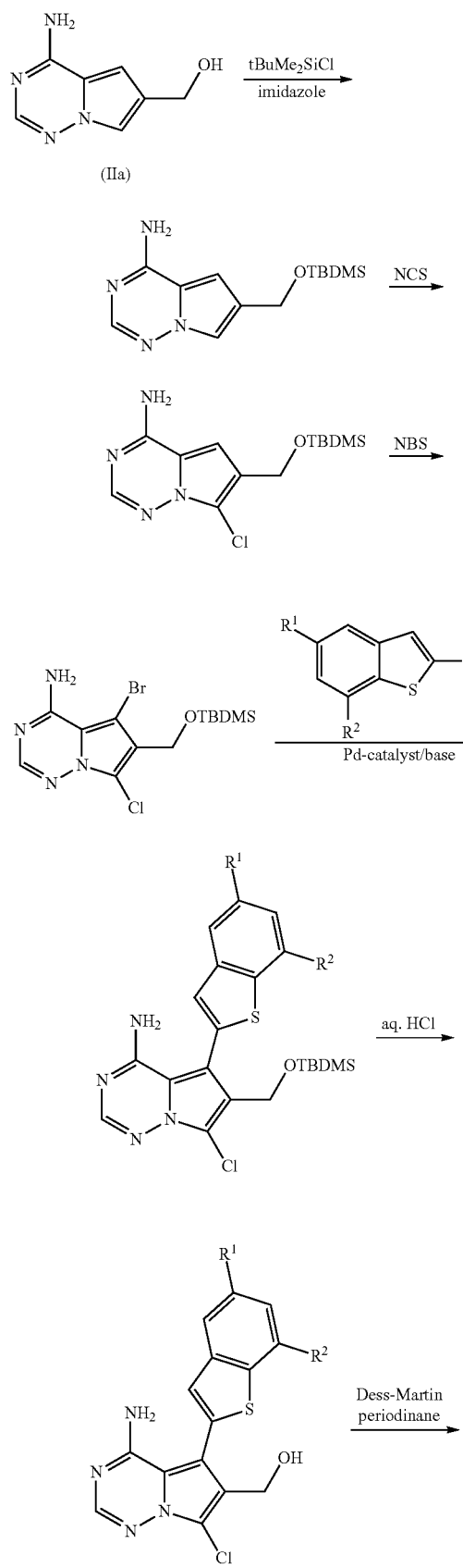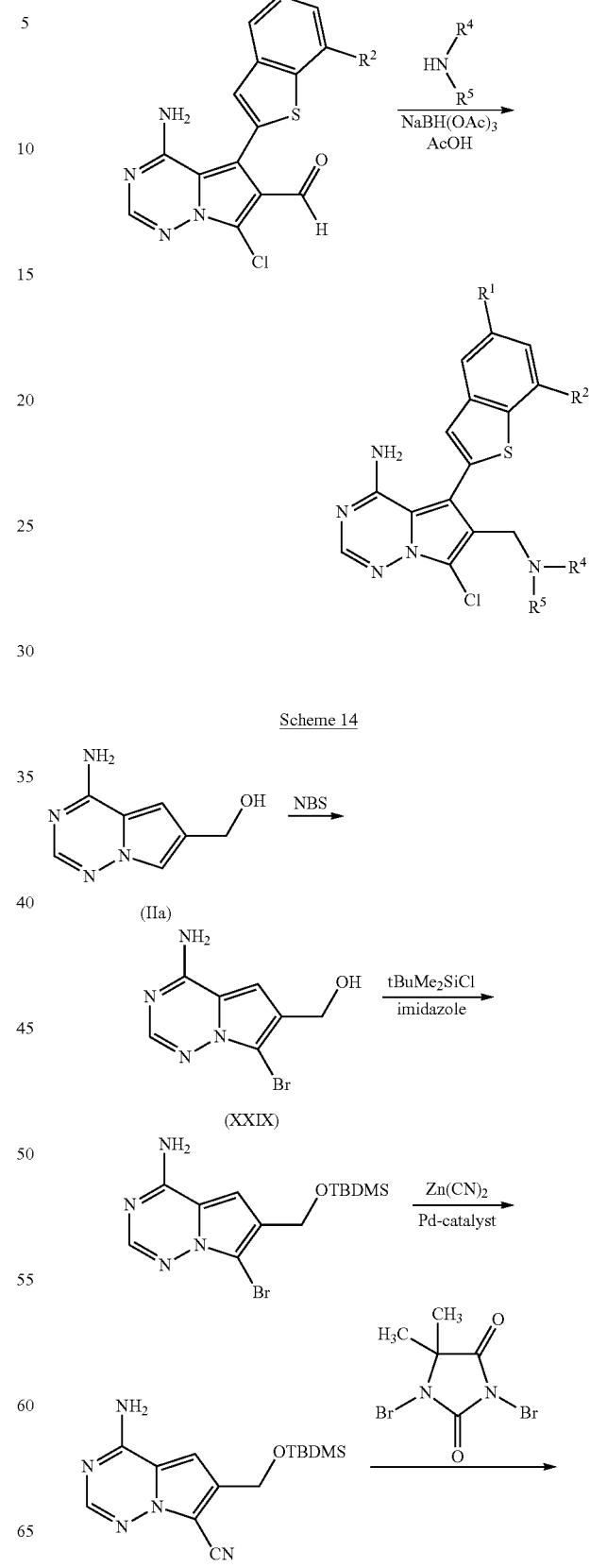

-continued

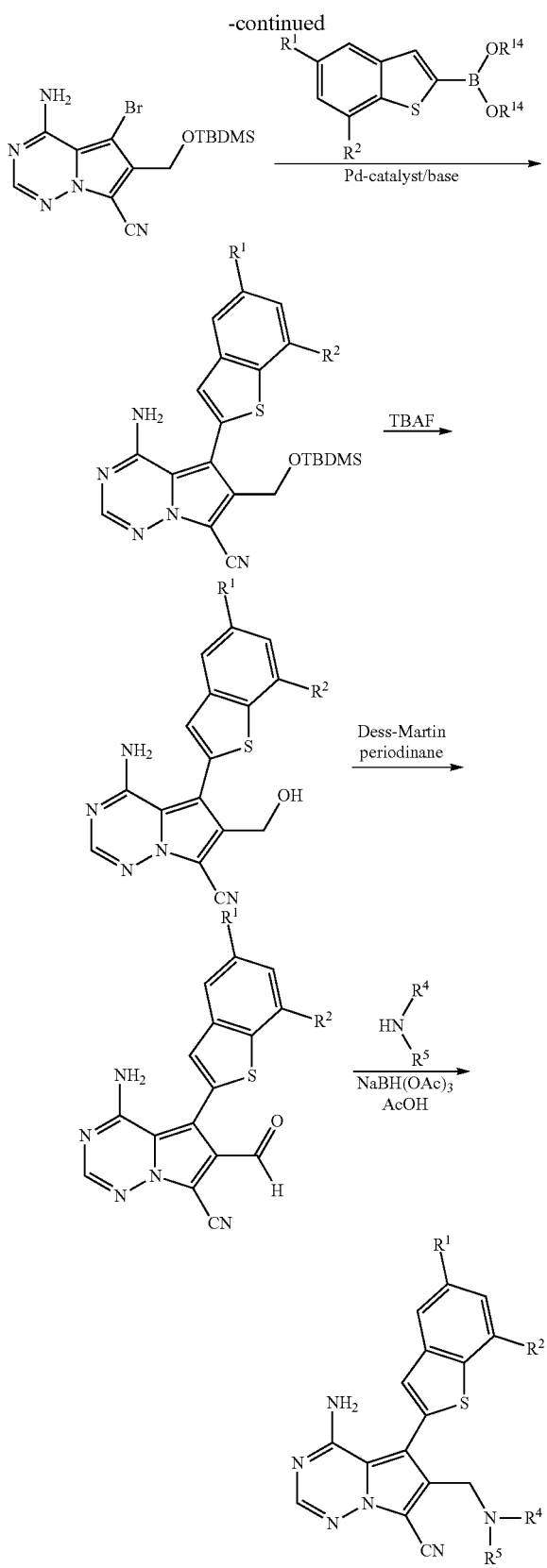

The compounds of the present invention have valuable pharmacological properties and can be used for the prevention and treatment of disorders in humans and other mammals.

The compounds of the present invention are potent inhibitors of the activity or expression of receptor tyrosine kinases, particularly of the FGFR kinases, and most notably of the FGFR-1 and FGFR-3 kinases. Accordingly, in another embodiment, the present invention provides a method of treating disorders relating to or mediated by the activity of FGFR kinases in a patient in need of such treatment, comprising administering to the patient an effective amount of a compound of formula (I) as defined above. In certain embodiments, the disorders relating to the activity of FGFR kinases are proliferative disorders, in particular cancer and tumor diseases.

In the context of the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing a disease, disorder, condition, or state, the development and/or progression thereof, and/or the symptoms thereof. The term prevention includes prophylaxis. Treatment or prevention of a disorder, disease, condition, or state may be partial or complete.

The term "proliferative disorder" includes disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

Throughout this document, for the sake of simplicity, the use of singular language is given preference over plural language, but is generally meant to include the plural language if not otherwise stated. For example, the expression "A method of treating a disease in a patient, comprising administering to a patient an effective amount of a compound of formula (I)" is meant to include the simultaneous treatment of more than one disease as well as the administration of more than one compound of formula (I).

Proliferative disorders that can be treated and/or prevented with the compounds of the present invention particularly include, but are not limited to, the group of cancer and tumor diseases. These are understood as meaning, in particular, the following diseases, but without being limited to them: mammary carcinomas and mammary tumors (ductal and lobular forms, also in situ), tumors of the respiratory tract (small cell and non-small cell lung carcinoma, parvicellular and non-parvicellular carcinoma, bronchial carcinoma, bronchial adenoma, pleuropulmonary blastoma), cerebral tumors (e.g. of the brain stem and of the hypothalamus, astrocytoma, glioblastoma, medulloblastoma, ependymoma, and neuroectodermal and pineal tumors), tumors of the digestive organs (oesophagus, stomach, gall bladder, small intestine, large intestine, rectum, anus), liver tumors (inter alia hepatocellular carcinoma, cholangiocellular carcinoma and mixed hepatocellular and cholangiocellular carcinoma), tumors of the head and neck region (larynx, hypopharynx, nasopharynx, oropharynx, lips and oral cavity), skin tumors (squamous epithelial carcinoma, Kaposi sarcoma, malignant melanoma, Merkel cell skin cancer and non-melanomatous skin cancer), tumors of soft tissue (inter alia soft tissue sarcomas, osteosarcomas, malignant fibrous histiocytomas, lymphosarcomas and rhabdomyosarcomas), tumors of the eyes (inter alia intraocular melanoma, uveal melanoma and retinoblastoma), tumors of the endocrine and exocrine glands (e.g. thyroid and parathyroid glands, pancreas and salivary gland), tumors of the urinary tract (tumors of the bladder, penis, kidney, renal pelvis and ureter), tumors of the reproductive organs (carcinomas of the endometrium, cervix, ovary, vagina, vulva and uterus in women, and carcinomas of the prostate and testicles in men), as well as distant metastases thereof. These disorders also include proliferative blood diseases in solid form and as circulating blood cells, such as lymphomas, leukaemias and myeloproliferative diseases, e.g. acute myeloid, acute lymphoblastic, chronic lymphocytic, chronic myelogenic and hairy cell leukaemia, and AIDS-related lymphomas, Hodgkin's lymphomas, non-Hodgkin's lymphomas, cutaneous T-cell lymphomas, Burkitt's lymphomas, and lymphomas in the central nervous system.

Due to their activity and selectivity profile, the compounds of the present invention are believed to be particularly suitable for the treatment of breast (mammary), lung, stomach (gastric), bladder and ovary cancer and tumor diseases. Furthermore, the compounds of the present invention may be especially suited for the prevention or suppression of tumor metastasis in general.

Other proliferative disorders that can be treated and/or prevented with the compounds and methods of the present invention include psoriasis, keloids and other hyperplasias affecting the skin, bullous disorders associated with subepidermal blister formation including bullous pemphigoid, erythema multiforme and dermatitis herpetiformis, fibrotic disorders such as lung fibrosis, atherosclerosis, restenosis and hepatic cirrhosis, renal diseases including mesangial cell proliferative disorders, glomerulopathies, glomerulonephritis, diabetic nephropathy, malignant nephrosclerosis and polycystic kidney disease, benign prostate hyperplasia (BPH), angiogenic or blood vessel proliferative disorders, and thrombotic microangiopathy syndromes.

The compounds of the present invention are also useful for the treatment and/or prevention of ophthalmological diseases such as, for example, age-related macular degeneration (AMD), dry macular degeneration, ischemic retinal vein occlusion, diabetic macula edema, diabetic retinopathy, retinopathy of prematurity, and other retinopathies.

Other conditions that may be treated and/or prevented by administering a compound of the present invention include gynaecological diseases such as endometriosis, myoma and ovarian cysts, metabolic disorders related to adipogenesis, bile metabolism, phosphate metabolism, calcium metabolism and/or bone mineralization, skeletal disorders such as, for example, dwarfism, achondrodysplasia and Pfeiffer syndrome, cartilage diseases such as osteoarthritis and polyarthritis, rheumatoid arthritis, calvities, and transplant rejection.

The diseases mentioned above have been well characterized in humans, but also exist with a comparable aetiology in other mammals, and can be treated in those with the compounds and methods of the present invention.

Thus, the present invention further relates to the use of the compounds according to the invention for the treatment and/or prevention of disorders, especially of the aforementioned disorders.

The present invention further relates to the use of the compounds according to the invention for preparing a pharmaceutical composition for the treatment and/or prevention of disorders, especially of the aforementioned disorders.

The present invention further relates to the use of the compounds according to the invention in a method for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

Compounds of the present invention may be administered as the sole pharmaceutical agent or in combination with one or more additional therapeutic agents as long as this combination does not lead to undesirable and/or unacceptable side effects. Such combination therapy includes administration of a single pharmaceutical dosage formulation which contains a compound of formula (I), as defined above, and one or more additional therapeutic agents, as well as administration of a compound of formula (I) and each additional therapeutic agent in its own separate pharmaceutical dosage formulation. For example, a compound of formula (I) and a therapeutic agent may be administered to the patient together in a single (fixed) oral dosage composition such as a tablet or capsule, or each agent may be administered in separate dosage formulations.

Where separate dosage formulations are used, the compound of formula (I) and one or more additional therapeutic agents may be administered at essentially the same time (i.e., concurrently) or at separately staggered times (i.e., sequentially).

In particular, the compounds of the present invention may be used in fixed or separate combination with other anti-cancer agents such as alkylating agents, anti-metabolites, plant-derived anti-tumor agents, hormonal therapy agents, topoisomerase inhibitors, tubulin inhibitors, kinase inhibitors, targeted drugs, antibodies, antibody-drug conjugates (ADCs), immunologicals, biological response modifiers, anti-angiogenic compounds, and other anti-proliferative, cytostatic and/or cytotoxic substances. In this regard, the following is a non-limiting list of examples of secondary agents that may be used in combination with the compounds of the present invention:

Abarelix, abiraterone, aclarubicin, afatinib, aflibercept, aldesleukin, alemtuzumab, alitretinoin, alpharadin, altretamine, aminoglutethimide, amonafide, amrubicin, amsacrine, anastrozole, andromustine, arglabin, asparaginase, axitinib, 5-azacitidine, basiliximab, belotecan, bendamustine, bevacizumab, bexarotene, bicalutamide, bisantrene, bleomycin, bortezomib, bosutinib, brivanib alaninate, buserelin, busulfan, cabazitaxel, CAL-101, calcium folinate, calcium levofolinate, camptothecin, capecitabine, carboplatin, carmofur, carmustine, catumaxomab, cediranib, celmoleukin, cetuximab, chlorambucil, chlormadinone, chlormethine, cidofovir, cisplatin, cladribine, clodronic acid, clofarabine, combretastatin, crisantaspase, crizotinib, cyclophosphamide, cyproterone, cytarabine, dacarbazine, dactinomycin, darbepoetin alfa, darinaparsin, dasatinib, daunorubicin, decitabine, degarelix, denileukin diftitox, denosumab, deslorelin, dibrospidium chloride, docetaxel, dovitinib, doxifluridine, doxorubicin, dutasteride, eculizumab, edrecolomab, eflornithine, elliptinium acetate, eltrombopag, endostatin, enocitabine, epimbicin, epirubicin, epitiostanol, epoetin alfa, epoetin beta, epothilone, eptaplatin, eribulin, erlotinib, estradiol, estramustine, etoposide, everolimus, exatecan, exemestane, exisulind, fadrozole, fenretinide, filgrastim, finasteride, flavopiridol, fludarabine, 5-fluorouracil, fluoxymesterone, flutamide, foretinib, formestane, fotemustine, fulvestrant, ganirelix, gefitinib, gemcitabine, gemtuzumab, gimatecan, gimeracil, glufosfamide, glutoxim, goserelin, histrelin, hydroxyurea, ibandronic acid, ibritumomab tiuxetan, idarubicin, ifosfamide, imatinib, imiquimod, improsulfan, intedanib, interferon alpha, interferon alpha-2a, interferon alpha-2b, interferon beta, interferon gamma, interleukin-2, ipilimumab, irinotecan, ixabepilone, lanreotide, lapatinib, lasofoxifene, lenalidomide, lenograstim, lentinan, lenvatinib, lestaurtinib, letrozole, leuprorelin, levamisole, linifanib, linsitinib, lisuride, lobaplatin, lomustine, lonidamine, lurtotecan, mafosfamide, mapatumumab, masitinib, masoprocol, medroxyprogesterone, megestrol, melarsoprol, melphalan, mepitiostane, mercaptopurine, methotrexate, methylaminolevulinate, methyltestosterone, mifamurtide, mifepristone, miltefosine, miriplatin, mitobronitol, mitoguazone, mitolactol, mitomycin, mitotane, mitoxantrone, molgramostim, motesanib, nandrolone, nedaplatin, nelarabine, neratinib, nilotinib, nilutamide, nimotuzumab, nimustine, nitracrine, nolatrexed, ofatumumab, oprelvekin, oxaliplatin, paclitaxel, palifermin, pamidronic acid, panitumumab, pazopanib, pegaspargase, peg-epoetin beta, pegfilgastrim, peginterferon alpha-2b, pelitrexol, pemetrexed, pemtumomab, pentostatin, peplomycin, perfosfamide, perifosine, pertuzumab, picibanil, pirambicin, pirarubicin, plerixafor, plicamycin, poliglusam, polyestradiol phosphate, ponatinib, porfimer sodium, pralatrexate, prednimustine, procarbazine, procodazole, PX-866, quinagolide, raloxifene, raltitrexed, ranibizumab, ranimustine, razoxane, regorafenib, risedronic acid, rituximab, romidepsin, romiplostim, rubitecan, saracatinib, sargramostim, satraplatin, selumetinib, sipuleucel-T, sirolimus, sizofuran, sobuzoxane, sorafenib, streptozocin, sunitinib, talaporfin, tamibarotene, tamoxifen, tandutinib, tasonermin, teceleukin, tegafur, telatinib, temoporfin, temozolomide, temsirolimus, teniposide, testolactone, testosterone, tetrofosmin, thalidomide, thiotepa, thymalfasin, tioguanine, tipifarnib, tivozanib, toceranib, tocilizumab, topotecan, toremifene, tositumomab, trabectedin, trastuzumab, treosulfan, tretinoin, triapine, trilostane, trimetrexate, triptorelin, trofosfamide, ubenimex, valrubicin, vandetanib, vapreotide, varlitinib, vatalanib, vemurafenib, vidarabine, vinblastine, vincristine, vindesine, vinflunine, vinorelbine, volociximab, vorinostat, zinostatin, zoledronic acid, and zorubicin.

Generally, the following aims may be pursued with the combination of compounds of the present invention with other anti-cancer agents:

improved activity in slowing down the growth of a tumor, in reducing its size or even in its complete elimination compared with treatment with a single active compound;

possibility of employing the chemotherapeutics used in a lower dosage than in monotherapy;

possibility of a more tolerable therapy with few side effects compared with individual administration;

possibility of treatment of a broader spectrum of cancer and tumor diseases;

achievement of a higher rate of response to therapy;

longer survival time of the patient compared with standard therapy.

Thus, in a further embodiment, the present invention relates to pharmaceutical compositions comprising at least one of the compounds according to the invention and one or more additional therapeutic agents for the treatment and/or prevention of disorders, especially of the aforementioned disorders.

In cancer treatment, the compounds of the present invention may also be employed in conjunction with radiation therapy and/or surgical intervention.

Furthermore, the compounds of formula (I) may be utilized, as such or in compositions, in research and diagnostics, or as analytical reference standards, and the like, which are well known in the art.

When the compounds of the present invention are administered as pharmaceuticals, to humans and other mammals, they can be given per se or as a pharmaceutical composition containing, for example, 0.1% to 99.5% (more preferably, 0.5% to 90%) of active ingredient in combination with one or more pharmaceutically acceptable excipients.

Thus, in another aspect, the present invention relates to pharmaceutical compositions comprising at least one of the compounds according to the invention, conventionally together with one or more inert, non-toxic, pharmaceutically suitable excipients, and to the use thereof for the treatment and/or prevention of disorders, especially of the aforementioned disorders.

The compounds according to the invention can act systemically and/or locally. For this purpose, they can be administered in a suitable way such as, for example, by the oral, parenteral, pulmonary, nasal, lingual, sublingual, buccal, rectal, dermal, transdermal, conjunctival, otic or topical route, or as an implant or stent.

For these application routes, the compounds of the invention can be administered in suitable application forms.

Suitable for oral administration are application forms which function according to the prior art and deliver the compounds according to the invention rapidly and/or in modified fashion, and which contain the compounds according to the invention in crystalline, amorphous and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (e.g. hard or soft gelatin capsules), sugar-coated tablets, granules, pellets, powders, emulsions, suspensions, aerosols or solutions.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include, for example, inhalatory pharmaceutical forms (e.g. powder inhalers, nebulizers), nasal drops, solutions or sprays, tablets or capsules to be administered lingually, sublingually or buccally (e.g. troches, lozenges), suppositories, ear and eye preparations (e.g. drops, ointments), vaginal capsules, aqueous suspensions (lotions, shaking mixtures), lipophilic suspensions, ointments, creams, milks, pastes, foams, dusting powders, transdermal therapeutic systems (e.g. patches), implants and stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The compounds according to the invention can be converted into the recited application forms in a manner known per se by mixing with inert, non-toxic, pharmaceutically suitable excipients. These excipients include, inter alia, carriers (e.g. microcrystalline cellulose, lactose, mannitol), solvents (e.g. liquid polyethylene glycols), emulsifiers (e.g. sodium dodecyl sulfate), surfactants (e.g. polyoxysorbitan oleate), dispersants (e.g. polyvinylpyrrolidone), synthetic and natural polymers (e.g. albumin), stabilizers (e.g. antioxidants such as, for example, ascorbic acid), colorants (e.g. inorganic pigments such as, for example, iron oxides), and taste and/or odour masking agents.

A preferred dose of the compound of the present invention is the maximum that a patient can tolerate and not develop serious side effects. Illustratively, the compound of the present invention may be administered parenterally at a dose of about 0.001 mg/kg to about 1 mg/kg, preferably of about 0.01 mg/kg to about 0.5 mg/kg of body weight. On oral administration, an exemplary dose range is about 0.01 to 100 mg/kg, preferably about 0.01 to 20 mg/kg, and more preferably about 0.1 to 10 mg/kg of body weight. Ranges intermediate to the above-recited values are also intended to be part of the invention.

Nevertheless, actual dosage levels and time course of administration of the active ingredients in the pharmaceutical compositions of the invention may be varied so as to obtain an amount of the active ingredient which is effective to achieve the desired therapeutic response for a particular patient, composition and mode of administration, without being toxic to the patient. It may therefore be necessary where appropriate to deviate from the stated amounts, in particular as a function of age, gender, body weight, diet and general health status of the patient, the bioavailability and pharmacodynamic characteristics of the particular compound and its mode and route of administration, the time or interval over which administration takes place, the dose regimen selected, the response of the individual patient to the active ingredient, the specific disease involved, the degree of or the involvement or severity of the disease, the kind of concurrent treatment (i.e., the interaction of the compound of the invention with other co-administered therapeutics), and other relevant circumstances.

Thus, it may be satisfactory in some cases to manage with less than the aforementioned minimum amount, whereas in other cases the stated upper limit must be exceeded. Treatment can be initiated with smaller dosages, which are less than the optimum dose of the compound. Thereafter, the dosage may be increased by small increments until the optimum effect under the circumstances is reached. For convenience, the total daily dosage may be divided and administered in individual portions spread over the day.

The following exemplary embodiments illustrate the invention. The invention is not restricted to the examples.

The percentages in the following tests and examples are, unless stated otherwise, by weight; parts are by weight. Solvent ratios, dilution ratios and concentrations reported for liquid/liquid solutions are each based on volume.

A. EXAMPLES

Abbreviations and Acronyms

Ac acetyl
$Ac_2O$ acetic anhydride
AcOH acetic acid
aq. aqueous (solution)
Boc tert-butoxycarbonyl
br. broad ($^1$H-NMR signal)
Bu butyl
cat. catalytic
conc. concentrated
d doublet ($^1$H-NMR signal)
DBDMH 1,3-dibromo-5,5-dimethylhydantoin
DCI direct chemical ionization (MS)
DCM dichloromethane
Dess-Martin periodinane 1,1,1-triacetoxy-1,1-dihydro-1,2-benziodoxol-3 (1H)-one
DIPEA N,N-diisopropylethylamine
DMF N,N-dimethylformamide
DMSO dimethylsulfoxide
EI electron impact ionization (MS)
eq. equivalent(s)
ESI electro-spray ionization (MS)
Et ethyl
EtOAc ethyl acetate
GC-MS gas chromatography-coupled mass spectroscopy
h hour(s)
Hal halogen
$^1$H-NMR proton nuclear magnetic resonance spectroscopy
HPLC high performance liquid chromatography
iPr isopropyl
LC-MS liquid chromatography-coupled mass spectroscopy
Me methyl
MeOH methanol
min minute(s)
MS mass spectroscopy
m/z mass-to-charge ratio (MS)
NBS N-bromosuccinimide
n-Bu n-butyl
NCS N-chlorosuccinimide
of th. of theory (chemical yield)
Pd/C palladium on charcoal
$PdCl_2$(dppf) [1,1'-bis(diphenylphosphino)ferrocene]dichloropalladium(II)
Pd(dba)$_2$ bis(dibenzylideneacetone)palladium
Ph phenyl
PPA polyphosphoric acid
q quartet ($^1$H-NMR signal)
quant. quantitative (yield)
rac racemic
$R^f$ TLC retention factor
RP reverse phase (HPLC)
rt room temperature
$R_t$ retention time (HPLC)
s singlet ($^1$H-NMR signal)
sat. saturated (solution)
t triplet ($^1$H-NMR signal)
TBAF tetra-n-butylammonium fluoride
TBDMS tert-butyldimethylsilyl
TBTU N-[(1H-benzotriazol-1-yloxy)(dimethylamino)methylene]-N-methylmethanaminium tetrafluoroborate
tBu tert-butyl
tert tertiary
TFA trifluoroacetic acid
THF tetrahydrofuran
TLC thin layer chromatography LC-MS and GC-MS Methods:

Method 1 (LC-MS):

Instrument: Micromass Quattro Premier with Waters UPLC Acquity; column: Thermo Hypersil GOLD 1.9µ, 50 mm×1 mm; eluent A: 1 L water+0.5 mL 50% aq. formic acid, eluent B: 1 L acetonitrile+0.5 ml 50% aq. formic acid; gradient: 0.0 min 90% A→0.1 min 90% A→1.5 min 10% A→2.2 min 10% A; temperature: 50° C.; flow rate: 0.33 mL/min; UV detection: 210 nm.

Method 2 (LC-MS):

Instrument: Waters Acquity SQD UPLC System; column: Waters Acquity UPLC HSS T3 1.8µ, 50 mm×1 mm; eluent A: 1 L water+0.25 mL 99% formic acid, eluent B: 1 L acetonitrile+0.25 mL 99% formic acid; gradient: 0.0 min 90%

A→1.2 min 5% A→2.0 min 5% A; oven: 50° C.; flow rate: 0.40 mL/min; UV detection: 210-400 nm.

Method 3 (LC-MS):

Instrument: Micromass Quattro Micro with HPLC Agilent 1100 Series; column: YMC-Triart C18 3µ, 50 mm×3 mm; eluent A: 1 L water+0.01 mol ammonium carbonate, eluent B: 1 L acetonitrile; gradient: 0.0 min 100% A→2.75 min 5% A→4.5 min 5% A; oven: 40° C.; flow rate: 1.25 mL/min; UV detection: 210 nm.

Method 4 (LC-MS):

Instrument: Waters Acquity SQD UPLC System; column: Waters Acquity UPLC HSS T3 1.8µ, 30 mm×2 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow rate: 0.60 mL/min; UV detection: 208-400 nm.

Method 5 (LC-MS):

Instrument: Micromass Quattro Premier with Waters UPLC Acquity; column: Thermo Hypersil GOLD 1.9µ, 50 mm×1 mm; eluent A: 1 L water+0.5 mL 50% aq. formic acid, eluent B: 1 L acetonitrile+0.5 ml 50% aq. formic acid; gradient: 0.0 min 97% A→0.5 min 97% A→3.2 min 5% A→4.0 min 5% A; temperature: 50° C.; flow rate: 0.3 mL/min; UV detection: 210 nm.

Method 6 (GC-MS):

Instrument: Micromass GCT, GC6890; column: Restek RTX-35, 15 m×200 µm×0.33 µm; constant flow with helium: 0.88 mL/min; oven: 70° C.; inlet: 250° C.; gradient: 70° C., 30° C./min→310° C. (maintain for 3 min).

Method 7 (LC-MS):

Instrument MS: Waters Micromass QM; Instrument HPLC: Agilent 1100 series; column: Agilent ZORBAX Extend-C18 3.0 mm×50 mm, 3.5µ; eluent A: 1 L water+0.01 mol ammonium carbonate, eluent B: 1 L acetonitrile; gradient: 0.0 min 98% A→0.2 min 98% A→3.0 min 5% A→4.5 min 5% A; temperature: 40° C.; flow rate: 1.75 mL/min; UV detection: 210 nm.

Method 8 (LC-MS):

Instrument MS: Waters Micromass ZQ; Instrument HPLC: Agilent 1100 series; column: Agilent ZORBAX Extend-C18 3.0 mm×50 mm, 3.5µ; eluent A: 1 L water+0.01 mol ammonium carbonate, eluent B: 1 L acetonitrile; gradient: 0.0 min 98% A→0.2 min 98% A→3.0 min 5% A→4.5 min 5% A; temperature: 40° C.; flow rate: 1.75 mL/min; UV detection: 210 nm.

General Purification Methods (see Table I and II Below):

Method P1:

Preparative RP-HPLC (Reprosil C18, gradient acetonitrile/0.2% aq. trifluoroacetic acid).

Method P2:

Preparative RP-HPLC(XBridge C18, gradient acetonitrile/water+0.1% aq. ammonia).

Method P3:

Preparative RP-HPLC (Sunfire C18, gradient acetonitrile/water).

Method P4:

Preparative RP-HPLC (XBridge C18, gradient acetonitrile/water+0.05% aq. ammonia).

Method P5:

The product obtained from the preceding RP-HPLC purification is dissolved in methanol and filtered through an anion exchange cartridge (Stratospheres SPE, PL-HCO$_3$ MP-resin). The cartridge is eluted with methanol, and the filtrate is evaporated.

Method P6:

A solution of the product in ethyl acetate is washed with sat. aq. sodium hydrogencarbonate solution followed by sat. aq. sodium chloride solution, dried over magnesium sulfate, filtered and evaporated.

Starting Materials and Intermediates

Intermediate 1A

2-Methoxy-4-methylaniline

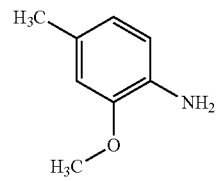

A mixture of 5-methyl-2-nitroanisol (265 g, 1.58 mol) and 10% Pd/C (39.75 g) in THF (1.32 L) was stirred overnight at rt under 1 atm of hydrogen. Filtration over kieselguhr and evaporation afforded 216.1 g of the crude product which was used in the next step without further purification.

LC-MS (method 3): R$_t$=2.39 min; MS (ESIpos): m/z=138 (M+H)$^+$ $^1$H-NMR (400 MHz, DMSO-d$_6$): δ=6.45-6.63 (m, 3H), 4.46 (s, 2H), 3.72 (s, 3H), 2.16 (s, 3H) ppm.

Intermediate 2A

2-Methoxy-4-methylbenzenethiol

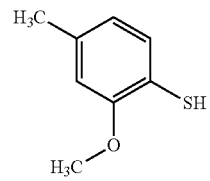

Method 1:

A solution of sodium nitrite (7 g, 101.4 mmol) in water (25 ml) was added dropwise to a cooled (0°-5° C.) solution of Intermediate 1A (13.7 g, 100 mmol) in concentrated hydrochloric acid (30 ml) and water (85 ml). After stirring at 0° C. for 10 min, sodium acetate (15 g, 182.8 mmol) was added. The resulting mixture was added dropwise to a hot solution (70°-80° C.) of potassium O-ethyl dithiocarbonate (30 g, 187.1 mmol) in water (140 ml), stirred between 70° C. and 80° C. for 1 h and then cooled to rt. The mixture was extracted twice with ethyl acetate, and the combined organic extracts were dried over sodium sulfate and evaporated. The residue was taken up in a 1.3 M solution of potassium hydroxide in ethanol (300 ml). Glucose (8 g) was added, and the resulting mixture was refluxed for 3 h. Then, the ethanol solvent was evaporated, and the residue was diluted with water and acidified with 6 N aqueous sulfuric acid. Zinc powder (15 g) was added carefully, and the resulting mixture was heated to 50° C. for 30 min. The mixture was then cooled to rt, diluted with dichloromethane and filtered. The filtrate was extracted twice with dichloromethane, and the combined organic extracts were dried over sodium sulfate and evaporated affording 14.3 g of the crude product which was used in the next step without further purification.

Method 2:

To 2.9 L of THF was added a warm solution of 355 ml (6.67 mol) concentrated sulfuric acid in 1.1 L of water. At 50° C., 293 g (1.33 mol) 2-methoxy-4-methylbenzenesulfonyl chloride were added under stirring. Then, 521 g (7.97 mol) of zinc powder were added carefully in portions (foaming), and the slightly exothermic reaction was cooled in a water bath to maintain a temperature of 50°-55° C. The mixture was subsequently stirred at 55° C. for 3 h. The progress of the reaction was monitored by TLC (silica gel, petrolether/ethyl acetate 95:5). The reaction mixture was poured into 13.6 L of water, 6.8 L dichloromethane were added, and the mixture was stirred for 5 min. After decanting from remaining zinc and phase separation, the aqueous phase was extracted once more with 6.8 L dichloromethane. The combined organic phases were washed with 10% brine, dried and evaporated at 40° C. under reduced pressure yielding 237 g of crude product. This material was used in the next step without further purification. An analytical sample was obtained by silica gel chromatography with petrolether/ethyl acetate (97:3) as eluent.

LC-MS (method 1): $R_t$=1.21 min; MS (ESIneg): m/z=153 (M−H)$^-$ $^1$H-NMR (400 MHz, DMSO-d$_6$): δ=7.17 (d, 1H), 6.81 (s, 1H), 6.66 (d, 1H), 4.63 (br. s, 1H), 3.80 (s, 3H), 2.26 (s, 3H) ppm.

Intermediate 3A

1-[(2,2-Diethoxyethyl)sulfanyl]-2-methoxy-4-methylbenzene

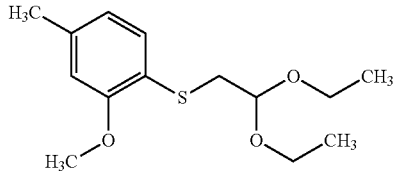 [SMILES: CCOC(CSc1ccc(C)cc1OC)OCC]

237 g crude material from Intermediate 2A, 287 g (1.46 mol) bromoacetaldehyde-diethylacetal and 862 g (2.65 mol) caesium carbonate were suspended in 2 L DMF. The reaction temperature increased initially to 40° C., then stirring was continued overnight at ambient temperature. The reaction mixture was partitioned between 10 L of water and 2.7 L of ethyl acetate. The aqueous phase was extracted with another portion of 2.7 L ethyl acetate. The combined organic phases were washed with 10% brine, dried and evaporated. The resulting oily residue was purified by silica gel chromatography with petrolether/ethyl acetate (95:5) as eluent.

Yield: 236 g of an oil (66% of th.)

GC-MS (method 6): $R_t$=6.03 min; MS (EIpos): m/z=270 (M)$^+$ $^1$H-NMR (400 MHz, DMSO-d$_6$): δ=7.16 (d, 1H), 6.82 (s, 1H), 6.73 (d, 1H), 4.55 (t, 1H), 3.80 (s, 3H), 3.52-3.64 (m, 2H), 3.39-3.51 (m, 2H), 2.96 (d, 2H), 2.33 (s, 3H), 1.09 (t, 6H) ppm.

Intermediate 4A

7-Methoxy-5-methyl-1-benzothiophene

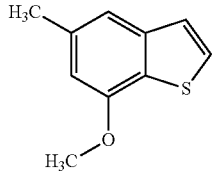

To a refluxing mixture of 13 g polyphosphoric acid and 150 ml chlorobenzene was added dropwise a solution of 5.2 g (19.2 mmol) of Intermediate 3A, and refluxing was continued overnight. After cooling, the organic layer was decanted, and the residue and flask were rinsed twice with DCM. The combined organic phases were evaporated at reduced pressure. The residue (3.76 g) was chromatographed on silica gel with isohexane/0-10% ethyl acetate as eluent.

Yield: 1.69 g of an oil (49% of th.)

GC-MS (method 6): $R_t$=5.20 min; MS (EIpos): m/z=178 (M)$^+$ $^1$H-NMR (400 MHz, DMSO-d$_6$): δ=7.68 (d, 1H), 7.34 (d, 1H), 7.28 (s, 1H), 6.78 (s, 1H), 3.93 (s, 3H), 2.43 (s, 3H) ppm.

Intermediate 5A (7-Methoxy-5-methyl-1-benzothiophen-2-yl)boronic acid

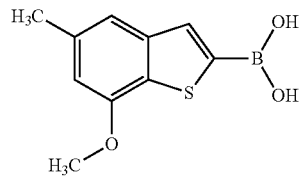

Under argon atmosphere, 26.7 g (150 mmol) of Intermediate 4A were dissolved in 270 ml of THF and cooled to −70° C. Between −70° C. and −65° C., 66 ml (165 mmol) of a 2.5 N solution of n-butyllithium in hexane were added dropwise within 20 min, resulting in formation of a white precipitate. After stirring for 1 h at −70° C., 41.5 ml (180 mmol) triisopropyl borate were added at this temperature within 10 min (resulting in a thick suspension). Stirring was continued for 1 h at −70° C., before the reaction mixture was allowed to warm up to rt overnight. Then, 400 ml of saturated aq. ammonium chloride solution were added, the layers were separated, and the aqueous layer was extracted once more with THF. The combined organic phases were evaporated under reduced pressure. To the residue thus obtained, 200 ml of water and 86 ml of 2 N aq. sodium hydroxide solution were added. The solution was washed twice with DCM, then acidified with 35 ml of 3 M sulfuric acid, and the resulting suspension was stirred vigorously for 1 h. The precipitate was filtered off by suction and dried overnight at 45° C. in vacuo.

Yield: 28.25 g of a colorless solid (94% pure by LC-MS, 80% of th.)

LC-MS (method 2): $R_t$=0.87 min; MS (ESIpos): m/z=223 (M+H)$^+$ $^1$H-NMR (400 MHz, DMSO-d$_6$): δ=7.17 (d, 1H), 6.81 (s, 1H), 6.66 (d, 1H), 4.63 (br. s, 1H), 3.80 (s, 3H), 2.26 (s, 3H) ppm.

Intermediate 6A 2-(7-Methoxy-5-methyl-1-benzothiophen-2-yl)-6-methyl-1,3,6,2-dioxazaborocane-4,8-dione

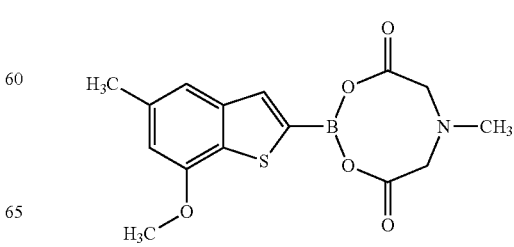

6.3 g (28.4 mmol) of Intermediate 5A and 4.2 g (28.4 mmol) 2,2'-(methylimino)diacetic acid were dissolved in a mixture of 45 ml DMSO and 400 ml toluene and refluxed for 16 h using a Dean-Stark trap. After evaporation, the residue was taken up in ethyl acetate and washed three times with water and once with brine. The organic phase was dried over magnesium sulfate and evaporated to a volume of about 200 ml. A white solid precipitated which was filtered, washed with ethyl acetate and dried in vacuo to give a first crop (5.52 g) of the title compound. A second crop (3.32 g) was obtained after evaporation of the mother liquor and flash-chromatography over a layer of silica gel using cyclohexane/0-100% ethyl acetate as the eluent.

Yield: 8.84 g (overall purity 92.5% by LC-MS, 87% of th.)

LC-MS (method 2): $R_t$=0.93 min; MS (ESIpos): m/z=334 (M+H)$^+$ $^1$H-NMR (400 MHz, DMSO-d$_6$): δ=7.42 (s, 1H), 7.26 (s, 1H), 6.76 (s, 1H), 4.40 (d, 2H), 4.17 (d, 2H), 3.92 (s, 3H), 2.63 (s, 3H), 2.42 (s, 3H) ppm.

Intermediate 7A

Ethyl 4-aminopyrrolo[2,1-f][1,2,4]triazine-6-carboxylate

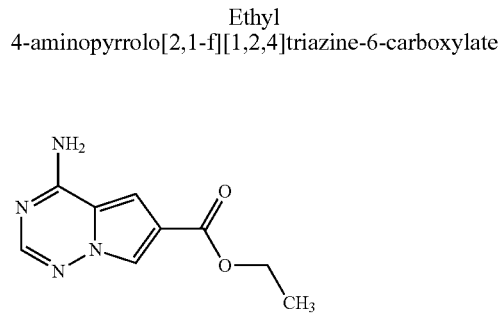

A solution of 4-aminopyrrolo[2,1-f][1,2,4]triazine-6-carbonitrile (3.9 g, 24.5 mmol; preparation described in PCT Int. Pat. Appl. WO 2007/064883) in ethanol (124.8 ml) was stirred with concentrated sulfuric acid (62.4 ml) at 80° C. overnight. After cooling to rt, the reaction mixture was poured onto 800 g of ice and brought to pH 6-7 with concentrated aq. sodium hydroxide solution. Ethyl acetate (500 ml) and dichloromethane (500 ml) were added to the suspension, and the resulting mixture was filtered over kieselguhr. The organic layer was separated from the aqueous layer. The solid was dissolved in hot water (1 L), and the aqueous layer was extracted twice with ethyl acetate. The combined organic layers were dried over sodium sulfate and evaporated. The residue was triturated with an isopropanol/diethylether mixture, and the solid was filtered off yielding 2.5 g (49% of th.) of the title compound.

LC-MS (method 2): $R_t$=0.59 min; MS (ESIpos): m/z=206 (M+H)$^+$ $^1$H-NMR (400 MHz, DMSO-d$_6$): δ=8.11-7.97 (m, 3H), 7.88 (s, 1H), 7.34 (br. s, 1H), 4.27 (q, 2H), 1.30 (t, 3H) ppm.

Intermediate 8A (4-Aminopyrrolo[2,1-f][1,2,4]triazin-6-yl)methanol

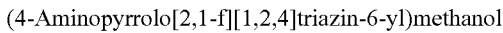
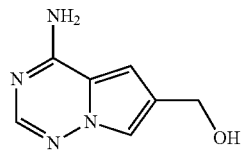 [SMILES: Nc1ncnn2cc(CO)cc12]

An ice-cooled solution of Intermediate 7A (3.0 g, 14.5 mmol) in THF (30 ml) was treated with a 1 M solution of lithium triethylborohydride in THF (58 ml) and stirred at rt for 45 min. The reaction mixture was then cooled to 0° C., quenched with methanol, warmed slowly to rt and adsorbed on kieselguhr. Purification by column chromatography over silica gel (dichloromethane/methanol 20:1→4:1 gradient) afforded 2.21 g (92.5% of th.) of the title compound.

LC-MS (method 3): $R_t$=1.46 min; MS (ESIpos): m/z=164 (M+H)$^+$ $^1$H-NMR (400 MHz, DMSO-d$_6$): δ=7.75 (s, 1H), 7.64 (br. s, 2H), 7.50 (br. d, 1H), 6.79 (br. d, 1H), 5.01 (t, 1H), 4.50 (d, 2H) ppm.

Intermediate 9A tert-Butyl[2-cyano-4-(hydroxymethyl)-1H-pyrrol-1-yl]carbamate

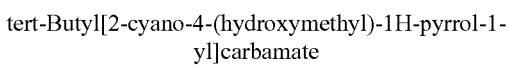
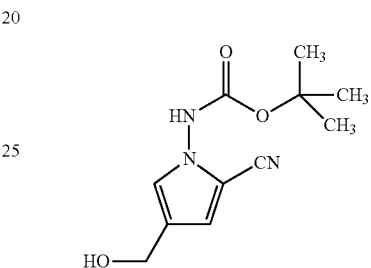

Under argon, a 1 M solution of methylmagnesium bromide in THF (13.3 ml) was added over 15 min to a solution of tert-butyl (4-bromo-2-cyano-1H-pyrrol-1-yl)carbamate (3.7 g, 12.09 mmol; preparation described in PCT Int. Pat. Appl. WO 2007/064883, Intermediate AAE, Step 3) in THF (37 ml) cooled to −60° C. After 30 min, a 1.6 M solution of n-butyllithium in hexane (15.1 ml, 24.2 mmol) was added over 10 min to the reaction, and the resulting mixture was stirred between −60° C. and −40° C. for 1 h. Then, paraformaldehyde (1.09 g, 36.3 mmol) was added to the reaction, and the reaction mixture was slowly warmed to rt and stirred overnight. After quenching with sat. aq. ammonium chloride solution, the aqueous layer was extracted twice with ethyl acetate. The combined organic phases were washed with sat. aq. sodium chloride solution, dried over sodium sulfate and evaporated. Purification by column chromatography on silica gel (cyclohexane/ethyl acetate 2:1→1:1) afforded 2.04 g (69% of th.) of the title compound.

LC-MS (method 4): $R_t$=0.70 min; MS (ESIpos): m/z=238 (M+H)$^+$ $^1$H-NMR (400 MHz, DMSO-d$_6$): δ=10.79 (br. s, 1H), 7.09 (d, 1H), 6.86 (d, 1H), 4.97 (t, 1H), 4.28 (d, 2H), 1.45 (s, 9H) ppm.

Intermediate 10A 6-(Methoxymethyl)pyrrolo[2,1-f][1,2,4]triazin-4-amine

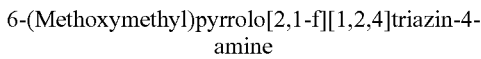
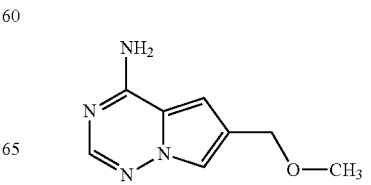

Method 1:

A solution of Intermediate 8A (1.3 g, 7.9 mmol) in THF (25 ml) was treated with thionyl chloride (1.15 ml, 15.8 mmol) and stirred at rt for 2 h. After evaporation, the residue was dissolved in methanol (25 ml) and treated with sodium acetate (1.3 g, 15.8 mmol). The mixture was stirred for 3 h at 65° C. and then evaporated again. Purification by column chromatography on silica gel (dichloromethane/methanol 100:2) afforded 787 mg (55% of th.) of the title compound.

Method 2:

A solution of Intermediate 9A (6.14 g, 25.88 mmol) in a 4 M solution of hydrogen chloride in 1,4-dioxane (15 ml) was stirred at rt for 5 h. After dilution with methanol (73 ml), stirring at rt was continued overnight. Then, potassium phosphate (54.9 g, 258.65 mmol) and formamidinium acetate (13.46 g, 129.32 mmol) were added, and the resulting mixture was stirred at 65° C. for 17 h. The reaction mixture was evaporated, sat. aq. sodium chloride solution was added, and the mixture was extracted with dichloromethane followed by ethyl acetate. The combined organic phases were dried over sodium sulfate and evaporated. Purification by column chromatography on silica gel (dichloromethane/methanol 40:1→20:1) afforded 2.36 g (49% of th.) of the title compound.

LC-MS (method 3): $R_t$=1.72 min; MS (ESIpos): m/z=179 (M+H)$^+$ $^1$H-NMR (400 MHz, DMSO-d$_6$): δ=7.77 (s, 1H), 7.69 (br. s, 2H), 7.57 (s, 1H), 6.81 (s, 1H), 4.42 (s, 2H), 3.25 (s, 3H) ppm.

Intermediate 11A

4-Amino-6-(methoxymethyl)pyrrolo[2,1-f][1,2,4]triazine-7-carbaldehyde

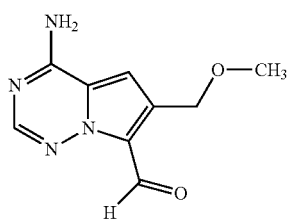

Phosphoryl chloride (13.7 ml, 147.18 mmol) was added to a solution of Intermediate 10A (5.24 g, 29.43 mmol) in DMF (80 ml) at 0° C. The resulting mixture was stirred at 60° C. for 8 h, then carefully quenched with water and neutralized with 4 M aq. sodium hydroxide solution. The aqueous layer was extracted with ethyl acetate. The combined organic phases were washed with sat. aq. sodium chloride solution, dried over magnesium sulfate and evaporated. A solution of the residue in methanol (50 ml) was treated with sodium acetate (2.41 g, 29.43 mmol) and refluxed overnight. The reaction mixture was diluted with water and extracted with ethyl acetate. The combined organic phases were washed with sat. aq. sodium chloride solution, dried over magnesium sulfate and evaporated, affording 2.66 g of the crude product which was used in the next step without further purification.

LC-MS (method 4): $R_t$=0.50 min; MS (ESIpos): m/z=207 (M+H)$^+$ $^1$H-NMR (400 MHz, DMSO-d$_6$): δ=10.35 (s, 1H), 8.20 (br. s, 2H), 8.07 (s, 1H), 7.06 (s, 1H), 4.72 (s, 2H), 3.39 (s, 3H) ppm.

Intermediate 12A

4-Amino-5-bromo-6-(methoxymethyl)pyrrolo[2,1-f][1,2,4]triazine-7-carbaldehyde

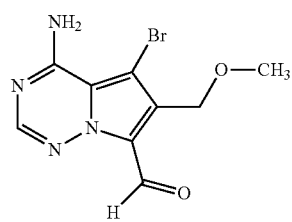 [SMILES: COCc1c(Br)c2c(N)ncnn2c1C=O]

A solution of Intermediate 11A (crude, 2.66 g) in DMF (30 ml), cooled to −30° C., was treated with a solution of N-bromosuccinimide (NBS; 2.52 g, 14.19 mmol) in DMF (14 ml). The resulting mixture was slowly warmed to 0° C. After 1 hour, the mixture was warmed to rt, stirred for further 15 min and then quenched with 1 M aq. sodium thiosulfate solution. The precipitate was filtered off and washed with ethyl acetate, affording 1.1 g (100% purity, 30% of th.) as a first crop of the title compound. The remaining filtrate was extracted with ethyl acetate. The combined organic phases were washed with sat. aq. sodium chloride solution, dried over sodium sulfate and evaporated. Purification of the residue by column chromatography on silica gel (cyclohexane/ethyl acetate 1:1→1:3) afforded further 1.39 g (70% purity, 26% of th.) of the title compound.

LC-MS (method 2): $R_t$=0.67 min; MS (ESIpos): m/z=283/285 (M+H)$^+$ $^1$H-NMR (400 MHz, DMSO-d$_6$): δ=10.36 (s, 1H), 8.63 (br. s, 1H), 8.13 (s, 1H), 7.23 (br. s, 1H), 4.64 (s, 2H), 3.26 (s, 3H) ppm.

Intermediate 13A

4-Amino-6-(methoxymethyl)-5-(7-methoxy-5-methyl-1-benzothiophen-2-yl)pyrrolo[2,1-f][1,2,4]-triazine-7-carbaldehyde

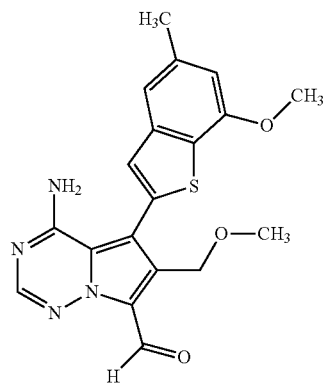 [SMILES: COCc1c(-c2cc3cc(C)cc(OC)c3s2)c2c(N)ncnn2c1C=O]

Under argon, a degassed 0.5 M aq. potassium phosphate solution (9.9 ml) was added to a solution of Intermediate 12A (710 mg, 2.49 mmol), Intermediate 5A (921 mg, 3.73 mmol) and (2'-aminobiphenyl-2-yl)(chloro)palladium-dicyclohexyl (2',4',6'-triisopropylbiphenyl-2-yl)phosphine (1:1; 196 mg, 249 µmol; see S. L. Buchwald et al., *J. Am. Chem. Soc.* 132 (40), 14073-14075 (2010)) in degassed THF (28.4 ml). The resulting mixture was stirred at 60° C. for 2 h and then evaporated. Purification of the residue by column chromatography on silica gel (cyclohexane/ethyl actetate 5:1→1:1) afforded 550 mg (51% of th.) of the title compound.

LC-MS (method 2): $R_t$=1.06 min; MS (ESIpos): m/z=383 (M+H)$^+$ $^1$H-NMR (400 MHz, DMSO-d$_6$): δ=10.50 (s, 1H), 8.43 (br. s, 1H), 8.21 (s, 1H), 7.42 (s, 1H), 7.33 (s, 1H), 6.87 (s, 1H), 6.09 (br. s, 1H), 4.58 (s, 2H), 3.96 (s, 3H), 3.19 (s, 3H), 2.46 (s, 3H) ppm.

Intermediate 14A 6-(Ethoxymethyl)pyrrolo[2,1-f][1,2,4]triazin-4-amine

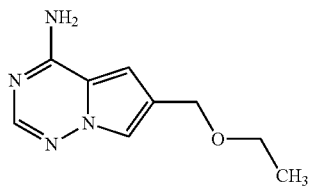

Method 1:

To a suspension of 2 g (12.2 mmol) of Intermediate 8A in 40 ml THF were added 1.78 ml (24.4 mmol) thionyl chloride at rt within 20 sec. The mixture was stirred for 1.5 h, then evaporated to dryness, and the residue was dissolved in 40 ml ethanol. 2 g (24.4 mmol) sodium acetate were added, and the mixture was stirred at 70° C. for 1 h 45 min. The reaction mixture was evaporated again, and sat. aq. sodium hydrogencarbonate solution was added. The mixture was extracted five times with ethyl acetate. The combined organic phases were washed with sat. aq. sodium chloride solution, dried with magnesium sulfate and evaporated to dryness, giving 2.02 g of crude product which was purified by column chromatography on silica gel with dichloromethane/methanol (0-2%) as the eluent.

Yield: 1.37 g (58% of th.).

Method 2:

Step 1: A solution of Intermediate 9A (2.3 g, 9.69 mmol) in 1,4-dioxane (5 ml) was treated with a 4 M solution of hydrogen chloride in 1,4-dioxane (24 ml, 96.9 mmol) and stirred at rt for 130 min. Then, the suspension was filtered, and the precipitate was washed with 1,4-dioxane (5 ml) and dried in vacuo yielding 1.01 g (54% of th.) of the intermediate compound 1-amino-4-(chloromethyl)-1H-pyrrole-2-carbonitrile hydrochloride.

Step 2: Freshly prepared 1-amino-4-(chloromethyl)-1H-pyrrole-2-carbonitrile hydrochloride from Step 1 (0.3 g, 1.82 mmol) was dissolved in ethanol (10 ml) and stirred at rt for 5 min. The clear solution was treated with formamidine acetate (813 mg, 7.81 mmol) and potassium phosphate (1.66 g, 7.81 mmol) and stirred first at rt for 3 days, then at 80° C. for 10.5 h. More formamidine acetate (488 mg, 4.69 mmol) was added, and the mixture was stirred for further 18 h at 80° C. The mixture was then cooled to rt, and water and ethyl acetate were added. The organic phase was separated, and the aqueous phase was extracted twice with ethyl acetate. The combined organic phases were washed with sat. aq. sodium chloride solution, dried with magnesium sulfate and evaporated. The residue was dissolved in a mixture of methanol and dichloromethane, adsorbed on diatomaceous earth, dried in vacuo and finally purified by chromatography on silica gel (gradient 0-10% methanol/dichloromethane) yielding 260 mg (78% of th.) of the title compound.

LC-MS (method 3): $R_t$=2.02 min; MS (ESIpos): m/z=193 (M+H)$^+$ $^1$H-NMR (400 MHz, DMSO-d$_6$): δ=7.77 (s, 1H), 7.59-7.74 (br. s, 2H), 7.56 (s, 1H), 6.82 (s, 1H), 5.76 (s, 1H), 4.46 (s, 2H), 3.46 (q, 2H), 1.13 (t, 3H) ppm.

Intermediate 15A

4-Amino-6-(ethoxymethyl)pyrrolo[2,1-f][1,2,4]triazine-7-carbaldehyde

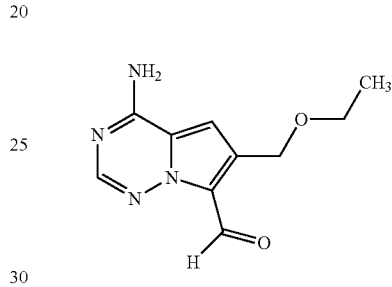

To a solution of 2.1 g (10.9 mmol) of Intermediate 14A in 40 ml dry DMF, 5.1 ml (54.6 mmol) phosphoryl chloride were added dropwise at 0° C. under an argon atmosphere. The mixture was stirred at 60° C. for 10 h. Then, water was added carefully, and the mixture was stirred at ambient temperature until all reactive intermediates were destroyed (HPLC control). The acidic solution was neutralized with 1 M aq. sodium hydroxide solution and extracted three times with ethyl acetate. The combined organic phases were washed with sat. aq. sodium chloride solution, dried over magnesium sulfate and evaporated at reduced pressure.

Yield: 1.94 g (purity 90%, 81% of th.)

LC-MS (method 5): $R_t$=1.49 min; MS (ESIpos): m/z=221 (M+H)$^+$ $^1$H-NMR (400 MHz, DMSO-d$_6$): δ=10.35 (s, 1H), 8.14-8.26 (m, 2H), 8.07 (s, 1H), 7.07 (s, 1H), 4.76 (s, 2H), 3.58 (q, 2H), 1.20 (t, 3H) ppm.

Intermediate 16A

4-Amino-5-bromo-6-(ethoxymethyl)pyrrolo[2,1-f][1,2,4]triazine-7-carbaldehyde

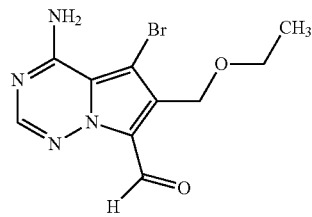 [SMILES: CCOCc1c(Br)c2c(N)ncnn2c1C=O]

To a solution of 73 g (0.33 mol) of Intermediate 15A in 1.9 L DMF was added dropwise a solution of 65 g (0.37 mol)

NBS in 200 ml DMF at −15° C. The mixture was allowed to warm to 0° C. and stirred for 3 h at this temperature. The reaction mixture was poured into 2% aq. sodium thiosulfate solution under stirring, and the precipitate was filtered off, washed with water and dried over phosphorous pentoxide in vacuo.

Yield: 85.6 g (86% of th.)

LC-MS (method 2): $R_t$=0.76 min; MS (ESIpos): m/z=299/301 (M+H)$^+$ $^1$H-NMR (400 MHz, DMSO-d$_6$): δ=10.36 (s, 1H), 8.62 (br. s, 1H), 8.13 (s, 1H), 7.22 (br. s, 1H), 4.68 (s, 2H), 3.49 (q, 2H), 1.10 (t, 3H) ppm.

Intermediate 17A

4-Amino-6-(ethoxymethyl)-5-(7-methoxy-5-methyl-1-benzothiophen-2-yl)pyrrolo[2,1-f][1,2,4]-triazine-7-carbaldehyde

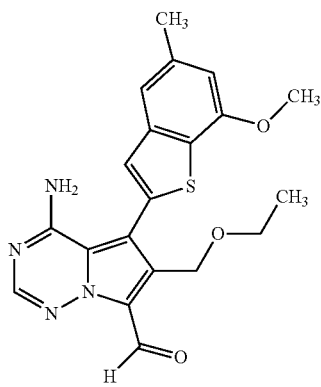 [SMILES: CCOCc1c(-c2cc3cc(C)cc(OC)c3s2)c2c(N)ncnn2c1C=O]

Under an argon atmosphere, 714 mg (purity 85%, 2.03 mmol) of Intermediate 16A, 946 mg (2.84 mmol) of Intermediate 6A and 160 mg (0.2 mmol) (2'-aminobiphenyl-2-yl)(chloro)palladium-dicyclohexyl(2',4',6'-triisopropylbiphenyl-2-yl)phosphine (1:1; see S. L. Buchwald et al., *J. Am. Chem. Soc.* 132 (40), 14073-14075 (2010)) were suspended in 15.5 ml THF. Then, 15.5 ml of a degassed 0.5 M aq. potassium phosphate solution were added, and the mixture was stirred at 50° C. for 16 h. After addition of water, the mixture was extracted with ethyl acetate, and the combined organic phases were dried over magnesium sulfate and evaporated under reduced pressure. The residue was purified by column chromatography on silica gel (100 g) with 10-50% ethyl acetate/cyclohexane as the eluent.

Yield: 452 mg (75% pure by HPLC, 42% of th.)

LC-MS (method 5): $R_t$=2.38 min; MS (ESIpos): m/z=397 (M+H)$^+$ $^1$H-NMR (400 MHz, DMSO-d$_6$): δ=10.50 (s, 1H), 8.42 (br. s, 1H), 8.21 (s, 1H), 7.43 (s, 1H), 7.33 (s, 1H), 6.87 (s, 1H), 6.07 (br. s, 1H), 4.63 (s, 2H), 3.96 (s, 3H), 3.40 (q, 2H), 2.46 (s, 3H), 1.02 (t, 3H) ppm.

Intermediate 18A (4-Amino-5,7-dibromopyrrolo[2,1-f][1,2,4]triazin-6-yl)methanol

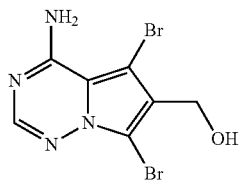 [SMILES: Nc1ncnn2c(Br)c(CO)c(Br)c12]

A solution of Intermediate 8A (5 g, 30.4 mmol) in THF (100 ml) was treated with 1,3-dibromo-5,5-dimethylhydantoin (9.58 g, 33.5 mmol) and stirred at rt for 2 h. The precipitate was filtered off and dried in vacuo to afford 6.60 g (64% of th.) of the title compound.

LC-MS (method 2): $R_t$=0.56 min; MS (ESIpos): m/z=321/323/325 (M+H)$^+$ $^1$H-NMR (400 MHz, DMSO-d$_6$): δ=8.23 (br. s, 1H), 7.96 (s, 1H), 6.94 (br. s, 1H), 5.09 (br. s, 1H), 4.43 (s, 2H) ppm.

Intermediate 19A (4-Amino-5-bromopyrrolo[2,1-f][1,2,4]triazin-6-yl)methanol

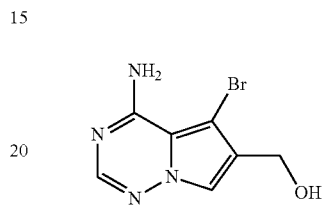

A suspension of Intermediate 18A (3.7 g, 11.5 mmol) in THF (800 ml) was heated under stirring until complete dissolution. The mixture was then cooled to −78° C., and a 1.6 M solution of n-butyllithium in hexanes (20 ml, 32.1 mmol) was added dropwise. After 5 min, a further portion of 1.6 M n-butyllithium solution (1.5 ml, 2.29 mmol) was added. The resulting mixture was stirred at −78° C. for 5 min, then quenched with methanol (5 ml) and warmed to rt. The reaction mixture was diluted with sat. aq. ammonium chloride solution, sat. aq. sodium hydrogencarbonate solution, sat. aq. sodium chloride solution and ethyl acetate. After phase separation, the organic layer was washed with sat. aq. sodium chloride solution. The combined aqueous phases were re-extracted with ethyl acetate. The combined organic phases were washed again with sat. aq. sodium chloride solution, dried over magnesium sulfate and evaporated to afford 2.87 g of the crude product which was used in subsequent steps without further purification.

LC-MS (method 3): $R_t$=1.73 min; MS (ESIpos): m/z=243/245 (M+H)$^+$ $^1$H-NMR (400 MHz, DMSO-d$_6$): δ=8.41-7.89 (br. s, 1H), 7.82 (s, 1H), 7.66 (s, 1H), 7.13-6.48 (br. s, 1H), 5.11 (t, 1H), 4.45 (d, 2H) ppm.

Intermediate 20A

[4-Amino-5-(7-methoxy-5-methyl-1-benzothiophen-2-yl)pyrrolo[2,1-f][1,2,4]triazin-6-yl]methanol

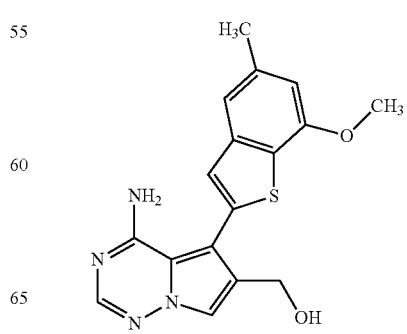

A suspension of Intermediate 19A (70% purity, 2.52 g, 7.26 mmol), Intermediate 6A (3.63 g, 10.9 mmol) and caesium fluoride (5.51 g, 36.3 mmol) in a THF/water mixture (10:1; 80 ml) was degassed under argon. 4-(Di-tert-butylphosphino)-N,N-dimethylaniline-dichloropalladium (2:1; 176 mg, 0.248 mmol) was added, and the resulting mixture was degassed again and stirred at 50° C. for 16 h. The reaction mixture was then washed with sat. aq. sodium chloride solution, and the organic layer was separated, dried over magnesium sulfate, filtered and evaporated. The residue was suspended in methanol, and the resulting solid was filtered off and dried in vacuo to afford 1.97 g (90% purity, 72% of th.) of the title compound.

LC-MS (method 2): $R_t$=0.85 min; MS (ESIpos): m/z=340 $(M+H)^+$ $^1$H-NMR (400 MHz, DMSO-$d_6$): δ=7.91 (s, 1H), 7.5-8.1 (br. s, 1H), 7.72 (s, 1H), 7.35 (s, 1H), 7.30 (s, 1H), 6.84 (s, 1H), 5.5-6.0 (br. s, 1H), 5.06 (t, 1H), 4.49 (d, 2H), 3.95 (s, 3H), 2.45 (s, 3H) ppm.

Intermediate 21A 6-(Methoxymethyl)-5-(7-methoxy-5-methyl-1-benzothiophen-2-yl)pyrrolo[2,1-f][1,2,4]triazin-4-amine

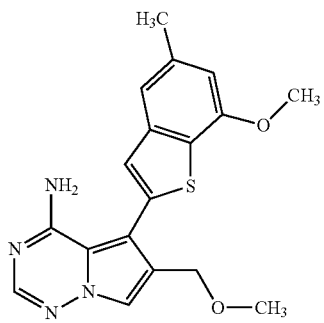 [SMILES: COCc1cn2ncnc(N)c2c1-c1cc2cc(C)cc(OC)c2s1]

A solution of Intermediate 20A (400 mg, 1.17 mmol) in dichloromethane (12 ml) was treated with thionyl chloride (128 μl, 1.76 mmol) and stirred at rt for 15 min. After evaporation, the residue was taken up in methanol (12 ml) and treated with DIPEA (409 μl, 2.35 mmol). The mixture was refluxed overnight and then evaporated again. Purification by column chromatography on silica gel (dichloromethane/methanol 98:2→95:5) afforded 388 mg (93% of th.) of the title compound.

LC-MS (method 2): $R_t$=1.00 min; MS (ESIpos): m/z=355 $(M+H)^+$ $^1$H-NMR (400 MHz, DMSO-$d_6$): δ=7.93 (s, 1H), 7.82 (s, 1H), 7.35 (s, 1H), 7.31 (s, 1H), 6.84 (s, 1H), 4.38 (s, 2H), 3.95 (s, 3H), 3.22 (s, 3H), 2.45 (s, 3H) ppm.

Intermediate 22A 6-(Ethoxymethyl)-5-(7-methoxy-5-methyl-1-benzothiophen-2-yl)pyrrolo[2,1-f][1,2,4]triazin-4-amine

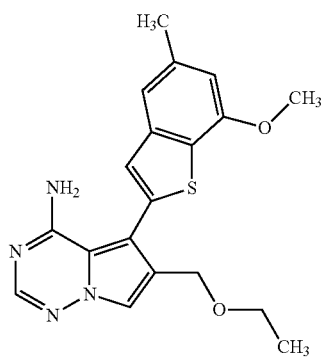 [SMILES: CCOCc1cn2ncnc(N)c2c1-c1cc2cc(C)cc(OC)c2s1]

Intermediate 20A (200 mg, 587 μmol) in dichloromethane (5 ml) was treated with thionyl chloride (64 μl, 881 μmol) and stirred at rt for 15 min. After evaporation, the residue was refluxed in ethanol (5 ml) for 1 h, then treated with DIPEA (204 μl, 1.17 mmol) and refluxed again overnight. The reaction mixture was evaporated, and the crude product was purified by column chromatography on silica gel (dichloromethane/methanol 98:2→95:5) affording 202 mg (90% of th.) of the title compound.

LC-MS (method 5): $R_t$=2.32 min; MS (ESIpos): m/z=369 $(M+H)^+$ $^1$H-NMR (400 MHz, DMSO-$d_6$): δ=8.31-7.59 (br. s, 1H), 7.93 (s, 1H), 7.81 (s, 1H), 7.35 (s, 1H), 7.30 (s, 1H), 6.84 (s, 1H), 6.20-5.50 (br. s, 1H), 4.41 (s, 2H), 3.95 (s, 3H), 3.41 (q, 2H), 2.45 (s, 3H), 1.08 (t, 3H) ppm.

Intermediate 23A tert-Butyl 4-{[4-amino-6-(hydroxymethyl)-5-(7-methoxy-5-methyl-1-benzothiophen-2-yl)pyrrolo-[2,1-f][1,2,4]triazin-7-yl]methyl}piperazine-1-carboxylate

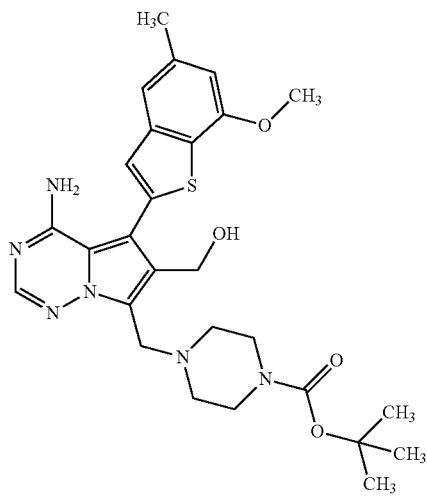 [SMILES: COc1cc(C)cc2cc(-c3c(CO)c(CN4CCN(C(=O)OC(C)(C)C)CC4)n4ncnc(N)c34)sc12]

A solution of Intermediate 20A (9.5 g, 27.9 mmol) in acetic acid (136.8 ml) was treated with tert-butyl piperazine-1-carboxylate (6.24 g, 33.49 mmol) and 37% aq. formaldehyde solution (2.5 ml, 33.49 mmol). The mixture was stirred at 60° C. for 2.5 h. After evaporation, the residue was taken up in ethyl acetate, and the mixture was washed twice with sat. aq. sodium hydrogencarbonate solution, dried over sodium sulfate and evaporated. The residue was triturated in boiling ethanol (100 ml). The solid was filtered off and washed with ethanol and diethylether affording 9.70 g (58% of th.) of the title compound.

LC-MS (method 2): $R_t$=0.88 min; MS (ESIpos): m/z=539 (M+H)$^+$ $^1$H-NMR (400 MHz, CDCl$_3$): δ=7.94 (s, 1H), 7.13-7.35 (m, 2H, overlap with CHCl$_3$ peak), 6.67 (s, 1H), 5.86 (br. s, 1H), 5.54 (br. s, 2H), 4.68 (s, 2H), 4.08 (s, 2H), 4.00 (s, 3H), 3.45 (br. s, 4H), 2.59-2.48 (m, 7H), 1.45 (s, 9H) ppm.

Intermediate 24A tert-Butyl 4-({4-amino-5-(7-methoxy-5-methyl-1-benzothiophen-2-yl)-6-[(2-methoxy-2-oxoethoxy)methyl]pyrrolo[2,1-f][1,2,4]triazin-7-yl}methyl)piperazine-1-carboxylate

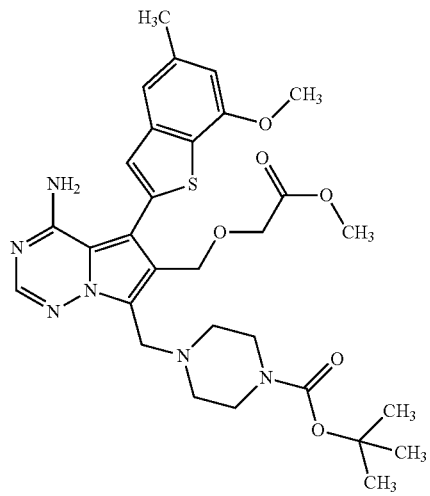 [SMILES: COC(=O)COCc1c(-c2cc3cc(C)cc(OC)c3s2)c2c(N)ncnn2c1CN1CCN(C(=O)OC(C)(C)C)CC1]

A solution of Intermediate 23A (300 mg, 556 μmol) in dichloromethane (12 ml) was treated with thionyl chloride (81 μl, 1.11 mmol) and stirred at rt for 15 min. After evaporation, the residue was dissolved in freshly distilled methylglycolate (2.5 ml) and treated with DIPEA (485 μl, 2.78 mmol). The mixture was stirred at 70° C. for 2 h, then evaporated again, and excess methylglycolate was removed by distillation. Purification of the residue by column chromatography on silica gel (cyclohexane/ethyl acetate 1:5) afforded 136 mg (33% of th.) of the title compound.

LC-MS (method 2): $R_t$=0.88 min; MS (ESIpos): m/z=611 (M+H)$^+$ $^1$H-NMR (400 MHz, DMSO-d$_6$): δ=7.99 (s, 1H), 7.39 (s, 1H), 7.31 (s, 1H), 6.85 (s, 1H), 4.58 (s, 2H), 4.11 (s, 2H), 3.96 (s, 3H), 3.93 (s, 2H), 3.57 (s, 3H), 3.30-3.24 (m, 4H), 2.45-2.38 (m, 7H), 1.39 (s, 9H) ppm.

Intermediate 25A tert-Butyl 4-{[4-amino-6-formyl-5-(7-methoxy-5-methyl-1-benzothiophen-2-yl)pyrrolo[2,1-f]-[1,2,4]triazin-7-yl]methyl}piperazine-1-carboxylate

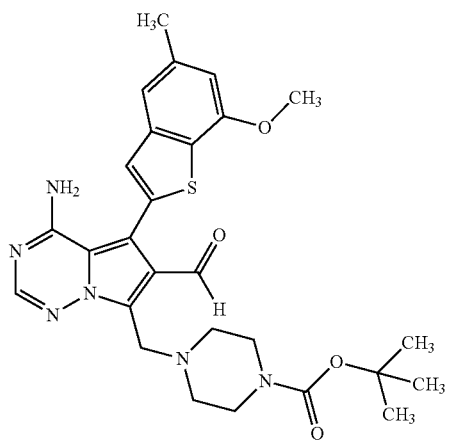 [SMILES: COc1cc(C)cc2cc(-c3c(C=O)c(CN4CCN(C(=O)OC(C)(C)C)CC4)n4ncnc(N)c34)sc12]

A solution of Intermediate 23A (300 mg, 556 μmol) in dichloromethane (4.2 ml) was treated with Dess-Martin periodinane (1,1,1-triacetoxy-1,1-dihydro-1,2-benziodoxol-3(1H)-one; 307 mg, 724 μmol) and stirred at rt for 2 h. The reaction mixture was quenched with sat. aq. sodium hydrogencarbonate solution and sat. aq. sodium thiosulfate solution (1:1) and stirred at rt for 30 min. The aqueous layer was extracted three times with dichloromethane, and the combined organic layers were dried over magnesium sulfate and evaporated. Purification by column chromatography on silica gel (cyclohexane/ethyl acetate 1:1→100% ethyl acetate) afforded 273 mg (87% of th.) of the title compound.

LC-MS (method 2): $R_t$=0.87 min; MS (ESIpos): m/z=537 (M+H)$^+$ $^1$H-NMR (400 MHz, DMSO-d$_6$): δ=10.02 (s, 1H), 8.44-8.18 (br. s, 1H), 8.08 (s, 1H), 7.51 (s, 1H), 7.32 (s, 1H), 6.88 (s, 1H), 6.01-5.74 (br. s, 1H), 4.16 (s, 2H), 3.96 (s, 3H), 3.30-3.22 (m, 4H), 2.48-2.40 (m, 7H), 1.38 (s, 9H) ppm.

Intermediate 26A

4-Amino-5-(7-methoxy-5-methyl-1-benzothiophen-2-yl)-7-(piperazin-1-ylmethyl)pyrrolo[2,1-f]-[1,2,4]triazine-6-carbaldehyde bis(formiate)

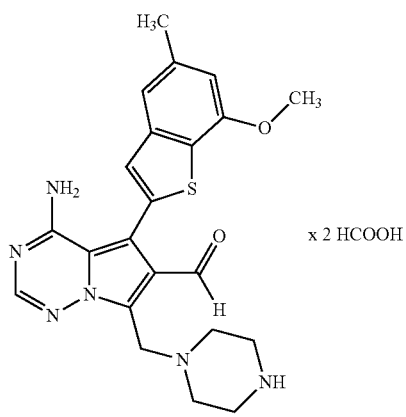 [SMILES: COc1cc(C)cc2cc(-c3c(C=O)c(CN4CCNCC4)n4ncnc(N)c34)sc12]

x 2 HCOOH

A solution of Intermediate 23A (80 mg, 148 µmol) in THF (3.9 ml) was treated with Dess-Martin periodinane (1,1,1-triacetoxy-1,1-dihydro-1,2-benziodoxol-3(1H)-one; 94 mg, 222 µmol) and stirred at rt for 30 min. The reaction mixture was quenched with sat. aq. sodium hydrogencarbonate solution and sat. aq. sodium thiosulfate solution (1:1). The aqueous layer was extracted three times with ethyl acetate, and the combined organic layers were dried over magnesium sulfate and evaporated. The residue was dissolved in a 4 M solution of hydrogen chloride in 1,4-dioxane (4 ml) and stirred at rt for 1 h. After evaporation, the residue was purified by preparative RP-HPLC (Reprosil C18, gradient 10-95% acetonitrile/0.1% aq. formic acid) affording 34 mg (52% of th.) of the title compound.

LC-MS (method 2): $R_t$=0.78 min; MS (ESIpos): m/z=437 (M+H)$^+$ $^1$H-NMR (400 MHz, DMSO-d$_6$): δ=10.02 (s, 1H), 8.29 (br. s, 2H), 8.09 (s, 1H), 7.50 (s, 1H), 7.33 (s, 1H), 6.88 (s, 1H), 4.17 (s, 2H), 3.96 (s, 3H), 2.90-2.81 (m, 4H), 2.63-2.56 (m, 4H), 2.46 (s, 3H) ppm.

Intermediate 27A tert-Butyl 4-({4-amino-5-(7-methoxy-5-methyl-1-benzothiophen-2-yl)-6-[(3-oxopiperazin-1-yl)methyl]pyrrolo[2,1-f][1,2,4]triazin-7-yl}methyl)piperazine-1-carboxylate

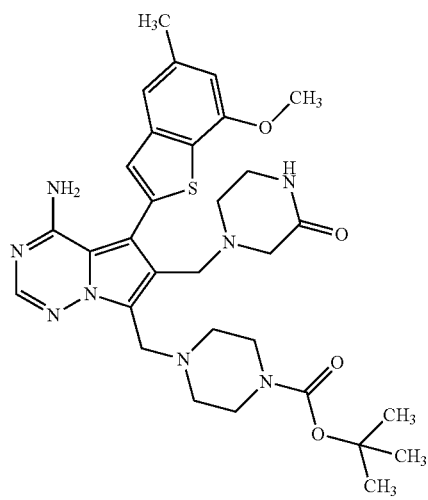 [SMILES: COc1cc(C)cc2cc(-c3c(CN4CCNC(=O)C4)c(CN4CCN(C(=O)OC(C)(C)C)CC4)n4ncnc(N)c34)sc12]

A solution of Intermediate 25A (185 mg, 344 µmol) in THF (4.6 ml) was treated with 2-oxopiperazine (344 mg, 3.4 mmol), sodium triacetoxyborohydride (365 mg, 1.7 mmol) and acetic acid (39 µl, 689 µmol). The resulting mixture was stirred at rt for 2 h, then adsorbed on kieselguhr and purified by column chromatography on silica gel (dichloromethane→dichloromethane/methanol 100:8) affording 221 mg (quant.) of the title compound.

LC-MS (method 4): $R_t$=0.77 min; MS (ESIpos): m/z=621 (M+H)$^+$.

Intermediate 28A

N-Ethylethanaminium 4-amino-7-{[4-(tert-butoxycarbonyl)piperazin-1-yl]carbonyl}-5-(7-methoxy-5-methyl-1-benzothiophen-2-yl)pyrrolo[2,1-f][1,2,4]triazine-6-carboxylate

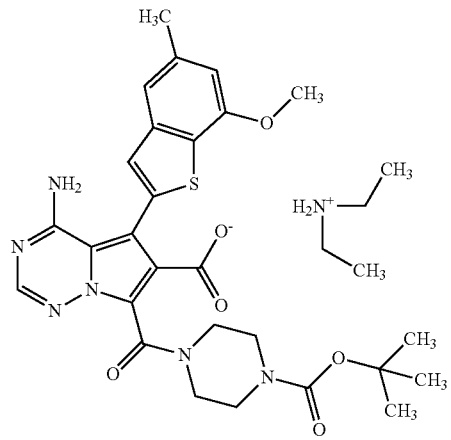

A solution of Intermediate 25A (70 mg, 130 µmol) in THF/water (10:1, 4.85 ml) was treated with a 2 M solution of 2-methyl-2-buten in THF (521 µl, 1.04 mmol) and sodium dihydrogenphosphate (107 mg, 783 µmol) and stirred at rt for 5 min. Sodium chlorite (70 mg, 783 µmol) was added, and the resulting mixture was stirred at rt overnight. After dilution with water, the aqueous phase was extracted three times with ethyl acetate. The combined organic layers were dried over sodium sulfate and evaporated, and the residue was purified by preparative RP-HPLC (XBridge C18, gradient 5-50% acetonitrile/water+0.05% diethylamine) affording 18 mg (21% of th.) of the title compound.

LC-MS (method 1): $R_t$=1.14 min; MS (ESIpos): m/z=567 (M+H)$^+$ $^1$H-NMR (400 MHz, DMSO-d$_6$): inter al. δ=8.26-7.89 (br. s, 1H), 7.94 (s, 1H), 7.33 (s, 1H), 7.28 (s, 1H), 6.83 (s, 1H), 5.64-5.33 (br. s, 1H), 3.95 (s, 3H), 2.80 (q, 4H), 2.45 (s, 3H), 1.40 (s, 9H), 1.09 (t, 6H) ppm.

Intermediate 29A tert-Butyl 4-{[4-amino-6-(azidomethyl)-5-(7-methoxy-5-methyl-1-benzothiophen-2-yl)pyrrolo-[2,1-f][1,2,4]triazin-7-yl]methyl}piperazine-1-carboxylate

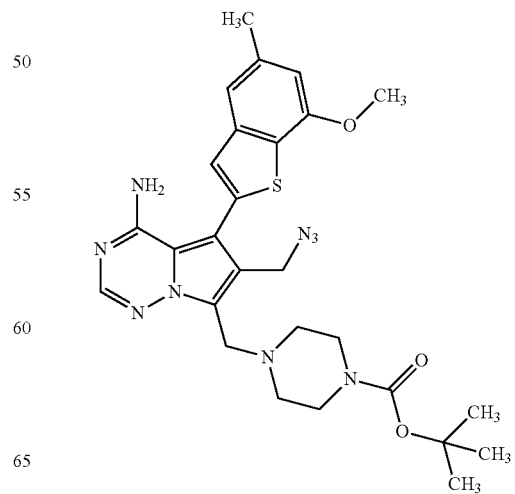

A solution of Intermediate 23A (150 mg, 0.278 mmol) in dichloromethane (7.5 ml) was treated with thionyl chloride (40 µl, 0.56 mmol) and stirred at rt for 15 min. After evaporation, the residue was dissolved in DMF (6 ml) and treated with sodium azide (362 mg, 5.57 mmol) and sodium iodide (208 mg, 1.39 mmol). The mixture was heated to 80° C. for 1 h, then diluted with water and extracted three times with ethyl acetate. The combined organic layers were washed with water and with sat. aq. sodium chloride solution, dried over magnesium sulfate and evaporated. Purification by column chromatography on silica gel (cyclohexane/ethyl acetate 98:2→100% ethyl acetate) afforded 95.8 mg (57% of th.) of the title compound.

LC-MS (method 4): $R_t$=0.99 min; MS (ESIpos): m/z=564 (M+H)$^+$ $^1$H-NMR (400 MHz, DMSO-d$_6$): δ=8.20-7.80 (br. s, 1H), 8.01 (s, 1H), 7.39 (s, 1H), 7.33 (s, 1H), 6.86 (s, 1H), 6.05-5.55 (br. s, 1H), 4.50 (s, 2H), 3.96 (s, 3H), 3.94 (s, 2H), 3.32-3.25 (m, 4H), 2.45 (s, 3H), 2.43-2.36 (m, 4H), 1.39 (s, 9H) ppm.

Intermediate 30A tert-Butyl 4-{[6-(acetamidomethyl)-4-amino-5-(7-methoxy-5-methyl-1-benzothiophen-2-yl)pyrrolo[2,1-f][1,2,4]triazin-7-yl]methyl}piperazine-1-carboxylate

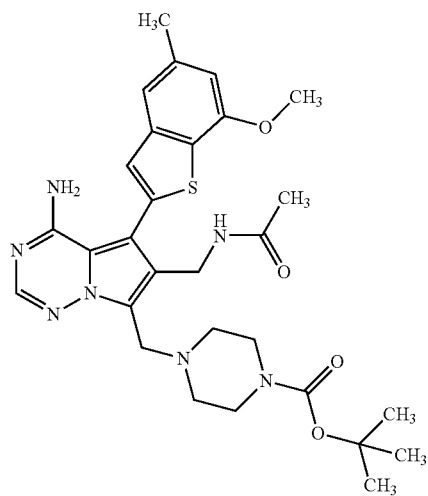 [SMILES: COc1cc(C)cc2cc(-c3c(CNC(C)=O)c(CN4CCN(C(=O)OC(C)(C)C)CC4)n4ncnc(N)c34)sc12]

A mixture of Intermediate 29A (320 mg, 567 mmol), 10% Pd/C (320 mg) and acetic anhydride (106 µl, 1.13 mmol) in methanol (32 ml) was stirred for 90 min under 1 atm of hydrogen at rt. The mixture was then filtered through kieselguhr, and the filtrate was evaporated. Purification by column chromatography on silica gel (cyclohexane/ethyl acetate 1:1→100% ethyl acetate) afforded 440 mg (quant.) of the title compound.

LC-MS (method 2): $R_t$=0.91 min; MS (ESIpos): m/z=580 (M+H)$^+$ $^1$H-NMR (400 MHz, DMSO-d$_6$): δ=8.02-7.97 (m, 2H), 7.38 (s, 1H), 7.31 (s, 1H), 6.85 (s, 1H), 4.27 (br. d, 2H), 3.95 (s, 3H), 3.89 (s, 2H), 3.31-3.24 (m, 4H), 2.45 (s, 3H), 2.43-2.36 (m, 4H), 1.74 (s, 3H), 1.39 (s, 9H) ppm.

Intermediate 31A

7-[(4-Acetylpiperazin-1-yl)methyl]-4-amino-5-(7-methoxy-5-methyl-1-benzothiophen-2-yl)pyrrolo[2,1-f][1,2,4]triazine-6-carbaldehyde

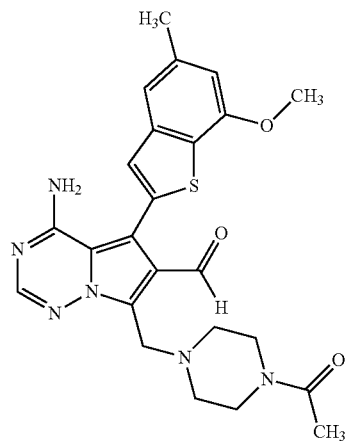 [SMILES: COc1cc(C)cc2cc(-c3c(C=O)c(CN4CCN(C(C)=O)CC4)n4ncnc(N)c34)sc12]

A solution of Example 55 (678 mg, purity 89%, 1.26 mmol) in dichloromethane (4 ml) containing molecular sieves (4 Å) was treated with Dess-Martin periodinane (1,1,1-triacetoxy-1,1-dihydro-1,2-benziodoxol-3(1H)-one; 623 mg, 1.47 mmol) and stirred at rt for 5 min. The reaction mixture was then adsorbed on diatomaceous earth and purified by column chromatography on silica gel (gradient of 30-100% ethyl acetate/cyclohexane, then 0-10% methanol/dichloromethane) yielding 449 mg (49% of th.) of the title compound.

LC-MS (method 4): $R_t$=0.70 min; MS (ESIpos): m/z=479 (M+H)$^+$.

Intermediate 32A

4-{[4-Amino-6-(azidomethyl)-5-(7-methoxy-5-methyl-1-benzothiophen-2-yl)pyrrolo[2,1-f][1,2,4]-triazin-7-yl]methyl}piperazin-2-one

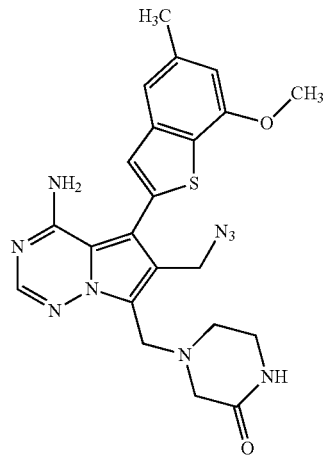 [SMILES: COc1cc(C)cc2cc(-c3c(CN=[N+]=[N-])c(CN4CCNC(=O)C4)n4ncnc(N)c34)sc12]

A solution of Example 13 (59 mg, 130 μmol) in dichloromethane (3.5 ml) was treated with thionyl chloride (19 μl, 261 μmol) and stirred at rt for 15 min. After evaporation, the residue was dissolved in DMF (2.8 ml) and treated with sodium iodide (97 mg, 652 μmol) and sodium azide (169 mg, 2.6 mmol). The mixture was stirred at 80° C. for 1 h. After dilution with sat. aq. sodium chloride solution, the aqueous phase was extracted four times with ethyl acetate, and the combined organic layers were dried over magnesium sulfate and evaporated. Purification by column chromatography on silica gel (dichloromethane/methanol 98:2→90:10) afforded 35 mg (56% of th.) of the title compound.

LC-MS (method 5): $R_t$=2.04 min; MS (ESIpos): m/z=478 (M+H)$^+$ $^1$H-NMR (400 MHz, DMSO-d$_6$): δ=8.02 (s, 1H), 7.75 (br. s, 1H), 7.41 (s, 1H), 7.33 (s, 1H), 6.86 (s, 1H), 4.51 (s, 2H), 4.01 (s, 2H), 3.96 (s, 3H), 3.16-3.08 (m, 2H), 3.04-2.98 (m, 2H), 2.65-2.58 (m, 2H), 2.45 (s, 3H) ppm.

Intermediate 33A

4-Amino-5-(7-methoxy-5-methyl-1-benzothiophen-2-yl)-7-(morpholin-4-ylmethyl)pyrrolo[2,1-f]-[1,2,4]triazine-6-carbaldehyde

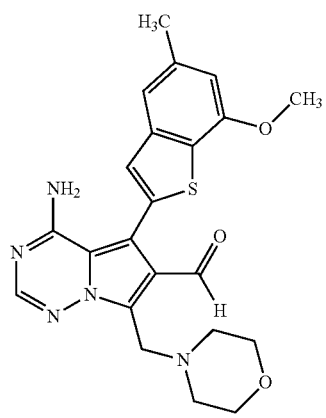 [SMILES: COc1cc(C)cc2cc(-c3c(C=O)c(CN4CCOCC4)n4ncnc(N)c34)sc12]

A solution of Example 50 (710 mg, purity 70%, 1.13 mmol) in dichloromethane (5 ml) containing molecular sieves (4 Å) was treated with Dess-Martin periodinane (1,1,1-triacetoxy-1,1-dihydro-1,2-benziodoxol-3(1H)-one; 623 mg, 1.47 mmol) and stirred at rt for 5 min. The reaction mixture was then adsorbed on diatomaceous earth and purified by column chromatography on silica gel (gradient of 30-100% ethyl acetate/cyclohexane) yielding 386 mg (72% of th.) of the title compound.

LC-MS (method 2): $R_t$=0.76 min; MS (ESIpos): m/z=438 (M+H)$^+$.

Intermediate 34A (4-Amino-7-bromopyrrolo[2,1-f][1,2,4]triazin-6-yl)methanol

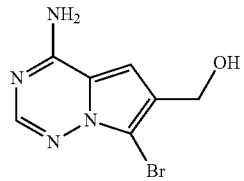 [SMILES: Nc1ncnn2c(Br)c(CO)cc12]

A solution of 1,3-dibromo-5,5-dimethylhydantoin (87 mg, 0.305 mmol) in THF (1 ml) was added dropwise to a solution of Intermediate 8A (100 mg, 0.609 mmol) in THF (4 ml) and methanol (2 ml) at −78° C. The mixture was stirred at −78° C. for 16 h, then diluted with water and extracted with ethyl acetate. The combined organic layers were washed with sat. aq. sodium chloride solution, dried over magnesium sulfate and evaporated. Purification by column chromatography on silica gel (dichloromethane/methanol 20:1→10:1) afforded 55 mg (32% of th.) of the title compound.

LC-MS (method 3): $R_t$=1.71 min; MS (ESIpos): m/z=243/245 (M+H)$^+$ $^1$H-NMR (400 MHz, DMSO-d$_6$): δ=7.74-7.94 (m, 3H), 7.04 (s, 1H), 5.12 (t, 1H), 4.48 (d, 2H) ppm.

Intermediate 35A

7-Bromo-6-({[tert-butyl(dimethyl)silyl]oxy}methyl)pyrrolo[2,1-f][1,2,4]triazin-4-amine

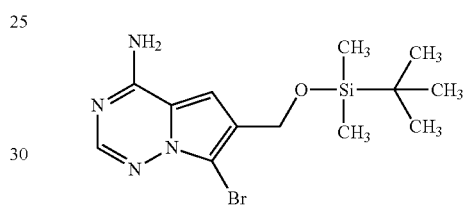

A solution of Intermediate 34A (885 mg, 3.64 mmol) in DMF (11 ml) was treated with tert-butyldimethylsilyl chloride (823 mg, 5.46 mmol) and imidazole (743 mg, 10.92 mmol) and stirred at rt for 2 h. The reaction mixture was combined with the reaction mixture of a 100 mg test run, diluted with water and extracted twice with ethyl acetate. The combined organic phases were washed with water and sat. aq. sodium chloride solution, dried over magnesium sulfate and evaporated. Purification by column chromatography on silica gel (cyclohexane/ethyl acetate 2:1→100% ethyl acetate) afforded 1.36 g (93% of th.) of the title compound.

LC-MS (method 2): $R_t$=1.13 min; MS (ESIpos): m/z=357/359 (M+H)$^+$ $^1$H-NMR (400 MHz, DMSO-d$_6$): δ=7.98-7.68 (m, 3H), 7.04 (s, 1H), 4.68 (s, 2H), 0.89 (s, 9H), 0.09 (s, 6H) ppm.

Intermediate 36A

4-Amino-6-({[tert-butyl(dimethyl)silyl]oxy}methyl)pyrrolo[2,1-f][1,2,4]triazine-7-carbonitrile

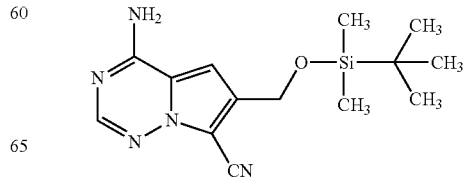

Under argon, a mixture of Intermediate 35A (880 mg, 2.46 mmol), [1,1'-bis(diphenylphosphino)ferrocene]dichloropalladium(II)-dichloromethane complex [PdCl₂(dppf)×DCM] (120 mg, 0.148 mmol), bis(dibenzylideneacetone)palladium [Pd(dba)₂] (135 mg, 0.148 mmol), zinc cyanide (578 mg, 4.92 mmol), zinc powder (64 mg, 0.985 mmol) and zinc acetate (180 mg, 0.985 mmol) in degassed DMF/water (100:1, 9.2 ml) was stirred at 160° C. overnight. The reaction mixture was then combined with the reaction mixture of a 100 mg test run, and the combined mixtures were adsorbed on kieselguhr, filtered over another layer of kieselguhr and eluted with tert-butyl methyl ether. The filtrate was washed with sat. aq. sodium hydrogencarbonate solution, and the aqueous layer was re-extracted three times with tert-butyl methyl ether. The combined organic phases were dried over sodium sulfate and evaporated. Purification by column chromatography on silica gel (cyclohexane/ethyl acetate 1:1) afforded 453 mg (44% of th.) of the title compound.

LC-MS (method 2): $R_t$=1.09 min; MS (ESIpos): m/z=304 (M+H)⁺

¹H-NMR (400 MHz, DMSO-d₆): δ=8.22-8.35 (m, 2H), 8.06 (s, 1H), 6.95 (s, 1H), 4.83 (s, 2H), 0.91 (s, 9H), 0.11 (s, 6H) ppm.

Intermediate 37A

4-Amino-5-bromo-6-({[tert-butyl(dimethyl)silyl]oxy}methyl)pyrrolo[2,1-f][1,2,4]triazine-7-carbonitrile

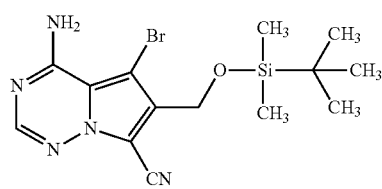 [SMILES: CC(C)(C)[Si](C)(C)OCc1c(Br)c2c(N)ncnn2c1C#N]

A solution of 1,3-dibromo-5,5-dimethylhydantoin (621 mg, 2.17 mmol) in THF (20 ml) was added dropwise to a solution of Intermediate 36A (1.1 g, 3.62 mmol) in THF (80 ml) at −50° C. The resulting mixture was slowly warmed to rt, stirred for 2 h and then quenched with 10% aq. sodium thiosulfate solution and sat. aq. sodium hydrogencarbonate solution. The aqueous phase was extracted three times with ethyl acetate. A solid precipitating from the ethyl acetate solution was filtered off and washed with ethyl acetate, affording 508 mg (100% purity, 36% of th.) as a first crop of the title compound. The remaining filtrate was dried over sodium sulfate and evaporated. The residue was precipitated from DMSO and washed with DMSO and ethyl acetate affording further 498 mg (85% purity, 26% of th.) of the title compound.

LC-MS (method 5): $R_t$=2.70 min; MS (ESIpos): m/z=382/384 (M+H)⁺

¹H-NMR (400 MHz, DMSO-d₆): δ=8.10 (s, 1H), 4.76 (s, 2H), 0.90 (s, 9H), 0.12 (s, 6H) ppm.

Intermediate 38A

4-Amino-6-({[tert-butyl(dimethyl)silyl]oxy}methyl)-5-(7-methoxy-5-methyl-1-benzothiophen-2-yl)pyrrolo[2,1-f][1,2,4]triazine-7-carbonitrile

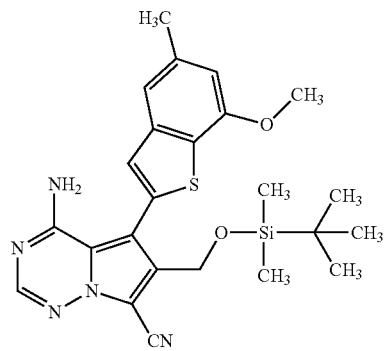 [SMILES: COc1cc(C)cc2cc(-c3c(CO[Si](C)(C)C(C)(C)C)c(C#N)n4ncnc(N)c34)sc12]

Under argon, a solution of Intermediate 37A (459 mg, 1.29 mmol) in degassed THF (14.8 ml) was added to (2'-aminobiphenyl-2-yl)(chloro)palladium-dicyclohexyl(2',4',6'-triisopropylbiphenyl-2-yl)phosphine (1:1; 152 mg, 0.19 mmol; see S. L. Buchwald et al., *J. Am. Chem. Soc.* 132 (40), 14073-14075 (2010)) and Intermediate 6A (647 mg, 1.94 mmol). Degassed 0.5 M aq. potassium phosphate solution (5.1 ml) was added dropwise, and the resulting mixture was stirred at 60° C. for 2 h. The reaction mixture was then combined with the reaction mixtures of previous 70 mg, 90 mg and 500 mg test runs and evaporated. Purification of the residue by column chromatography on silica gel (cyclohexane/ethyl acetate 3:1→100% ethyl acetate) afforded 1.0 g (58% of th.) of the title compound.

LC-MS (method 2): $R_t$=1.49 min; MS (ESIpos): m/z=480 (M+H)⁺

¹H-NMR (400 MHz, DMSO-d₆): δ=8.57-8.35 (br. s, 1H), 8.18 (s, 1H), 7.41 (s, 1H), 7.30 (s, 1H), 6.86 (s, 1H), 6.28-6.03 (br. s, 1H), 4.74 (s, 2H), 3.95 (s, 3H), 2.44 (s, 3H), 0.83 (s, 9H), 0.00 (s, 6H) ppm.

Intermediate 39A

4-Amino-6-formyl-5-(7-methoxy-5-methyl-1-benzothiophen-2-yl)pyrrolo[2,1-f][1,2,4]triazine-7-carbonitrile

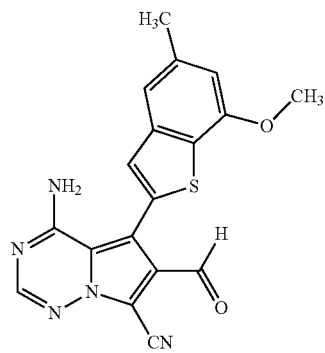 [SMILES: COc1cc(C)cc2cc(-c3c(C=O)c(C#N)n4ncnc(N)c34)sc12]

A solution of Example 68 (250 mg, 0.684 mmol) in dichloromethane (5 ml) was treated with Dess-Martin periodinane (1,1,1-triacetoxy-1,1-dihydro-1,2-benziodoxol-3(1H)-one; 377 mg, 0.889 mmol) and stirred at rt for 1 h. The reaction mixture was combined with the reaction mixture from a 50 mg test run, quenched with sat. aq. sodium hydrogencarbonate solution and sat. aq. sodium thiosulfate solution (1:1) and stirred at rt for 30 min. The aqueous phase was extracted three times with ethyl acetate, and the combined organic phases were dried over sodium sulfate and evaporated. Purification by column chromatography on silica gel (cyclohexane/25% ethyl acetate→100% ethyl acetate) afforded 102 mg (24% of th.) of the title compound.

LC-MS (method 2): $R_t$=1.02 min; MS (ESIpos): m/z=364 (M+H)$^+$ $^1$H-NMR (400 MHz, DMSO-d$_6$): δ=9.86 (s, 1H), 8.78 (br. s, 1H), 8.30 (s, 1H), 7.62 (s, 1H), 7.36 (s, 1H), 6.91 (s, 1H), 6.51 (br. s, 1H), 3.97 (s, 3H), 2.46 (s, 3H) ppm.

Intermediate 40A

4-Amino-6-(azidomethyl)-5-(7-methoxy-5-methyl-1-benzothiophen-2-yl)pyrrolo[2,1-f][1,2,4]-triazine-7-carbonitrile

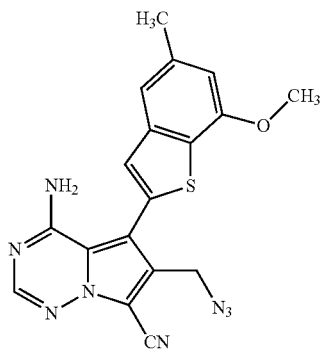 [SMILES: COc1cc(C)cc2cc(-c3c(CN=[N+]=[N-])c(C#N)n4ncnc(N)c34)sc12]

A solution of Example 68 (100 mg, 273 μmol) in dichloromethane (5 ml) was treated with thionyl chloride (39 μl, 547 μmol) and stirred at rt for 15 min. After evaporation, the residue was dissolved in DMF (6 ml) and treated with sodium iodide (205 mg, 1.36 mmol) and sodium azide (355 mg, 5.47 mmol). The mixture was stirred at 80° C. overnight, then diluted with water and extracted three times with ethyl acetate. The combined organic layers were washed with water, followed by sat. aq. sodium chloride solution, dried over sodium sulfate and evaporated affording 91 mg of the crude product which was used in the next step without further purification.

LC-MS (method 2): $R_t$=1.13 min; MS (ESIpos): m/z=391 (M+H)$^+$ $^1$H-NMR (400 MHz, DMSO-d$_6$): δ=8.65-8.45 (br. s, 1H), 8.23 (s, 1H), 7.46 (s, 1H), 7.34 (s, 1H), 6.88 (s, 1H), 6.41-6.10 (br. s, 2H), 4.57 (s, 2H), 3.96 (s, 3H), 2.46 (s, 3H) ppm.

Intermediate 41A 5,7-Dibromo-6-({[tert-butyl(dimethyl)silyl]oxy}methyl)pyrrolo[2,1-f][1,2,4]triazin-4-amine

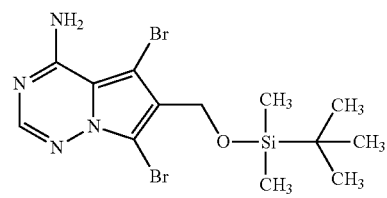 [SMILES: CC(C)(C)[Si](C)(C)OCc1c(Br)c2c(N)ncnn2c1Br]

A solution of Intermediate 18A (2 g, 6.21 mmol) in DMF (20 ml) was treated with imidazole (846 mg, 12.4 mmol) and tert-butyldimethylsilyl chloride (1.12 g, 7.45 mmol) and stirred at rt for 20 h. The reaction mixture was then diluted with water (200 ml) and stirred at rt for further 2 h. Filtration of the solid afforded 2.46 g (88% of th.) of the title compound.

LC-MS (method 2): $R_t$=1.37 min; MS (ESIpos): m/z=437 (M+H)$^+$ $^1$H-NMR (400 MHz, DMSO-d$_6$): δ=8.49-8.05 (br. s, 1H), 7.96 (s, 1H), 7.15-6.76 (br. s, 1H), 4.64 (s, 2H), 0.87 (s, 9H), 0.09 (s, 6H) ppm.

Intermediate 42A

2-[4-Amino-5-bromo-6-({[tert-butyl(dimethyl)silyl]oxy}methyl)pyrrolo[2,1-f][1,2,4]triazin-7-yl]-propan-2-ol

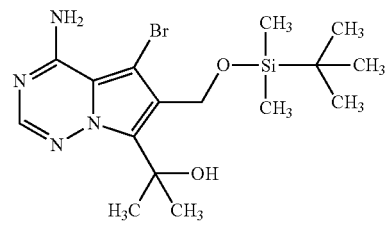 [SMILES: CC(C)(O)c1c(CO[Si](C)(C)C(C)(C)C)c(Br)c2c(N)ncnn12]

Under argon, a solution of Intermediate 41A (1 g, 2.29 mmol) in THF (40 ml) was cooled to −78° C. and treated with a 1.6 M solution of methyllithium in diethylether (1.5 ml, 2.40 mmol). After stirring for 10 min at −78° C., a 1.6 M solution of n-butyllithium in hexanes (1.58 ml, 2.52 mmol) was added, and stirring was continued for 10 min. Acetone (1.68 ml, 22.92 mmol) was added, and the resulting mixture was slowly warmed to rt and stirred at rt for 18 h. The reaction was then quenched with water, and the aqueous phase was extracted twice with ethyl acetate. The combined organic phases were washed with sat. aq. sodium chloride solution, dried over magnesium sulfate and evaporated. Purification by flash chromatography on silica gel (cyclohexane/ethyl acetate 2:1) afforded 306 mg (30% of th.) of the title compound.

LC-MS (method 4): $R_t$=1.39 min; MS (ESIpos): m/z=415/417 (M+H)$^+$ $^1$H-NMR (400 MHz, DMSO-d$_6$): δ=8.23-7.85 (br. s, 1H), 7.89 (s, 1H), 7.05-6.82 (br. s, 1H), 5.49 (s, 1H), 4.88 (s, 2H), 1.66 (s, 6H), 0.87 (s, 9H), 0.08 (s, 6H) ppm.

Intermediate 43A

2-[4-Amino-5-bromo-6-(hydroxymethyl)pyrrolo[2,1-f][1,2,4]triazin-7-yl]propan-2-ol

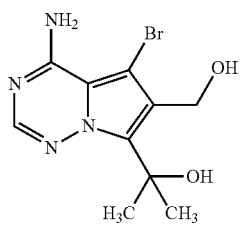 [SMILES: CC(C)(O)c1c(CO)c(Br)c2c(N)ncnn12]

A solution of Intermediate 42A (304 mg, 0.732 mmol) in THF (15 ml) was treated with a 1 M solution of tetra-n-butylammonium fluoride in THF (768 µl, 768 µmol) and stirred at rt for 2 min. The reaction mixture was diluted with acetonitrile (20 ml), then evaporated, and the residue was purified by preparative RP-HPLC (Reprosil C18, gradient 10-30% acetonitrile/0.2% aq. TFA). The product thus obtained was dissolved in methanol and filtered through an anion exchange cartridge (Stratospheres SPE, PL-HCO₃ MP-resin). The cartridge was eluted with methanol, and the filtrate was evaporated affording 180 mg (67% of th.) of the title compound.

LC-MS (method 2): $R_t$=0.55 min; MS (ESIpos): m/z=301/303 (M+H)⁺

¹H-NMR (400 MHz, DMSO-d₆): δ=8.21-7.90 (m, 1H), 7.87 (s, 1H), 7.09-6.60 (br. s, 1H), 5.90 (br. s, 1H), 5.03 (br. s, 1H), 4.63 (s, 2H), 1.66 (s, 6H) ppm.

Intermediate 44A

4-Amino-7-(2-hydroxypropan-2-yl)-5-(7-methoxy-5-methyl-1-benzothiophen-2-yl)pyrrolo[2,1-f]-[1,2,4]triazine-6-carbaldehyde

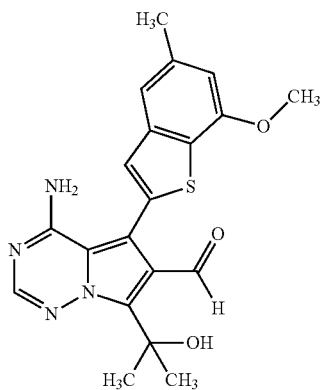 [SMILES: COc1cc(C)cc2cc(-c3c(C=O)c(C(C)(C)O)n4ncnc(N)c34)sc12]

A solution of Example 73 (135 mg, purity 89%, 302 µmol) in dichloromethane (7 ml) was treated with Dess-Martin periodinane (1,1,1-triacetoxy-1,1-dihydro-1,2-benziodoxol-3(1H)-one; 166 mg, 392 µmol) and stirred at rt for 70 min. The reaction mixture was combined with the reaction mixture of a 18 mg (45 µmol) test run and quenched with sat. aq. sodium hydrogencarbonate solution and sat. aq. sodium thiosulfate solution (1:1). The aqueous phase was extracted three times with dichloromethane. The combined organic phases were washed with sat. aq. sodium chloride solution, dried over magnesium sulfate and evaporated yielding 143 mg (purity 77%, 92% of th.) of the title compound.

LC-MS (method 2): $R_t$=1.08 min; MS (ESIpos): m/z=397 (M+H)⁺.

Intermediate 45A 6-({[tert-Butyl(dimethyl)silyl]oxy}methyl)pyrrolo[2,1-f][1,2,4]triazin-4-amine

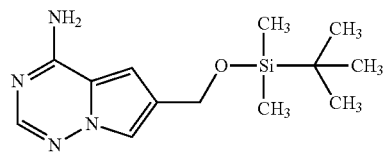 [SMILES: CC(C)(C)[Si](C)(C)OCc1cc2c(N)ncnn2c1]

A solution of 1.5 g (9.14 mmol) of Intermediate 8A in 15 ml dry DMF was treated with 1.65 g (10.96 mmol) tert-butyldimethylsilyl chloride and 1.24 g (18.27 mmol) imidazole and stirred at rt overnight. The reaction mixture was poured into 250 ml water and stirred for 5 min. The resulting precipitate was filtered off and dried in vacuo at 45° C. Yield: 2.28 g (90% of th.).

LC-MS (method 5): $R_t$=2.12 min; MS (ESIpos): m/z=279 (M+H)⁺.

Intermediate 46A 6-({[tert-Butyl(dimethyl)silyl]oxy}methyl)-7-chloro-pyrrolo[2,1-f][1,2,4]triazin-4-amine

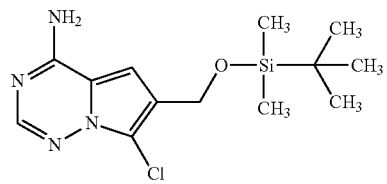 [SMILES: CC(C)(C)[Si](C)(C)OCc1cc2c(N)ncnn2c1Cl]

A solution of 2 g (7.18 mmol) of Intermediate 45A in 20 ml THF was treated with 893 mg (6.47 mmol) N-chlorosuccinimide in 6 portions over 60 min at −10° C. Stirring was continued for 15 min at −10° C., then the mixture was allowed to warm to rt. Another 192 mg (1.44 mmol) N-chlorosuccinimide were added at rt, and stirring was continued overnight. About one-tenth of the reaction mixture was evaporated to dryness, and the residue was purified by preparative RP-HPLC (Reprosil C18, gradient 10-95% acetonitrile/0.1% aq. formic acid) furnishing 94 mg (4% of th.) of the title compound. The major part of the reaction mixture was adsorbed on silica gel and subjected to chromatography on silica gel with isohexane/ethyl acetate 5-66% as eluent, yielding 899 mg (40% of th.) of the title compound. Total yield: 993 mg (44% of th.).

LC-MS (method 5): $R_t$=2.45 min; MS (ESIpos): m/z=313 (M+H)⁺

¹H-NMR (400 MHz, DMSO-d₆): δ=7.69-8.04 (m, 3H), 7.0 (s, 1H), 4.70 (s, 2H), 0.88 (s, 9H), 0.08 (s, 6H) ppm.

Intermediate 47A

5-Bromo-6-({[tert-butyl(dimethyl)silyl]oxy}methyl)-7-chloropyrrolo[2,1-f][1,2,4]triazin-4-amine

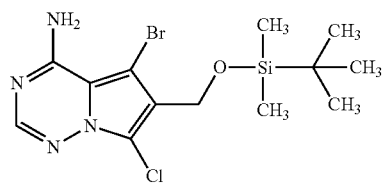 [SMILES: CC(C)(C)[Si](C)(C)OCc1c(Br)c2c(N)ncnn2c1Cl]

A solution of 890 mg (2.85 mmol) of Intermediate 46A in 20 ml DMF was treated with 506 mg (2.85 mmol) N-bromosuccinimide in portions over 1 h at −10° C. Stirring was continued for 3 h at −10° C. and then overnight at rt. Water (200 ml) was added, and the mixture was stirred for 2 h. The precipitated solid was filtered off, washed with water and dried in vacuo at 45° C. Yield: 997 mg (89% of th.).

LC-MS (method 5): $R_t$=2.82 min; MS (ESIpos): m/z=391/393/395 (M+H)$^+$ $^1$H-NMR (400 MHz, DMSO-d$_6$): δ=8.32 (br. s, 1H), 7.97 (s, 1H), 6.97 (br. s, 1H), 4.66 (s, 2H), 0.87 (s, 9H), 0.09 (s, 6H) ppm.

Intermediate 48A 6-({[tert-Butyl(dimethyl)silyl]oxy}methyl)-7-chloro-5-(7-methoxy-5-methyl-1-benzothiophen-2-yl)pyrrolo[2,1-f][1,2,4]triazin-4-amine

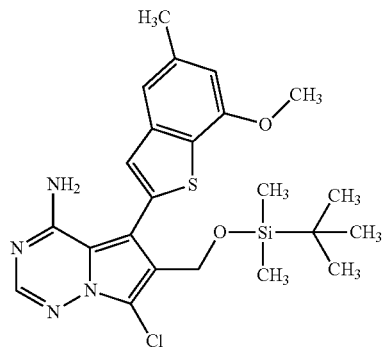 [SMILES: COc1cc(C)cc2cc(-c3c(CO[Si](C)(C)C(C)(C)C)c(Cl)n4ncnc(N)c34)sc12]

Under an argon atmosphere, a flask was charged with 800 mg (2.04 mmol) of Intermediate 47A, 680 mg (2.04 mmol) of Intermediate 6A, 80 mg (0.1 mmol) (2'-aminobiphenyl-2-yl)(chloro)palladium-dicyclohexyl(2',4',6'-triisopropylbiphenyl-2-yl)phosphine (1:1; see S. L. Buchwald et al., *J. Am. Chem. Soc.* 132 (40), 14073-14075 (2010)) and 1.3 g (6.13 mmol) potassium phosphate.

Then, 30 ml of a degassed 1,4-dioxane/water mixture (5:1) were added, and the solution was stirred at 70° C. for 1 h. Further 680 mg (2.04 mmol) of Intermediate 6A and 32 mg (0.04 mmol) (2'-aminobiphenyl-2-yl)(chloro)palladium-dicyclohexyl(2',4',6'-triisopropylbiphenyl-2-yl)phosphine (1:1) were added, and stirring at 70° C. was continued for another 1 h. This procedure was repeated three times until the starting material was consumed (control by LC-MS). With the last portion of reagents, also 1.6 ml of 5 M aq. sodium hydroxide solution were added to achieve a pH value of 8-9. At the end of the reaction period, 30 ml water and 5 M aq. formic acid were added (pH 3-4) whereupon an oil separated. A part of this oil was purified by preparative RP-HPLC (Reprosil C18, gradient 10-95% acetonitrile/0.1% aq. formic acid). Two fractions of the title compound were obtained: 103 mg of a solid (89% purity by LC-MS, 9% of th.), and 23 mg of a solid (100% purity by LC-MS, 2% of th.). The rest of the oil and the supernatant were diluted with water, adjusted to pH 8-9 with sat. aq. sodium hydrogencarbonate solution and extracted three times with dichloromethane. The combined organic phases were washed with water, dried and evaporated under reduced pressure, yielding 2.1 g of an oil. This material was purified by column chromatography on silica gel with dichloromethane/0-5% methanol as eluent to afford further 709 mg (43% purity by LC-MS, 31% of th.) of the title compound. Total yield: 42% of th.

LC-MS (method 2): $R_t$=1.57 min; MS (ESIpos): m/z=489 (M+H)$^+$ $^1$H-NMR (400 MHz, DMSO-d$_6$): δ=8.08 (s, 1H), 7.43 (s, 1H), 7.32 (s, 1H), 6.88 (s, 1H), 4.66 (s, 2H), 3.98 (s, 3H), 2.47 (s, 3H), 0.84 (s, 9H), −0.03 (s, 6H) ppm.

Intermediate 49A

4-Amino-7-chloro-5-(7-methoxy-5-methyl-1-benzothiophen-2-yl)pyrrolo[2,1-f][1,2,4]triazine-6-carbaldehyde

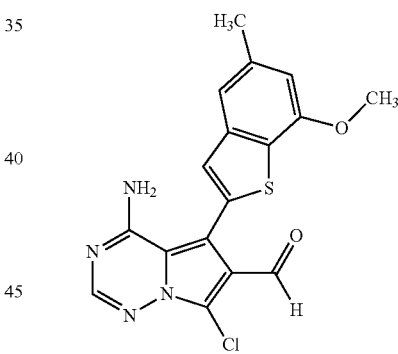

To a suspension of 166 mg (0.44 mmol) of Example 79 and molecular sieves (3 Å) in 3 ml dichloromethane were added 207 mg (0.49 mmol) Dess-Martin periodinane (1,1,1-triacetoxy-1,1-dihydro-1,2-benziodoxol-3(1H)-one) at 0-5° C. The mixture was stirred for 10 min at this temperature, then further 56 mg (0.13 mmol) Dess-Martin periodinane were added, and stirring was continued for 15 min at 5° C. and 10 min at ambient temperature. After this, the mixture was adsorbed on diatomaceous earth and purified by column chromatography on silica gel with dichloromethane/0-10% methanol as eluent. Yield: 100 mg of a solid (92.7% pure by LC-MS, 56% of th.).

LC-MS (method 2): $R_t$=1.08 min; MS (ESIpos): m/z=373 (M+H)$^+$ $^1$H-NMR (400 MHz, DMSO-d$_6$): δ=9.90 (s, 1H), 8.46 (br. s, 1H), 8.15 (s, 1H), 7.54 (s, 1H), 7.34 (s, 1H), 6.89 (s, 1H), 6.07 (br. s, 1H), 3.96 (s, 3H), 2.46 (s, 3H) ppm.

Intermediate 50A

7-Chloro-6-(chloromethyl)-5-(7-methoxy-5-methyl-1-benzothiophen-2-yl)pyrrolo[2,1-f][1,2,4]-triazin-4-amine

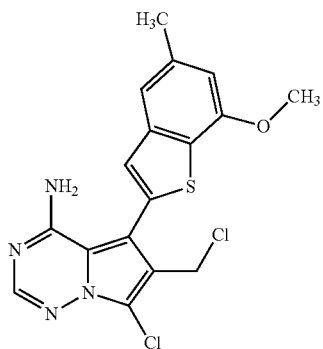 [SMILES: COc1cc(C)cc2cc(-c3c(CCl)c(Cl)n4ncnc(N)c34)sc12]

The title compound was isolated as a by-product in the preparation of Example 79 (see below). Yield: 9.2 mg (10% of th.).

LC-MS (method 3): $R_t$=2.98 min; MS (ESIpos): m/z=393/395 (M+H)$^+$.

Intermediate 51A 6-({[tert-Butyl(dimethyl)silyl]oxy}methyl)-7-methylpyrrolo[2,1-f][1,2,4]triazin-4-amine

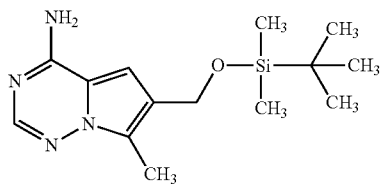 [SMILES: Cc1c(CO[Si](C)(C)C(C)(C)C)cc2c(N)ncnn12]

To a solution of 3 g (8.4 mmol) of Intermediate 35A in 60 ml 1,4-dioxane under an argon atmosphere were added 171 mg (0.21 mmol) of PdCl$_2$(dppf)×DCM and then dropwise over 10 min 16.8 ml of a 2 M solution of dimethylzinc in toluene (causing a rise in temperature from 22° C. to 31° C.). Stirring was continued first for 10 min at ambient temperature, then for 13 h at 90° C. After this, water (10 ml) was added to the reaction mixture at rt, and the suspension was stirred for 1 h. The mixture was evaporated under reduced pressure, and the residue was taken up in water and ethyl acetate and stirred for another 1 h. The precipitate was filtered off and discarded, the phases were separated, and the aqueous layer was extracted twice with ethyl acetate. The combined organic phases were dried and evaporated affording 2.45 g (92% purity by LC-MS, 92% of th.) of the title compound.

LC-MS (method 5): $R_t$=2.18 min; MS (ESIpos): m/z=293 (M+H)$^+$ $^1$H-NMR (400 MHz, DMSO-d$_6$): δ=7.98-7.78 (m, 3H), 7.04 (s, 1H), 4.68 (s, 2H), 0.89 (s, 9H), 0.09 (s, 6H) ppm.

Intermediate 52A (4-Amino-7-methylpyrrolo[2,1-f][1,2,4]triazin-6-yl)methanol

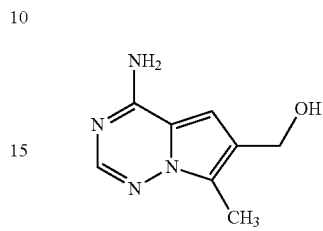

Method 1:

To a solution of 100 mg (0.28 mmol) of Intermediate 35A in 2 ml 1,4-dioxane under an argon atmosphere were added 6 mg (0.01 mmol) PdCl$_2$(dppf)×DCM and then dropwise over 10 min 0.56 ml of a 2 M solution of dimethylzinc in toluene. The mixture was stirred at 90° C. overnight, then evaporated, and the residue was treated with acetonitrile and 5 M aq. formic acid. The precipitate was filtered off, the filtrate was evaporated, and the residue was taken up in DMSO/acetonitrile and purified by preparative RP-HPLC (Reprosil C18, gradient 10-95% acetonitrile/0.1% aq. formic acid). Yield: 33 mg (66% of th.).

$^1$H-NMR (400 MHz, DMSO-d$_6$): δ=7.79 (s, 1H), 7.47 (br. s, 2H), 6.80 (s, 1H), 4.84 (t, 1H), 4.49 (d, 2H), 2.36 (s, 3H) ppm.

Method 2:

Under an argon atmosphere, a microwave reaction vessel was charged with 750 mg (3.1 mmol) of Intermediate 34A, 515 µl (3.7 mmol) trimethylboroxine, 786 mg (3.7 mmol) potassium phosphate and 73 mg (0.09 mmol) (2'-aminobiphenyl-2-yl)(chloro)palladium-dicyclohexyl(2',4',6'-triisopropylbiphenyl-2-yl)phosphine (1:1; see S. L. Buchwald et al., J. Am. Chem. Soc. 132 (40), 14073-14075 (2010)). Then, 13 ml of a degassed 1,4-dioxane/water mixture (5:1) were added, the vessel was sealed, and the mixture was heated to 140° C. for 20 min in the microwave (4 bar, 50 watt). Further 50 mg (2'-aminobiphenyl-2-yl)(chloro)palladium-dicyclohexyl(2',4',6'-triisopropylbiphenyl-2-yl)phosphine (1:1) were added, and the mixture was heated again to 140° C. for 20 min in the microwave. Another portion of 515 µl trimethylboroxine was added, and the vessel was heated again to 140° C. for 20 min. The latter procedure was repeated two more times with heating periods of 30 min each until LC-MS showed only minor amounts of starting material left. The mixture was filtered over kieselguhr, washed with 1,4-dioxane, and the combined filtrates were evaporated to dryness. This residue was combined with a previous 100 mg test run and purified by preparative RP-HPLC (XBridge C18, gradient 5-42% acetonitrile/0.05% aq. ammonium hydroxide solution). Yield: 238 mg (38% of th.).

LC-MS (method 5): $R_t$=0.51 min; MS (ESIneg): m/z=177 (M−H)$^-$ $^1$H-NMR (400 MHz, DMSO-d$_6$): δ=7.79 (s, 1H), 7.48 (br. s, 2H), 6.80 (s, 1H), 4.84 (t, 1H), 4.49 (d, 2H), 2.36 (s, 3H) ppm.

Intermediate 53A (4-Amino-5-bromo-7-methylpyrrolo[2,1-f][1,2,4]triazin-6-yl)methanol

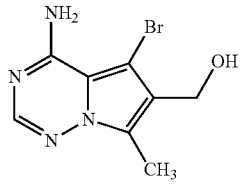

A solution of 245 mg (1.38 mmol) of Intermediate 52A in 8.8 ml DMF was treated with 288 mg (1.62 mmol) N-bromosuccinimide in portions over 2 h at −10° C. Stirring was continued at −10° C. for 30 min and then for 2 h at ambient temperature. The mixture was poured into 50 ml water and extracted with ethyl acetate. The combined organic phases were dried and evaporated. The residue was flash-chromatographed on silica gel with dichloromethane/0-15% methanol as eluent. Yield: 148 mg (42% of th.).

LC-MS (method 4): R$_t$=0.42 min; MS (ESIpos): m/z=257/259 (M+H)$^+$ $^1$H-NMR (400 MHz, DMSO-d$_6$): δ=7.85 (s, 1H), 6.14-8.22 (broad, 2H), 4.88 (t, 1H), 4.45 (d, 2H), 2.43 (s, 3H) ppm.

Intermediate 54A

4-Amino-5-(7-methoxy-5-methyl-1-benzothiophen-2-yl)-7-methylpyrrolo[2,1-f][1,2,4]triazine-6-carbaldehyde

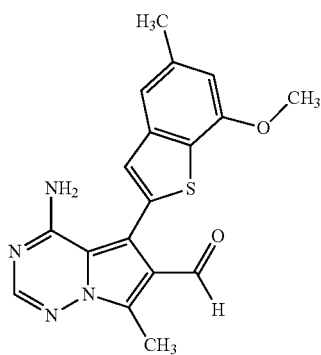 [SMILES: COc1cc(C)cc2cc(-c3c(C=O)c(C)n4ncnc(N)c34)sc12]

To a suspension of 175 mg (0.49 mmol) of Example 75 and molecular sieves (3 Å) in 3.5 ml dichloromethane were added 230 mg (0.54 mmol) Dess-Martin periodinane (1,1,1-triacetoxy-1,1-dihydro-1,2-benziodoxol-3(1H)-one) at 0-5° C. The mixture was stirred for 5 min at this temperature, followed by 30 min at rt. After this, the mixture was adsorbed on diatomaceous earth and purified by flash-chromatography on silica gel with isohexane/10-100% ethyl acetate as eluent.

Yield: 139 mg of a solid (79% of th.).

LC-MS (method 5): R$_t$=2.34 min; MS (ESIpos): m/z=353 (M+H)$^+$ $^1$H-NMR (400 MHz, DMSO-d$_6$): δ=9.93 (s, 1H), 8.06 (s, 1H), 7.50 (s, 1H), 7.33 (s, 1H), 6.88 (s, 1H), 3.96 (s, 3H), 2.71 (s, 3H), 2.46 (s, 3H) ppm.

Intermediate 55A tert-Butyl 4-[(4-amino-6-methylpyrrolo[2,1-f][1,2,4]triazin-7-yl)methyl]piperazine-1-carboxylate

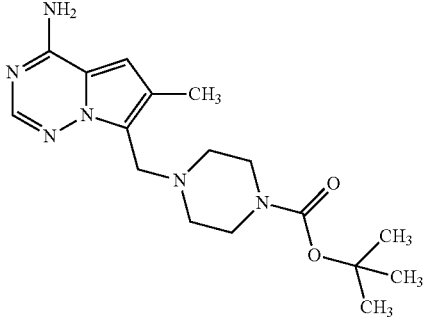 [SMILES: Cc1cc2c(N)ncnn2c1CN1CCN(C(=O)OC(C)(C)C)CC1]

A solution of 6-methylpyrrolo[2,1-f][1,2,4]triazin-4-amine (500 mg, 3.3 mmol; preparation described in PCT Int. Pat. Appl. WO 2007/056170) in acetic acid (8 ml) was treated with 37% aq. formaldehyde solution (328 µl, 4.04 mmol) and tert-butyl piperazine-1-carboxylate (754 mg, 4.04 mmol). The mixture was stirred at 60° C. overnight. After evaporation, the residue was taken up in ethyl acetate and washed with sat. aq. sodium hydrogencarbonate solution. The aqueous layer was extracted twice with ethyl acetate. The combined organic phases were dried over magnesium sulfate and evaporated affording 1.2 g of the crude product which was used in the next step without further purification.

LC-MS (method 2): R$_t$=0.56 min; MS (ESIpos): m/z=347 (M+H)$^+$ $^1$H-NMR (400 MHz, DMSO-d$_6$): δ=7.79 (s, 1H), 7.51 (br. s, 2H), 6.67 (s, 1H), 3.76 (br. s, 2H), 3.29-3.17 (m, 4H), 2.36-2.29 (m, 4H), 2.22 (s, 3H), 1.37 (s, 9H) ppm.

Intermediate 56A tert-Butyl-4-[(4-amino-5-bromo-6-methylpyrrolo[2,1-f][1,2,4]triazin-7-yl)methyl]piperazine-1-carboxylate

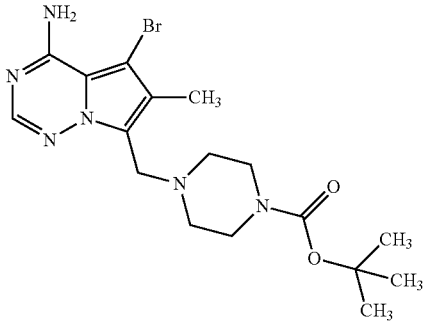 [SMILES: Cc1c(Br)c2c(N)ncnn2c1CN1CCN(C(=O)OC(C)(C)C)CC1]

A solution of Intermediate 55A (1.17 g, 3.37 mmol) in THF (20 ml) was cooled to −60° C. and treated with 1,3-dibromo-5,5-dimethylhydantoin (5.78 mg, 2.02 mmol). The mixture was stirred for 4 h at −60° C. to −20° C. After this, the reaction mixture was quenched with 10% aq. sodium thiosulfate solution. Most of the THF solvent was evaporated whereupon a solid precipitated. Filtration and recrystallization from acetone afforded 862 mg (59% of th.) of the title compound.

LC-MS (method 2): $R_t$=0.66 min; MS (ESIpos): m/z=425/427 (M+H)$^+$ $^1$H-NMR (400 MHz, DMSO-d$_6$): δ=8.29-7.62 (br. s, 1H), 7.85 (s, 1H), 7.17-6.44 (br. s, 1H), 3.80 (s, 2H), 3.29-3.22 (m, 4H), 2.37-2.27 (m, 4H), 2.16 (s, 3H), 1.37 (s, 9H) ppm.

Intermediate 57A tert-Butyl 4-{[4-amino-5-(7-methoxy-5-methyl-1-benzothiophen-2-yl)-6-methylpyrrolo[2,1-f]-[1,2,4]triazin-7-yl]methyl}piperazine-1-carboxylate

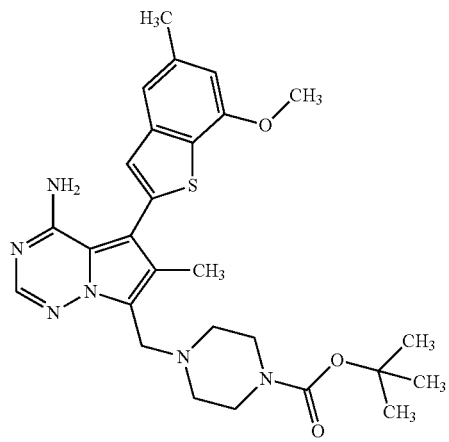 [SMILES: COc1cc(C)cc2cc(-c3c(C)c(CN4CCN(C(=O)OC(C)(C)C)CC4)n4ncnc(N)c34)sc12]

A solution of Intermediate 56A (100 mg, 235 µmol) in degassed 1,4-dioxane (3 ml) was treated with Intermediate 6A (93 mg, 282 µmol), dicyclohexyl(2',6'-dimethoxybiphenyl-2-yl)phosphine (S-Phos; 9.6 mg, 23 µmol) and palladium diacetate (2.6 mg, 11 Degassed 3 M aq. potassium phosphate solution (588 µl) was added, and the resulting mixture was stirred at 60° C. for 1 h. A further portion of Intermediate 6A (78 mg, 235 µmol) was added, and stirring at 60° C. was continued overnight. The reaction mixture was quenched with 2 M aq. sodium hydroxide solution, and the aqueous phase was extracted with ethyl acetate. The combined organic phases were washed with sat. aq. sodium chloride solution, dried over magnesium sulfate and evaporated. Purification by column chromatography on silica gel (cyclohexane/ethyl acetate 3:2) afforded 82 mg (62% of th.) of the title compound.

LC-MS (method 2): $R_t$=0.97 min; MS (ESIpos): m/z=523 (M+H)$^+$ $^1$H-NMR (400 MHz, DMSO-d$_6$): δ=7.94 (s, 1H), 7.34 (s, 1H), 7.30 (s, 1H), 6.84 (s, 1H), 3.95 (s, 3H), 3.84 (s, 2H), 3.30-3.23 (m, 4H, overlap with water peak), 2.45 (s, 3H), 2.42-2.33 (m, 4H), 2.19 (s, 3H), 1.39 (s, 9H) ppm.

Intermediate 58A tert-Butyl 4-[(4-amino-6-chloropyrrolo[2,1-f][1,2,4]triazin-7-yl)methyl]piperazine-1-carboxylate

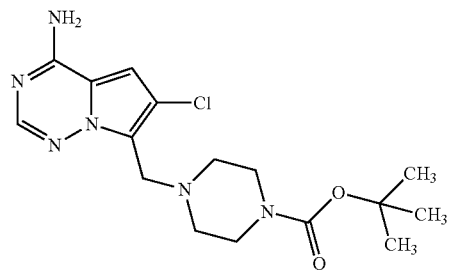 [SMILES: CC(C)(C)OC(=O)N1CCN(Cc2c(Cl)cc3c(N)ncnn23)CC1]

Following the procedure of Intermediate 55A, 4 g (23.7 mmol) 6-chloropyrrolo[2,1-f][1,2,4]triazin-4-amine (preparation described in PCT Int. Pat. Appl. WO 2007/064883) were reacted to give 11.2 g of the title compound as crude material which was used in the next step without further purification.

LC-MS (method 5): $R_t$=0.74 min; MS (ESIpos): m/z=367 (M+H)$^+$

A sample of 67 mg of the corresponding formiate salt, tert-butyl 4-[(4-amino-6-chloropyrrolo-[2,1-f][1,2,4]triazin-7-yl)methyl]piperazine-1-carboxylate formiate, was isolated after preparative RP-HPLC (Reprosil C18, gradient 10-95% acetonitrile/0.1% aq. formic acid) of 100 mg of the crude material obtained above.

$^1$H-NMR (400 MHz, DMSO-d$_6$): inter al. δ=8.14 (s, 1H), 7.91 (s, 1H), 7.83 (br. s, 2H), 6.95 (s, 1H), 3.80 (s, 2H), 3.17 (s, 2H), 2.38 (br. s, 4H), 1.37 (s, 9H) ppm.

Intermediate 59A tert-Butyl 4-[(4-amino-5-bromo-6-chloropyrrolo[2,1-f][1,2,4]triazin-7-yl)methyl]piperazine-1-carboxylate

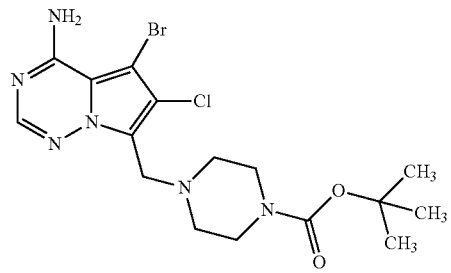 [SMILES: CC(C)(C)OC(=O)N1CCN(Cc2c(Cl)c(Br)c3c(N)ncnn23)CC1]

Following the procedure of Intermediate 56A, 11 g (30 mmol) of Intermediate 58A were reacted to give 1.17 g (9% of th.) of the title compound after flash-chromatography on silica gel (dichloromethane/methanol 10:1) and subsequent preparative RP-HPLC (Daiso C18, gradient 40-65% acetonitrile/water).

LC-MS (method 2): $R_t$=0.74 min; MS (ESIpos): m/z=445/447/449 (M+H)$^+$ $^1$H-NMR (400 MHz, DMSO-d$_6$): inter al. δ=7.96 (s, 1H), 3.84 (s, 2H), 2.37 (br. s, 4H), 1.37 (s, 9H) ppm.

Intermediate 60A tert-Butyl 4-{[4-amino-6-chloro-5-(7-methoxy-5-methyl-1-benzothiophen-2-yl)pyrrolo[2,1-f]-[1,2,4]triazin-7-yl]methyl}piperazine-1-carboxylate

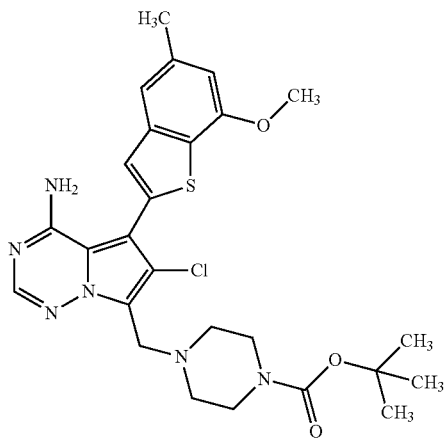 [SMILES: COc1cc(C)cc2cc(-c3c(Cl)c(CN4CCN(C(=O)OC(C)(C)C)CC4)n4ncnc(N)c34)sc12]

Under an argon atmosphere, a flask was charged with 140 mg (0.31 mmol) of Intermediate 59A, 102 mg (0.46 mmol) of Intermediate 5A, 16 mg (0.02 mmol) PdCl$_2$(dppf)×DCM and 122 mg (1.15 mmol) sodium carbonate. After addition of 3 ml degassed 1,2-dimethoxyethane/water (3:1), the suspension was stirred at 60° C. for 2.5 h. Further portions of Intermediate 5A (50 mg, 0.23 mmol) and PdCl$_2$(dppf)×DCM (8 mg, 0.01 mmol) were added, and stirring was continued at 40° C. for 2.5 h. The latter procedure was repeated once more until the starting material was consumed. Then, the reaction mixture was partially evaporated under reduced pressure, water was added, and the mixture was extracted with dichloromethane. The combined organic phases were washed with water and sat. aq. sodium chloride solution, dried and evaporated under reduced pressure. The residue (322 mg) was purified by preparative RP-HPLC (Reprosil C18, gradient 10-95% acetonitrile/0.1% aq. formic acid) to give 49 mg of a mixture of the title compound and the Boc-deprotected derivative, 6-chloro-5-(7-methoxy-5-methyl-1-benzothiophen-2-yl)-7-(piperazin-1-yl-methyl)pyrrolo[2,1-f][1,2,4]triazin-4-amine. This mixture was used as such in the next reaction step (see Example 85).

LC-MS (method 2): R$_t$=1.00 min; MS (ESIpos): m/z=543 (M+H)$^+$, and R$_t$=0.81 min; MS (ESIpos): m/z=443 (M+H)$^+$.

Intermediate 61A

4-{[4-Amino-6-(methoxymethyl)pyrrolo[2,1-f][1,2,4]triazin-7-yl]methyl}piperazin-2-one

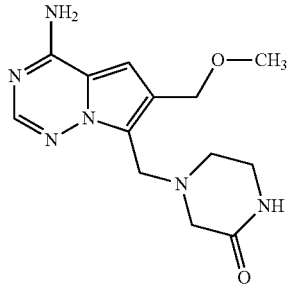 [SMILES: COCc1cc2c(N)ncnn2c1CN1CCNC(=O)C1]

A solution of Intermediate 10A (5 g, 28.1 mmol) and piperazin-2-one (3.09 g, 30.9 mmol) in acetic acid (85 ml) was treated with 37% aq. formaldehyde solution (3.15 ml, 42.1 mmol) and stirred at 60° C. for 16 h. The volatiles were evaporated under reduced pressure, and the residue was dissolved in methanol and adsorbed on diatomaceous earth. Purification by column chromatography on silica gel (5-10% methanol/dichloromethane) afforded 3.91 g (46% of th.) of the title compound.

LC-MS (method 3): R$_t$=1.68 min; MS (ESIpos): m/z=291 (M+H)$^+$.

Intermediate 62A

4-{[4-Amino-5-bromo-6-(methoxymethyl)pyrrolo[2,1-f][1,2,4]triazin-7-yl]methyl}piperazin-2-one

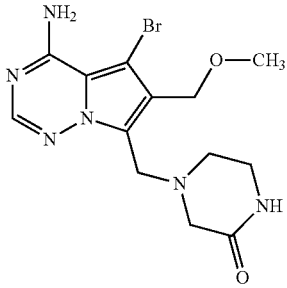 [SMILES: COCc1c(Br)c2c(N)ncnn2c1CN1CCNC(=O)C1]

A solution of Intermediate 61A (3.9 g, 13.4 mmol) in DMF (50 ml) was cooled to 0° C. and treated with a solution of N-bromosuccinimide (2.63 g, 14.8 mmol) in DMF (6 ml). The mixture was stirred at 0° C. for 1 h. Then, the solvent was evaporated, and the residue was dissolved in methanol and adsorbed on diatomaceous earth. Purification by column chromatography on silica gel (5-10% methanol/dichloromethane) afforded 1.99 g (39% of th.) of the title compound.

LC-MS (method 3): R$_t$=1.86 min; MS (ESIpos): m/z=369/371 (M+H)$^+$ $^1$H-NMR (400 MHz, DMSO-d$_6$): δ=7.96-8.23 (br. s, 1H), 7.90 (s, 1H), 7.71 (s, 1H), 6.72-6.98 (br. s, 1H), 4.45 (s, 2H), 3.91 (s, 2H), 3.27 (s, 3H), 3.07 (br. s, 2H), 2.96 (s, 2H), 2.56 (br. s, 2H) ppm.

Intermediate 63A 7-(Chloromethyl)-6-(ethoxymethyl)-5-(7-methoxy-5-methyl-1-benzothiophen-2-yl)pyrrolo[2,1-f]-[1,2,4]triazin-4-amine hydrochloride

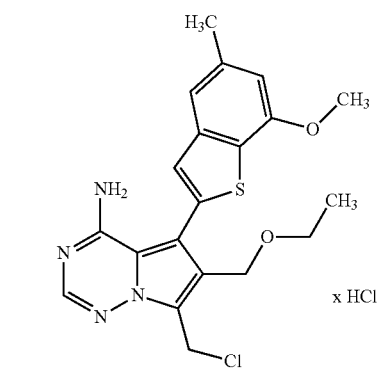 [SMILES: CCOCc1c(-c2cc3cc(C)cc(OC)c3s2)c2c(N)ncnn2c1CCl]

A suspension of Example 86 (1 g, 2.51 mmol) in toluene (60 ml) was treated dropwise with thionyl chloride (1.83 ml, 25.1 mmol), and the mixture was stirred at rt overnight. The volatiles were evaporated under reduced pressure. The residue was co-evaporated with toluene under reduced pressure for three times affording 0.85 g (74% of th.) of the title compound which was immediately used for the next step without further purification.

Intermediate 64A

4-Amino-6-(ethoxymethyl)-5-(7-methoxy-5-methyl-1-benzothiophen-2-yl)pyrrolo[2,1-f][1,2,4]triazine-7-carboxylic acid

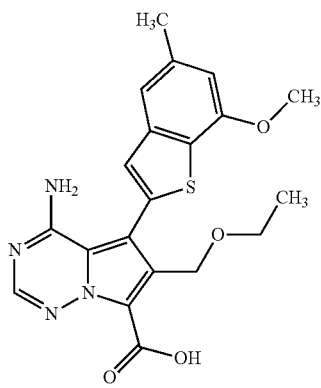 [SMILES: CCOCc1c(-c2cc3cc(C)cc(OC)c3s2)c2c(N)ncnn2c1C(=O)O]

A suspension of Intermediate 17A (5 g, 12.6 mmol) in THF/water (10:1, 220 ml) was treated with a 2 M solution of 2-methyl-2-butene in THF (31.5 ml, 63.1 mmol) and with sodium dihydrogenphosphate (6.96 g, 50.4 mmol). The mixture was stirred at rt for 5 min. Then, sodium chlorite (4.56 g, 50.44 mmol) was added, and the resulting mixture was stirred at rt for 20 h. The suspension was filtered, and the resulting solid was washed with water affording 4.24 g (74% of th.) of the title compound which was used in the next step without further purification.

LC-MS (method 4): $R_t$=1.06 min; MS (ESIpos): m/z=413 (M+H)$^+$ $^1$H-NMR (400 MHz, DMSO-d$_6$): δ=13.22 (br. s, 1H), 8.53-8.00 (br. s, 1H), 8.14 (s, 1H), 7.41 (s, 1H), 7.33 (s, 1H), 6.86 (s, 1H), 6.28-5.65 (br. s, 1H), 4.61 (s, 2H), 3.96 (s, 3H), 3.36 (q, 2H), 2.46 (s, 3H), 1.01 (t, 3H) ppm.

Intermediate 65A 5,7-Dimethoxy-1-benzothiophene

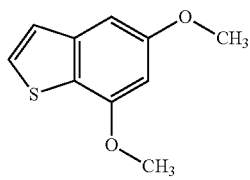

To a solution of 1-benzothiophene-5,7-diol (1.16 g, 6.98 mmol) in acetone (20 ml) under argon were added potassium carbonate (2.89 g, 20.9 mmol) and iodomethane (912 µl, 14.6 mmol). The resulting mixture was stirred under reflux for 18 h. After cooling to rt, the mixture was treated with a 7 M solution of ammonia in methanol (10 ml) for 30 min and then adsorbed on silica gel. Purification by column chromatography over silica gel (cyclohexane/ethyl acetate 40:1) afforded 0.52 g (32% of th.) of the title compound.

LC-MS (method 4): $R_t$=1.02 min; MS (ESIpos): m/z=195 (M+H)$^+$ $^1$H-NMR (400 MHz, DMSO-d$_6$): δ=7.69 (d, 1H), 7.35 (d, 1H), 7.02 (d, 1H), 6.57 (d, 1H), 3.92 (s, 3H), 3.81 (s, 3H) ppm.

Intermediate 66A (5,7-Dimethoxy-1-benzothiophen-2-yl)boronic acid

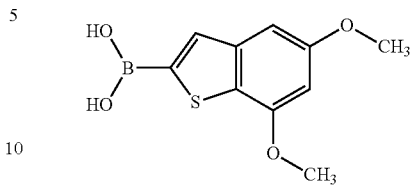

Under an argon atmosphere, a 1.6 M solution of n-butyl-lithium in hexane (1.84 ml, 2.95 mmol) was added dropwise to a solution of Intermediate 65A (520 mg, 2.68 mmol) in dry THF (5 ml) at −70° C. After 1 h at −70° C., triisopropyl borate (742 µl, 3.21 mmol) was added, and the mixture was stirred for 16 h while slowly warming up to rt. Dichloromethane and sat. aq. ammonium chloride solution were added, and the pH value was adjusted to 6 by addition of 1 M hydrochloric acid. The organic phase was separated, and the aqueous phase was extracted with dichloromethane. The combined organic phases were dried with magnesium sulfate, filtered and evaporated. The resulting residue was purified by column chromatography over silica gel (at first eluting with dichloromethane/methanol 40:1, then methanol, finally methanol/4 M hydrogen chloride in 1,4-dioxane 10:1) yielding 631 mg (71% purity, 71% of th.) of the title compound.

LC-MS (method 4): $R_t$=0.83 min; MS (ESIpos): m/z=239 (M+H)$^+$.

Intermediate 67A

4-Amino-6-(chloromethyl)pyrrolo[2,1-f][1,2,4]triazine-7-carbaldehyde

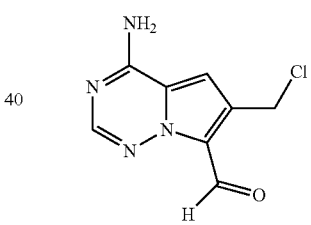

Intermediate 67A was isolated as a side-product of the synthesis of Intermediate 11A after column chromatography on silica gel (dichloromethane/acetone 8:2→7:3).

LC-MS (method 2): $R_t$=0.6 min; MS (ESIpos): m/z=211/213 (M+H)$^+$.

Intermediate 68A

4-Amino-6-[(3-oxopiperazin-1-yl)methyl]pyrrolo[2,1-f][1,2,4]triazine-7-carbaldehyde

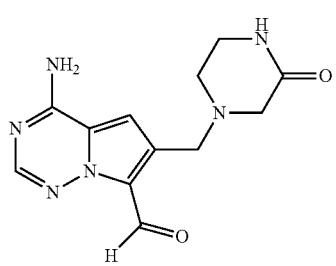 [SMILES: Nc1ncnn2c(C=O)c(CN3CCNC(=O)C3)cc12]

A solution of Intermediate 67A (11.03 g, 52.4 mmol) and 2-oxopiperazine (6.82 g, 68.1 mmol) in 331 ml DMF was treated at rt with DIPEA (13.7 ml, 78.6 mmol) and stirred overnight. The precipitate was filtered off, washed with DMF and diethylether and then dried in vacuo to yield 11.64 g of the title compound (89% purity, 72% of th.).

LC-MS (method 7): $R_t$=1.30 min; MS (ESIpos): m/z=275 (M+H)$^+$.

Intermediate 69A

4-{[4-Amino-7-(hydroxymethyl)pyrrolo[2,1-f][1,2,4]triazin-6-yl]methyl}piperazin-2-one

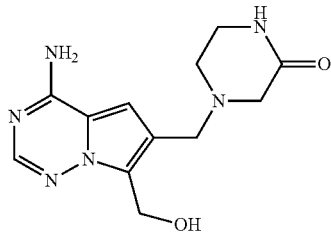 [SMILES: Nc1ncnn2c(CO)c(CN3CCNC(=O)C3)cc12]

To a solution of Intermediate 68A (10.17 g, 89% purity, 33.01 mmol) in 1 M hydrochloric acid (370 ml) and methanol (370 ml) at rt was added zinc dust (12.1 g, 185 mmol), and the mixture was stirred at rt for 18 h. Silica gel (100 g) was added, and the volatiles were evaporated under reduced pressure. The residue was suspended in methanol, the volatiles were evaporated under reduced pressure again, and the residue was dried in vacuo. The solid was subjected to column chromatography on silica gel (gradient dichloromethane/7 M ammonia in methanol 10:1→3:1) to yield 6.39 g of the title compound (60% of th.).

LC-MS (method 8): $R_t$=1.12 min; MS (ESIpos): m/z=277 (M+H)$^+$ $^1$H-NMR (400 MHz, DMSO-d$_6$): δ=7.83 (s, 1H), 7.76 (br. s, 1H), 7.64 (br. s, 2H), 6.83 (s, 1H), 5.01 (br. s, 1H), 4.74 (s, 2H), 3.64 (br. s, 2H), 3.14 (br. s, 2H), 2.95 (br. s, 2H), 2.58 (br. s, 2H) ppm.

Intermediate 70A

4-{[4-Amino-5-bromo-7-(hydroxymethyl)pyrrolo[2,1-f][1,2,4]triazin-6-yl]methyl}piperazin-2-one trifluoroacetate

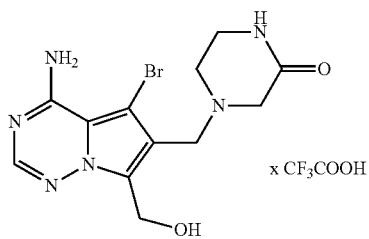 [SMILES: Nc1ncnn2c(CO)c(CN3CCNC(=O)C3)c(Br)c12]

A suspension of Intermediate 69A (1 g) in methanol/water (10:1, 33 ml) was treated with trifluoroacetic acid (0.56 ml, 7.24 mmol) to result in a clear solution. A solution of N-bromosuccinimide (708 mg, 3.98 mmol) in methanol (30 ml) was added dropwise at 0° C., and the mixture was stirred at 0° C. for 1 h. The formed precipitate was filtered off and dried in vacuo to yield 700 mg of the title compound (41% of th.).

LC-MS (method 7): $R_t$=1.38 min; MS (ESIpos): m/z=355/357 (M+H)$^+$ $^1$H-NMR (400 MHz, D$_2$O): δ=7.90 (s, 1H), 5.00 (s, 2H), 4.44 (s, 2H), 3.85 (s, 2H), 3.58 (br. t, 2H), 3.50 (br. t, 2H) ppm.

PREPARATION EXAMPLES

Example 1

4-{[4-Amino-6-(methoxymethyl)-5-(7-methoxy-5-methyl-1-benzothiophen-2-yl)pyrrolo[2,1-f]-[1,2,4]triazin-7-yl]methyl}piperazin-2-one

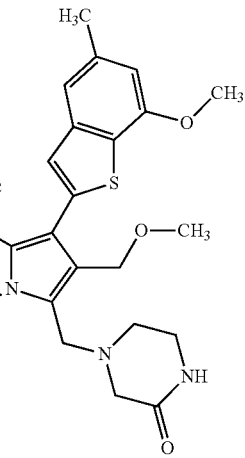

Method 1:

A solution of Intermediate 13A (3 g, 7.84 mmol) in methanol (87 ml) was treated with acetic acid (0.898 ml, 15.68 mmol), 2-oxopiperazine (1.17 g, 11.76 mmol) and sodium triacetoxyborohydride (4.98 g, 23.53 mmol). The mixture was stirred at rt for 4.5 h. Further portions of 2-oxopiperazine (392 mg, 3.9 mmol) and sodium triacetoxyborohydride (3.3 g, 15.68 mmol) were added, and the resulting mixture was stirred at 60° C. overnight. After evaporation, the residue was taken up in sat. aq. sodium hydrogencarbonate solution and extracted with ethyl acetate. The combined organic phases were dried over sodium sulfate and evaporated, and the residue was purified by column chromatography on silica gel (dichloromethane/methanol 40:1→10:1). The product thus obtained was triturated in methanol and filtered off affording 540 mg (14% of th.) of the title compound. The methanolic mother liquor was evaporated and the residue purified by two-fold RP-HPLC (Reprosil C18, gradient 10-95% acetonitrile/0.1% aq. formic acid). The fractions containing pure product were combined and neutralized with sat. aq. sodium hydrogencarbonate solution. The acetonitrile solvent was evaporated, and the aqueous phase was extracted with ethyl acetate. The combined organic phases were dried over sodium sulfate and evaporated affording 395 mg (13% of th.) as a second batch of the title compound.

Method 2:

A solution of Intermediate 21A (291 mg, 0.82 mmol) in acetic acid (2.9 ml) was treated with 37% aq. formaldehyde solution (104 μl, 1.39 mmol) and 2-oxopiperazine (139 mg, 1.39 mmol). The mixture was stirred at 60° C. for 3 h and then evaporated. Purification by preparative RP-HPLC (Reprosil C18, gradient 10-95% acetonitrile/0.1% aq. formic acid) afforded 184 mg (44% of th.) of the title compound.

LC-MS (method 4): $R_t$=0.77 min; MS (ESIpos): m/z=467 (M+H)⁺

¹H-NMR (400 MHz, DMSO-d₆): δ=8.00 (s, 1H), 7.73 (br. s, 1H), 7.37 (s, 1H), 7.31 (s, 1H), 6.84 (s, 1H), 4.41 (s, 2H), 3.97 (s, 2H), 3.96 (s, 3H), 3.20 (s, 3H), 3.15-3.08 (br. s, 2H), 3.01 (s, 2H), 2.64 (br. t, 2H), 2.45 (s, 3H) ppm.

Example 2

4-{[4-Amino-6-(methoxymethyl)-5-(7-methoxy-5-methyl-1-benzothiophen-2-yl)pyrrolo[2,1-f]-[1,2,4]triazin-7-yl]methyl}piperazin-2-one dihydrochloride

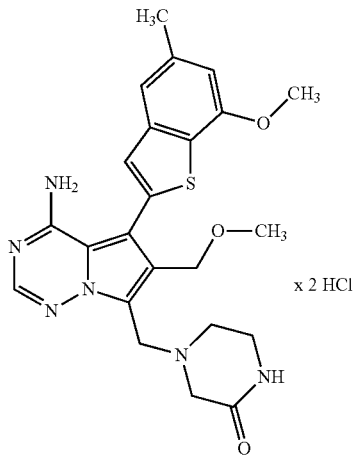 [SMILES: COCc1c(-c2cc3cc(C)cc(OC)c3s2)c2c(N)ncnn2c1CN1CCNC(=O)C1]

A solution of Example 1 (100 mg, 214 µmol) in 1,4-dioxane (2 ml) was treated with a 4 M solution of hydrogen chloride in 1,4-dioxane (2 ml, 8 mmol). The solvent was evaporated leaving 130 mg (quant.) of the title compound.

LC-MS (method 2): $R_t$=0.79 min; MS (ESIpos): m/z=467 (M+H)⁺

¹H-NMR (400 MHz, DMSO-d₆): δ=8.39 (br. s, 1H), 8.31-8.53 (br. s, 1H), 8.17 (s, 1H), 7.38 (s, 1H), 7.34 (s, 1H), 6.87 (s, 1H), 6.21-6.42 (br. s, 1H), 4.81 (br. s, 2H), 4.52 (br. s, 2H), 3.96 (s, 3H), 3.57 (s, 2H), 3.32-3.72 (m, 4H), 3.26 (s, 3H), 2.46 (s, 3H) ppm.

Example 3

(3R)-3-({[4-Amino-6-(methoxymethyl)-5-(7-methoxy-5-methyl-1-benzothiophen-2-yl)pyrrolo-[2,1-f][1,2,4]triazin-7-yl]methyl}amino)pyrrolidin-2-one dihydrochloride

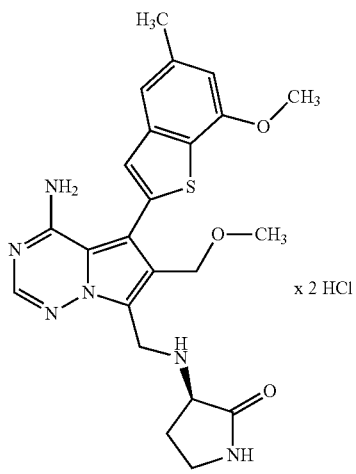 [SMILES: COCc1c(-c2cc3cc(C)cc(OC)c3s2)c2c(N)ncnn2c1CN[C@@H]1CCNC1=O]

A solution of Intermediate 13A (520 mg, 1.36 mmol) in methanol (15 ml) and acetic acid (156 µl, 2.7 mmol) was treated with (R)-3-aminopyrrolidin-2-one (503 mg, 5.0 mmol) and triacetoxyborohydride (1.06 g, 5.0 mmol). The mixture was stirred at rt overnight and then evaporated. Purification by preparative RP-HPLC (Reprosil C18, gradient 10-95% acetonitrile/0.1% aq. formic acid) and lyophilization of the product thus obtained from a 4 M solution of hydrogen chloride in 1,4-dioxane afforded 272 mg (36% of th.) of the title compound.

LC-MS (method 2): $R_t$=0.70 min; MS (ESIpos): m/z=467 (M+H)⁺

¹H-NMR (400 MHz, DMSO-d₆): δ=9.62 (br. s, 1H), 9.46 (br. s, 1H), 8.56-8.22 (br. s, 1H), 8.44 (s, 1H), 8.19 (s, 1H), 7.38 (s, 1H), 7.34 (s, 1H), 6.87 (s, 1H), 6.54-6.12 (br. s, 1H), 4.89-4.65 (m, 2H), 4.58-4.46 (m, 2H), 4.17-4.07 (br. s, 1H, overlap with water peak), 3.96 (s, 3H), 3.36-3.16 (m, 2H), 3.25 (s, 3H), 2.48-2.39 (m, 1H), 2.46 (s, 3H), 2.23-2.06 (m, 1H) ppm.

Example 4

(3R)-3-({[4-Amino-6-(methoxymethyl)-5-(7-methoxy-5-methyl-1-benzothiophen-2-yl)pyrrolo-[2,1-f][1,2,4]triazin-7-yl]methyl}amino)pyrrolidin-2-one

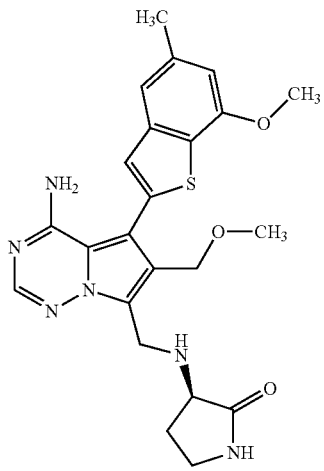 [SMILES: COCc1c(-c2cc3cc(C)cc(OC)c3s2)c2c(N)ncnn2c1CN[C@@H]1CCNC1=O]

A solution of Intermediate 13A (2.0 g, 5.2 mmol) in methanol (58 ml) and acetic acid (0.6 ml) was treated with (R)-3-aminopyrrolidin-2-one (785 mg, 7.8 mmol) and triacetoxyborohydride (3.32 g, 15.6 mmol). The mixture was stirred at rt overnight. After this, the reaction mixture was diluted with sat. aq. sodium hydrogencarbonate solution and extracted three times with ethyl acetate. The combined organic phases were dried over sodium sulfate and evaporated. The residue was purified by two-fold column chromatography on silica gel (dichloromethane/methanol 40:1 to 10:1) to afford 957 mg (37% of th.) of the title compound.

LC-MS (method 4): $R_t$=0.72 min; MS (ESIpos): m/z=467 (M+H)⁺

¹H-NMR (400 MHz, DMSO-d₆): δ=8.01 (s, 1H), 7.75 (s, 1H), 7.35 (s, 1H), 7.31 (s, 1H), 6.85 (s, 1H), 4.46-4.34 (m, 2H), 4.24-4.02 (m, 2H), 3.96 (s, 3H), 3.24-3.04 (m, 3H), 3.21 (s, 3H), 2.45 (s, 3H), 2.40-2.27 (m, 1H), 1.80-1.65 (m, 1H) ppm.

Example 5

4-{[4-Amino-6-(ethoxymethyl)-5-(7-methoxy-5-methyl-1-benzothiophen-2-yl)pyrrolo[2,1-f]-[1,2,4]triazin-7-yl]methyl}piperazin-2-one

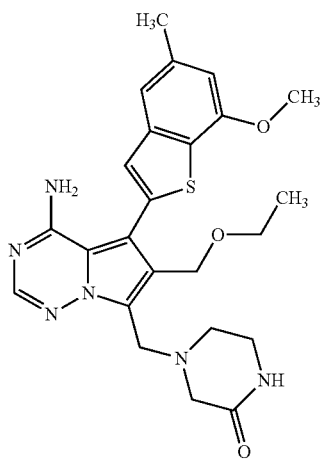 [SMILES: CCOCc1c(-c2cc3cc(C)cc(OC)c3s2)c2c(N)ncnn2c1CN1CCNC(=O)C1]

Method 1:

A solution of Intermediate 17A (2 g, 5.05 mmol) in THF (100 ml) was treated at 0° C. with 2-oxopiperazine (1.01 g, 10.1 mmol), sodium triacetoxyborohydride (1.07 g, 5.04 mmol) and acetic acid (0.29 ml, 5.04 mmol). The resulting mixture was stirred at 0° C. for 30 min. Four additional portions of sodium triacetoxyborohydride (1.07 g, 5.04 mmol) and of acetic acid (0.29 ml, 5.04 mmol) were added every 30 minutes, and the resulting mixture was stirred for further 30 min at 0° C., then for 25 min at 35° C. and finally at rt overnight. The reaction was quenched with 10% aq. sodium chloride solution and extracted twice with ethyl acetate. The combined organic layers were evaporated. The residue was purified by column chromatography over silica gel (dichloromethane/methanol 95:5→90:10) affording 360 mg (17% of th.) of the compound described in Example 86 (see below) and 1.82 g of the title compound in separate fractions. The title product thus obtained was suspended in ethanol (20 ml), refluxed for 2 h and then cooled to 15° C. The solid was filtered off and washed with ethanol affording 1.63 g (67% of th.) of the pure title compound.

Method 2:

A solution of Example 13 (930 mg, 1.9 mmol) in dichloromethane (18 ml) was treated with thionyl chloride (210 µl, 2.8 mmol) and stirred at rt for 15 min. After evaporation, the residue was dissolved in ethanol (18 ml) and treated with DIPEA (670 µl, 3.8 mmol). The mixture was stirred at 70° C. for 2 h and then evaporated. The residue was purified by column chromatography on silica gel (dichloromethane/methanol 98:2→90:10). The product thus obtained was triturated in an acetonitrile/diethylether mixture and filtered. The filtrate was evaporated, and the residue was re-purified by column chromatography on silica gel (dichloromethane/methanol 98:2→90:10). Again, the product thus obtained was triturated in acetonitrile/diethylether and filtered. This procedure was repeated one more time. The three batches of solids obtained in this way were combined, triturated in acetonitrile/diethylether once again and finally filtered off affording 600 mg (62% of th.) of the title compound.

Method 3:

A solution of Intermediate 22A (720 mg, purity 89%, 1.74 mmol) in acetic acid (10 ml) was stirred with piperazin-2-one (261 mg, 2.61 mmol) at 60° C. To this, 37% aq. formaldehyde solution (260 µl, 3.48 mmol) was added in three portions after 0, 3 and 12 h, respectively, and the mixture was stirred at 60° C. for a total of 24 h. Then, the volatiles were removed under reduced pressure, and the residue was partitioned between ethyl acetate and sat. aq. sodium hydrogencarbonate solution. The organic phase was washed with sat. aq. sodium chloride solution, dried with magnesium sulfate and evaporated. The residue was dissolved in a mixture of methanol and dichloromethane, adsorbed on diatomaceous earth, dried in vacuo and purified by flash-chromatography on silica gel (gradient 0-6% methanol/dichloromethane). The product fractions were combined, evaporated and re-purified by preparative RP-HPLC (Reprosil C18, gradient 30-50% acetonitrile/0.2% aq. TFA). The product fractions were combined again, diluted with sat. aq. sodium hydrogencarbonate solution and extracted with ethyl acetate. The organic phase was washed with sat. aq. sodium chloride solution, dried with magnesium sulfate and evaporated yielding 281 mg (31% of th.) of the title compound.

LC-MS (method 2): $R_t$=0.86 min; MS (ESIpos): m/z=481 $(M+H)^+$ $^1$H-NMR (400 MHz, DMSO-$d_6$): δ=8.01 (s, 1H), 7.8-8.05 (br. s, 1H), 7.74 (br. s, 1H), 7.38 (s, 1H), 7.31 (s, 1H), 6.85 (s, 1H), 5.6-5.9 (br. s, 1H), 4.45 (s, 2H), 3.97 (s, 2H), 3.94 (s, 3H), 3.41 (q, 2H), 3.09-3.13 (m, 2H), 3.02 (s, 2H), 2.63-2.69 (br. s, 2H), 2.45 (s, 3H), 1.07 (t, 3H) ppm.

Example 6

4-{[4-Amino-6-(ethoxymethyl)-5-(7-methoxy-5-methyl-1-benzothiophen-2-yl)pyrrolo-[2,1-f][1,2,4]triazin-7-yl]methyl}piperazin-2-one dihydrochloride

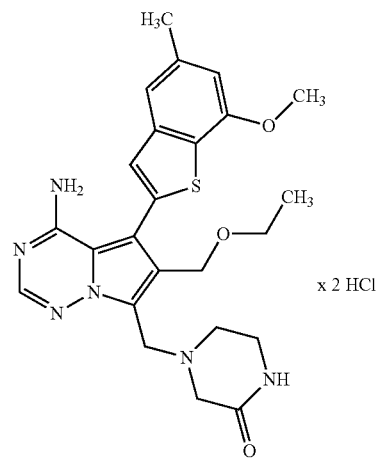 [SMILES: CCOCc1c(-c2cc3cc(C)cc(OC)c3s2)c2c(N)ncnn2c1CN1CCNC(=O)C1]

A solution of Intermediate 17A (60 mg, purity 69%, 104 µmol) in methanol (6 ml) was treated with 2-oxopiperazine (22 mg, 209 µmol), sodium cyanoborohydride (33 mg, 522 mmol) and acetic acid (12 µl, 209 µmol). The mixture was stirred at 60° C. for 16 h and then filtered. The filtrate and the residue were purified separately by preparative RP-HPLC (Reprosil C18, gradient 40-60% acetonitrile/0.2% aq. TFA). The product fractions were combined, diluted with 1 M hydrochloric acid (3 ml) and evaporated to dryness yielding 46 mg (79% of th.) of the title compound.

LC-MS (method 2): $R_t$=0.87 min; MS (ESIpos): m/z=481 $(M+H)^+$ $^1$H-NMR (400 MHz, DMSO-$d_6$): δ=8.37 (br. s, 1H), 8.31 (br. s, 1H), 8.14 (s, 1H), 7.38 (s, 1H), 7.33 (s, 1H), 6.87 (s, 1H), 6.13 (br. s, 1H), 4.80 (br. s, 2H), 4.52 (s, 2H), 3.96 (s, 3H), 3.86 (br. s, 2H), 3.36-3.51 (m, 5H), 2.46 (s, 3H), 1.11 (t, 3H) ppm.

Example 7

(3R)-3-({[4-Amino-6-(ethoxymethyl)-5-(7-methoxy-5-methyl-1-benzothiophen-2-yl)pyrrolo-[2,1-f][1,2,4]triazin-7-yl]methyl}amino)pyrrolidin-2-one dihydrochloride

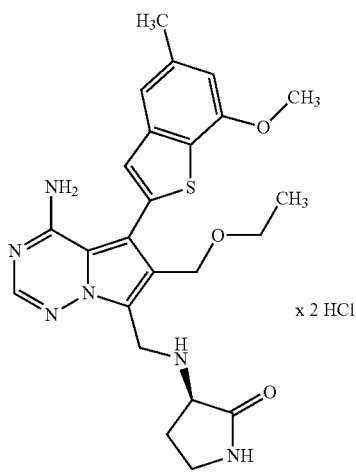 [SMILES: CCOCc1c(-c2cc3cc(C)cc(OC)c3s2)c2c(N)ncnn2c1CN[C@@H]1CCNC1=O]

A solution of Intermediate 17A (60 mg, purity 69%, 104 μmol) in methanol (3 ml) was treated with (R)-3-aminopyrrolidin-2-one (22 mg, 209 μmol), sodium cyanoborohydride (33 mg, 522 μmol) and acetic acid (12 μl, 209 μmol). The mixture was stirred at 60° C. for 4 h and then filtered. The filtrate was purified by preparative RP-HPLC (Reprosil C18, gradient 40-60% acetonitrile/0.2% aq. TFA). The product fractions were combined, diluted with 1 M hydrochloric acid and evaporated to dryness yielding 46 mg (79% of th.) of the title compound.

LC-MS (method 4): $R_t$=0.74 min; MS (ESIpos): m/z=481 (M+H)$^+$ $^1$H-NMR (400 MHz, DMSO-d$_6$): δ=9.58-9.75 (m, 1H), 9.33-9.54 (m, 1H), 8.44 (s, 1H), 8.27-8.71 (br. s, 1H), 8.19 (s, 1H), 7.38 (s, 1H), 6.87 (s, 1H), 6.18-6.48 (br. s, 1H), 4.68-4.87 (m, 2H), 4.49-4.62 (q, 2H), 3.96 (s, 3H), 3.45 (q, 2H), 3.18-3.35 (m, 2H), 2.46 (s, 4H), 2.08-2.22 (m, 1H), 1.10 (t, 3H) ppm.

Example 8

(3R)-3-({[4-Amino-6-(ethoxymethyl)-5-(7-methoxy-5-methyl-1-benzothiophen-2-yl)pyrrolo-[2,1-f][1,2,4]triazin-7-yl]methyl}amino)pyrrolidin-2-one

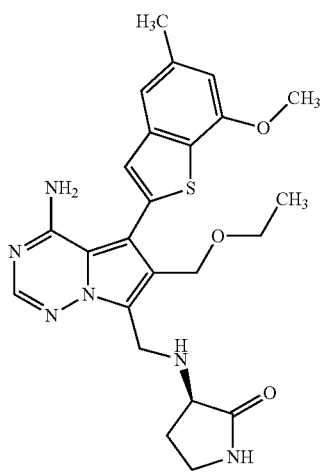 [SMILES: CCOCc1c(-c2cc3cc(C)cc(OC)c3s2)c2c(N)ncnn2c1CN[C@@H]1CCNC1=O]

A solution of Intermediate 17A (226 mg, purity 75%, 428 μmol) in methanol (4 ml) was treated with (R)-3-aminopyrrolidin-2-one (85 mg, 855 μmol), sodium cyanoborohydride (134 mg, 2.14 mmol) and acetic acid (49 μl, 855 μmol). The mixture was stirred at rt for 1.5 h. After this, the mixture was directly separated by preparative RP-HPLC (Reprosil C18, gradient 40-60% acetonitrile/0.2% aq. TFA). The product fractions were combined, diluted with sat. aq. sodium hydrogencarbonate solution and extracted with ethyl acetate. The combined organic phases were washed with sat. aq. sodium chloride solution, dried over magnesium sulfate and evaporated to dryness yielding 180 mg (88% of th.) of the title compound.

LC-MS (method 4): $R_t$=0.74 min; MS (ESIpos): m/z=481 (M+H)$^+$ $^1$H-NMR (400 MHz, DMSO-d$_6$): δ=8.00 (s, 1H), 7.76 (s, 1H), 7.8-8.1 (br. s, 1H), 7.35 (s, 1H), 7.31 (s, 1H), 6.84 (s, 1H), 5.6-5.9 (br. s, 1H), 4.39-4.49 (m, 2H), 4.04-4.23 (m, 2H), 3.96 (s, 3H), 3.41 (q, 2H), 3.05-3.23 (m, 3H), 2.45 (s, 3H), 2.31-2.40 (m, 1H), 1.68-1.79 (m, 1H), 1.08 (t, 3H) ppm.

Example 9

N$^2$-{[4-Amino-6-(ethoxymethyl)-5-(7-methoxy-5-methyl-1-benzothiophen-2-yl)pyrrolo[2,1-f]-[1,2,4]triazin-7-yl]methyl}glycinamide dihydrochloride

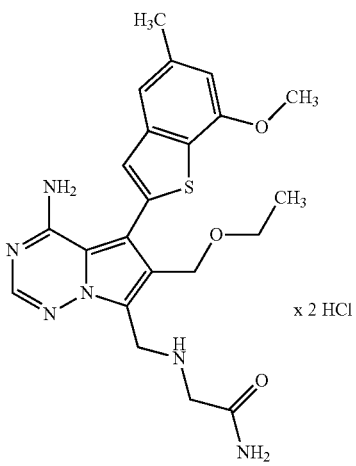 [SMILES: CCOCc1c(-c2cc3cc(C)cc(OC)c3s2)c2c(N)ncnn2c1CNCC(N)=O]

A solution of Intermediate 17A (60 mg, purity 69%, 104 μmol) in methanol (3 ml) was treated with glycinamide hydrochloride (23 mg, 209 μmol), sodium cyanoborohydride (32 mg, 522 mmol) and acetic acid (12 μl, 209 μmol). The mixture was stirred at 60° C. for 16 h. After filtration, the filtrate was separated by preparative RP-HPLC (Reprosil C18, gradient 20-40% acetonitrile/0.2% aq. TFA). The product fractions were combined, diluted with 1 M hydrochloric acid, evaporated to dryness and combined with the residue from the filtration step. This material was re-purified by twofold preparative RP-HPLC (Reprosil C18, gradient 20-40% acetonitrile/0.2% aq. TFA). The product fractions were combined again, diluted with 1 M hydrochloric acid and evaporated to dryness yielding 7.4 mg (13% of th.) of the title compound.

LC-MS (method 2): $R_t$=0.80 min; MS (ESIpos): m/z=455 (M+H)$^+$ $^1$H-NMR (500 MHz, DMSO-d$_6$): δ=9.33 (br. s, 2H), 9.05 (br. s, 1H), 8.31 (s, 1H), 7.93 (br. s, 1H), 7.58 (br. s, 1H), 7.40 (s, 1H), 7.35 (s, 1H), 7.05 (br. s, 1H), 6.88 (s, 1H), 4.65 (br. m, 2H), 4.56 (s, 2H), 3.96 (s, 3H), 3.74 (br. m, 2H), 3.46 (q, 2H), 2.46 (s, 3H), 1.10 (t, 3H) ppm.

Example 10

6-(Ethoxymethyl)-5-(7-methoxy-5-methyl-1-benzothiophen-2-yl)-7-(morpholin-4-ylmethyl)pyrrolo[2,1-f][1,2,4]triazin-4-amine

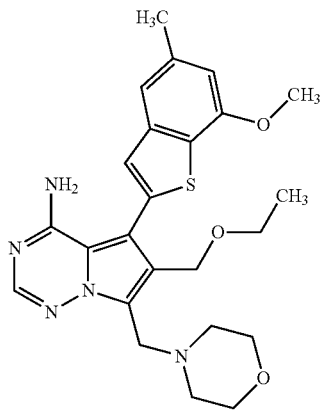

A solution of Intermediate 17A (55 mg, purity 73%, 101 µmol) in methanol (3 ml) was treated with morpholine (18 mg, 202 µmol), sodium cyanoborohydride (19 mg, 303 mmol) and acetic acid (18 µl, 304 µmol). The mixture was stirred at 60° C. for 18 h. Further amounts of morpholine (18 mg, 202 µmol), sodium cyanoborohydride (19 mg, 303 mmol) and acetic acid (18 µl, 304 µmol) were added, and stirring at 60° C. was continued for another 3 h. The resulting mixture was diluted with THF to dissolve precipitates and separated by preparative RP-HPLC (Reprosil C18, gradient 20-40% acetonitrile/0.2% aq. TFA). The product fractions were combined and evaporated to dryness. The residue was dissolved in methanol and filtered through an anion exchange cartridge (Stratospheres SPE, PL-HCO$_3$ MP-resin). The cartridge was eluted with methanol, and the filtrate was evaporated yielding 32 mg (68% of th.) of the title compound.

LC-MS (method 2): R$_t$=0.78 min; MS (ESIpos): m/z=468 (M+H)$^+$ $^1$H-NMR (400 MHz, DMSO-d$_6$): δ=7.98 (s, 1H), 7.9 (br. s, 1H), 7.37 (s, 1H), 7.31 (s, 1H), 6.84 (s, 1H), 5.75 (br. s, 1H), 4.45 (s, 2H), 3.95 (s, 3H), 3.88 (s, 2H), 3.51-3.56 (m, 4H), 3.40 (q, 2H), 2.4-2.5 (m, 4H), 2.45 (s, 3H), 1.06 (t, 3H) ppm.

Example 11

1-(4-{[4-Amino-6-(ethoxymethyl)-5-(7-methoxy-5-methyl-1-benzothiophen-2-yl)pyrrolo[2,1-f]-[1,2,4]triazin-7-yl]methyl}piperazin-1-yl)ethanone dihydrochloride

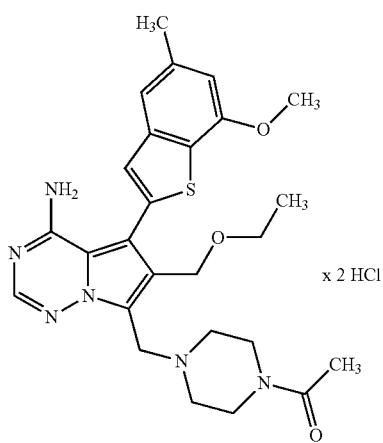 [SMILES: CCOCc1c(-c2cc3cc(C)cc(OC)c3s2)c2c(N)ncnn2c1CN1CCN(C(C)=O)CC1]

A solution of Intermediate 17A (130 mg, 0.328 mmol) in methanol (8 ml) was treated with N-acetylpiperazine (63 mg, 0.492 mmol), sodium cyanoborohydride (103 mg, 1.63 mmol) and acetic acid (37 µl, 0.655 mmol). The mixture was stirred at 60° C. for 3 h. It was then combined with the reaction mixture of a 30 mg test run, evaporated and purified by preparative RP-HPLC (Reprosil C18, gradient 10-95% acetonitrile/0.1% aq. formic acid). The product thus obtained was lyophilized from 1,4-dioxane, then dissolved in ethyl acetate and washed with sat. aq. sodium hydrogencarbonate solution. The organic layer was dried over magnesium sulfate, evaporated and lyophilized again from 1,4-dioxane. Re-purification by preparative RP-HPLC (Reprosil C18, gradient 10-95% acetonitrile/0.1% aq. formic acid), followed by two-fold column chromatography on silica gel (dichloromethane/methanol 98:2→4:1) and lyophilization from a 4 M solution of hydrogen chloride in 1,4-dioxane afforded 49 mg (18% of th.) of the title compound.

LC-MS (method 2): R$_t$=0.82 min; MS (ESIpos): m/z=509 (M+H)$^+$ $^1$H-NMR (400 MHz, DMSO-d$_6$): inter al. δ=8.65-8.26 (br. s, 1H), 8.17 (s, 1H), 7.38 (s, 1H), 7.34 (s, 1H), 6.87 (s, 1H), 6.53-6.05 (br. s, 1H), 4.75 (br. s, 2H), 4.56 (br. s, 2H), 3.96 (s, 3H), 3.45 (q, 2H, overlap with water peak), 2.46 (s, 3H), 2.03 (s, 3H), 1.09 (t, 3H) ppm.

Example 12

[4-Amino-5-(7-methoxy-5-methyl-1-benzothiophen-2-yl)-7-(piperazin-1-ylmethyl)pyrrolo[2,1-f]-[1,2,4]triazin-6-yl]methanol bis(formiate)

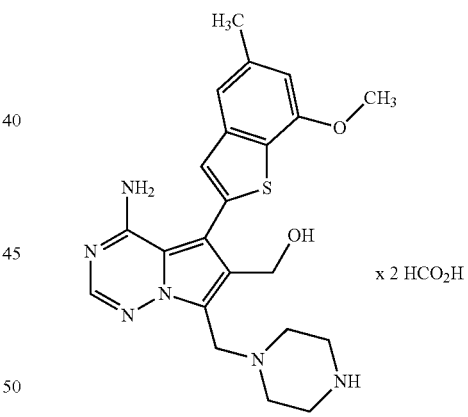

A solution of Intermediate 23A (95 mg, 152 µmol) in a 4 M solution of hydrogen chloride in 1,4-dioxane (3.7 ml) was stirred at rt for 2 h. After evaporation, the residue was purified by preparative RP-HPLC (Reprosil C18, gradient 10-95% acetonitrile/0.1% aq. formic acid) affording 44 mg (62% of th.) of the title compound.

LC-MS (method 2): R$_t$=0.63 min; MS (ESIpos): m/z=439 (M+H)$^+$ $^1$H-NMR (400 MHz, DMSO-d$_6$): δ=8.28 (br. s, 2H), 7.98 (s, 1H), 7.37 (s, 1H), 7.31 (s, 1H), 6.85 (s, 1H), 4.50 (s, 2H, overlap with water peak), 3.98 (s, 2H, overlap with water peak), 3.95 (s, 3H, overlap with water peak), 2.95-2.84 (m, 4H), 2.61-2.55 (m, 4H, overlap with DMSO peak), 2.45 (s, 3H) ppm.

Example 13

4-{[4-Amino-6-(hydroxymethyl)-5-(7-methoxy-5-methyl-1-benzothiophen-2-yl)pyrrolo[2,1-f]-[1,2,4]triazin-7-yl]methyl}piperazin-2-one

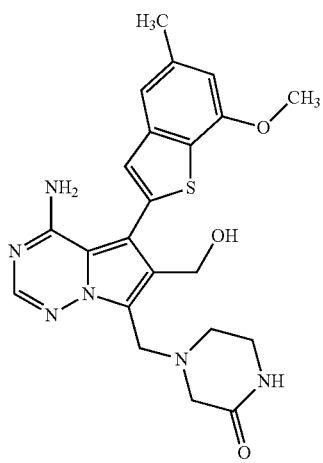 [SMILES: COc1cc(C)cc2cc(-c3c(CO)c(CN4CCNC(=O)C4)n4ncnc(N)c34)sc12]

A solution of Intermediate 20A (1.34 g, 3.96 mmol) in acetic acid (13.9 ml) was treated with 37% aq. formaldehyde solution (501 µl, 6.6 mmol) and 2-oxopiperazine (670 mg, 6.6 mmol). The mixture was stirred at 50° C. for 2 h and then evaporated. Purification by column chromatography on silica gel (dichloromethane/methanol 98:2→90:10) afforded 942 mg (49% of th.) of the title compound.

LC-MS (method 2): $R_t$=0.67 min; MS (ESIpos): m/z=453 $(M+H)^+$ $^1$H-NMR (400 MHz, DMSO-$d_6$): δ=7.99 (s, 1H), 7.76 (br. s, 1H), 7.39 (s, 1H), 7.31 (s, 1H), 6.84 (s, 1H), 4.51 (s, 2H), 4.03 (br. s, 2H), 3.95 (s, 3H), 3.18-3.13 (m, 2H), 3.07-2.98 (m, 2H), 2.72-2.60 (m, 2H), 2.45 (s, 3H) ppm.

Example 14

7-{[(3S)-3-Amino-3-methylpyrrolidin-1-yl]methyl}-6-(methoxymethyl)-5-(7-methoxy-5-methyl-1-benzothiophen-2-yl)pyrrolo[2,1-f][1,2,4]triazin-4-amine trihydrochloride

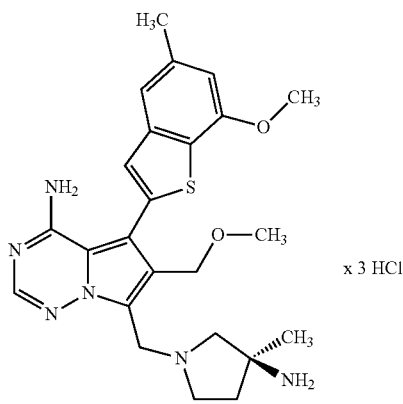 [SMILES: COCc1c(-c2cc3cc(C)cc(OC)c3s2)c2c(N)ncnn2c1CN1CC[C@](C)(N)C1]

A solution of Intermediate 21A (100 mg, 0.28 mmol) in acetic acid (1 ml) was treated with 37% aq. formaldehyde solution (25 µl, 0.33 mmol) and tert-butyl [(3S)-3-methylpyrrolidin-3-yl]carbamate (Yoshida et al., Chem. Pharm. Bull. 1996, 44 (7), 1376-1386; 67 mg, 0.33 mmol). The mixture was stirred at rt for 3 h and then evaporated. The residue was diluted with sat. aq. sodium hydrogencarbonate solution, and solid potassium carbonate was added until no more gas generation occurred. The aqueous phase was extracted three times with ethyl acetate. The combined organic phases were dried over sodium sulfate and evaporated. The residue was dissolved in a 4 M solution of hydrogen chloride in 1,4-dioxane (2 ml) and stirred at rt for 2 h. After evaporation, the residue was purified by two-fold preparative RP-HPLC (first Reprosil C18, gradient 10-95% acetonitrile/0.1% aq. formic acid; then Shield RP18, gradient 5-50% methanol+0.1% aq. TFA/0.1% aq. TFA). The product thus obtained was lyophilized from a 4 M solution of hydrogen chloride in 1,4-dioxane affording 14 mg (8% of th.) of the title compound.

LC-MS (method 2): $R_t$=0.67 min; MS (ESIpos): m/z=467 $(M+H)^+$ $^1$H-NMR (400 MHz, DMSO-$d_6$): inter al. δ=8.50-8.22 (br. s, 1H), 8.14 (s, 1H), 7.36 (s, 1H), 7.34 (s, 1H), 6.87 (s, 1H), 6.36-6.01 (br. s, 1H), 4.88 (br. s, 2H), 4.56 (br. s, 2H), 3.96 (s, 3H, overlap with water peak), 3.26 (s, 3H), 2.46 (s, 3H), 1.52 (s, 3H) ppm.

Example 15

7-{[(3S)-3-Amino-3-methylpyrrolidin-1-yl]methyl}-6-(ethoxymethyl)-5-(7-methoxy-5-methyl-1-benzothiophen-2-yl)pyrrolo[2,1-f][1,2,4]triazin-4-amine

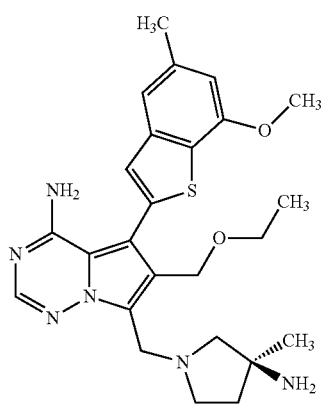 [SMILES: CCOCc1c(-c2cc3cc(C)cc(OC)c3s2)c2c(N)ncnn2c1CN1CC[C@](C)(N)C1]

A solution of Intermediate 17A (100 mg, 271 µmol) in acetic acid (1 ml) was treated with 37% aq. formaldehyde solution (24 µl, 326 µmol) and tert-butyl [(3S)-3-methylpyrrolidin-3-yl]carbamate (Yoshida et al., Chem. Pharm. Bull. 1996, 44 (7), 1376-1386; 65 mg, 326 µmol). The mixture was stirred at 60° C. for 4 h. Then, further amounts of 37% aq. formaldehyde solution (10 µl, 136 µmol) and tert-butyl [(3S)-3-methylpyrrolidin-3-yl]carbamate (27 mg, 136 µmol) were added, and stirring at 60° C. was continued overnight. After evaporation, the residue was partitioned between ethyl acetate and sat. aq. sodium hydrogencarbonate solution. Solid potassium carbonate was added until no more gas generation occurred. The aqueous phase was extracted three times with ethyl acetate. The combined organic phases were dried over sodium sulfate, evaporated and purified by preparative RP-HPLC (Reprosil C18, gradient 10-95% acetonitrile/0.1% aq. formic acid). The product thus obtained was dissolved in a 4 M solution of hydrogen chloride in 1,4-dioxane (2 ml) and stirred at rt for 1 h. After evaporation, the residue was purified by preparative RP-HPLC (Reprosil C18, gradient 10-95% acetonitrile/0.1% aq. formic acid) affording 24 mg (18% of th.) of the title compound.

LC-MS (method 4): $R_t$=0.70 min; MS (ESIpos): m/z=481 $(M+H)^+$ $^1$H-NMR (400 MHz, DMSO-$d_6$): inter al. δ=8.19 (s, 1H), 7.38 (s, 1H), 7.34 (s, 1H), 6.87 (s, 1H), 4.90 (br. s, 2H), 3.96 (s, 3H), 3.46 (q, 3H), 2.46 (s, 3H), 1.54 (s, 3H), 1.14-1.05 (m, 3H) ppm.

Example 16

1-(4-{[4-Amino-6-(methoxymethyl)-5-(7-methoxy-5-methyl-1-benzothiophen-2-yl)pyrrolo[2,1-f]-[1,2,4]triazin-7-yl]methyl}piperazin-1-yl)ethanone dihydrochloride

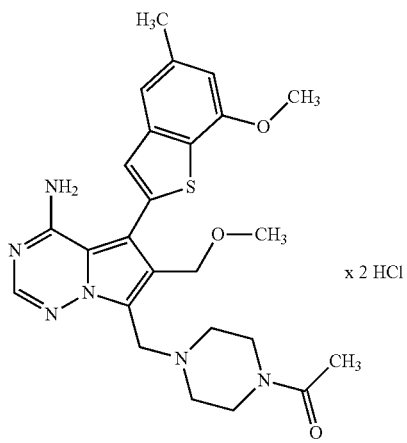 [SMILES: COCc1c(-c2cc3cc(C)cc(OC)c3s2)c2c(N)ncnn2c1CN1CCN(C(C)=O)CC1]

x 2 HCl

A solution of Intermediate 21A (50 mg, 141 μmol) in acetic acid (1 ml) was treated with 37% aq. formaldehyde solution (4.6 μl, 169 μmol) and N-acetylpiperazine (21.6 mg, 169 μmol). The mixture was stirred at 75° C. for 3 h. After evaporation, the residue was purified by preparative RP-HPLC (Reprosil C18, gradient 10-95% acetonitrile/0.1% aq. formic acid). Lyophilization from a 4 M solution of hydrogen chloride in 1,4-dioxane afforded 34 mg (39% of th.) of the title compound.

LC-MS (method 5): $R_t$=1.78 min; MS (ESIpos): m/z=495 (M+H)$^+$ $^1$H-NMR (400 MHz, DMSO-d$_6$): inter al. δ=8.70-8.35 (br. s, 1H), 8.18 (s, 1H), 7.37 (s, 1H), 7.34 (s, 1H), 6.86 (s, 1H), 6.61-6.19 (br. s, 1H), 4.74 (br. s, 2H), 4.54 (br. s, 2H), 3.96 (s, 3H), 3.25 (s, 3H), 2.46 (s, 3H), 2.03 (s, 3H) ppm.

Example 17

6-(Methoxymethyl)-5-(7-methoxy-5-methyl-1-benzothiophen-2-yl)-7-(piperazin-1-ylmethyl)pyrrolo[2,1-f][1,2,4]triazin-4-amine formiate

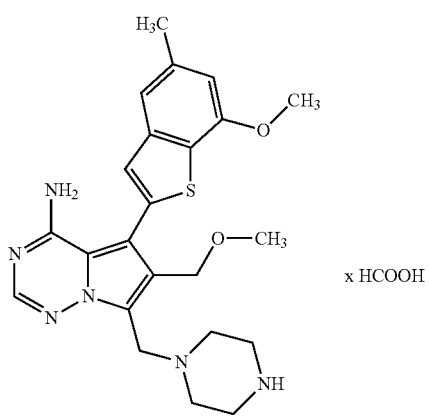 [SMILES: COCc1c(-c2cc3cc(C)cc(OC)c3s2)c2c(N)ncnn2c1CN1CCNCC1]

x HCOOH

A solution of Intermediate 23A (110 mg, 204 μmol) in dichloromethane (2.2 ml) was treated with thionyl chloride (29 μl, 408 μmol) and stirred at rt for 15 min. After evaporation, the residue was dissolved in methanol (2.2 ml) and treated with DIPEA (39 μl, 224 μmol). The mixture was stirred at 70° C. for 1 h and then evaporated. The residue was taken up in a 4 M solution of hydrogen chloride in 1,4-dioxane (2.2 ml) and stirred at rt for 2 h. Evaporation and purification by preparative RP-HPLC (Reprosil C18, gradient 10-95% acetonitrile/0.1% aq. formic acid) afforded 44.9 mg (46% of th.) of the title compound.

LC-MS (method 2): $R_t$=0.73 min; MS (ESIpos): m/z=453 (M+H)$^+$ $^1$H-NMR (400 MHz, DMSO-d$_6$): δ=8.28 (br. s, 1H), 8.00 (s, 1H), 7.35 (s, 1H), 7.31 (s, 1H), 6.85 (s, 1H), 4.41 (s, 2H), 4.00-3.90 (m, 5H), 3.00-2.90 (m, 4H), 2.65-2.56 (m, 4H), 2.45 (s, 3H) ppm.

Example 18

6-(Ethoxymethyl)-5-(7-methoxy-5-methyl-1-benzothiophen-2-yl)-7-(piperazin-1-ylmethyl)pyrrolo-[2,1-f][1,2,4]triazin-4-amine

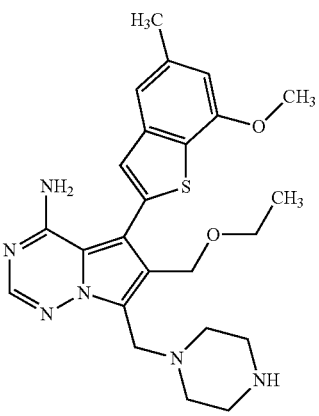

A solution of Intermediate 23A (80 mg, 317 μmol) in dichloromethane (2 ml) was treated with thionyl chloride (22 μl, 297 μmol) and stirred at rt for 15 min. After evaporation, the residue was dissolved in ethanol (2 ml) and treated with DIPEA (28 μl, 163 μmol). The mixture was stirred at 70° C. for 1 h and then evaporated. The residue was taken up in a 4 M solution of hydrogen chloride in 1,4-dioxane (2 ml) and stirred at rt for 1 h. Evaporation and purification by preparative RP-HPLC (Reprosil C18, gradient 10-95% acetonitrile/ 0.1% aq. formic acid) afforded 35 mg (50% of th.) of the title compound.

LC-MS (method 2): $R_t$=0.82 min; MS (ESIpos): m/z=467 (M+H)$^+$ $^1$H-NMR (400 MHz, DMSO-d$_6$): inter al. δ=8.09 (br. s, 1H), 7.36 (s, 1H), 7.32 (s, 1H), 6.86 (s, 1H), 4.50 (br. s, 2H), 3.96 (s, 3H), 3.42 (q, 2H, overlap with water peak), 2.45 (s, 3H), 1.05 (t, 3H) ppm.

Example 19

6-(Ethoxymethyl)-5-(7-methoxy-5-methyl-1-benzothiophen-2-yl)-7-(piperazin-1-ylmethyl)pyrrolo-[2,1-f][1,2,4]triazin-4-amine dihydrochloride

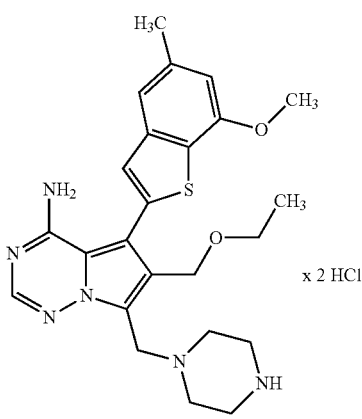 [SMILES: CCOCc1c(-c2cc3cc(C)cc(OC)c3s2)c2c(N)ncnn2c1CN1CCNCC1]

x 2 HCl

A solution of Example 18 (50 mg, 107 μmol) in a 4 M solution of hydrogen chloride in 1,4-dioxane (1 ml) was stirred at rt for 15 min. After evaporation 55 mg (93% of th.) of the title compound were obtained.

LC-MS (method 4): $R_t$=0.74 min; MS (ESIpos): m/z=467 (M+H)$^+$ $^1$H-NMR (400 MHz, DMSO-d$_6$): inter al. δ=8.18 (s, 1H), 7.37 (s, 1H), 7.34 (s, 1H), 6.87 (s, 1H), 4.76 (br. s, 2H), 4.60 (br. s, 2H), 3.96 (s, 3H), 3.45 (q, 2H), 2.46 (s, 3H), 1.09 (t, 3H) ppm.

Example 20

1-(4-{[4-Amino-6-(ethoxymethyl)-5-(7-methoxy-5-methyl-1-benzothiophen-2-yl)pyrrolo[2,1-f]-[1,2,4]triazin-7-yl]methyl}piperazin-1-yl)ethanone

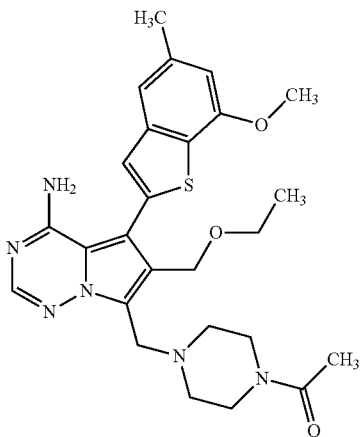 [SMILES: CCOCc1c(-c2cc3cc(C)cc(OC)c3s2)c2c(N)ncnn2c1CN1CCN(C(C)=O)CC1]

A solution of Example 18 (70 mg, 150 μmol) in dichloromethane (2 ml) and THF (0.8 ml) was treated with acetyl chloride (21 μl, 300 μmol) and sodium carbonate (127 mg, 1.2 mmol). The mixture was stirred at rt overnight. After evaporation, the residue was purified by preparative RP-HPLC (Reprosil C18, gradient 10-95% acetonitrile/0.1% aq. formic acid) affording 27 mg (31% of th.) of the title compound.

LC-MS (method 4): $R_t$=0.77 min; MS (ESIpos): m/z=509 (M+H)$^+$ $^1$H-NMR (400 MHz, DMSO-d$_6$): δ=7.98 (s, 1H), 7.37 (s, 1H), 7.31 (s, 1H), 6.84 (s, 1H), 4.45 (s, 2H), 3.95 (s, 3H), 3.92 (s, 2H), 3.45-3.36 (m, 6H), 2.48-2.38 (m, 7H, overlap with DMSO peak), 1.97 (s, 3H), 1.06 (t, 3H) ppm.

Example 21

4-({4-Amino-6-[(2-hydroxyethoxy)methyl]-5-(7-methoxy-5-methyl-1-benzothiophen-2-yl)pyrrolo-[2,1-f][1,2,4]triazin-7-yl}methyl)piperazin-2-one formiate

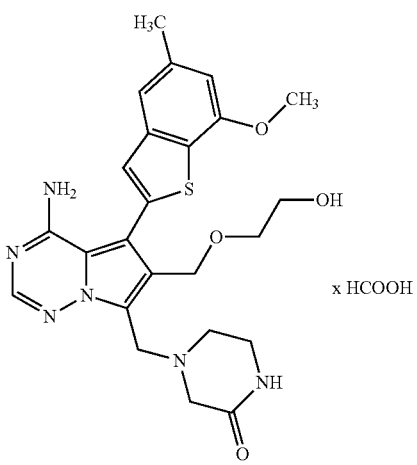 [SMILES: COc1cc(C)cc2cc(-c3c(COCCO)c(CN4CCNC(=O)C4)n4ncnc(N)c34)sc12]

x HCOOH

A solution of Example 13 (60 mg, 132 mmol) in dichloromethane (2 ml) was treated with thionyl chloride (14 μl, 198 mmol). The mixture was stirred at rt for 15 min and then evaporated. The residue was dissolved in ethylene glycol (500 μl) and stirred at 100° C. for 90 min. Purification by preparative RP-HPLC (Reprosil C18, gradient 10-95% acetonitrile/0.1% aq. formic acid) afforded 34 mg (47% of th.) of the title compound.

LC-MS (method 2): $R_t$=0.69 min; MS (ESIpos): m/z=497 (M+H)$^+$ $^1$H-NMR (400 MHz, DMSO-d$_6$): δ=8.14 (s, 1H), 8.00 (s, 1H), 7.74 (br. s, 1H), 7.42 (s, 1H), 7.31 (s, 1H), 6.84 (s, 1H), 4.49 (s, 2H), 3.99 (s, 2H), 3.96 (s, 3H), 3.50-3.43 (m, 2H), 3.42-3.36 (m, 2H, overlap with water peak), 3.15-3.07 (m, 2H), 3.03 (s, 2H), 2.69-2.61 (m, 2H), 2.45 (s, 3H) ppm.

Example 22

2-{[4-Amino-5-(7-methoxy-5-methyl-1-benzothiophen-2-yl)-7-(piperazin-1-ylmethyl)pyrrolo-[2,1-f][1,2,4]triazin-6-yl]methoxy}ethanol dihydrochloride

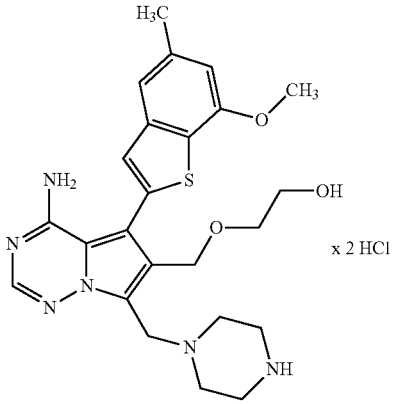 [SMILES: COc1cc(C)cc2cc(-c3c(COCCO)c(CN4CCNCC4)n4ncnc(N)c34)sc12]

x 2 HCl

A solution of Intermediate 23A (100 mg, 185 μmol) in dichloromethane (4 ml) was treated with thionyl chloride (27 μl, 371 μmol). The mixture was stirred at rt for 20 min and then evaporated. The residue was dissolved in ethylene glycol/THF (2:1, 1.5 ml) and stirred at 100° C. for 2 h. After evaporation, the residue was purified by preparative RP-HPLC (Reprosil C18, gradient 10-95% acetonitrile/0.1% aq. formic acid), followed by column chromatography on silica gel (dichloromethane/methanol+0.1% aq. ammonia 98:2→90:10). Lyophilization from a 4 M solution of hydrogen chloride in 1,4-dioxane afforded 67 mg (64% of th.) of the title compound.

LC-MS (method 2): $R_t$=0.66 min; MS (ESIpos): m/z=483 (M+H)$^+$ $^1$H-NMR (400 MHz, DMSO-d$_6$): δ=8.16 (s, 1H), 7.49 (s, 1H), 7.43 (s, 1H), 6.98 (s, 1H), 4.86 (s, 2H), 4.69 (s, 2H), 4.03 (s, 3H), 3.81-3.49 (m, 12H), 2.50 (s, 3H) ppm.

Example 23

6-(Butoxymethyl)-5-(7-methoxy-5-methyl-1-benzothiophen-2-yl)-7-(piperazin-1-ylmethyl)pyrrolo-[2,1-f][1,2,4]triazin-4-amine formiate

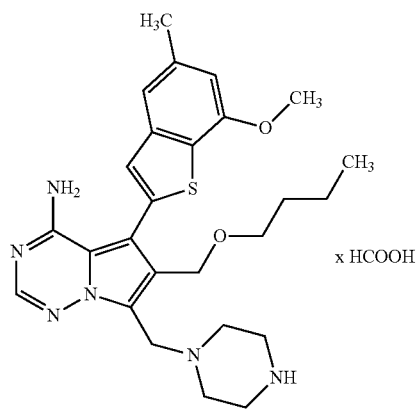 [SMILES: CCCCOCc1c(-c2cc3cc(C)cc(OC)c3s2)c2c(N)ncnn2c1CN1CCNCC1]

x HCOOH

A solution of Intermediate 23A (100 mg, 185 μmol) in dichloromethane (2 ml) was treated with thionyl chloride (27 μl, 371 μmol). The mixture was stirred at rt for 15 min and then evaporated. The residue was dissolved in 1-butanol (2 ml) and heated to 70° C. for 1 h. After evaporation, the residue was taken up in a 4 M solution of hydrogen chloride in 1,4-dioxane (2 ml) and stirred at rt for 2 h. Evaporation and purification by preparative RP-HPLC (Reprosil C18, gradient 10-95% acetonitrile/0.1% aq. formic acid) afforded 22 mg (24% of th.) of the title compound.

LC-MS (method 2): $R_t$=0.82 min; MS (ESIpos): m/z=495 (M+H)$^+$ $^1$H-NMR (400 MHz, DMSO-d$_6$): δ=8.29 (s, 1H), 7.99 (s, 1H), 7.35 (s, 1H), 7.29 (s, 1H), 6.84 (s, 1H), 4.43 (s, 2H), 3.95 (s, 3H), 3.92 (s, 2H), 3.35 (t, 2H), 2.90-2.79 (m, 4H), 2.45 (s, 3H), 1.47-1.37 (m, 2H), 1.31-1.18 (m, 2H), 0.80 (t, 3H) ppm.

Example 24

5-(7-Methoxy-5-methyl-1-benzothiophen-2-yl)-7-(piperazin-1-ylmethyl)-6-(propoxymethyl)pyrrolo[2,1-f][1,2,4]triazin-4-amine bis(formiate)

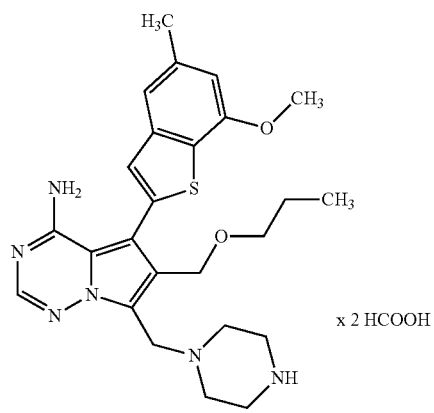 [SMILES: CCCOCc1c(-c2cc3cc(C)cc(OC)c3s2)c2c(N)ncnn2c1CN1CCNCC1]

x 2 HCOOH

A solution of Intermediate 23A (100 mg, 185 μmol) in dichloromethane (2 ml) was treated with thionyl chloride (27 μl, 371 μmol). The mixture was stirred at rt for 15 min and then evaporated. The residue was dissolved in 1-propanol (2 ml), treated with DIPEA (48 μl, 278 μmol) and stirred at rt for 1 h. After evaporation, the residue was taken up in a 4 M solution of hydrogen chloride in 1,4-dioxane (2 ml) and stirred at rt for 2 h. Evaporation and purification by preparative RP-HPLC (Reprosil C18, gradient 10-95% acetonitrile/0.1% aq. formic acid) afforded 15 mg (16% of th.) of the title compound.

LC-MS (method 2): $R_t$=0.78 min; MS (ESIpos): m/z=481 (M+H)$^+$ $^1$H-NMR (400 MHz, DMSO-d$_6$): δ=8.26 (br. s, 2H), 7.98 (s, 1H), 7.36 (s, 1H), 7.30 (s, 1H), 6.84 (s, 1H), 4.44 (s, 2H), 3.95 (s, 3H), 3.92 (s, 2H), 3.32 (t, 2H), 2.87-2.79 (m, 4H), 1.52-1.39 (m, 2H), 0.81 (t, 3H) ppm.

Example 25

6-[(Cyclopropylmethoxy)methyl]-5-(7-methoxy-5-methyl-1-benzothiophen-2-yl)-7-(piperazin-1-ylmethyl)pyrrolo[2,1-f][1,2,4]triazin-4-amine bis(formiate)

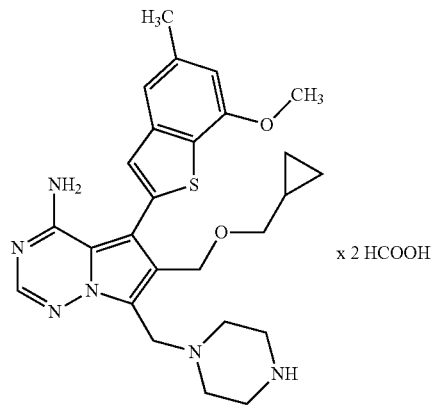 [SMILES: COc1cc(C)cc2cc(-c3c(COCC4CC4)c(CN4CCNCC4)n4ncnc(N)c34)sc12]

x 2 HCOOH

A solution of Intermediate 23A (100 mg, 185 μmol) in dichloromethane (2 ml) was treated with thionyl chloride (27 μl, 371 μmol). The mixture was stirred at rt for 15 min and then evaporated. The residue was dissolved in cyclopropylmethanol (2 ml), treated with DIPEA (48 μl, 278 μmol) and stirred at 70° C. for 2 h. After evaporation, the residue was taken up in a 4 M solution of hydrogen chloride in 1,4-dioxane (2 ml) and stirred at rt for 2 h. Evaporation and purification by preparative RP-HPLC (Reprosil C18, gradient 10-95% acetonitrile/0.1% aq. formic acid) afforded 29 mg (30% of th.) of the title compound.

LC-MS (method 2): $R_t$=0.78 min; MS (ESIpos): m/z=493 $(M+H)^+$ $^1$H-NMR (400 MHz, DMSO-$d_6$): δ=8.28 (br. s, 2H), 7.99 (s, 1H), 7.37 (s, 1H), 7.30 (s, 1H), 6.84 (s, 1H), 4.45 (s, 2H), 3.95 (s, 3H), 3.93 (s, 2H), 3.21 (d, 2H), 2.95-2.83 (m, 4H), 2.61-2.56 (m, 4H), 2.45 (s, 3H), 1.01-0.91 (m, 1H), 0.46-0.37 (m, 2H), 0.15-0.08 (m, 2H) ppm.

Example 26

6-[(Cyclobutyloxy)methyl]-5-(7-methoxy-5-methyl-1-benzothiophen-2-yl)-7-(piperazin-1-ylmethyl)pyrrolo[2,1-f][1,2,4]triazin-4-amine

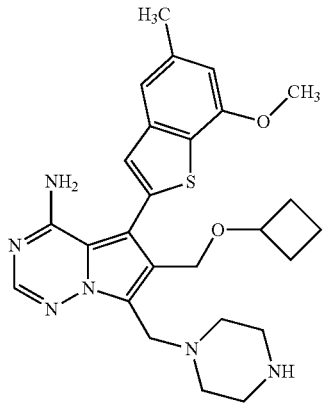 [SMILES: COc1cc(C)cc2cc(-c3c(COC4CCC4)c(CN4CCNCC4)n4ncnc(N)c34)sc12]

A solution of Intermediate 23A (85 mg, 157 μmol) in dichloromethane (1.7 ml) was treated with thionyl chloride (23 μl, 315 μmol). The mixture was stirred at rt for 15 min and then evaporated. The residue was dissolved in cyclobutanol (1.7 ml), treated with DIPEA (41 μl, 236 μmol) and stirred at 70° C. for 2 h. After evaporation, the residue was taken up in a 4 M solution of hydrogen chloride in 1,4-dioxane (1.7 ml) and stirred at rt for 2 h. Evaporation and purification by preparative RP-HPLC (Reprosil C18, gradient 10-95% acetonitrile/0.1% aq. formic acid) afforded 23 mg (28% of th.) of the title compound.

LC-MS (method 2): $R_t$=0.82 min; MS (ESIpos): m/z=493 $(M+H)^+$ $^1$H-NMR (400 MHz, DMSO-$d_6$): δ=8.01 (s, 1H), 7.37 (s, 1H), 7.32 (s, 1H), 6.85 (s, 1H), 4.37 (s, 2H), 4.06-3.86 (m, 6H), 3.14-2.97 (m, 4H), 2.80-2.62 (m, 4H), 2.45 (s, 3H), 2.10-1.96 (m, 2H), 1.83-1.69 (m, 2H), 1.65-1.52 (m, 1H), 1.49-1.33 (m, 1H) ppm.

Example 27

6-(Isopropoxymethyl)-5-(7-methoxy-5-methyl-1-benzothiophen-2-yl)-7-(piperazin-1-ylmethyl)pyrrolo[2,1-f][1,2,4]triazin-4-amine formiate

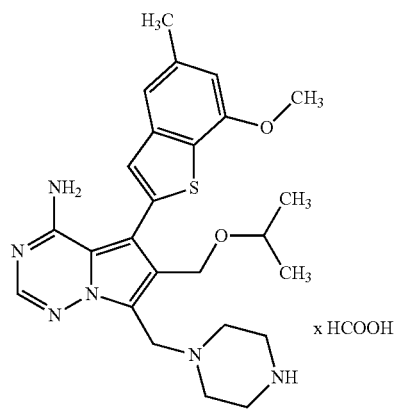 [SMILES: COc1cc(C)cc2cc(-c3c(COC(C)C)c(CN4CCNCC4)n4ncnc(N)c34)sc12]

A solution of Intermediate 23A (65 mg, 120 μmol) in dichloromethane (1.3 ml) was treated with thionyl chloride (17 μl, 241 μmol). The mixture was stirred at rt for 15 min and then evaporated. The residue was dissolved in 2-propanol (1.3 ml), treated with DIPEA (23 μl, 132 μmol) and stirred at 70° C. for 1 h. Further DIPEA (23 μl, 132 μmol) was added, and the mixture was stirred again at 70° C. for 1 h. Then, another portion of DIPEA (63 μl, 362 μmol) was added, and stirring was continued at 90° C. for 3 h. After evaporation, the residue was taken up in a 4 M solution of hydrogen chloride in 1,4-dioxane (1.3 ml) and stirred at rt for 2 h. Evaporation and purification by preparative RP-HPLC (Reprosil C18, gradient 10-95% acetonitrile/0.1% aq. formic acid) afforded 23 mg (34% of th.) of the title compound.

LC-MS (method 4): $R_t$=0.74 min; MS (ESIpos): m/z=481 $(M+H)^+$ $^1$H-NMR (400 MHz, DMSO-$d_6$): δ=8.30 (s, 1H), 7.98 (s, 1H), 7.37 (s, 1H), 7.30 (s, 1H), 6.84 (s, 1H), 4.43 (s, 2H), 3.95 (s, 3H), 3.90 (s, 2H), 3.57 (m, 1H, overlap with water peak), 2.88-2.78 (m, 4H), 2.45 (s, 3H), 1.04 (d, 6H) ppm.

Example 28

6-[(2-Methoxyethoxy)methyl]-5-(7-methoxy-5-methyl-1-benzothiophen-2-yl)-7-(piperazin-1-ylmethyl)pyrrolo[2,1-f][1,2,4]triazin-4-amine formiate

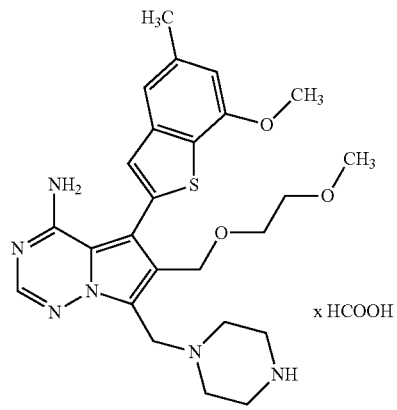 [SMILES: COCCOCc1c(-c2cc3cc(C)cc(OC)c3s2)c2c(N)ncnn2c1CN1CCNCC1]

A solution of Intermediate 23A (100 mg, 185 μmol) in dichloromethane (2 ml) was treated with thionyl chloride (27 μl, 371 μmol). The mixture was stirred at rt for 15 min and then evaporated. The residue was dissolved in 2-methoxyethanol (2 ml), treated with DIPEA (35 μl, 204 μmol) and stirred at 70° C. for 1 h. After evaporation, the residue was taken up in a 4 M solution of hydrogen chloride in 1,4-dioxane (2 ml) and stirred at rt for 2 h. Evaporation and purification by preparative RP-HPLC (Reprosil C18, gradient 10-95% acetonitrile/0.1% aq. formic acid) afforded 50 mg (50% of th.) of the title compound.

LC-MS (method 2): $R_t$=0.75 min; MS (ESIpos): m/z=497 (M+H)$^+$ $^1$H-NMR (400 MHz, DMSO-d$_6$): δ=8.26 (br. s, 1H), 7.99 (s, 1H), 7.39 (s, 1H), 7.30 (s, 1H), 6.84 (s, 1H), 4.48 (s, 2H), 3.95 (s, 3H), 3.94 (s, 2H), 3.52-3.46 (m, 2H, overlap with water peak), 3.44-3.37 (m, 2H, overlap with water peak), 3.20 (s, 3H), 2.94-2.84 (m, 4H), 2.61-2.54 (m, 4H, overlap with DMSO peak), 2.45 (s, 3H) ppm.

Example 29

5-(7-Methoxy-5-methyl-1-benzothiophen-2-yl)-7-(piperazin-1-ylmethyl)-6-[(2,2,2-trifluoroethoxy)methyl]pyrrolo[2,1-f][1,2,4]triazin-4-amine formiate

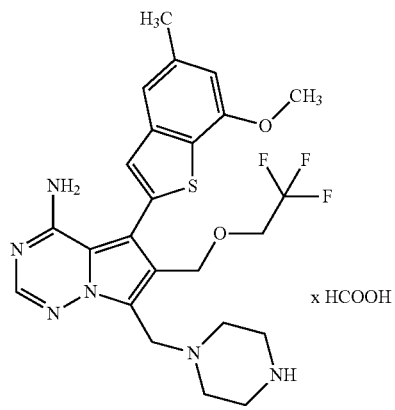 [SMILES: COc1cc(C)cc2cc(-c3c(COCC(F)(F)F)c(CN4CCNCC4)n4ncnc(N)c34)sc12]

A solution of Intermediate 23A (100 mg, 185 μmol) in dichloromethane (2 ml) was treated with thionyl chloride (27 μl, 371 μmol). The mixture was stirred at rt for 15 min and then evaporated. The residue was dissolved in 2,2,2-trifluoroethanol (2 ml), treated with DIPEA (35 μl, 204 μmol) and stirred at 70° C. for 1 h. Further DIPEA (35 μl, 204 μmol) was added, and stirring was continued at rt for 1 h. After evaporation, the residue was taken up in a 4 M solution of hydrogen chloride in 1,4-dioxane (2 ml) and stirred at rt for 2 h. Evaporation and purification by preparative RP-HPLC (Reprosil C18, gradient 10-95% acetonitrile/0.1% aq. formic acid) afforded 23 mg (23% of th.) of the title compound.

LC-MS (method 2): $R_t$=0.79 min; MS (ESIpos): m/z=521 (M+H)$^+$ $^1$H-NMR (400 MHz, DMSO-d$_6$): δ=8.28 (br. s, 1H), 8.00 (s, 1H), 7.37 (s, 1H), 7.30 (s, 1H), 6.85 (s, 1H), 4.66 (s, 2H), 4.08 (q, 2H), 3.95 (s, 3H), 3.92 (s, 2H), 2.85-2.75 (m, 4H), 2.45 (s, 3H) ppm.

Example 30

6-[(2-Aminoethoxy)methyl]-5-(7-methoxy-5-methyl-1-benzothiophen-2-yl)-7-(piperazin-1-ylmethyl)pyrrolo[2,1-f][1,2,4]triazin-4-amine trihydrochloride

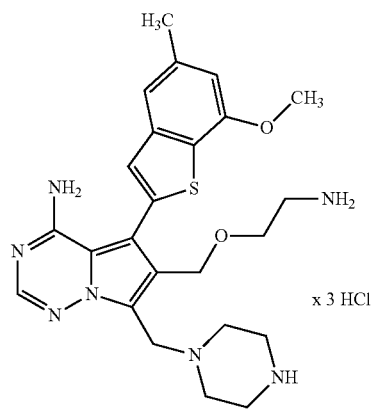 [SMILES: COc1cc(C)cc2cc(-c3c(COCCN)c(CN4CCNCC4)n4ncnc(N)c34)sc12]

A solution of Intermediate 23A (150 mg, 278 μmol) in dichloromethane (5 ml) was treated with thionyl chloride (40 μl, 556 μmol). The mixture was stirred at rt for 15 min and then evaporated. The residue was dissolved in THF (0.5 ml) and treated with tert-butyl (2-hydroxyethyl)carbamate (1 ml) and DIPEA (242 μl, 1.39 mmol). The mixture was stirred at 100° C. overnight. After evaporation, the residue was taken up in 1,4-dioxane (10 ml), treated with a 4 M solution of hydrogen chloride in 1,4-dioxane (10 ml) and stirred at rt for 1 h. The volatiles were removed under reduced pressure, and the residue was purified by preparative RP-HPLC (Reprosil C18, gradient 10-95% acetonitrile/0.1% aq. formic acid). Further purification by preparative RP-HPLC (Shield RP18, 25% acetonitrile/75% 0.01% aq. TFA) followed by lyophilization from a 4 M solution of hydrogen chloride in 1,4-dioxane afforded 10 mg (6% of th.) of the title compound.

LC-MS (method 2): $R_t$=0.58 min; MS (ESIpos): m/z=482 (M+H)$^+$ $^1$H-NMR (400 MHz, D$_2$O): δ=8.12 (s, 1H), 7.50 (s, 1H), 7.44 (s, 1H), 6.99 (s, 1H), 4.61 (s, 2H), 4.04 (s, 3H), 3.88-3.80 (m, 1H), 3.70-3.60 (m, 3H), 3.52-3.46 (m, 4H), 3.40-3.34 (m, 4H), 3.07 (t, 2H), 2.51 (s, 3H) ppm.

Example 31

Methyl{[4-amino-5-(7-methoxy-5-methyl-1-benzothiophen-2-yl)-7-(piperazin-1-ylmethyl)pyrrolo[2,1-f][1,2,4]triazin-6-yl]methoxy}acetate

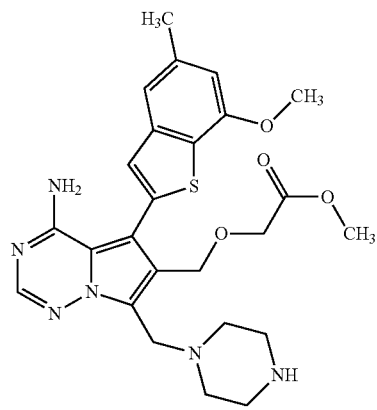 [SMILES: COC(=O)COCc1c(-c2cc3cc(C)cc(OC)c3s2)c2c(N)ncnn2c1CN1CCNCC1]

A solution of Intermediate 23A (50 mg, 92 μmol) in dichloromethane (2 ml) was treated with thionyl chloride (13 μl, 186 μmol). The mixture was stirred at rt for 15 min and then evaporated. The residue was dissolved in methylglycolate (1 ml), treated with DIPEA (80 μl, 464 μmol) and stirred at 70° C. for 2 h. After evaporation, the residue was taken up in dichloromethane (1.6 ml), treated with trifluoroacetic acid (400 μl, 5.19 mmol) and stirred at rt for 1 h. Then, the mixture was evaporated, and the residue was purified by preparative RP-HPLC (Reprosil C18, gradient 10-95% acetonitrile/0.1% aq. TFA). Fractions containing the title compound were neutralized with sat. aq. sodium hydrogencarbonate solution and evaporated. The residue was taken up in water, and the mixture was extracted three times with dichloromethane. The combined organic phases were dried over sodium sulfate and evaporated affording 21 mg (43% of th.) of the title compound.

LC-MS (method 2): $R_t$=0.72 min; MS (ESIpos): m/z=511 $(M+H)^+$ $^1$H-NMR (400 MHz, DMSO-$d_6$): δ=7.99 (s, 1H), 7.39 (s, 1H), 7.31 (s, 1H), 6.85 (s, 1H), 4.59 (s, 2H), 4.11 (s, 2H), 3.95 (s, 3H), 3.90 (s, 2H), 3.57 (s, 3H), 2.81-2.69 (m, 4H), 2.48-2.39 (m, 7H) ppm.

Example 32

{[4-Amino-5-(7-methoxy-5-methyl-1-benzothiophen-2-yl)-7-(piperazin-1-ylmethyl)pyrrolo[2,1-f]-[1,2,4]triazin-6-yl]methoxy}acetic acid

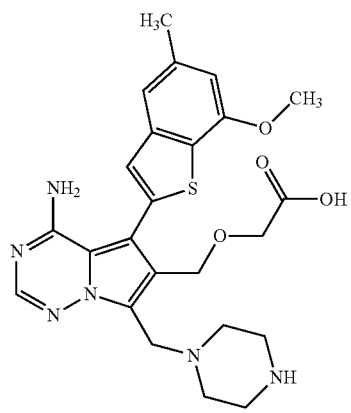 [SMILES: COc1cc(C)cc2cc(-c3c(COCC(=O)O)c(CN4CCNCC4)n4ncnc(N)c34)sc12]

A solution of Intermediate 24A (200 mg, 327 μmol) in THF (14 ml) was treated with 2.5 M aq. lithium hydroxide solution (16 ml) and stirred at 80° C. for 2 h. The mixture was then combined with the reaction mixture of a 27 mg test run. The aqueous phase was extracted twice with THF, and the combined organic phases were evaporated. The residue was dissolved in a 4 M solution of hydrogen chloride in 1,4-dioxane (2 ml) and stirred at rt for 3 h. After evaporation, the residue was purified by preparative RP-HPLC (Reprosil C18, gradient 10-95% acetonitrile/0.1% aq. TFA). Lyophilization from a 4 M solution of hydrogen chloride in 1,4-dioxane and re-purification by preparative RP-HPLC (XBridge C18, gradient 5-95% acetonitrile/0.1% aq. ammonium hydroxide solution) afforded 13 mg (7% of th.) of the title compound.

LC-MS (method 2): $R_t$=0.69 min; MS (ESIpos): m/z=497 $(M+H)^+$ $^1$H-NMR (400 MHz, DMSO-$d_6$): δ=8.00 (s, 1H), 7.38 (s, 1H), 7.30 (s, 1H), 6.84 (s, 1H), 4.54 (s, 2H), 4.08 (s, 2H), 3.95 (s, 3H), 3.79 (s, 2H), 2.99-2.89 (m, 4H), 2.73-2.63 (m, 4H), 2.44 (s, 3H) ppm.

Example 33

2-{[4-Amino-5-(7-methoxy-5-methyl-1-benzothiophen-2-yl)-7-(piperazin-1-ylmethyl)pyrrolo[2,1-f][1,2,4]triazin-6-yl]methoxy}acetamide

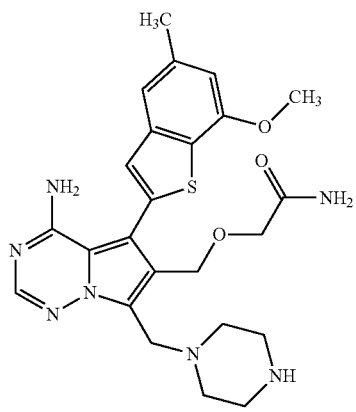 [SMILES: COc1cc(C)cc2cc(-c3c(COCC(N)=O)c(CN4CCNCC4)n4ncnc(N)c34)sc12]

Intermediate 24A (200 mg, 327 μmol) was treated with a 7 M solution of ammonia in methanol (10 ml) and stirred at rt overnight. The mixture was then combined with the reaction mixture of a 20 mg test run, and the solvents were evaporated. The residue was treated with a 4 M solution of hydrogen chloride in 1,4-dioxane (2 ml) and stirred at rt for 2 h. Evaporation and subsequent purifications by preparative RP-HPLC (first Reprosil C18, gradient 10-95% acetonitrile/0.1% aq. TFA; then XBridge C18, gradient 5-95% acetonitrile/0.1% aq. ammonium hydroxide solution) afforded 5.5 mg (3% of th.) of the title compound.

LC-MS (method 2): $R_t$=0.69 min; MS (ESIpos): m/z=496 $(M+H)^+$ $^1$H-NMR (400 MHz, DMSO-$d_6$): δ=8.14-7.59 (br. s, 1H), 7.99 (s, 1H), 7.39 (s, 1H), 7.35-7.22 (m, 3H), 6.85 (s, 1H), 4.54 (s, 2H), 3.95 (s, 3H), 3.90 (s, 2H), 3.79 (s, 2H), 2.73-2.66 (m, 4H), 2.45 (s, 3H), 2.43-2.35 (m, 4H) ppm.

Example 34

2-({7-[(4-Acetylpiperazin-1-yl)methyl]-4-amino-5-(7-methoxy-5-methyl-1-benzothiophen-2-yl)pyrrolo[2,1-f][1,2,4]triazin-6-yl}methoxy)acetamide

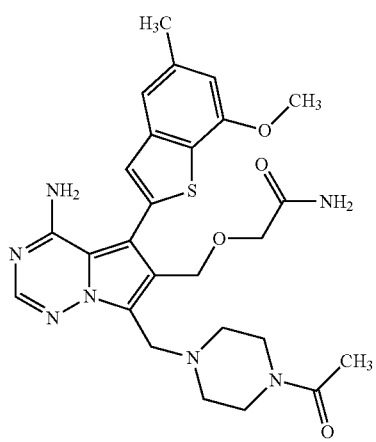 [SMILES: COc1cc(C)cc2cc(-c3c(COCC(N)=O)c(CN4CCN(C(C)=O)CC4)n4ncnc(N)c34)sc12]

A solution of Example 33 (105 mg, 68% purity, 144 μmol) in THF/dichloromethane (1:2.5, 3.9 ml) was treated with sodium carbonate (179 mg, 1.6 mmol) and stirred at rt for 30 min. Acetyl chloride (30 μl, 424 μmol) was added, and the resulting mixture was stirred at rt for 30 min, then quenched with methanol (2 ml) and evaporated. Purification by preparative RP-HPLC (Reprosil C18, gradient 10-95% acetonitrile/ 0.1% aq. formic acid) afforded 30 mg (85% purity, 34% of th.) of the title compound.

LC-MS (method 5): $R_t$=1.67 min; MS (ESIpos): m/z=538 (M+H)$^+$ $^1$H-NMR (400 MHz, DMSO-d$_6$): δ=7.99 (s, 1H), 7.40 (s, 1H), 7.33-7.19 (m, 3H), 6.85 (s, 1H), 4.55 (s, 2H), 3.96 (s, 5H), 3.80 (s, 2H), 3.43-3.36 (m, 4H), 2.47-2.38 (m, 7H), 1.97 (s, 3H) ppm.

Example 35

5-(7-Methoxy-5-methyl-1-benzothiophen-2-yl)-6-(phenoxymethyl)-7-(piperazin-1-ylmethyl)pyrrolo[2,1-f][1,2,4]triazin-4-amine bis(formiate)

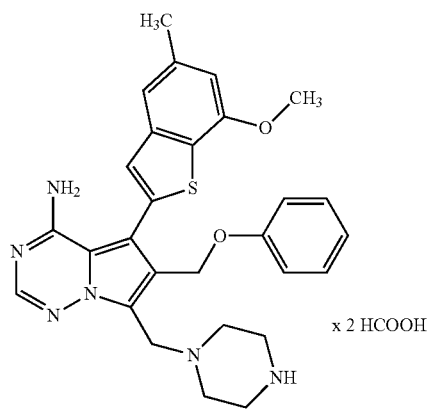 [SMILES: COc1cc(C)cc2cc(-c3c(COc4ccccc4)c(CN4CCNCC4)n4ncnc(N)c34)sc12]

A solution of Intermediate 23A (100 mg, 185 μmol) in dichloromethane (2 ml) was treated with thionyl chloride (27 μl, 371 μmol). The mixture was stirred at rt for 15 min and then evaporated. The residue was dissolved in THF (2 ml), treated with phenol (174 mg, 1.85 mmol) and DIPEA (48 μl, 278 μmol) and stirred at 70° C. for 2 h. Further amounts of phenol (174 mg, 1.85 mmol) and DIPEA (64 μl, 371 μmol) were added, and stirring was continued at 70° C. overnight. After evaporation, the residue was taken up in a 4 M solution of hydrogen chloride in 1,4-dioxane (2 ml) and stirred at rt for 2 h. Evaporation and purification by preparative RP-HPLC (Reprosil C18, gradient 10-95% acetonitrile/0.1% aq. formic acid) afforded 8 mg (8% of th.) of the title compound.

LC-MS (method 2): $R_t$=0.84 min; MS (ESIpos): m/z=515 (M+H)$^+$ $^1$H-NMR (400 MHz, DMSO-d$_6$): δ=8.26 (s, 2H), 8.02 (s, 1H), 7.36 (s, 1H), 7.30-7.22 (m, 3H), 6.99-6.89 (m, 3H), 6.81 (m, 1H), 5.04 (s, 2H), 3.93 (s, 5H), 2.78-2.71 (m, 4H), 2.42 (s, 3H) ppm.

Example 36

5-(7-Methoxy-5-methyl-1-benzothiophen-2-yl)-6-[(methylamino)methyl]-7-(piperazin-1-ylmethyl) pyrrolo[2,1-f][1,2,4]triazin-4-amine trihydrochloride

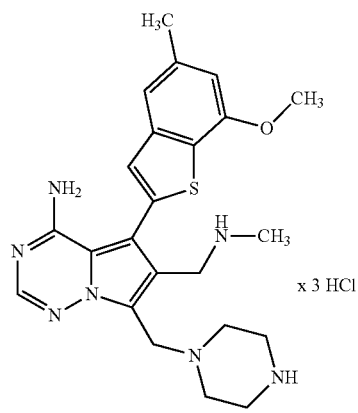 [SMILES: CNCc1c(-c2cc3cc(C)cc(OC)c3s2)c2c(N)ncnn2c1CN1CCNCC1]

Intermediate 25A (150 mg, 279 μmol) in THF (3 ml) was treated with acetic acid (32 μl, 559 μmol), a 2 M solution of methylamine in THF (698 μl, 1.39 mmol) and sodium triacetoxyborohydride (296 mg, 1.39 mmol). The mixture was stirred at 60° C. for 2 h and then evaporated. The residue was dissolved in a 4 M solution of hydrogen chloride in 1,4-dioxane (1.87 ml) and stirred at rt for 2 h. After evaporation, the residue was purified by preparative RP-HPLC (Reprosil C18, gradient 10-95% acetonitrile/0.1% aq. TFA). Lyophilization from a 4 M solution of hydrogen chloride in 1,4-dioxane afforded 79 mg (49% of th.) of the title compound.

LC-MS (method 2): $R_t$=0.56 min; MS (ESIpos): m/z=452 (M+H)$^+$ $^1$H-NMR (400 MHz, D$_2$O): δ=8.17 (s, 1H), 7.57 (s, 1H), 7.46 (s, 1H), 7.01 (s, 1H), 4.52 (s, 2H), 4.46 (s, 2H), 4.04 (s, 3H), 3.48-3.39 (m, 4H), 3.25-3.15 (m, 4H), 2.59 (s, 3H), 2.51 (s, 3H) ppm.

Example 37

6-[(Dimethylamino)methyl]-5-(7-methoxy-5-methyl-1-benzothiophen-2-yl)-7-(piperazin-1-ylmethyl)pyrrolo[2,1-f][1,2,4]triazin-4-amine trihydrochloride

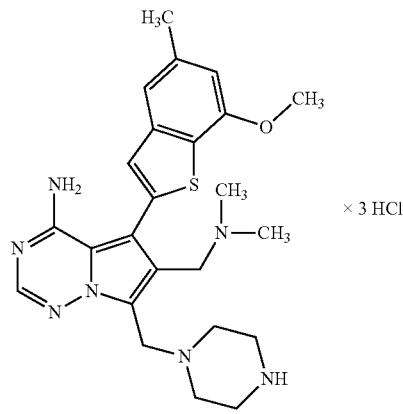 [SMILES: COc1cc(C)cc2cc(-c3c(CN(C)C)c(CN4CCNCC4)n4ncnc(N)c34)sc12]

A solution of Intermediate 25A (150 mg, 279 μmol) in THF (3 ml) was treated with acetic acid (32 μl, 559 μmol), a 2 M solution of dimethylamine in THF (698 μl, 1.39 mmol) and sodium triacetoxyborohydride (296 mg, 1.39 mmol). The mixture was stirred at 60° C. for 2 h and then evaporated. The residue was dissolved in a 4 M solution of hydrogen chloride in 1,4-dioxane (1.88 ml) and stirred at rt for 2 h. After evaporation, the residue was purified by preparative RP-HPLC (Reprosil C18, gradient 10-95% acetonitrile/0.1% aq. TFA). Lyophilization from a 4 M solution of hydrogen chloride in 1,4-dioxane afforded 83 mg (50% of th.) of the title compound.

LC-MS (method 4): $R_t$=0.50 min; MS (ESIpos): m/z=466 (M+H)$^+$ $^1$H-NMR (400 MHz, D$_2$O): δ=8.17 (s, 1H), 7.57 (s, 1H), 7.45 (s, 1H), 7.01 (s, 1H), 4.57 (s, 2H), 4.50 (s, 2H), 4.04 (s, 3H), 3.47-3.36 (m, 4H), 3.21-3.12 (m, 4H), 2.80 (s, 6H), 2.51 (s, 3H) ppm.

Example 38

6-[(Ethylamino)methyl]-5-(7-methoxy-5-methyl-1-benzothiophen-2-yl)-7-(piperazin-1-ylmethyl)pyrrolo[2,1-f][1,2,4]triazin-4-amine trihydrochloride

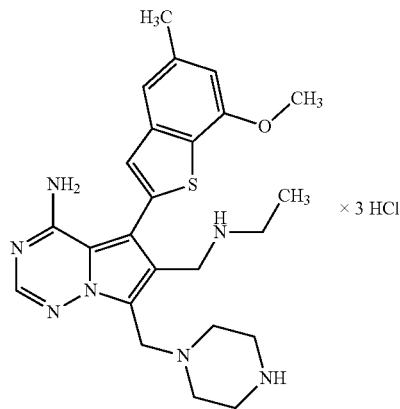 [SMILES: CCNCc1c(-c2cc3cc(C)cc(OC)c3s2)c2c(N)ncnn2c1CN1CCNCC1]

A solution of Intermediate 25A (60 mg, 111.8 μmol) in THF (1 ml) was treated with a 2 M solution of ethylamine in THF (83 μl, 167 μmol), sodium triacetoxyborohydride (118 mg, 559 mmol) and acetic acid (83 μl, 167 μmol). The mixture was stirred at 60° C. for 90 min. Further amounts of 2 M ethylamine solution (83 μl, 167 μmol) and sodium triacetoxyborohydride (71 mg, 335 mmol) were added, and stirring at 60° C. was continued for another 2 h. After evaporation, the residue was dissolved in a 4 M solution of hydrogen chloride in 1,4-dioxane (3 ml) and stirred at rt overnight. The mixture was evaporated, and the residue was purified by preparative RP-HPLC (Reprosil C18, gradient 10-95% acetonitrile/0.1% aq. formic acid) and lyophilized from a 4 M solution of hydrogen chloride in 1,4-dioxane. Re-purification by preparative RP-HPLC (Sunfire C18, 20% acetonitrile/80% 0.02% aq. TFA) and re-lyophilization from a 4 M solution of hydrogen chloride in 1,4-dioxane afforded 19 mg (29% of th.) of the title compound.

LC-MS (method 2): $R_t$=0.56 min; MS (ESIpos): m/z=466 (M+H)$^+$ $^1$H-NMR (400 MHz, D$_2$O): δ=8.14 (s, 1H), 7.56 (s, 1H), 7.45 (s, 1H), 7.01 (s, 1H), 4.45 (s, 4H), 4.04 (s, 3H), 3.45-3.32 (m, 4H), 3.18-3.05 (m, 4H), 2.99 (q, 2H), 2.51 (s, 3H), 1.10 (t, 3H) ppm.

Example 39

2-({[4-Amino-5-(7-methoxy-5-methyl-1-benzothiophen-2-yl)-7-(piperazin-1-ylmethyl)pyrrolo[2,1-f][1,2,4]triazin-6-yl]methyl}amino)ethanol trihydrochloride

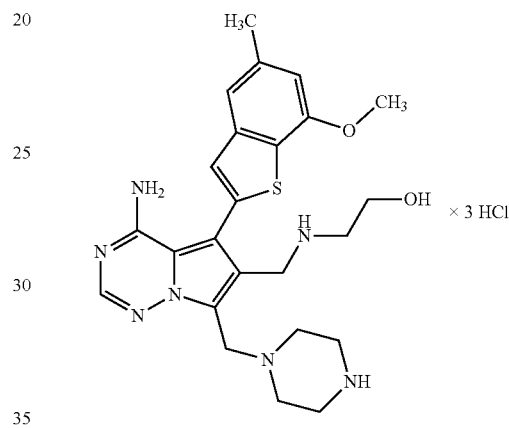

A solution of Intermediate 25A (150 mg, 279 μmol) in THF (3 ml) was treated with 2-aminoethanol (84 μl, 1.39 mmol), sodium triacetoxyborohydride (296 mg, 1.39 mmol) and acetic acid (32 μl, 559 μmol). The mixture was stirred at 60° C. for 2 h and then evaporated. The residue was dissolved in a 4 M solution of hydrogen chloride in 1,4-dioxane (1.87 ml) and stirred at rt for 2 h. After evaporation, the residue was purified by preparative RP-HPLC (Reprosil C18, gradient 10-95% acetonitrile/0.1% aq. TFA). Lyophilization from a 4 M solution of hydrogen chloride in 1,4-dioxane afforded 140 mg (80% of th.) of the title compound.

LC-MS (method 2): $R_t$=0.54 min; MS (ESIpos): m/z=482 (M+H)$^+$ $^1$H-NMR (400 MHz, D$_2$O): δ=8.15 (s, 1H), 7.56 (s, 1H), 7.45 (s, 1H), 7.00 (s, 1H), 4.47 (s, 2H), 4.37 (s, 2H), 4.04 (s, 3H), 3.79-3.71 (m, 2H), 3.42-3.34 (m, 4H), 3.19-3.12 (m, 2H), 3.06-2.97 (m, 4H), 2.51 (s, 3H) ppm.

General Procedure for Reductive Amination Reactions with Intermediate 25A (GP1):

A 0.1 M solution of Intermediate 25A in THF was treated with 5 eq. of the respective amine component, 5 eq. of sodium triacetoxyborohydride and 2 eq. of acetic acid. The resulting mixture was stirred at 60° C. for 2 h and then evaporated. A 0.15 M solution of the residue thus obtained in a 4 M solution of hydrogen chloride in 1,4-dioxane was stirred at rt for 1-2 h. After evaporation, the residue was purified as described below.

Example 40 rac-1-{[4-Amino-5-(7-methoxy-5-methyl-1-benzothiophen-2-yl)-7-(piperazin-1-ylmethyl)pyrrolo[2,1-f][1,2,4]triazin-6-yl]methyl}piperidin-3-ol trihydrochloride

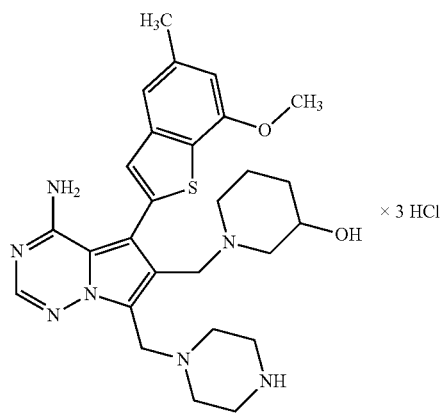 [SMILES: COc1cc(C)cc2cc(-c3c(CN4CCCC(O)C4)c(CN4CCNCC4)n4ncnc(N)c34)sc12]

According to GP1, Intermediate 25A (150 mg, 279 µmol) was reacted with 3-hydroxypiperidine (141 mg, 1.39 mmol). Purification by preparative RP-HPLC (Reprosil C18, gradient 10-95% acetonitrile/0.1% aq. TFA) and lyophilization from a 4 M solution of hydrogen chloride in 1,4-dioxane afforded 178 mg (quant.) of the title compound.

LC-MS (method 2): $R_t$=0.54 min; MS (ESIpos): m/z=522 (M+H)$^+$ $^1$H-NMR (400 MHz, D$_2$O): δ=8.16 (s, 1H), 7.55 (s, 1H), 7.45 (s, 1H), 7.01 (s, 1H), 4.66-4.16 (m, 5H), 4.04 (s, 3H), 3.55-2.71 (m, 11H), 2.51 (s, 3H), 1.96-1.42 (m, 4H), 1.64-1.50 (m, 1H) ppm.

Example 41

1-{[4-Amino-5-(7-methoxy-5-methyl-1-benzothiophen-2-yl)-7-(piperazin-1-ylmethyl)pyrrolo[2,1-f][1,2,4]triazin-6-yl]methyl}piperidin-4-ol trihydrochloride

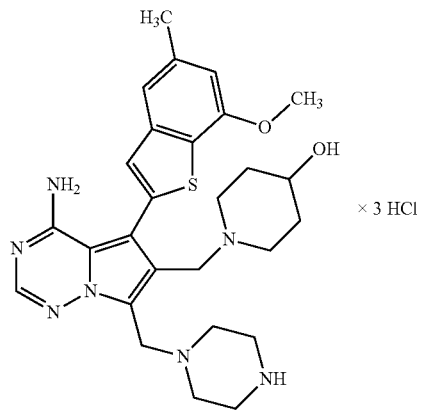 [SMILES: COc1cc(C)cc2cc(-c3c(CN4CCC(O)CC4)c(CN4CCNCC4)n4ncnc(N)c34)sc12]

According to GP1, Intermediate 25A (150 mg, 279 µmol) was reacted with 4-hydroxypiperidine (141 mg, 1.39 mmol). Purification by preparative RP-HPLC (Reprosil C18, gradient 10-95% acetonitrile/0.1% aq. TFA) and lyophilization from a 4 M solution of hydrogen chloride in 1,4-dioxane afforded 162 mg (91% of th.) of the title compound.

LC-MS (method 4): $R_t$=0.48 min; MS (ESIpos): m/z=522 (M+H)$^+$ $^1$H-NMR (400 MHz, D$_2$O): δ=8.16 (s, 1H), 7.58 (br. s, 1H), 7.46 (s, 1H), 7.01 (s, 1H), 4.67-4.48 (m, 4H), 4.04 (s, 4H), 3.59-2.78 (m, 12H), 2.51 (s, 3H), 2.14-1.38 (m, 4H) ppm.

Example 42 rac-1-{[4-Amino-5-(7-methoxy-5-methyl-1-benzothiophen-2-yl)-7-(piperazin-1-ylmethyl)pyrrolo[2,1-f][1,2,4]triazin-6-yl]methyl}pyrrolidin-3-ol trihydrochloride

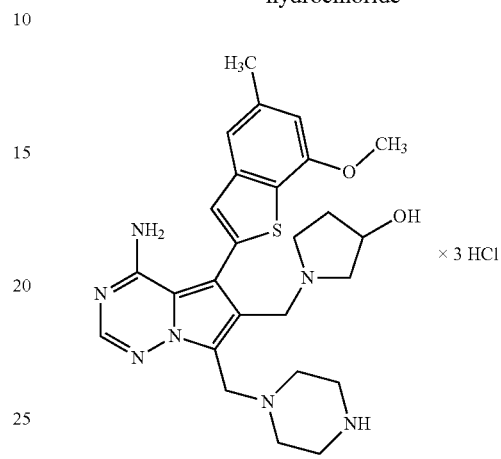

According to GP1, Intermediate 25A (150 mg, 279 mmol) was reacted with 3-hydroxypyrrolidine (113 µl, 1.39 mmol). Purification by preparative RP-HPLC (Reprosil C18, gradient 10-95% acetonitrile/0.1% aq. TFA) and lyophilization from a 4 M solution of hydrogen chloride in 1,4-dioxane afforded 148 mg (85% of th.) of the title compound.

LC-MS (method 4): $R_t$=0.46 min; MS (ESIpos): m/z=508 (M+H)$^+$ $^1$H-NMR (400 MHz, D$_2$O): δ=8.18 (s, 1H), 7.58 (s, 1H), 7.46 (s, 1H), 7.01 (s, 1H), 4.71-4.30 (m, 5H), 4.04 (s, 3H), 3.70-2.95 (m, 12H), 2.51 (s, 3H), 2.32-2.14 (m, 1H), 2.03-1.87 (m, 1H) ppm.

Example 43

6-[(Diethylamino)methyl]-5-(7-methoxy-5-methyl-1-benzothiophen-2-yl)-7-(piperazin-1-ylmethyl)pyrrolo[2,1-f][1,2,4]triazin-4-amine trihydrochloride

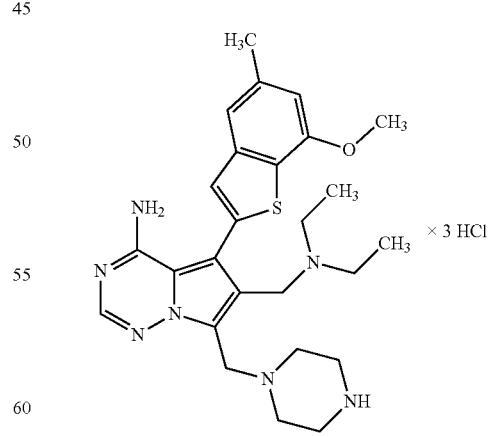

According to GP1, Intermediate 25A (150 mg, 279 µmol) was reacted with diethylamine (144 µl, 1.39 mmol). Purification by preparative RP-HPLC (Reprosil C18, gradient 10-95% acetonitrile/0.1% aq. TFA) and lyophilization from a 4 M solution of hydrogen chloride in 1,4-dioxane afforded 127 mg (69% of th.) of the title compound.

LC-MS (method 2): R$_t$=0.55 min; MS (ESIpos): m/z=494 (M+H)$^+$ $^1$H-NMR (400 MHz, D$_2$O): δ=8.19 (s, 1H), 7.61 (s, 1H), 7.47 (s, 1H), 7.01 (s, 1H), 4.59 (s, 2H), 4.51 (s, 2H), 4.04 (s, 3H), 3.47-3.35 (m, 4H), 3.29-3.00 (m, 8H), 2.51 (s, 3H), 1.07 (t, 6H) ppm.

Example 44

6-[(Cyclobutylamino)methyl]-5-(7-methoxy-5-methyl-1-benzothiophen-2-yl)-7-(piperazin-1-ylmethyl)pyrrolo[2,1-f][1,2,4]triazin-4-amine trihydrochloride

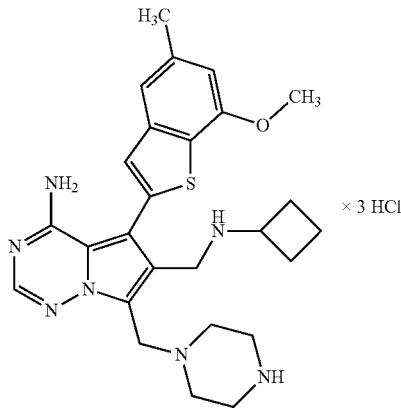 [SMILES: COc1cc(C)cc2cc(-c3c(CNC4CCC4)c(CN4CCNCC4)n4ncnc(N)c34)sc12]

According to GP1, Intermediate 25A (150 mg, 279 mmol) was reacted with cyclobutylamine (119 μl, 1.39 mmol). Purification by preparative RP-HPLC (Reprosil C18, gradient 10-95% acetonitrile/0.1% aq. TFA) and lyophilization from a 4 M solution of hydrogen chloride in 1,4-dioxane afforded 127 mg (72% of th.) of the title compound.

LC-MS (method 2): R$_t$=0.58 min; MS (ESIpos): m/z=492 (M+H)$^+$ $^1$H-NMR (400 MHz, D$_2$O): δ=8.16 (s, 1H), 7.59 (s, 1H), 7.47 (s, 1H), 7.00 (s, 1H), 4.40 (s, 2H), 4.37 (s, 2H), 4.04 (s, 3H), 3.69-3.58 (m, 1H), 3.44-3.33 (m, 4H), 3.21-3.12 (m, 4H), 2.51 (s, 3H), 2.02-1.87 (m, 4H), 1.81-1.62 (m, 2H) ppm.

Example 45

5-(7-Methoxy-5-methyl-1-benzothiophen-2-yl)-7-(piperazin-1-ylmethyl)-6-(pyrrolidin-1-ylmethyl)pyrrolo[2,1-f][1,2,4]triazin-4-amine trihydrochloride

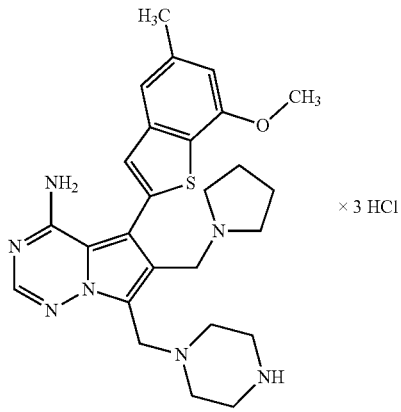 [SMILES: COc1cc(C)cc2cc(-c3c(CN4CCCC4)c(CN4CCNCC4)n4ncnc(N)c34)sc12]

According to GP1, Intermediate 25A (150 mg, 279 μmol) was reacted with pyrrolidine (116 μl, 1.39 mmol). Purification by preparative RP-HPLC (Reprosil C18, gradient 10-95% acetonitrile/0.1% aq. TFA) and lyophilization from a 4 M solution of hydrogen chloride in 1,4-dioxane afforded 112 mg (64% of th.) of the title compound.

LC-MS (method 2): R$_t$=0.54 min; MS (ESIpos): m/z=492 (M+H)$^+$ $^1$H-NMR (400 MHz, D$_2$O): δ=8.19 (s, 1H), 7.60 (s, 1H), 7.46 (s, 1H), 7.01 (s, 1H), 4.70-4.61 (m, 4H), 4.04 (s, 3H), 3.55-3.40 (m, 6H), 3.35-3.26 (m, 4H), 3.02-2.87 (m, 2H), 2.51 (s, 3H), 1.97-1.83 (m, 4H) ppm.

Example 46

6-[(Cyclopropylamino)methyl]-5-(7-methoxy-5-methyl-1-benzothiophen-2-yl)-7-(piperazin-1-ylmethyl)pyrrolo[2,1-f][1,2,4]triazin-4-amine trihydrochloride

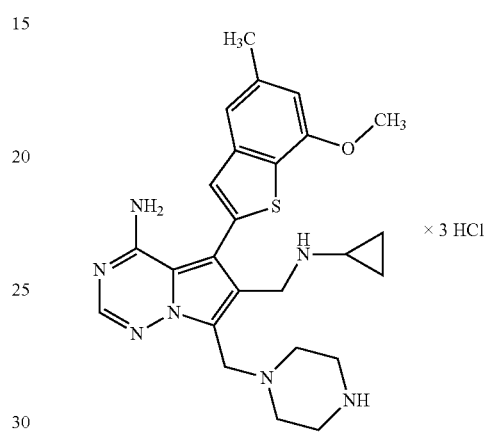

According to GP1, Intermediate 25A (200 mg, 372 μmol) was reacted with cyclopropylamine (129 μl, 1.86 mmol). Purification by preparative RP-HPLC (Reprosil C18, gradient 10-95% acetonitrile/0.1% aq. TFA) and lyophilization from a 4 M solution of hydrogen chloride in 1,4-dioxane afforded 140 mg (62% of th.) of the title compound.

LC-MS (method 5): R$_t$=1.42 min; MS (ESIpos): m/z=478 (M+H)$^+$ $^1$H-NMR (400 MHz, D$_2$O): δ=8.16 (s, 1H), 7.56 (s, 1H), 7.46 (s, 1H), 7.01 (s, 1H), 4.57 (s, 2H), 4.47 (s, 2H), 4.04 (s, 3H), 3.46-3.34 (m, 4H), 3.19-3.07 (m, 4H), 2.61-2.54 (m, 1H), 2.51 (s, 3H), 0.75-0.64 (m, 4H) ppm.

Example 47

6-{[(Cyclopropylmethyl)amino]methyl}-5-(7-methoxy-5-methyl-1-benzothiophen-2-yl)-7-(piperazin-1-ylmethyl)pyrrolo[2,1-f][1,2,4]triazin-4-amine trihydrochloride

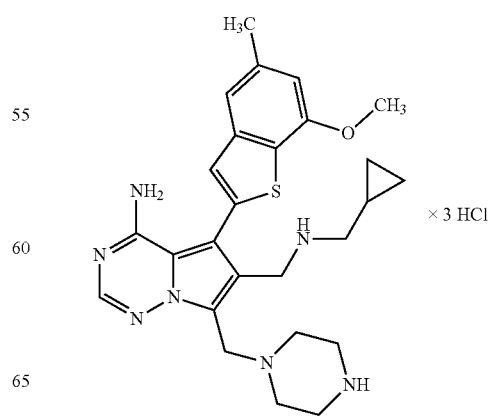

According to GP1, Intermediate 25A (200 mg, 372 mmol) was reacted with cyclopropylmethylamine (161 µl, 1.86 mmol). Purification by preparative RP-HPLC (Reprosil C18, gradient 10-95% acetonitrile/0.1% aq. TFA) and lyophilization from a 4 M solution of hydrogen chloride in 1,4-dioxane afforded 163 mg (69% of th.) of the title compound.

LC-MS (method 2): $R_t$=0.60 min; MS (ESIpos): m/z=492 (M+H)$^+$ $^1$H-NMR (400 MHz, D$_2$O): δ=8.14 (s, 1H), 7.57 (s, 1H), 7.45 (s, 1H), 7.00 (s, 1H), 4.50 (s, 2H), 4.44 (s, 2H), 4.04 (s, 3H), 3.42-3.34 (m, 4H), 3.16-3.07 (m, 4H), 2.86 (d, 2H), 2.50 (s, 3H), 0.89-0.76 (m, 1H), 0.55-0.45 (m, 2H), 0.23-0.14 (m, 2H) ppm.

Example 48

N-{[4-Amino-5-(7-methoxy-5-methyl-1-benzothiophen-2-yl)-7-(piperazin-1-ylmethyl)pyrrolo-[2,1-f][1,2,4]triazin-6-yl]methyl}glycine trihydrochloride

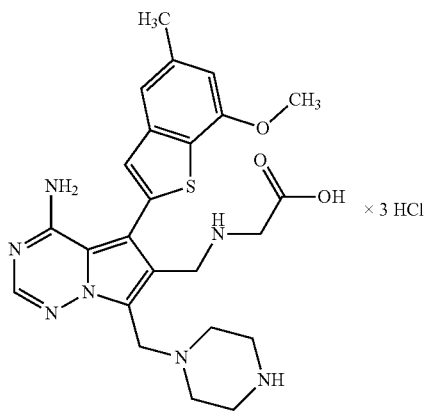 [SMILES: COc1cc(C)cc2cc(-c3c(CNCC(=O)O)c(CN4CCNCC4)n4ncnc(N)c34)sc12]

A solution of Intermediate 25A (161 mg, 300 µmol) in THF (3.2 ml) was treated with 2-aminoacetic acid (112 mg, 1.5 mmol), sodium triacetoxyborohydride (317 mg, 1.5 mmol) and acetic acid (34 µl, 600 µmol). The resulting mixture was stirred at 60° C. for 2 h and then evaporated. The residue was purified by preparative RP-HPLC (Reprosil C18, gradient 10-95% acetonitrile/0.1% aq. TFA). The product thus obtained was dissolved in a 4 M solution of hydrogen chloride in 1,4-dioxane (2 ml) and stirred at rt for 1 h. After evaporation, the residue was purified by preparative RP-HPLC (Reprosil C18, gradient 10-95% acetonitrile/0.1% aq. TFA). Subsequent lyophilization from a 4 M solution of hydrogen chloride in 1,4-dioxane afforded 18 mg (9% of th.) of the title compound.

LC-MS (method 2): $R_t$=0.63 min; MS (ESIpos): m/z=496 (M+H)$^+$ $^1$H-NMR (400 MHz, D$_2$O): δ=8.14 (s, 1H), 7.54 (s, 1H), 7.45 (s, 1H), 6.99 (s, 1H), 4.42 (s, 2H), 4.36 (s, 2H), 4.03 (s, 3H), 3.64 (s, 2H), 3.42-3.33 (m, 4H), 3.07-2.96 (m, 4H), 2.50 (s, 3H) ppm.

Example 49

4-{[4-Amino-5-(7-methoxy-5-methyl-1-benzothiophen-2-yl)-7-(piperazin-1-ylmethyl)pyrrolo-[2,1-f][1,2,4]triazin-6-yl]methyl}piperazin-2-one trihydrochloride

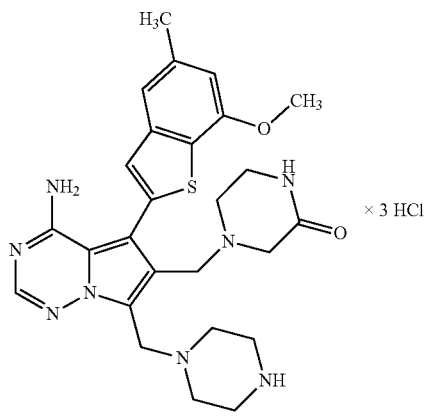 [SMILES: COc1cc(C)cc2cc(-c3c(CN4CCNC(=O)C4)c(CN4CCNCC4)n4ncnc(N)c34)sc12]

A solution of Intermediate 27A (220 mg, 354 µmol) in a 4 M solution of hydrogen chloride in 1,4-dioxane (2 ml) was stirred at rt for 2 h. Then, the mixture was evaporated leaving 235 mg of the crude product which was used in the next step without further purification.

LC-MS (method 4): $R_t$=0.60 min; MS (ESIpos): m/z=521 (M+H)$^+$.

Example 50

[4-Amino-5-(7-methoxy-5-methyl-1-benzothiophen-2-yl)-7-(morpholin-4-ylmethyl)pyrrolo-[2,1-f][1,2,4]triazin-6-yl]methanol

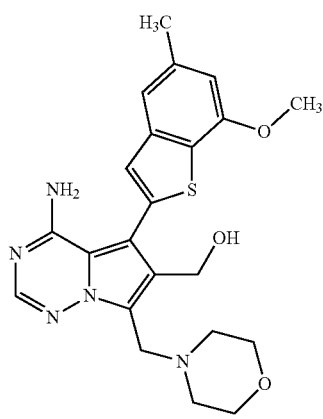 [SMILES: COc1cc(C)cc2cc(-c3c(CO)c(CN4CCOCC4)n4ncnc(N)c34)sc12]

A solution of Intermediate 20A (500 mg, purity 87%, 1.28 mmol) and 4-methylenemorpholin-4-ium chloride (347 mg, 2.56 mmol) in DMF (28 ml) was stirred at 70° C. for 1.5 h. The mixture was diluted with ethyl acetate and washed with sat. aq. sodium hydrogencarbonate solution and sat. aq. sodium chloride solution. The organic layer was dried with magnesium sulfate and evaporated under reduced pressure yielding 710 mg (purity 78%, 99% of th.) of the title compound.

LC-MS (method 2): $R_t$=0.65 min; MS (ESIpos): m/z=440 (M+H)$^+$.

Example 51

(3S)-3-({[4-Amino-5-(7-methoxy-5-methyl-1-benzothiophen-2-yl)-7-(morpholin-4-ylmethyl)pyrrolo[2,1-f][1,2,4]triazin-6-yl]methyl}amino)pyrrolidin-2-one

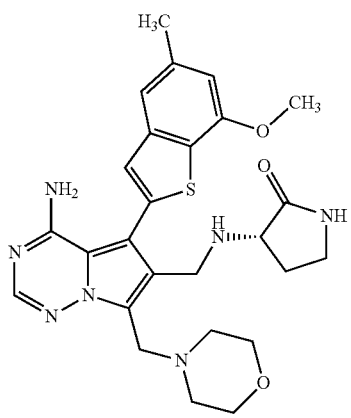 [SMILES: COc1cc(C)cc2cc(-c3c(CN[C@H]4CCNC4=O)c(CN4CCOCC4)n4ncnc(N)c34)sc12]

A solution of Intermediate 33A (65 mg, 149 µmol) in methanol (2 ml) was treated with (3S)-3-aminopyrrolidin-2-one (45 mg, 446 µmol), sodium cyanoborohydride (47 mg, 743 µmol) and acetic acid (26 µl, 446 µmol). After stirring at 60° C. for 16 h, the resulting mixture was separated by preparative RP-HPLC (Reprosil C18, gradient 20-40% acetonitrile/0.2% aq. TFA). The product thus obtained was dissolved in methanol and filtered through an anion exchange cartridge (Stratospheres SPE, PL-HCO$_3$ MP-resin). The cartridge was eluted with methanol, and the filtrate was evaporated yielding 49 mg (63% of th.) of the title compound.

LC-MS (method 2): R$_t$=0.71 min; MS (ESIpos): m/z=522 (M+H)$^+$ $^1$H-NMR (400 MHz, DMSO-d$_6$): δ=7.96 (s, 1H), 7.66 (s, 1H), 7.5-8.1 (br. s, 1H), 7.44 (s, 1H), 7.31 (s, 1H), 6.84 (s, 1H), 5.4-6.0 (br. s, 1H), 3.95 (s, 3H), 3.91 (s, 2H), 3.75 (d, 2H), 3.50-3.66 (m, 4H), 3.06-3.19 (m, 3H), 2.94-3.05 (m, 1H), 2.61 (t, 1H), 2.45 (t, 3H), 2.38-2.44 (m, 4H), 1.89-1.99 (m, 1H), 1.49-1.60 (m, 1H) ppm.

Example 52

4-{[4-Amino-5-(7-methoxy-5-methyl-1-benzothiophen-2-yl)-7-(morpholin-4-ylmethyl)pyrrolo[2,1-f][1,2,4]triazin-6-yl]methyl}piperazin-2-one

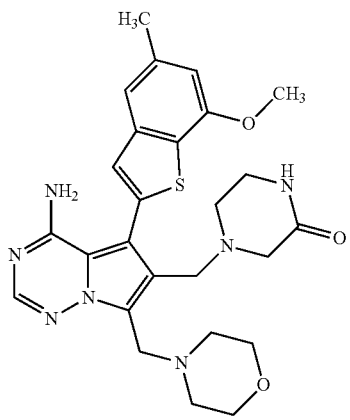 [SMILES: COc1cc(C)cc2cc(-c3c(CN4CCNC(=O)C4)c(CN4CCOCC4)n4ncnc(N)c34)sc12]

A solution of Intermediate 33A (65 mg, 149 µmol) in methanol (2 ml) was treated with 2-oxopiperazine (45 mg, 446 µmol), sodium cyanoborohydride (47 mg, 743 µmol) and acetic acid (26 µl, 446 µmol). After stirring at 60° C. for 16 h, the resulting mixture was separated by preparative RP-HPLC (Reprosil C18, gradient 20-40% acetonitrile/0.2% aq. TFA). The product thus obtained was dissolved in methanol and filtered through an anion exchange cartridge (Stratospheres SPE, PL-HCO$_3$ MP-resin). The cartridge was eluted with methanol, and the filtrate was evaporated yielding 41 mg (53% of th.) of the title compound.

LC-MS (method 2): R$_t$=0.70 min; MS (ESIpos): m/z=522 (M+H)$^+$ $^1$H-NMR (400 MHz, DMSO-d$_6$): δ=7.97 (s, 1H), 7.67 (br. s, 1H), 7.55-8.05 (br. s, 1H), 7.38 (s, 1H), 7.30 (s, 1H), 6.84 (s, 1H), 5.29-5.88 (br. s, 1H), 3.95 (s, 3H), 3.92 (s, 2H), 3.58 (s, 2H), 3.51-3.56 (m, 4H), 3.00-3.06 (m, 2H), 2.85 (s, 2H), 2.45 (s, 3H), 2.43-2.48 (m, 5H) ppm.

Example 53 rac-1-({[4-Amino-5-(7-methoxy-5-methyl-1-benzothiophen-2-yl)-7-(morpholin-4-ylmethyl)pyrrolo[2,1-f][1,2,4]triazin-6-yl]methyl}amino)propan-2-ol

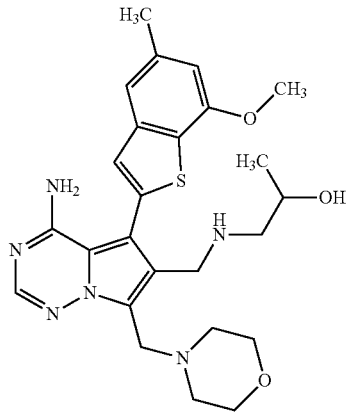 [SMILES: COc1cc(C)cc2cc(-c3c(CNCC(C)O)c(CN4CCOCC4)n4ncnc(N)c34)sc12]

A solution of Intermediate 33A (64 mg, 146 µmol) in methanol (2 ml) was treated with rac-1-aminopropan-2-ol (33 mg, 439 µmol), sodium cyanoborohydride (46 mg, 731 µmol) and acetic acid (25 µl, 439 µmol). After stirring at 60° C. for 16 h, the resulting mixture was separated by preparative RP-HPLC (Reprosil C18, gradient 20-40% acetonitrile/0.2% aq. TFA). The product thus obtained was dissolved in methanol and filtered through an anion exchange cartridge (Stratospheres SPE, PL-HCO$_3$ MP-resin). The cartridge was eluted with methanol, and the filtrate was evaporated yielding 42 mg (57% of th.) of the title compound.

LC-MS (method 5): R$_t$=1.63 min; MS (ESIpos): m/z=497 (M+H)$^+$ $^1$H-NMR (400 MHz, DMSO-d$_6$): δ=7.96 (s, 1H), 7.47-7.92 (br. s, 1H), 7.39 (s, 1H), 7.30 (s, 1H), 6.84 (s, 1H), 5.36-5.92 (br. s, 1H), 4.36 (d, 1H), 3.95 (s, 3H), 3.90 (s, 2H), 3.64-3.75 (m, 2H), 3.49-3.61 (m, 5H), 2.45 (s, 3H), 2.39-2.47 (m, 4H), 2.31-2.38 (m, 2H), 0.97 (d, 3H) ppm.

Example 54

1-({[4-Amino-5-(7-methoxy-5-methyl-1-benzothiophen-2-yl)-7-(morpholin-4-ylmethyl)pyrrolo[2,1-f][1,2,4]triazin-6-yl]methyl}amino)-2-methylpropan-2-ol

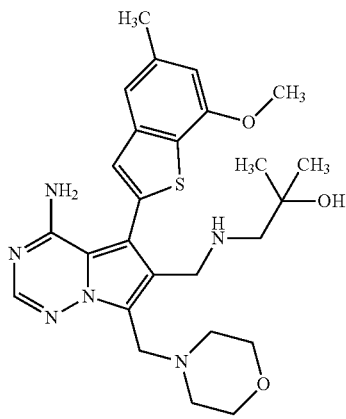 [SMILES: COc1cc(C)cc2cc(-c3c(CNCC(C)(C)O)c(CN4CCOCC4)n4ncnc(N)c34)sc12]

A solution of Intermediate 33A (80 mg, 183 µmol) in methanol (2 ml) was treated with 1-amino-2-methylpropan-2-ol (34 mg, 274 µmol), sodium cyanoborohydride (57 mg, 914 µmol) and acetic acid (21 µl, 366 µmol). After stirring at 60° C. for 16 h, the resulting mixture was separated by preparative RP-HPLC (Reprosil C18, gradient 20-40% acetonitrile/0.2% aq. TFA). The product thus obtained was dissolved in methanol and filtered through an anion exchange cartridge (Stratospheres SPE, PL-HCO₃ MP-resin). The cartridge was eluted with methanol, and the filtrate was evaporated yielding 29 mg (31% of th.) of the title compound.

LC-MS (method 2): $R_t$=0.65 min; MS (ESIpos): m/z=511 (M+H)⁺

$^1$H-NMR (400 MHz, DMSO-d₆): δ=7.96 (s, 1H), 7.50-8.02 (br. s, 1H), 7.42 (s, 1H), 7.28 (s, 1H), 6.84 (s, 1H), 5.4-6.0 (br. s, 1H), 4.11 (s, 1H), 3.95 (s, 3H), 3.90 (s, 2H), 3.70 (d, 2H), 3.51-3.58 (m, 4H), 2.45 (s, 3H), 2.39-2.46 (m, 4H), 2.33 (d, 2H), 1.83-1.92 (m, 1H), 1.03 (s, 6H) ppm.

Example 55

1-(4-{[4-Amino-6-(hydroxymethyl)-5-(7-methoxy-5-methyl-1-benzothiophen-2-yl)pyrrolo[2,1-f]-[1,2,4]triazin-7-yl]methyl}piperazin-1-yl)ethanone

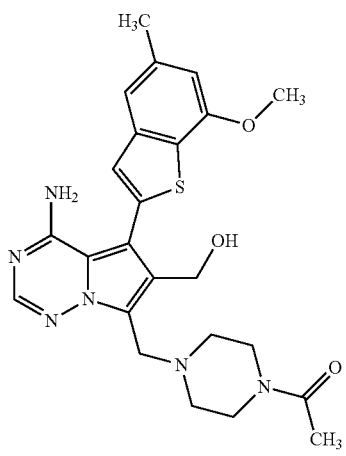 [SMILES: COc1cc(C)cc2cc(-c3c(CO)c(CN4CCN(C(C)=O)CC4)n4ncnc(N)c34)sc12]

A solution of Intermediate 20A (345 mg, 1.01 mmol) in acetic acid (5 ml) was treated with 37% aq. formaldehyde solution (91 µl, 1.22 mmol) and 1-acetylpiperazine (160 mg, 1.22 mmol). The mixture was stirred at 60° C. for 6 h and then evaporated. The residue was dissolved in a mixture of THF/1 M aq. lithium hydroxide solution (1:1, 10 ml) and stirred at rt for 2 h. The mixture was then combined with the reaction mixture of a 100 mg test run, and sat. aq ammonium chloride solution was added. The mixture was extracted with ethyl acetate, and the organic phase was washed with sat. aq. sodium chloride solution, dried over magnesium sulfate and evaporated under reduced pressure yielding 678 mg (purity 87%, 94% of th.) of the title compound.

LC-MS (method 2): $R_t$=0.71 min; MS (ESIpos): m/z=481 (M+H)⁺.

Example 56

(3R)-3-[({7-[(4-Acetylpiperazin-1-yl)methyl]-4-amino-5-(7-methoxy-5-methyl-1-benzothiophen-2-yl)pyrrolo[2,1-f][1,2,4]triazin-6-yl}methyl)amino]pyrrolidin-2-one

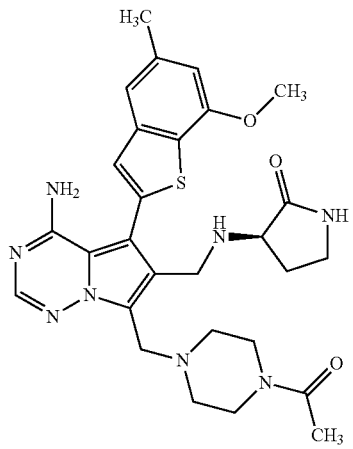 [SMILES: COc1cc(C)cc2cc(-c3c(CN[C@@H]4CCNC4=O)c(CN4CCN(C(C)=O)CC4)n4ncnc(N)c34)sc12]

A solution of Intermediate 31A (80 mg, 167 µmol) in methanol (1.4 ml) was treated with (3R)-3-aminopyrrolidin-2-one (21 mg, 251 µmol), sodium cyanoborohydride (52 mg, 836 µmol) and acetic acid (19 µl, 334 µmol). After stirring at 60° C. for 16 h, the resulting mixture was separated by preparative RP-HPLC (Reprosil C18, gradient 20-40% acetonitrile/0.2% aq. TFA). The product thus obtained was dissolved in methanol and filtered through an anion exchange cartridge (Stratospheres SPE, PL-HCO₃ MP-resin). The cartridge was eluted with methanol, and the filtrate was evaporated yielding 46 mg (49% of th.) of the title compound.

LC-MS (method 2): $R_t$=0.70 min; MS (ESIpos): m/z=563 (M+H)⁺

$^1$H-NMR (400 MHz, DMSO-d₆): δ=8.42 (s, 1H), 8.05 (s, 1H), 7.93-8.24 (br. s, 1H), 7.51 (s, 1H), 7.34 (s, 1H), 6.88 (s, 1H), 5.75-6.07 (br. s, 1H), 4.21-4.37 (m, 2H), 4.19 (s, 2H), 4.10 (t, 1H), 3.96 (s, 3H), 3.56-3.66 (m, 2H), 3.44-3.54 (m, 4H), 3.11-3.27 (m, 4H), 2.47 (s, 4H), 2.16-2.25 (m, 1H), 2.00 (s, 3H), 1.86-1.95 (m, 1H) ppm.

Example 57

1-(4-{[4-Amino-6-{[(2-hydroxy-2-methylpropyl)amino]methyl}-5-(7-methoxy-5-methyl-1-benzothiophen-2-yl)pyrrolo[2,1-f][1,2,4]triazin-7-yl]methyl}piperazin-1-yl)ethanone

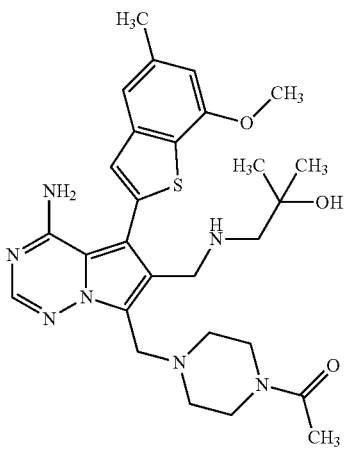 [SMILES: COc1cc(C)cc2cc(-c3c(CNCC(C)(C)O)c(CN4CCN(C(C)=O)CC4)n4ncnc(N)c34)sc12]

A solution of Intermediate 31A (80 mg, 183 µmol) in methanol (2 ml) was treated with 1-amino-2-methylpropan-2-ol (31 mg, 251 µmol), sodium cyanoborohydride (53 mg, 836 µmol) and acetic acid (19 µl, 334 µmol). After stirring at 60° C. for 16 h, the resulting mixture was separated by preparative RP-HPLC (Reprosil C18, gradient 20-40% acetonitrile/0.2% aq. TFA). The product thus obtained was dissolved in methanol and filtered through an anion exchange cartridge (Stratospheres SPE, PL-HCO$_3$ MP-resin). The cartridge was eluted with methanol, and the filtrate was evaporated yielding 29 mg (31% of th.) of the title compound.

LC-MS (method 2): R$_t$=0.71 min; MS (ESIpos): m/z=552 (M+H)$^+$ $^1$H-NMR (400 MHz, DMSO-d$_6$): δ=7.96 (s, 1H), 7.59-8.02 (br. s, 1H), 7.42 (s, 1H), 7.28 (s, 1H), 6.84 (s, 1H), 5.45-5.93 (br. s, 1H), 4.13 (br. s, 1H), 3.95 (s, 3H), 3.93 (s, 2H), 3.71 (s, 2H), 3.37-3.44 (m, 4H), 2.45 (s, 3H), 2.32-2.43 (m, 6H), 1.97 (s, 3H), 1.03 (s, 6H) ppm.

Example 58

4-({4-Amino-5-(7-methoxy-5-methyl-1-benzothiophen-2-yl)-6-[(3-oxopiperazin-1-yl)methyl]-pyrrolo[2,1-f][1,2,4]triazin-7-yl}methyl)piperazine-1-carbaldehyde formiate

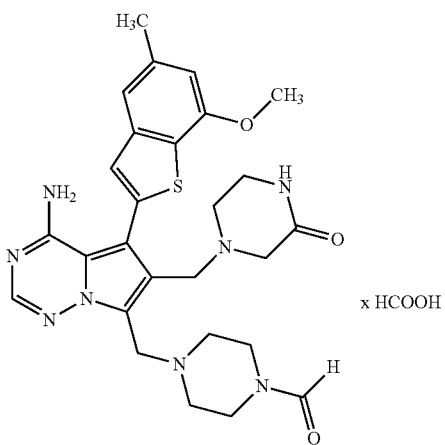 [SMILES: COc1cc(C)cc2cc(-c3c(CN4CCNC(=O)C4)c(CN4CCN(C=O)CC4)n4ncnc(N)c34)sc12]

Acetic acid anhydride (498 µl, 5.17 mmol) and formic acid (237 µl, 6.28 mmol) were stirred first 2 h at 50° C. and then overnight at rt. Subsequently, the mixture was diluted with dichloromethane (5.1 ml), and 1.16 ml of this solution were added to a solution of Example 49 (233 mg, 370 µmol) in pyridine (89 µl). After stirring at rt for 2 h, the mixture was diluted with methanol and then evaporated. The residue was purified by preparative RP-HPLC (Reprosil C18, gradient 10-95% acetonitrile/0.1% aq. formic acid) affording 77 mg (35% of th.) of title compound.

LC-MS (method 4): R$_t$=0.62 min; MS (ESIpos): m/z=549 (M+H)$^+$ $^1$H-NMR (400 MHz, DMSO-d$_6$): inter al. δ=8.14 (s, 1H), 7.97 (s, 2H), 7.67 (s, 1H), 7.38 (s, 1H), 7.30 (s, 1H), 6.84 (s, 1H), 3.96 (s, 2H), 3.95 (s, 3H), 3.58 (s, 2H), 3.04 (br. t, 2H), 2.86 (s, 2H), 2.45 (s, 3H), 2.42 (br. t, 2H) ppm.

Example 59

4-({7-[(4-Acetylpiperazin-1-yl)methyl]-4-amino-5-(7-methoxy-5-methyl-1-benzothiophen-2-yl)pyrrolo[2,1-f][1,2,4]triazin-6-yl}methyl)piperazin-2-one

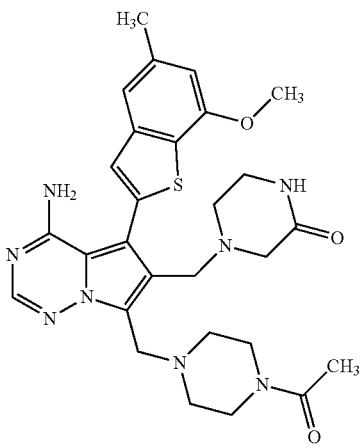 [SMILES: COc1cc(C)cc2cc(-c3c(CN4CCNC(=O)C4)c(CN4CCN(C(C)=O)CC4)n4ncnc(N)c34)sc12]

A suspension of Example 49 (310 mg, 522 µmol) in dichloromethane/THF (2.5:1, 9.64 ml) was treated with sodium carbonate (442 mg, 4.17 mmol) and stirred at rt for 30 min. Acetyl chloride (74 µl, 1.04 mmol) was added, and the resulting mixture was stirred at rt for 2 h. After quenching with methanol, the mixture was evaporated, and the residue was purified by preparative RP-HPLC (Reprosil C18, gradient 10-95% acetonitrile/0.1% aq. formic acid) affording 133 mg (45% of th.) of the title compound.

LC-MS (method 2): R$_t$=0.69 min; MS (ESIpos): m/z=563 (M+H)$^+$ $^1$H-NMR (400 MHz, methanol-d$_4$): δ=7.89 (s, 1H), 7.30 (s, 1H), 7.28 (s, 1H), 6.79 (s, 1H), 4.13 (s, 2H), 3.98 (s, 3H), 3.74 (s, 2H), 3.59 (t, 2H), 3.54 (t, 2H), 3.18 (t, 2H), 3.02 (s, 2H), 2.68-2.55 (m, 6H), 2.48 (s, 3H), 2.08 (s, 3H) ppm.

Example 60

Methyl 4-amino-5-(7-methoxy-5-methyl-1-benzothiophen-2-yl)-7-(piperazin-1-ylcarbonyl)pyrrolo[2,1-f][1,2,4]triazine-6-carboxylate bis(formiate)

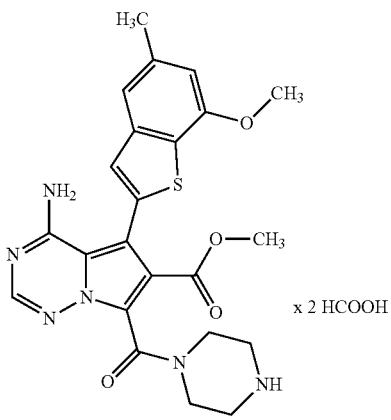 [SMILES: COC(=O)c1c(-c2cc3cc(C)cc(OC)c3s2)c2c(N)ncnn2c1C(=O)N1CCNCC1]

To a solution of Intermediate 28A (15 mg, 26 μmol) in a THF/methanol mixture (5:1, 180 μl), cooled to 0° C., was added (trimethylsilyl)diazomethane (2 M solution in hexane, 15 μl, 32 μmol). The resulting mixture was slowly warmed to rt over 30 min and then evaporated. The residue was dissolved in a 4 M solution of hydrogen chloride in 1,4-dioxane (0.5 ml) and stirred at rt for 1 h. After evaporation, the residue was purified by preparative RP-HPLC (Reprosil C18, gradient 10-95% acetonitrile/0.1% aq. formic acid) affording 4.8 mg (35% of th.) of the title compound.

LC-MS (method 2): $R_t$=0.66 min; MS (ESIpos): m/z=481 (M+H)$^+$ $^1$H-NMR (400 MHz, DMSO-d$_6$): inter al. δ=8.17 (s, 2H), 8.38-8.23 (br. s, 1H), 8.04 (s, 1H), 7.43 (s, 1H), 7.31 (s, 1H), 6.86 (s, 1H), 5.71-5.58 (br. s, 1H), 3.96 (s, 3H), 3.60 (s, 3H, overlap with water peak), 2.46 (s, 3H) ppm.

Example 61

5-(7-Methoxy-5-methyl-1-benzothiophen-2-yl)-6-(1,3-oxazol-5-yl)-7-(piperazin-1-ylmethyl)pyrrolo[2,1-f][1,2,4]triazin-4-amine trihydrochloride

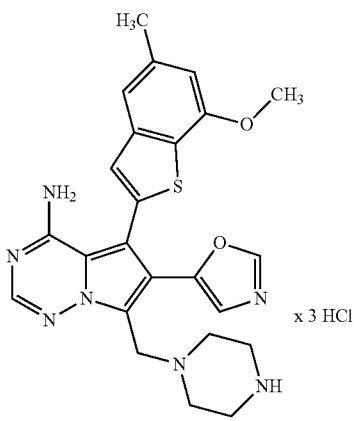 [SMILES: COc1cc(C)cc2cc(-c3c(-c4cnco4)c(CN4CCNCC4)n4ncnc(N)c34)sc12]

A solution of Intermediate 25A (100 mg, 0.19 mmol) in methanol (3.33 ml) was treated with (4-toluenesulfonyl)methylisocyanide (36 mg, 0.19 mmol) and potassium carbonate (25 mg, 186 μmol). The mixture was refluxed for 6 h. It was then combined with the reactions mixtures from three 30 mg test runs and evaporated. The residue was dissolved in a 4 M solution of hydrogen chloride in 1,4-dioxane (10 ml) and stirred at rt for 2 h. After evaporation, the residue was purified by two-fold preparative RP-HPLC (Reprosil C18, gradient 10-95% acetonitrile/0.1% aq. TFA). Further purification by column chromatography on silica gel (dichloromethane/methanol 5:1 with 0.5% aq. ammonia) and lyophilization from a 4 M solution of hydrogen chloride in 1,4-dioxane afforded 75 mg (34% of th.) of the title compound.

LC-MS (method 4): $R_t$=0.69 min; MS (ESIpos): m/z=476 (M+H)$^+$ $^1$H-NMR (400 MHz, DMSO-d$_6$): inter al. δ=8.40 (s, 1H), 8.20 (s, 1H), 7.46 (s, 1H), 7.35 (s, 1H), 6.96 (s, 1H), 6.89 (s, 1H), 3.95 (s, 3H), 2.46 (s, 3H) ppm.

Example 62

6-(Aminomethyl)-5-(7-methoxy-5-methyl-1-benzothiophen-2-yl)-7-(piperazin-1-ylmethyl)pyrrolo[2,1-f][1,2,4]triazin-4-amine trihydrochloride

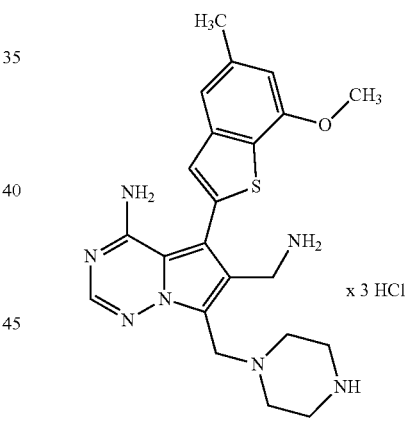

A suspension of Intermediate 29A (76 mg, 134 μmol) and 10% Pd/C (60 mg) in a 0.5 M solution of hydrogen chloride in methanol (20 ml) was stirred at rt for 3 h under 1 atm of hydrogen. The mixture was then filtered through kieselguhr, the filtrate was evaporated, and the residue was purified by preparative RP-HPLC (Reprosil C18, gradient 10-95% acetonitrile/0.1% aq. TFA). The product thus obtained was lyophilized from a 4 M solution of hydrogen chloride in 1,4-dioxane affording 34 mg (46% of th.) of the title compound.

LC-MS (method 2): $R_t$=0.55 min; MS (ESIpos): m/z=438 (M+H)$^+$ $^1$H-NMR (400 MHz, DMSO-d$_6$): inter al. δ=8.24 (br. s, 3H), 8.12 (s, 1H), 7.52 (s, 1H), 7.34 (s, 1H), 6.89 (s, 1H), 3.96 (s, 3H), 3.76-3.63 (m, 1H), 3.52-3.42 (m, 1H), 2.47 (s, 3H) ppm.

Example 63

N-{[4-Amino-5-(7-methoxy-5-methyl-1-benzothiophen-2-yl)-7-(piperazin-1-ylmethyl)pyrrolo-[2,1-f][1,2,4]triazin-6-yl]methyl}acetamide bis(trifluoroacetate)

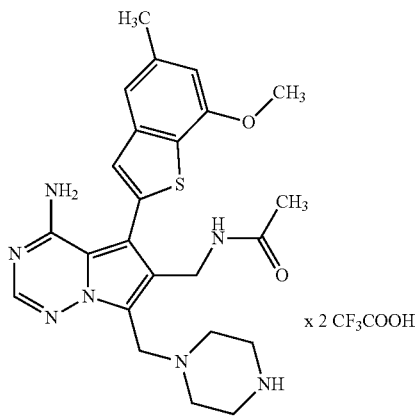 [SMILES: COc1cc(C)cc2cc(-c3c(CNC(C)=O)c(CN4CCNCC4)n4ncnc(N)c34)sc12]

x 2 CF₃COOH

A solution of Intermediate 30A (210 mg, 362 µmol) in dichloromethane (26 ml) was treated with trifluoroacetic acid (5.2 ml) and stirred at rt for 1 h. After evaporation at rt, the residue was purified by preparative RP-HPLC (Reprosil C18, gradient 10-95% acetonitrile/0.1% aq. TFA) affording 163 mg (63% of th.) of the title compound.

LC-MS (method 3): $R_t$=2.42 min; MS (ESIpos): m/z=480 (M+H)⁺

¹H-NMR (400 MHz, DMSO-$d_6$): inter al. δ=9.00-8.75 (br. s, 1H), 8.30-8.16 (br. s, 1H), 8.08 (s, 1H), 7.38 (s, 1H), 7.33 (s, 1H), 6.87 (s, 1H), 4.32 (br. d, 2H), 3.96 (s, 3H), 3.40-2.98 (m, 8H), 2.46 (s, 3H), 1.77 (s, 3H) ppm.

Example 64

N-{[4-Amino-5-(7-methoxy-5-methyl-1-benzothiophen-2-yl)-7-(piperazin-1-ylmethyl)pyrrolo-[2,1-f][1,2,4]triazin-6-yl]methyl}acetamide dihydrochloride

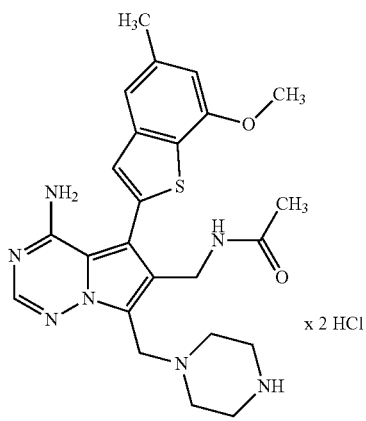 [SMILES: COc1cc(C)cc2cc(-c3c(CNC(C)=O)c(CN4CCNCC4)n4ncnc(N)c34)sc12]

x 2 HCl

A solution of Intermediate 30A (80 mg, 0.14 mmol) in dichloromethane (10 ml) and trifluoroacetic acid (2 ml) was stirred at rt for 1 h and then evaporated. Purification by preparative RP-HPLC (Reprosil C18, gradient 10-95% acetonitrile/0.1% aq. formic acid) and lyophilization from a mixture of methanol and 4 M solution of hydrogen chloride in 1,4-dioxane afforded 39 mg (50% of th.) of the title compound.

LC-MS (method 5): $R_t$=1.56 min; MS (ESIpos): m/z=480 (M+H)⁺

¹H-NMR (400 MHz, DMSO-$d_6$): inter al. δ=8.12 (s, 1H), 7.38 (s, 1H), 7.33 (s, 1H), 6.87 (s, 1H), 4.37 (br. d, 2H), 3.96 (s, 3H), 3.85-3.20 (m, 8H, overlap with water peak), 2.46 (s, 3H), 1.76 (s, 3H) ppm.

Example 65

N-({4-Amino-7-[(4-formylpiperazin-1-yl)methyl]-5-(7-methoxy-5-methyl-1-benzothiophen-2-yl)pyrrolo[2,1-f][1,2,4]triazin-6-yl}methyl)acetamide formiate

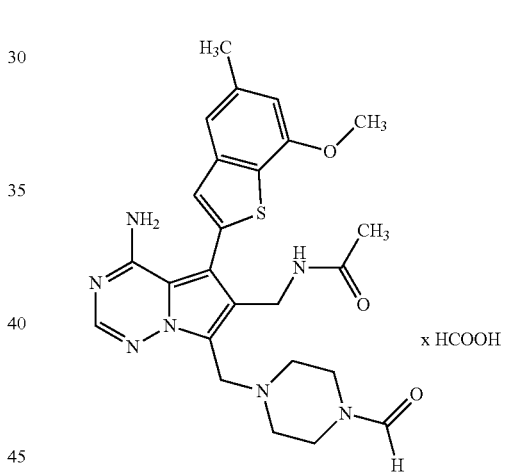

x HCOOH

Acetic acid anhydride (304 µl, 3.16 mmol) and formic acid (145 µl, 3.16 mmol) were stirred first 2 h at 50° C. and then overnight at rt. Subsequently, the mixture was diluted with dichloromethane (3.1 ml), and 663 µl of this solution were added to a solution of Example 63 (160 mg, 226 µmol) in pyridine (54 µl). The mixture was stirred at rt for 2 h, then diluted with methanol (1 ml), and stirring was continued at 40° C. for another 2 h. After evaporation, the residue was purified by preparative RP-HPLC (Reprosil C18, gradient 10-95% acetonitrile/0.1% aq. formic acid) affording 74 mg (61% of th.) of title compound.

LC-MS (method 4): $R_t$=0.65 min; MS (ESIpos): m/z=508 (M+H)⁺

¹H-NMR (400 MHz, DMSO-$d_6$): δ=8.13 (s, 1H), 8.06-7.89 (m, 3H), 7.38 (s, 1H), 7.31 (s, 1H), 6.85 (s, 1H), 4.28 (d, 2H), 4.01-3.88 (m, 5H), 2.47-2.34 (m, 7H), 1.75 (s, 3H) ppm.

Example 66

N-({7-[(4-Acetylpiperazin-1-yl)methyl]-4-amino-5-(7-methoxy-5-methyl-1-benzothiophen-2-yl)pyrrolo[2,1-f][1,2,4]triazin-6-yl}methyl)acetamide

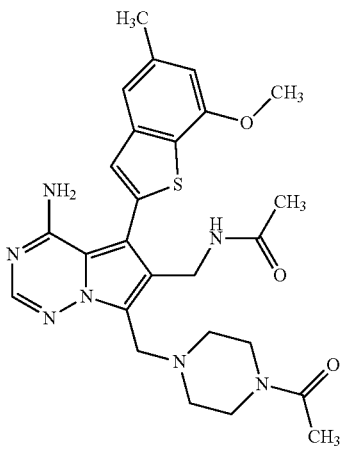 [SMILES: COc1cc(C)cc2cc(-c3c(CNC(C)=O)c(CN4CCN(C(C)=O)CC4)n4ncnc(N)c34)sc12]

A solution of Example 63 (110 mg, 229 μmol) and acetyl chloride (32 μl, 458 μmol) in THF/dichloromethane (1:2, 3 ml) was treated with sodium carbonate (194 mg, 1.83 mmol) and stirred at rt overnight. Then, the mixture was diluted with methanol (2 ml) and water (1 ml) and stirred at rt for 1 h. After evaporation, the residue was purified by preparative RP-HPLC (Reprosil C18, gradient 10-95% acetonitrile/0.1% aq. formic acid). Lyophilization from 1,4-dioxane and re-purification by column chromatography on silica gel (dichloromethane/methanol 50:1→100% methanol) afforded 35 mg (28% of th.) of the title compound.

LC-MS (method 2): $R_t$=0.70 min; MS (ESIpos): m/z=522 (M+H)$^+$ $^1$H-NMR (400 MHz, DMSO-d$_6$): δ=8.04-7.98 (m, 2H), 7.38 (s, 1H), 7.31 (s, 1H), 6.85 (s, 1H), 4.27 (d, 2H), 3.95 (s, 3H), 3.91 (s, 2H), 3.44-3.36 (m, 4H), 2.48-2.35 (m, 7H), 1.98 (s, 3H), 1.75 (s, 3H) ppm.

Example 67

N-({4-Amino-5-(7-methoxy-5-methyl-1-benzothiophen-2-yl)-7-[(3-oxopiperazin-1-yl)methyl]-pyrrolo[2,1-f][1,2,4]triazin-6-yl}methyl)acetamide

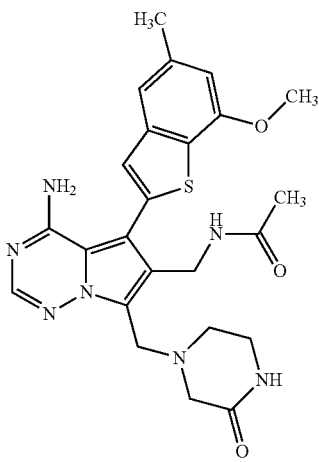 [SMILES: COc1cc(C)cc2cc(-c3c(CNC(C)=O)c(CN4CCNC(=O)C4)n4ncnc(N)c34)sc12]

A suspension of Intermediate 32A (35 mg, 73 μmol) in methanol (4.1 ml) was treated with acetic anhydride (13 μl, 146 μmol) and 10% Pd/C (41 mg) and stirred at rt for 1 h under 1 atm of hydrogen. Filtration over kieselguhr and evaporation of the filtrate afforded 30 mg (79% of th.) of the title compound.

LC-MS (method 5): $R_t$=1.65 min; MS (ESIpos): m/z=494 (M+H)$^+$ $^1$H-NMR (400 MHz, DMSO-d$_6$): δ=7.99 (s, 2H), 7.75 (br. s, 1H), 7.39 (s, 1H), 7.31 (s, 1H), 6.85 (s, 1H), 4.27 (s, 1H), 4.26 (s, 1H), 3.95 (s, 5H), 3.19-3.08 (m, 2H), 3.05-2.96 (m, 2H), 2.66-2.57 (m, 2H), 2.45 (s, 3H), 1.72 (s, 3H) ppm.

Example 68

4-Amino-6-(hydroxymethyl)-5-(7-methoxy-5-methyl-1-benzothiophen-2-yl)pyrrolo[2,1-f][1,2,4]-triazine-7-carbonitrile

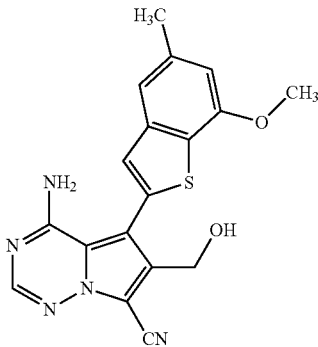 [SMILES: COc1cc(C)cc2cc(-c3c(CO)c(C#N)n4ncnc(N)c34)sc12]

A solution of Intermediate 38A (1 g, 2.08 mmol) in THF (10 ml) was treated with a 1 M solution of tetra-n-butylammonium fluoride in THF (12 ml, 12 mmol). The mixture was stirred at rt overnight and then evaporated. The residue was taken up in water and extracted three times with ethyl acetate. The combined organic phases were dried over magnesium sulfate and evaporated. The residue was triturated in tert-butyl methyl ether, and the solid was filtered off affording 680 mg (78% of th.) of the title compound.

LC-MS (method 2): $R_t$=0.95 min; MS (ESIpos): m/z=366 (M+H)$^+$ $^1$H-NMR (400 MHz, DMSO-d$_6$): δ=8.61-8.29 (br. s, 1H), 8.18 (s, 1H), 7.43 (s, 1H), 7.32 (s, 1H), 6.87 (s, 1H), 6.32-6.03 (br. s, 1H), 5.46 (t, 1H), 4.55 (d, 2H), 3.96 (s, 3H), 2.45 (s, 3H) ppm.

Example 69

4-Amino-6-(methoxymethyl)-5-(7-methoxy-5-methyl-1-benzothiophen-2-yl)pyrrolo[2,1-f][1,2,4]-triazine-7-carbonitrile

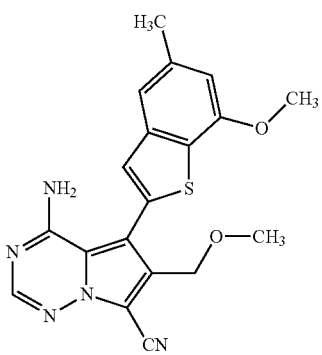 [SMILES: COCc1c(-c2cc3cc(C)cc(OC)c3s2)c2c(N)ncnn2c1C#N]

A solution of Example 68 (60 mg, 164 µmol) in dichloromethane (5 ml) was treated with thionyl chloride (18 µl, 246 µmol). The mixture was stirred at rt for 15 min and then evaporated. The residue was dissolved in methanol (2 ml) and treated with DIPEA (57 µl, 328 µmol). The mixture was stirred first 2 h at 60° C., then refluxed overnight and finally heated to 150° C. for 30 min in a microwave device. After this, the mixture was evaporated, and the residue was purified by preparative RP-HPLC (Reprosil C18, gradient 10-95% acetonitrile/0.1% aq. TFA). The product thus obtained was dissolved in methanol and filtered through an anion exchange cartridge (Stratospheres SPE, PL-HCO$_3$ MP-resin). The cartridge was eluted with methanol, and the filtrate was evaporated affording 18 mg (28% of th.) of the title compound.

LC-MS (method 4): R$_t$=1.12 min; MS (ESIpos): m/z=379 (M+H)$^+$ $^1$H-NMR (400 MHz, DMSO-d$_6$): δ=8.61-8.40 (br. s, 1H), 8.21 (s, 1H), 7.42 (s, 1H), 7.33 (s, 1H), 6.87 (s, 1H), 6.34-6.09 (br. s, 1H), 4.47 (s, 2H), 3.96 (s, 3H), 3.26 (s, 3H), 2.45 (s, 3H) ppm.

Example 70

4-Amino-6-(ethoxymethyl)-5-(7-methoxy-5-methyl-1-benzothiophen-2-yl)pyrrolo[2,1-f][1,2,4]-triazine-7-carbonitrile

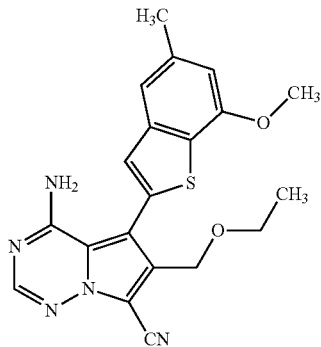 [SMILES: CCOCc1c(-c2cc3cc(C)cc(OC)c3s2)c2c(N)ncnn2c1C#N]

A solution of Example 68 (60 mg, 164 µmol) in dichloromethane (5 ml) was treated with thionyl chloride (18 µl, 246 µmol). The mixture was stirred at rt for 15 min and then evaporated. The residue was dissolved in ethanol (2 ml) and treated with DIPEA (57 µl, 328 µmol). The mixture was stirred at 60° C. overnight and then heated to 150° C. for 30 min in a microwave device. After this, the mixture was evaporated, and the residue was purified by preparative RP-HPLC (Reprosil C18, gradient 10-95% acetonitrile/0.1% aq. TFA). The product thus obtained was dissolved in ethanol (2 ml) and again heated to 150° C. for 30 min in the microwave oven. DIPEA (57 µl, 328 µmol) was added, and heating to 150° C. in the microwave oven was continued for further 30 min. After evaporation, the residue was purified by column chromatography on silica gel (dichloromethane/methanol 95:5) affording 16 mg (23% of th.) of the title compound.

LC-MS (method 2): R$_t$=1.18 min; MS (ESIpos): m/z=393 (M+H)$^+$ $^1$H-NMR (400 MHz, DMSO-d$_6$): δ=8.61-8.38 (br. s, 1H), 8.20 (s, 1H), 7.42 (s, 1H), 7.33 (s, 1H), 6.87 (s, 1H), 6.33-6.08 (br. s, 1H), 4.51 (s, 2H), 3.96 (s, 3H), 3.45 (q, 2H), 2.45 (s, 3H), 1.10 (t, 3H) ppm.

Example 71

4-Amino-5-(7-methoxy-5-methyl-1-benzothiophen-2-yl)-6-[(3-oxopiperazin-1-yl)methyl]pyrrolo-[2,1-f][1,2,4]triazine-7-carbonitrile

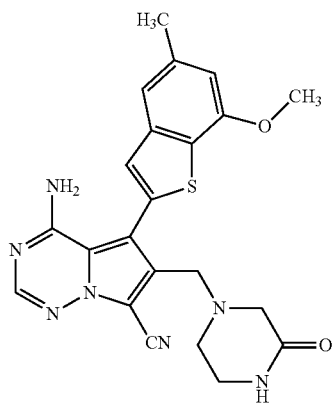 [SMILES: COc1cc(C)cc2cc(-c3c(CN4CCNC(=O)C4)c(C#N)n4ncnc(N)c34)sc12]

A solution of Intermediate 39A (20 mg, 55 µmol) in THF (0.73 ml) was treated with acetic acid (6 µl, 110 µmol), 2-oxopiperazine (27 mg, 275 µmol) and sodium triacetoxyborohydride (58 mg, 275 µmol). After stirring at rt for 3 h, further amounts of THF (1 ml), acetic acid (6 µl, 110 µmol), 2-oxopiperazine (27 mg, 275 µmol) and sodium triacetoxyborohydride (58 mg, 275 µmol) were added, and stirring at rt was continued overnight. After evaporation, the residue was purified by preparative RP-HPLC (Reprosil C18, gradient 10-95% acetonitrile/0.1% aq. TFA). The product thus obtained was dissolved in methanol and filtered through an anion exchange cartridge (Stratospheres SPE, PL-HCO$_3$ MP-resin). The cartridge was eluted with methanol, and the filtrate was evaporated affording 13 mg (52% of th.) of the title compound.

LC-MS (method 2): R$_t$=0.86 min; MS (ESIpos): m/z=447 (M+H)$^+$ $^1$H-NMR (400 MHz, DMSO-d$_6$): δ=8.60-8.31 (br. s, 1H), 8.19 (s, 1H), 7.74 (s, 1H), 7.44 (s, 1H), 7.33 (s, 1H), 6.87 (s, 1H), 6.25-5.98 (br. s, 1H), 3.96 (s, 3H), 3.62 (s, 2H), 3.13-3.07 (m, 2H), 2.91 (s, 2H), 2.45 (s, 3H) ppm.

Example 72

N,N'-{[4-Amino-5-(7-methoxy-5-methyl-1-benzothiophen-2-yl)pyrrolo[2,1-f][1,2,4]triazine-6,7-diyl]bis(methylene)}diacetamide

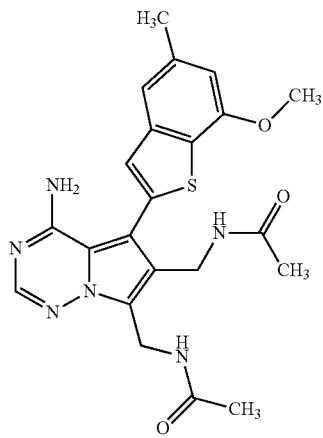 [SMILES: COc1cc(C)cc2cc(-c3c(CNC(C)=O)c(CNC(C)=O)n4ncnc(N)c34)sc12]

A suspension of Intermediate 40A (crude, 85 mg), 10% Pd/C (115 mg) and acetic anhydride (40 µl, 435 mmol) in methanol (12 ml) was stirred at rt under 1 atm of hydrogen. After 4 h, further amounts of 10% Pd/C (115 mg) and acetic anhydride (40 µl, 435 mmol) were added, and stirring at rt under 1 atm of hydrogen was continued for 2 h. The resulting mixture was filtered through kieselguhr, the filtrate was evaporated, and the residue was purified by preparative RP-HPLC (Reprosil C18, gradient 10-95% acetonitrile/0.1% aq. TFA). The product thus obtained was dissolved in methanol and filtered through an anion exchange cartridge (Stratospheres SPE, PL-HCO$_3$ MP-resin). The cartridge was eluted with methanol, and the filtrate was evaporated affording 18 mg (18% of th.) of the title compound.

LC-MS (method 2): R$_t$=0.73 min; MS (ESIpos): m/z=452 (M+H)$^+$ $^1$H-NMR (400 MHz, DMSO-d$_6$): δ=8.29 (br. t, 1H), 8.04 (br. t, 1H), 8.00 (s, 1H), 7.34 (s, 1H), 7.31 (s, 1H), 6.85 (s, 1H), 4.58 (d, 2H), 4.26 (d, 2H), 3.95 (s, 3H), 2.45 (s, 3H), 1.81 (s, 3H), 1.74 (s, 3H) ppm.

Example 73

2-[4-Amino-6-(hydroxymethyl)-5-(7-methoxy-5-methyl-1-benzothiophen-2-yl)pyrrolo[2,1-f]-[1,2,4]triazin-7-yl]propan-2-ol

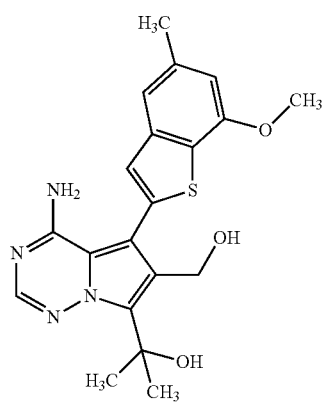 [SMILES: COc1cc(C)cc2cc(-c3c(CO)c(C(C)(C)O)n4ncnc(N)c34)sc12]

A flask containing a suspension of Intermediate 43A (180 mg, 598 µmol), Intermediate 6A (299 mg, 897 µmol) and caesium fluoride (454 mg, 2.99 mmol) in THF/water (10:1, 11 ml) was degassed under reduced pressure and then refilled with argon. 4-(Di-tert-butylphosphino)-N,N-dimethylaniline-dichloropalladium (2:1; 13 mg, 18 µmol) was added. The resulting mixture was degassed again and stirred under argon at 50° C. for 16 h. After this, the reaction mixture was separated by preparative RP-HPLC (Reprosil C18, gradient 30-50% acetonitrile/0.2% aq. TFA). The product fractions were diluted with a 7 M solution of ammonia in methanol and then concentrated under reduced pressure. The precipitate was filtered off, washed with water and dried in vacuo yielding 99 mg (42% of th.) of the title compound.

LC-MS (method 2): R$_t$=0.89 min; MS (ESIpos): m/z=399 (M+H)$^+$ $^1$H-NMR (400 MHz, DMSO-d$_6$): δ=7.96 (s, 1H), 7.51-8.02 (br. s, 1H), 7.37 (s, 1H), 7.31 (s, 1H), 6.86 (s, 1H), 5.99 (s, 1H), 5.23-5.82 (br. s, 1H), 5.04 (t, 1H), 4.53 (d, 2H), 3.96 (s, 3H), 2.45 (s, 3H), 1.73 (s, 6H) ppm.

Example 74

4-{[4-Amino-7-(2-hydroxypropan-2-yl)-5-(7-methoxy-5-methyl-1-benzothiophen-2-yl)pyrrolo-[2,1-f][1,2,4]triazin-6-yl]methyl}piperazin-2-one

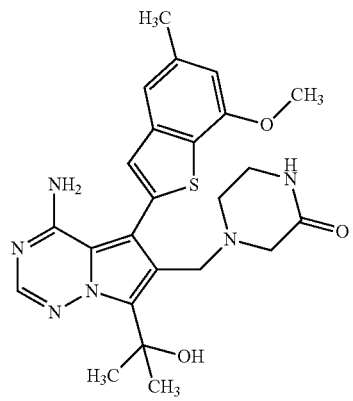 [SMILES: COc1cc(C)cc2cc(-c3c(CN4CCNC(=O)C4)c(C(C)(C)O)n4ncnc(N)c34)sc12]

A solution of Intermediate 44A (50 mg, 73% purity, 92 µmol) in methanol (4 ml) was treated with 2-oxopiperazine (28 mg, 276 µmol), sodium cyanoborohydride (23 mg, 368 µmol) and acetic acid (21 µl, 368 µmol). The mixture was stirred first 18 h at 60° C. and then 3 days at rt. After this, the mixture was separated by preparative RP-HPLC (Reprosil C18, gradient 20-40% acetonitrile/0.2% aq. TFA). The product fractions were diluted with a 7 M solution of ammonia in methanol and evaporated under reduced pressure. The residue was dissolved in ethyl acetate and washed with water. The organic phase was dried with sodium sulfate and concentrated under reduced pressure. The residue was dissolved in 1,4-dioxane and lyophilized yielding 24 mg (52% of th.) of the title compound.

LC-MS (method 5): R$_t$=1.85 min; MS (ESIpos): m/z=481 (M+H)$^+$ $^1$H-NMR (400 MHz, DMSO-d$_6$): δ=7.99 (s, 1H), 7.73-8.01 (br. s, 1H), 7.41 (s, 1H), 7.33 (s, 1H), 6.87 (s, 1H), 5.2-5.7 (br. s, 1H), 3.95 (s, 3H), 3.57 (s, 2H), 3.14 (br. s, 2H), 2.60 (br. s, 4H), 2.46 (s, 3H), 1.70 (br. s, 6H) ppm.

Example 75

[4-Amino-5-(7-methoxy-5-methyl-1-benzothiophen-2-yl)-7-methylpyrrolo[2,1-f][1,2,4]triazin-6-yl]methanol

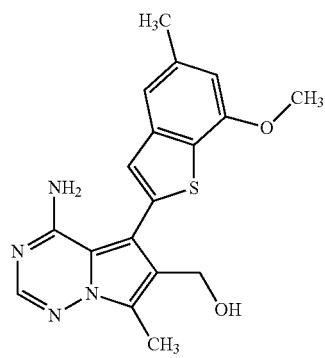 [SMILES: COc1cc(C)cc2cc(-c3c(CO)c(C)n4ncnc(N)c34)sc12]

Under an argon atmosphere, a flask was charged with 165 mg (0.64 mmol) of Intermediate 53A, 143 mg (0.64 mmol) of Intermediate 5A, 25 mg (0.03 mmol) (2'-aminobiphenyl-2-yl)(chloro)palladium-dicyclohexyl(2',4',6'-triisopropylbiphenyl-2-yl)phosphine (1:1; see S. L. Buchwald et al., *J. Am. Chem. Soc.* 132 (40), 14073-14075 (2010)) and 409 mg (1.93 mmol) potassium phosphate. Then, 7 ml of a degassed mixture of 1,4-dioxane and water (5:1) were added, and the solution was stirred at 70° C. for 1 h. Another portion of Intermediate 5A (142 mg, 0.64 mmol) and of (2'-aminobiphenyl-2-yl)(chloro)palladium-dicyclohexyl(2',4',6'-triisopropylbiphenyl-2-yl)phosphine (10 mg, 0.012 mmol) were added, and stirring was continued for 1 h. After this, the reaction mixture was partially evaporated under reduced pressure, water was added, and the mixture was extracted with ethyl acetate. The combined organic phases were evaporated under reduced pressure, and the residue was triturated with acetonitrile. The precipitate was filtered off and dried in vacuo yielding 180 mg (92% purity by LC-MS, 73% of th.) of the title compound. From the filtrate a second batch (41 mg, 18% of th.) was obtained by preparative RP-HPLC (Reprosil C18, gradient 10-95% acetonitrile/0.1% aq. formic acid). Total yield: 91% of th.

LC-MS (method 5): $R_t$=1.92 min; MS (ESIpos): m/z=355 (M+H)$^+$ $^1$H-NMR (400 MHz, DMSO-d$_6$): δ=7.95 (s, 1H), 7.35 (s, 1H), 7.30 (s, 1H), 6.83 (s, 1H), 4.82 (t, 1H), 4.44 (d, 2H), 3.95 (s, 3H), 2.45 (s, 3H) ppm.

Example 76

4-{[4-Amino-5-(7-methoxy-5-methyl-1-benzothiophen-2-yl)-7-methylpyrrolo[2,1-f][1,2,4]triazin-6-yl]methyl}piperazin-2-one

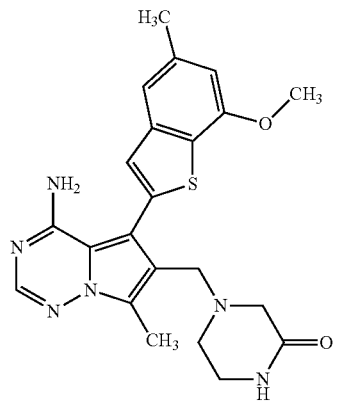

A suspension of 55 mg (0.16 mmol) of Intermediate 54A in THF (1.5 ml) was treated with 78 mg (0.78 mmol) piperazin-2-one, 18 µl (0.31 mmol) acetic acid and 166 mg (0.78 mmol) triacetoxyborohydride. The mixture was stirred at ambient temperature overnight. Then, 1.5 ml water were added, and most of the THF solvent was evaporated under reduced pressure. The remaining mixture was diluted with more water, and the precipitated solid was filtered off and dried (35 mg). This material was further purified by preparative RP-HPLC (Reprosil C18, gradient 10-95% acetonitrile/0.1% aq. formic acid). The product fractions were adjusted to pH 9 with solid potassium carbonate and partially concentrated under reduced pressure. The precipitated solid was filtered off and dried at 45° C. in vacuo to afford 16 mg (24% of th.) of the title compound.

LC-MS (method 5): $R_t$=1.74 min; MS (ESIpos): m/z=437 (M+H)$^+$ $^1$H-NMR (400 MHz, DMSO-d$_6$): δ=7.95 (s, 1H), 7.66 (br. s, 1H), 7.35 (s, 1H), 7.30 (s, 1H), 6.83 (s, 1H), 3.95 (s, 3H), 3.50 (s, 2H), 3.05 (m, 2H), 2.84 (s, 2H), 2.45 (m, 5H) ppm.

Example 77

1-({[4-Amino-5-(7-methoxy-5-methyl-1-benzothiophen-2-yl)-7-methylpyrrolo[2,1-f][1,2,4]triazin-6-yl]methyl}amino)-2-methylpropan-2-ol formiate

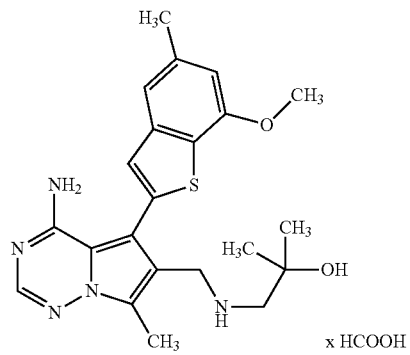 [SMILES: COc1cc(C)cc2cc(-c3c(CNCC(C)(C)O)c(C)n4ncnc(N)c34)sc12]

A suspension of 55 mg (0.16 mmol) of Intermediate 54A in THF (1.5 ml) was treated with 98 mg (0.78 mmol) 1-amino-2-methylpropan-2-ol hydrochloride, 39 mg (0.47 mmol) sodium acetate and 166 mg (0.78 mmol) sodium triacetoxyborohydride. The mixture was stirred at ambient temperature overnight. Then, 1.5 ml water were added, and the mixture was evaporated under reduced pressure. The residue was purified by preparative RP-HPLC (Reprosil C18, gradient 10-95% acetonitrile/0.1% aq. formic acid) to afford 38 mg (52% of th.) of the title compound.

LC-MS (method 5): $R_t$=1.68 min; MS (ESIpos): m/z=426 (M+H)$^+$ $^1$H-NMR (400 MHz, DMSO-d$_6$): δ=8.19 (s, 1H), 7.94 (s, 1H), 7.38 (s, 1H), 7.29 (s, 1H), 6.84 (s, 1H), 3.95 (s, 3H), 2.45 (s, 3H), 2.34 (s, 2H), 1.02 (s, 6H) ppm.

Example 78

1-({[4-Amino-5-(7-methoxy-5-methyl-1-benzothiophen-2-yl)-7-methylpyrrolo[2,1-f][1,2,4]triazin-6-yl]methyl}amino)-2-methylpropan-2-ol

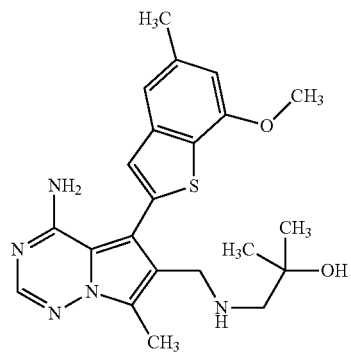 [SMILES: COc1cc(C)cc2cc(-c3c(CNCC(C)(C)O)c(C)n4ncnc(N)c34)sc12]

A solution of 29 mg (0.06 mmol) of Example 77 in 3 ml of methanol was run through a Stratospheres SPE PL-HCO₃ MP-resin cartridge, preconditioned with 2 ml of methanol. The cartridge was washed with 4 ml of methanol, and the eluate was evaporated to afford 21.5 mg (82% of th.) of the title compound.

LC-MS (method 4): $R_t$=0.68 min; MS (ESIpos): m/z=426 (M+H)$^+$ $^1$H-NMR (400 MHz, DMSO-d$_6$): δ=7.94 (s, 1H), 7.37 (s, 1H), 7.28 (s, 1H), 6.83 (s, 1H), 4.07 (s, 1H), 3.95 (s, 3H), 3.63-3.75 (m, 2H), 2.45 (s, 3H), 2.32 (m, 3H), 1.42-1.56 (m, 1H), 1.02 (s, 6H) ppm.

Example 79

[4-Amino-7-chloro-5-(7-methoxy-5-methyl-1-benzothiophen-2-yl)pyrrolo[2,1-f][1,2,4]triazin-6-yl]methanol

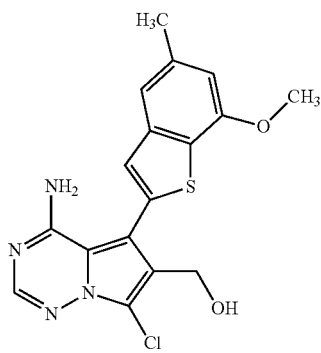 [SMILES: COc1cc(C)cc2cc(-c3c(CO)c(Cl)n4ncnc(N)c34)sc12]

A solution of Intermediate 48A (117 mg, 0.24 mmol) in 5 ml THF was treated with 5 ml conc. hydrochloric acid and stirred at ambient temperature overnight. Then, 12 ml of 5 M aq. sodium hydroxide solution as well as ethyl acetate were added, the layers were separated, and the aqueous layer was extracted twice with ethyl acetate. The combined organic phases were washed with sat. aq. sodium chloride solution, dried and evaporated. The residue was purified by preparative RP-HPLC (Reprosil C18, gradient 10-95% acetonitrile/0.1% aq. formic acid) to afford 30 mg (34% of th.) of the title compound.

LC-MS (method 2): $R_t$=0.90 min; MS (ESIpos): m/z=375 (M+H)$^+$ $^1$H-NMR (400 MHz, DMSO-d$_6$): δ=8.04 (s, 1H), 7.43 (s, 1H), 7.32 (s, 1H), 6.85 (s, 1H), 5.02 (t, 1H), 4.43 (d, 2H), 3.96 (s, 3H), 2.45 (s, 3H) ppm.

9.2 mg (10% of th.) of 7-chloro-6-(chloromethyl)-5-(7-methoxy-5-methyl-1-benzothiophen-2-yl)pyrrolo[2,1-f][1,2,4]triazin-4-amine were isolated as a by-product (cf. Intermediate 50A).

Example 80

4-{[4-Amino-7-chloro-5-(7-methoxy-5-methyl-1-benzothiophen-2-yl)pyrrolo[2,1-f][1,2,4]triazin-6-yl]methyl}piperazin-2-one

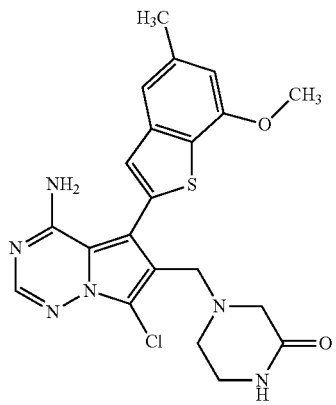 [SMILES: COc1cc(C)cc2cc(-c3c(CN4CCNC(=O)C4)c(Cl)n4ncnc(N)c34)sc12]

The title compound was prepared according to the procedure of Example 76 starting from 40 mg (0.11 mmol) of Intermediate 49A. Yield: 27 mg (55% of th.).

LC-MS (method 2): $R_t$=0.86 min; MS (ESIpos): m/z=457 (M+H)$^+$ $^1$H-NMR (400 MHz, DMSO-d$_6$): δ=8.05 (s, 1H), 7.68 (br. s, 1H), 7.44 (s, 1H), 7.31 (s, 1H), 6.85 (s, 1H), 3.96 (s, 3H), 3.52 (s, 2H), 3.05 (br. s, 2H), 2.86 (s, 2H), 2.45 (s, 3H) ppm.

Example 81

1-({[4-Amino-7-chloro-5-(7-methoxy-5-methyl-1-benzothiophen-2-yl)pyrrolo[2,1-f][1,2,4]triazin-6-yl]methyl}amino)-2-methylpropan-2-ol formiate

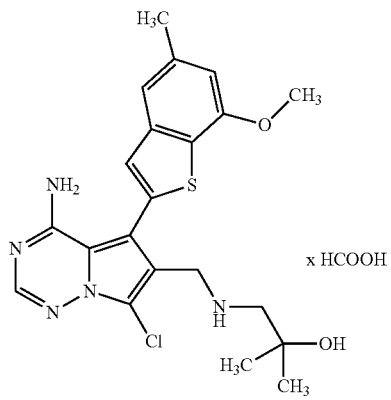 [SMILES: COc1cc(C)cc2cc(-c3c(CNCC(C)(C)O)c(Cl)n4ncnc(N)c34)sc12]

The title compound was prepared according to the procedure of Example 77 starting from 40 mg (0.11 mmol) of Intermediate 49A. Yield: 24 mg (45% of th.).

LC-MS (method 2): $R_t$=0.73 min; MS (ESIpos): m/z=446 (M+H)$^+$ $^1$H-NMR (400 MHz, DMSO-d$_6$): δ=8.15 (s, 1H), 8.04 (s, 1H), 7.45 (s, 1H), 7.30 (s, 1H), 6.85 (s, 1H), 3.96 (s, 3H), 3.73 (s, 2H), 2.45 (s, 3H), 2.32 (s, 2H), 1.00 (s, 6H) ppm.

Example 82

1-({[4-Amino-7-chloro-5-(7-methoxy-5-methyl-1-benzothiophen-2-yl)pyrrolo[2,1-f][1,2,4]triazin-6-yl]methyl}amino)-2-methylpropan-2-ol

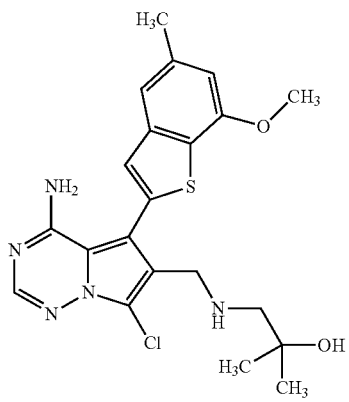 [SMILES: COc1cc(C)cc2cc(-c3c(CNCC(C)(C)O)c(Cl)n4ncnc(N)c34)sc12]

The title compound was prepared from Example 81 according to the procedure of Example 78.

LC-MS (method 2): $R_t$=0.72 min; MS (ESIpos): m/z=446 (M+H)$^+$ $^1$H-NMR (400 MHz, DMSO-d$_6$): δ=8.04 (s, 1H), 7.45 (s, 1H), 7.30 (s, 1H), 6.85 (s, 1H), 4.09 (br. s, 1H), 3.95 (s, 3H), 3.71 (s, 2H), 2.45 (s, 3H), 2.31 (s, 2H), 1.44-1.64 (m, 1H), 1.00 (s, 6H) ppm.

Example 83

7-Chloro-6-(ethoxymethyl)-5-(7-methoxy-5-methyl-1-benzothiophen-2-yl)pyrrolo[2,1-f][1,2,4]-triazin-4-amine

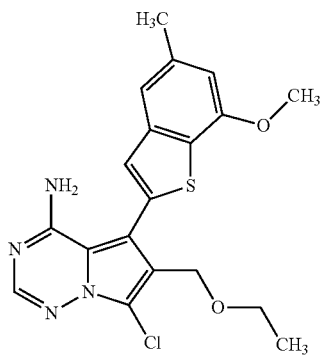 [SMILES: CCOCc1c(-c2cc3cc(C)cc(OC)c3s2)c2c(N)ncnn2c1Cl]

8.2 mg (0.02 mmol) of Intermediate 50A were suspended in 1 ml of ethanol, treated with 41 μl (0.11 mmol) of a 2.68 M solution of sodium ethanolate in ethanol and refluxed for 1 min. The clear solution was then evaporated, and the crude product was purified by preparative RP-HPLC (Reprosil C18, gradient 10-95% acetonitrile/0.1% aq. formic acid) to afford 5 mg (56% of th.) of the title compound.

LC-MS (method 4): $R_t$=1.25 min; MS (ESIpos): m/z=402 (M+H)$^+$ $^1$H-NMR (400 MHz, DMSO-d$_6$): δ=8.06 (s, 1H), 7.40 (s, 1H), 7.32 (s, 1H), 6.86 (s, 1H), 4.40 (s, 2H), 3.96 (s, 3H), 3.40 (q, 2H), 2.45 (s, 3H), 1.06 (t, 3H) ppm.

Example 84

5-(7-Methoxy-5-methyl-1-benzothiophen-2-yl)-6-methyl-7-(piperazin-1-ylmethyl)pyrrolo[2,1-f]-[1,2,4]triazin-4-amine formiate

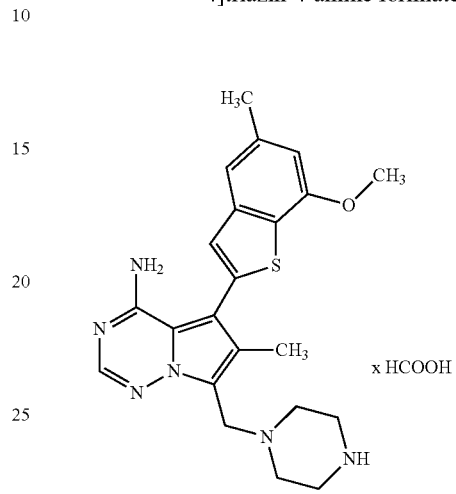

A solution of Intermediate 57A (100 mg, 191 μmol) in a 4 M solution of hydrogen chloride in 1,4-dioxane (2 ml) was stirred at rt for 3 h and then evaporated. Purification by two-fold preparative RP-HPLC (Reprosil C18, gradient 10-95% acetonitrile/0.1% aq. formic acid) afforded 71 mg (67% of th.) of the title compound.

LC-MS (method 2): $R_t$=0.81 min; MS (ESIpos): m/z=423 (M+H)$^+$ $^1$H-NMR (400 MHz, CDCl$_3$): δ=8.46 (br. s, 1H), 7.89 (s, 1H), 7.27 (s, 1H, overlap with CHCl$_3$ peak), 7.18 (s, 1H), 6.67 (s, 1H), 4.01 (s, 3H), 3.97 (s, 2H), 3.18-3.09 (m, 4H), 2.82-2.73 (m, 4H), 2.50 (s, 3H), 2.24 (s, 3H) ppm.

Example 85

6-Chloro-5-(7-methoxy-5-methyl-1-benzothiophen-2-yl)-7-(piperazin-1-ylmethyl)pyrrolo[2,1-f]-[1,2,4]triazin-4-amine trihydrochloride

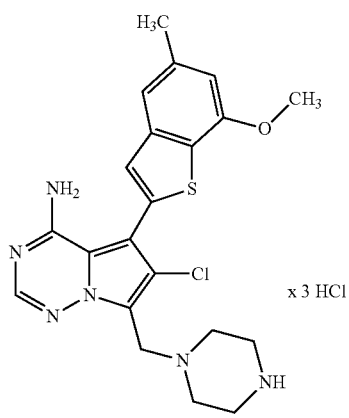 [SMILES: COc1cc(C)cc2cc(-c3c(Cl)c(CN4CCNCC4)n4ncnc(N)c34)sc12]

Intermediate 60A (65 mg, 0.12 mmol) was stirred in 1 ml of a 4 M solution of hydrogen chloride in 1,4-dioxane for 2 h at rt. The suspension was evaporated to dryness, and the crude product was purified by preparative RP-HPLC (Reprosil C18, gradient 10-95% acetonitrile/0.1% aq. hydrochloric acid) affording 49 mg (74% of th.) of the title compound.

LC-MS (method 2): $R_t$=0.81 min; MS (ESIpos): m/z=443 (M+H)$^+$ $^1$H-NMR (400 MHz, DMSO-d$_6$): inter al. δ=9.56 (br. s, 1H), 8.45 (br. s, 1H), 8.19 (s, 1H), 7.44 (s, 1H), 7.36 (s, 1H), 6.89 (s, 1H), 6.30 (br. s, 1H), 4.63 (br. s, 1H), 3.40 (br. s, 8H), 2.46 (s, 3H) ppm.

Example 86

[4-Amino-6-(ethoxymethyl)-5-(7-methoxy-5-methyl-1-benzothiophen-2-yl)pyrrolo[2,1-f][1,2,4]-triazin-7-yl]methanol

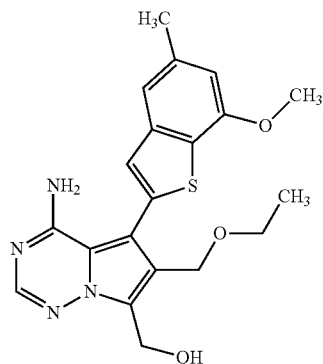 [SMILES: CCOCc1c(-c2cc3cc(C)cc(OC)c3s2)c2c(N)ncnn2c1CO]

The title compound (360 mg) was obtained as a side product in the preparation of Example 5 by preparation method 1.

LC-MS (method 2): $R_t$=0.99 min; MS (ESIpos): m/z=399 (M+H)$^+$ $^1$H-NMR (400 MHz, DMSO-d$_6$): δ=8.09-7.72 (br. s, 1H), 7.99 (s, 1H), 7.35 (s, 1H), 7.31 (s, 1H), 6.84 (s, 1H), 6.05-5.48 (br. s, 1H), 5.04 (br. s, 1H), 4.81 (d, 2H), 4.47 (s, 2H), 3.96 (s, 3H), 3.39 (q, 3H), 2.45 (s, 3H), 1.05 (t, 3H) ppm.

Example 87

1-{[4-Amino-6-(ethoxymethyl)-5-(7-methoxy-5-methyl-1-benzothiophen-2-yl)pyrrolo[2,1-f]-[1,2,4]triazin-7-yl]methyl}imidazolidin-2-one

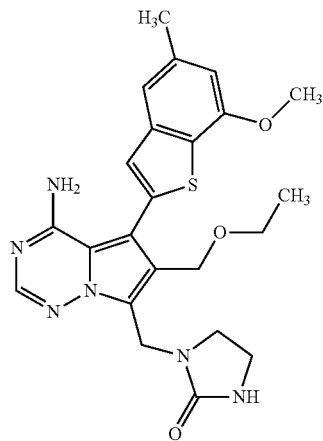 [SMILES: CCOCc1c(-c2cc3cc(C)cc(OC)c3s2)c2c(N)ncnn2c1CN1CCNC1=O]

A suspension of Intermediate 63A (100 mg, 0.221 mmol) in THF (5 ml) was treated with imidazolidin-2-one (57 mg, 0.662 mmol) and N,N-diisopropylethylamine (153 µl, 0.926 mmol), and the mixture was heated to 150° C. for 90 min in a microwave oven. After this, the reaction mixture was purified by preparative RP-HPLC (Reprosil C18, gradient 40-60% acetonitrile/0.2% aq. trifluoroacetic acid). The product thus obtained was dissolved in methanol and filtered through an anion exchange cartridge (Stratospheres SPE, PL-HCO$_3$ MP-resin). The cartridge was eluted with methanol, and the filtrate was evaporated. The product was purified once again by preparative thin layer chromatography over silica gel (cyclohexane/ethyl acetate 3:1) affording 24 mg (22% of th.) of the title compound.

LC-MS (method 2): $R_t$=0.99 min; MS (ESIpos): m/z=467 (M+H)$^+$ $^1$H-NMR (400 MHz, DMSO-d$_6$): δ=8.21-7.65 (br. s, 1H), 7.99 (s, 1H), 7.36 (s, 1H), 7.31 (s, 1H), 6.84 (s, 1H), 6.38 (s, 1H), 6.04-5.56 (br. s, 1H), 4.65 (s, 2H), 4.46 (s, 2H), 3.95 (s, 3H), 3.38 (q, 2H), 3.31-3.10 (m, 4H), 2.45 (s, 3H), 1.06 (t, 3H) ppm.

Example 88

4-{[4-Amino-5-(7-methoxy-1-benzothiophen-2-yl)-6-(methoxymethyl)pyrrolo[2,1-f][1,2,4]triazin-7-yl]methyl}piperazin-2-one

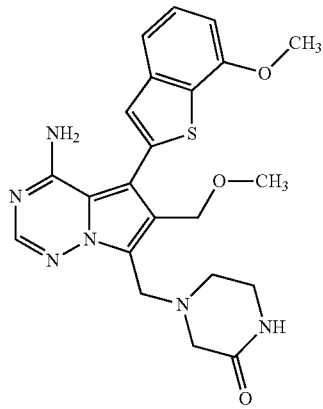 [SMILES: COCc1c(-c2cc3cccc(OC)c3s2)c2c(N)ncnn2c1CN1CCNC(=O)C1]

To a solution of Intermediate 62A (72.6 mg, 197 µmol), (7-methoxy-1-benzothiophen-2-yl)boronic acid (45 mg, 216 µmol) and caesium fluoride (149 mg, 983 µmol) in degassed THF/water (10:1, 2.2 ml) under argon was added (2'-amino-biphenyl-2-yl)(chloro)palladium-dicyclohexyl(2',4',6'-tri-isopropylbiphenyl-2-yl)phosphine (1:1; 7.7 mg, 9.8 µmol; see S. L. Buchwald et al., *J. Am. Chem. Soc.* 132 (40), 14073-14075 (2010)). The resulting mixture was degassed again and stirred under argon at 60° C. for 3 h. After this, the mixture was separated by preparative RP-HPLC (Reprosil C18, gradient 20-40% acetonitrile/0.1% aq. TFA). The product fractions were combined and evaporated to dryness. The residue was dissolved in methanol and filtered through an anion exchange cartridge (Stratospheres SPE, PL-HCO$_3$ MP-resin). The cartridge was eluted with methanol, and the filtrate was evaporated affording 31 mg (35% of th.) of the title compound.

LC-MS (method 2): $R_t$=0.71 min; MS (ESIpos): m/z=453 (M+H)$^+$ $^1$H-NMR (400 MHz, DMSO-d$_6$): δ=8.00 (s, 1H), 7.72 (s, 1H), 7.61-8.23 (br. s, 1H), 7.51 (d, 1H), 7.46 (s, 1H), 7.40 (t, 1H), 6.99 (d, 1H), 5.57-6.11 (br. s, 1H), 4.42 (s, 2H), 3.98 (s, 5H), 3.20 (s, 3H), 3.11 (br. m, 2H), 3.01 (s, 2H), 2.62-2.67 (m, 2H) ppm.

Example 89

4-{[4-Amino-6-(methoxymethyl)-5-(5-methyl-1-benzothiophen-2-yl)pyrrolo[2,1-f][1,2,4]triazin-7-yl]methyl}piperazin-2-one

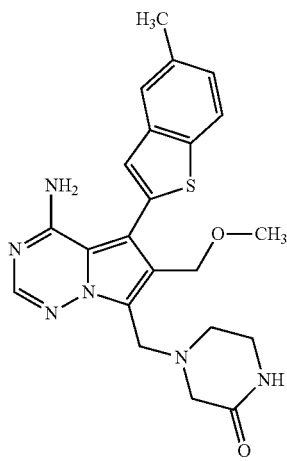 [SMILES: COCc1c(-c2cc3cc(C)ccc3s2)c2c(N)ncnn2c1CN1CCNC(=O)C1]

To a solution of Intermediate 62A (50 mg, 135 μmol), (5-methyl-1-benzothiophen-2-yl)boronic acid (28.6 mg, 149 μmol) and caesium fluoride (103 mg, 677 μmol) in degassed THF/water (10:1, 4.4 ml) under argon was added (2'-aminobiphenyl-2-yl)(chloro)palladium-dicyclohexyl(2',4',6'-triisopropylbiphenyl-2-yl)phosphine (1:1; 5.3 mg, 6.8 μmol; see S. L. Buchwald et al., *J. Am. Chem. Soc.* 132 (40), 14073-14075 (2010)). The resulting mixture was degassed again and stirred under argon at 60° C. for 16 h. After this, the mixture was separated by preparative RP-HPLC (Reprosil C18, gradient 30-50% acetonitrile/0.1% aq. TFA). The product fractions were combined and evaporated to dryness. The residue was dissolved in methanol and filtered through an anion exchange cartridge (StratoSpheres SPE, PL-HCO$_3$ MP-resin). The cartridge was eluted with methanol, and the filtrate was evaporated affording 27 mg (45% of th.) of the title compound.

LC-MS (method 2): $R_t$=0.79 min; MS (ESIpos): m/z=437 (M+H)$^+$ $^1$H-NMR (400 MHz, DMSO-d$_6$): δ=8.00 (s, 1H), 7.89 (d, 1H), 7.73 (s, 1H), 7.71 (s, 1H), 7.58-8.18 (br. s, 1H), 7.40 (s, 1H), 7.24 (dd, 1H), 5.58-6.03 (m, 1H), 4.42 (s, 2H), 3.97 (s, 2H), 3.21 (s, 3H), 3.11 (br. t, 2H), 3.01 (s, 2H), 2.64 (t, 2H), 2.44 (s, 3H) ppm.

Example 90

1-[4-Amino-6-(ethoxymethyl)-5-(7-methoxy-5-methyl-1-benzothiophen-2-yl)pyrrolo[2,1-f][1,2,4]triazin-7-yl]ethanol

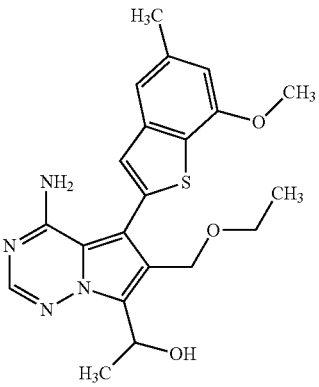 [SMILES: CCOCc1c(-c2cc3cc(C)cc(OC)c3s2)c2c(N)ncnn2c1C(C)O]

Under argon, a 1 M solution of methylmagnesium bromide in THF (630 μl, 630 μmol) was added dropwise at rt to a solution of Intermediate 17A (100 mg, 252 μmol) in THF (10 ml). The mixture was stirred at rt for 3 h and then treated with another portion of methylmagnesium bromide in THF (177 μl, 177 μmol). The reaction mixture was stirred for further 16 h, then quenched with sat. aq. ammonium chloride solution and extracted with ethyl acetate. The combined organic layers were washed with brine, dried with magnesium sulfate, filtered and evaporated. The residue was purified by preparative RP-HPLC (Reprosil C18, gradient 40-60% acetonitrile/0.1% aq. TFA). The product fractions were diluted with sat. aq. sodium hydrogencarbonate solution and extracted with ethyl acetate. The organic phase was washed with sat. aq. sodium chloride solution, dried with magnesium sulfate, filtered and evaporated yielding 39 mg (36% of th.) of the title compound.

LC-MS (method 4): $R_t$=1.07 min; MS (ESIpos): m/z=413 (M+H)$^+$ $^1$H-NMR (400 MHz, DMSO-d$_6$): δ=7.95 (s, 1H), 7.56-8.07 (br. s, 1H), 7.35 (s, 1H), 7.31 (s, 1H), 6.84 (s, 1H), 5.46-5.54 (m, 1H), 5.37-5.95 (br. s, 1H), 5.26 (d, 1H), 4.67 (d, 1H), 4.38 (d, 1H), 3.95 (s, 3H), 3.38 (q, 2H), 2.45 (s, 3H), 1.52 (d, 3H), 1.05 (t, 3H) ppm.

Example 91

[4-Amino-6-(ethoxymethyl)-5-(7-methoxy-5-methyl-1-benzothiophen-2-yl)pyrrolo[2,1-f][1,2,4]triazin-7-yl](cyclopropyl)methanol

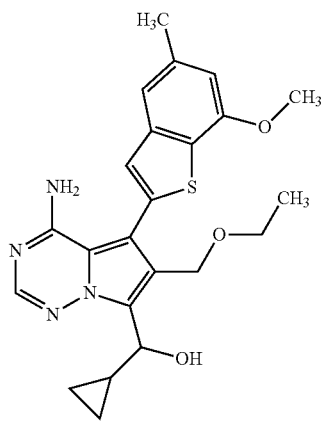 [SMILES: CCOCc1c(-c2cc3cc(C)cc(OC)c3s2)c2c(N)ncnn2c1C(O)C1CC1]

Under argon, a 0.5 M solution of cyclopropylmagnesium bromide in THF (1.26 ml, 630 μmol) was added dropwise at rt to a solution of Intermediate 17A (100 mg, 252 μmol) in THF (5 ml). The mixture was stirred at rt for 1 h, then quenched with sat. aq. ammonium chloride solution and extracted with ethyl acetate. The combined organic layers were washed with brine, dried with magnesium sulfate, filtered and evaporated. The residue was purified by preparative RP-HPLC (Reprosil C18, gradient 50-70% acetonitrile/0.1% aq. TFA). The product fractions were diluted with sat. aq. sodium hydrogencarbonate solution and extracted with ethyl acetate. The organic phase was washed with sat. aq. sodium chloride solution, dried with magnesium sulfate, filtered and evaporated yielding 10 mg (10% of th.) of the title compound.

LC-MS (method 2): $R_t$=1.13 min; MS (ESIpos): m/z=439 (M+H)$^+$ $^1$H-NMR (400 MHz, DMSO-d$_6$): δ=7.94 (s, 1H), 7.68-8.04 (br. s, 1H), 7.36 (s, 1H), 7.31 (s, 1H), 6.84 (s, 1H), 5.47-5.89 (br. s, 1H), 5.30 (d, 1H), 4.64 (d, 1H), 4.59-4.67 (m, 1H), 4.39 (d, 1H), 3.96 (s, 3H), 3.38 (q, 2H), 2.45 (s, 3H), 1.54-1.64 (m, 1H), 1.04 (t, 3H), 0.51-0.59 (m, 1H), 0.40-0.47 (m, 1H), 0.28-0.38 (m, 2H) ppm.

Example 92

(3S)-3-({[4-Amino-6-(methoxymethyl)-5-(7-methoxy-5-methyl-1-benzothiophen-2-yl)pyrrolo-[2,1-f][1,2,4]triazin-7-yl]methyl}amino)pyrrolidin-2-one

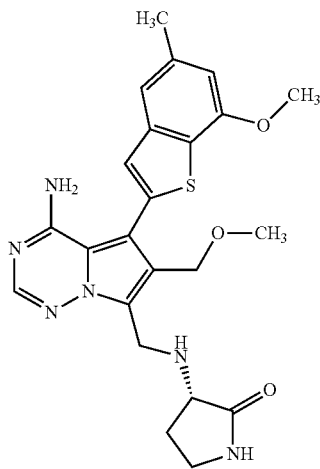 [SMILES: COCc1c(-c2cc3cc(C)cc(OC)c3s2)c2c(N)ncnn2c1CN[C@H]1CCNC1=O]

A suspension of Intermediate 13A (100 mg, 0.233 mmol) in THF (2 ml) was treated with (S)-3-aminopyrrolidin-2-one (35 mg, 0.349 mmol), sodium triacetoxyborohydride (148 mg, 0.698 mmol) and acetic acid (26.6 μl, 0.465 mmol). The resulting mixture was stirred at rt for 3 h and then directly purified by preparative RP-HPLC (Reprosil C18, gradient 40-60% acetonitrile/0.2% aq. trifluoroacetic acid). The product fractions were combined and evaporated to dryness. The residue was dissolved in methanol and filtered through an anion exchange cartridge (Stratospheres SPE, PL-HCO$_3$ MP-resin). The cartridge was eluted with methanol, and the filtrate was evaporated affording 56 mg (51% of th.) of the title compound.

LC-MS (method 4): $R_t$=0.72 min; MS (ESIpos): m/z=467 (M+H)$^+$ $^1$H-NMR (400 MHz, DMSO-d$_6$): δ=8.01 (s, 1H), 7.76 (s, 1H), 7.35 (s, 1H), 7.31 (s, 1H), 6.85 (s, 1H), 4.48 (d, 2H), 4.43 (d, 2H), 4.24-4.02 (m, 2H), 3.96 (s, 3H), 3.26-2.99 (m, 6H), 2.45 (s, 3H), 2.40-2.27 (m, 1H), 1.82-1.64 (m, 1H) ppm.

Example 93

(3S)-3-({[4-Amino-6-(ethoxymethyl)-5-(7-methoxy-5-methyl-1-benzothiophen-2-yl)pyrrolo[2,1-f]-[1,2,4]triazin-7-yl]methyl}amino)pyrrolidin-2-one

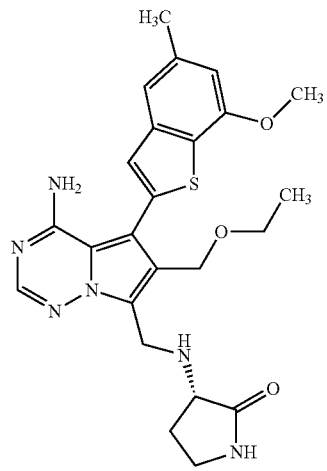 [SMILES: CCOCc1c(-c2cc3cc(C)cc(OC)c3s2)c2c(N)ncnn2c1CN[C@H]1CCNC1=O]

A suspension of Intermediate 17A (100 mg, 0.252 mmol) in THF (2 ml) was treated with (S)-3-aminopyrrolidin-2-one (38 mg, 378 μmol), sodium triacetoxyborohydride (160 mg, 757 μmol) and acetic acid (30 μl, 504 μmol). The resulting mixture was stirred at rt for 3 h and then directly purified by preparative RP-HPLC (Reprosil C18, gradient 30-50% acetonitrile/0.2% aq. trifluoroacetic acid). The product fractions were combined and evaporated to dryness. The residue was dissolved in methanol and filtered through an anion exchange cartridge (Stratospheres SPE, PL-HCO$_3$ MP-resin). The cartridge was eluted with methanol, and the filtrate was evaporated affording 84 mg (69% of th.) of the title compound.

LC-MS (method 4): $R_t$=0.75 min; MS (ESIpos): m/z=481 (M+H)$^+$ $^1$H-NMR (400 MHz, DMSO-d$_6$): δ=8.00 (s, 1H), 7.75 (s, 1H), 7.67-8.11 (br. s, 1H), 7.35 (s, 1H), 7.31 (s, 1H), 6.85 (s, 1H), 5.5-6.0 (br. s, 1H), 4.44 (q, 2H), 4.14-4.21 (m, 1H), 4.02-4.11 (m, 1H), 3.38-3.45 (q, 2H), 3.16-3.24 (m, 1H), 3.05-3.16 (m, 2H), 2.45 (s, 3H), 2.31-2.40 (m, 1H), 1.67-1.79 (m, 1H), 1.08 (t, 3H) ppm.

General Procedure for the Preparation of Examples 94-105 in Table I:

A 0.13 M suspension of Intermediate 17A in THF was treated with 1.5 eq. of the respective amine component, 3 eq. of sodium triacetoxyborohydride and 1.5 eq. of acetic acid. The resulting mixture was stirred at 60° C. for 3-20 h. After this, purification was carried out according to the methods indicated.

TABLE I
| Example No. | Structure | Purification method(s) | LC-MS data |
|---|---|---|---|
| 94 | 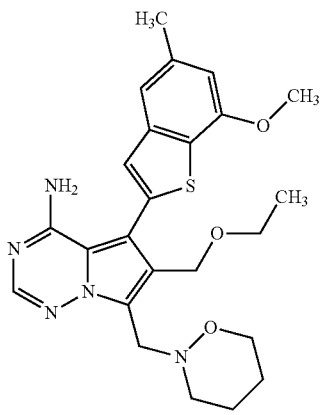 | P1, P5 | Method 4:<br>$R_t$ = 1.22 min;<br>MS (ESIpos): m/z = 468 (M + H)$^+$ |
| 95 | 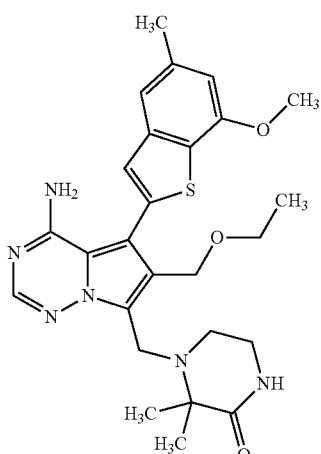 | P6, P3 | Method 2:<br>$R_t$ = 0.92 min;<br>MS (ESIpos): m/z = 509 (M + H)$^+$ |
| 96 | 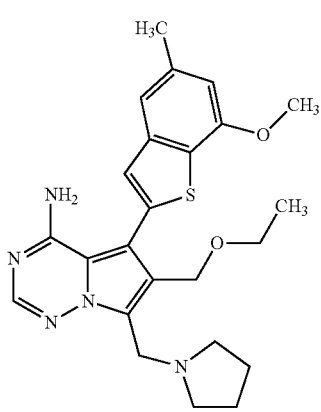 [SMILES: CCOCc1c(-c2cc3cc(C)cc(OC)c3s2)c2c(N)ncnn2c1CN1CCCC1] | P1, P5 | Method 4:<br>$R_t$ = 0.83 min;<br>MS (ESIpos): m/z = 452 (M + H)$^+$ |

TABLE I-continued

| Example No. | Structure | Purification method(s) | LC-MS data |
|---|---|---|---|
| 97 | 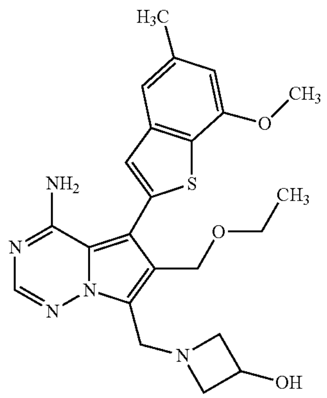 [SMILES: CCOCc1c(-c2cc3cc(C)cc(OC)c3s2)c2c(N)ncnn2c1CN1CC(O)C1] | P1, P5 | Method 5: $R_t$ = 1.84 min; MS (ESIpos): m/z = 454 (M + H)$^+$ |
| 98 | 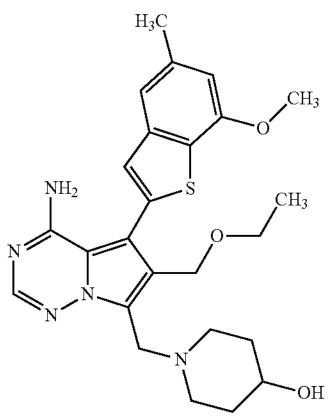 [SMILES: CCOCc1c(-c2cc3cc(C)cc(OC)c3s2)c2c(N)ncnn2c1CN1CCC(O)CC1] | P1, P5 | Method 5: $R_t$ = 1.82 min; MS (ESIpos): m/z = 482 (M + H)$^+$ |
| 99 | 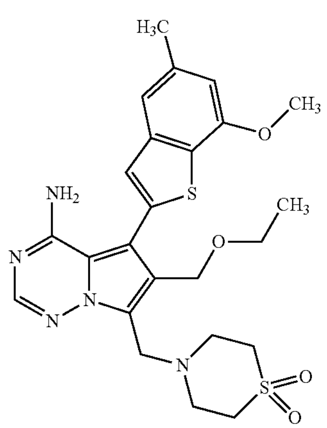 [SMILES: CCOCc1c(-c2cc3cc(C)cc(OC)c3s2)c2c(N)ncnn2c1CN1CCS(=O)(=O)CC1] | P1, P5 | Method 5: $R_t$ = 2.21 min; MS (ESIpos): m/z = 516 (M + H)$^+$ |

TABLE I-continued
| Example No. | Structure | Purification method(s) | LC-MS data |
|---|---|---|---|
| 100 | 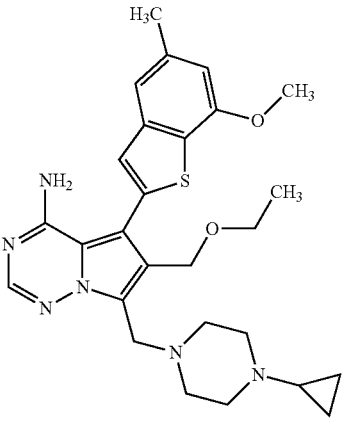 [SMILES: CCOCc1c(-c2cc3cc(C)cc(OC)c3s2)c2c(N)ncnn2c1CN1CCN(C2CC2)CC1] | P1, P5 | Method 2: $R_t$ = 0.86 min; MS (ESIpos): m/z = 507 (M + H)$^+$ |
| 101 | 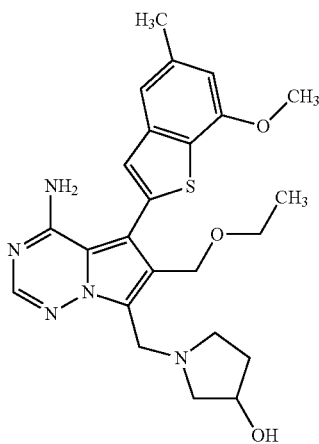 [SMILES: CCOCc1c(-c2cc3cc(C)cc(OC)c3s2)c2c(N)ncnn2c1CN1CCC(O)C1] | P1, P5 | Method 2: $R_t$ = 0.81 min; MS (ESIpos): m/z = 468 (M + H)$^+$ |
| 102 | 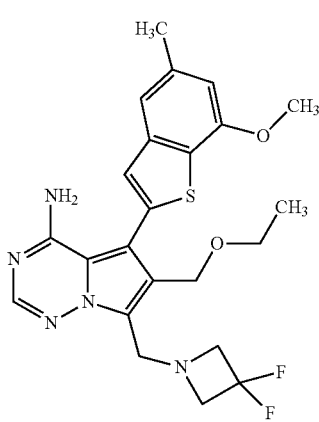 [SMILES: CCOCc1c(-c2cc3cc(C)cc(OC)c3s2)c2c(N)ncnn2c1CN1CC(F)(F)C1] | P1, P5, P4 | Method 2: $R_t$ = 1.03 min; MS (ESIpos): m/z = 474 (M + H)$^+$ |

TABLE I-continued
| Example No. | Structure | Purification method(s) | LC-MS data |
| --- | --- | --- | --- |
| 103 | 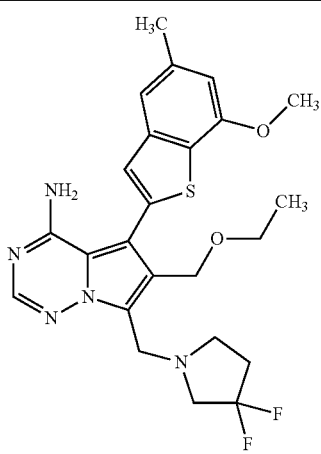 | P1, P5, P2 | Method 2:<br>$R_t$ = 1.05 min;<br>MS (ESIpos): m/z = 460 (M + H)$^+$ |
| 104 | 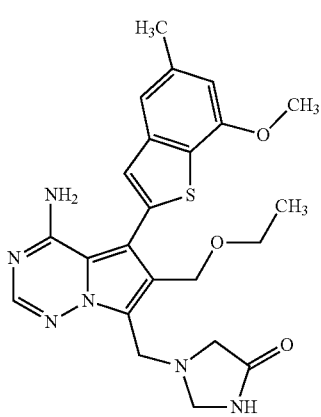 [SMILES: CCOCc1c(-c2cc3cc(C)cc(OC)c3s2)c2c(N)ncnn2c1CN1CNC(=O)C1] | P1, P6 | Method 2:<br>$R_t$ = 0.91 min;<br>MS (ESIpos): m/z = 467 (M + H)$^+$ |
| 105 | 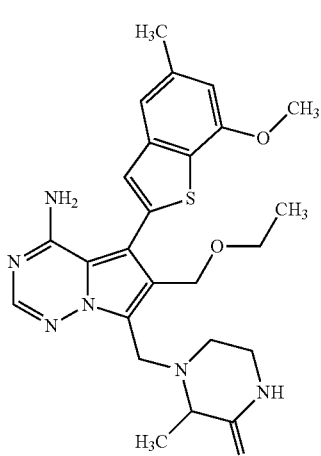 | P1, P6 | Method 2:<br>$R_t$ = 0.89 min;<br>MS (ESIpos): m/z = 495 (M + H)$^+$ |

Example 106

4-Amino-6-(ethoxymethyl)-5-(7-methoxy-5-methyl-1-benzothiophen-2-yl)-N-[(3R)-2-oxopyrrolidin-3-yl]pyrrolo[2,1-f][1,2,4]triazine-7-carboxamide

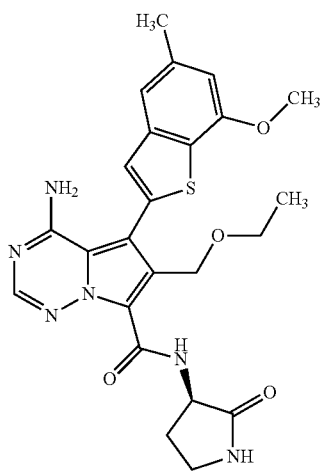 [SMILES: CCOCc1c(-c2cc3cc(C)cc(OC)c3s2)c2c(N)ncnn2c1C(=O)N[C@@H]1CCNC1=O]

A stirred solution of Intermediate 64A (50 mg, 121 µmol) in DMF (2 ml) was treated at rt with N-[(1H-benzotriazol-1-yloxy)(dimethylamino)methylene]-N-methylmethanaminium tetrafluoroborate (TBTU) (43 mg, 133 µmol) and DIPEA (53 µl, 303 µmol). After 15 min, (3R)-3-aminopyrrolidin-2-one (24 mg, 242 µmol) was added, and the resulting mixture was stirred at rt for further 2 h. After this, the mixture was separated by preparative RP-HPLC (Reprosil C18, gradient 30-50% acetonitrile/0.2% aq. trifluoroacetic acid). The product fractions were combined and evaporated to dryness. The residue was dissolved in methanol and filtered through an anion exchange cartridge (Stratospheres SPE, PL-HCO$_3$ MP-resin). The cartridge was eluted with methanol, and the filtrate was evaporated affording 36 mg (60% of th.) of the title compound.

LC-MS (method 2): $R_t$=0.91 min; MS (ESIpos): m/z=495 (M+H)$^+$ $^1$H-NMR (400 MHz, DMSO-d$_6$): δ=9.50 (d, 1H), 8.21-8.45 (br. s, 1H), 8.17 (s, 1H), 7.97 (s, 1H), 7.41 (s, 1H), 7.33 (s, 1H), 6.86 (s, 1H), 5.84-6.09 (br. s, 1H), 4.74 (dd, 2H), 4.47-4.56 (m, 1H), 3.96 (s, 3H), 3.37 (q, 2H), 3.22-3.29 (m, 2H), 2.54-2.61 (m, 1H), 2.46 (s, 3H), 1.90-2.03 (m, 1H), 1.00 (t, 3H) ppm.

Example 107

4-{[4-Amino-6-(ethoxymethyl)-5-(7-methoxy-5-methyl-1-benzothiophen-2-yl)pyrrolo[2,1-f]-[1,2,4]triazin-7-yl]carbonyl}piperazin-2-one

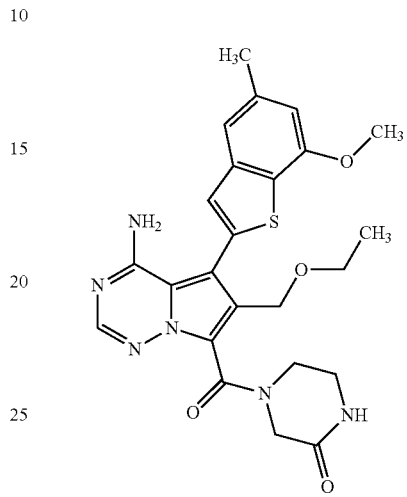

A stirred solution of Intermediate 64A (50 mg, 121 µmol) in DMF (2 ml) was treated at rt with TBTU (43 mg, 133 µmol) and DIPEA (53 µl, 303 µmol). After 15 min, piperazin-2-one (24 mg, 242 µmol) was added, and the resulting mixture was stirred at rt for further 16 h. After this, the mixture was separated by preparative RP-HPLC (Reprosil C18, gradient 40-60% acetonitrile/0.2% aq. trifluoroacetic acid). The product fractions were combined and evaporated to dryness. The residue was dissolved in methanol and filtered through an anion exchange cartridge (Stratospheres SPE, PL-HCO$_3$ MP-resin). The cartridge was eluted with methanol, and the filtrate was evaporated affording 45 mg (68% of th.) of the title compound.

LC-MS (method 2): $R_t$=0.92 min; MS (ESIpos): m/z=495 (M+H)$^+$ $^1$H-NMR (400 MHz, DMSO-d$_6$): δ=8.14 (br. s, 1H), 7.99-8.01 (m, 1H), 7.9-8.3 (br. s, 1H), 7.41 (d, 1H), 7.32 (s, 1H), 6.86 (s, 1H), 5.78-6.05 (br. s, 1H), 4.30-4.49 (m, 2H), 4.13-4.23 (m, 1H), 4.03-4.10 (m, 1H), 3.96 (s, 3H), 3.76-3.87 (m, 1H), 3.57-3.74 (m, 1H), 3.35-3.43 (m, 2H), 3.14-3.25 (m, 1H), 2.45 (s, 3H), 0.96-1.05 (m, 3H) ppm.

General Procedure for the Preparation of Examples 108-123 in Table II:

A 0.13 M solution of Intermediate 64A in DMF was treated with 1.1 eq. TBTU and 2.5 eq. DIPEA and stirred at rt for 15 min. 2 eq. of the respective amine were added, and the resulting mixture was stirred at rt for further 18 h. After this, purification was carried out according to the methods indicated.

TABLE II
| Example No. | Structure | Purification method(s) | LC-MS data |
|---|---|---|---|
| 108 | 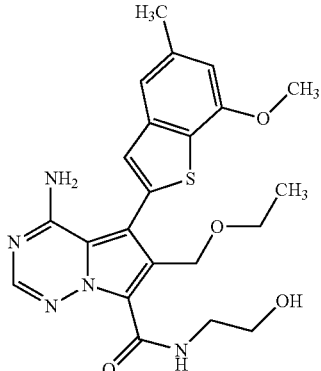 | P1 | Method 2: $R_t$ = 1.02 min; MS (ESIpos): m/z = 456 (M + H)$^+$ |
| 109 | 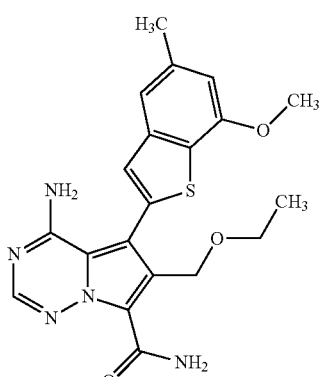 | P1 | Method 4: $R_t$ = 0.97 min; MS (ESIpos): m/z = 412 (M + H)$^+$ |
| 110 | 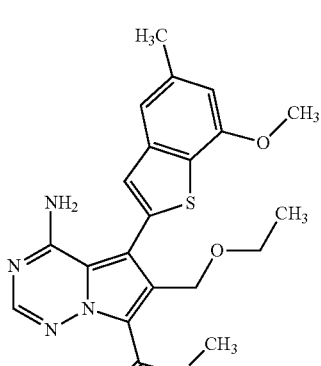 | P1, P5 | Method 2: $R_t$ = 1.01 min; MS (ESIpos): m/z = 426 (M + H)$^+$ |
| 111 | 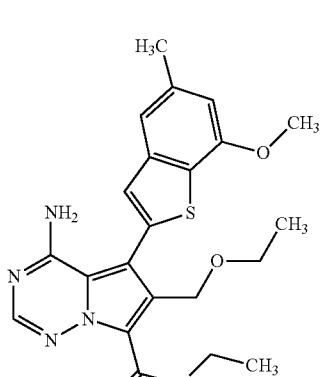 | P1, P5 | Method 4: $R_t$ = 1.11 min; MS (ESIpos): m/z = 440 (M + H)$^+$ |

TABLE II-continued

| Example No. | Structure | Purification method(s) | LC-MS data |
|---|---|---|---|
| 112 | 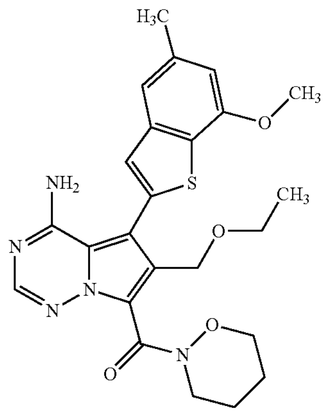 [SMILES: CCOCc1c(-c2cc3cc(C)cc(OC)c3s2)c2c(N)ncnn2c1C(=O)N1CCCCO1] | P1 | Method 4:<br>$R_t$ = 1.07 min;<br>MS (ESIpos): m/z = 482 (M + H)$^+$ |
| 113 | 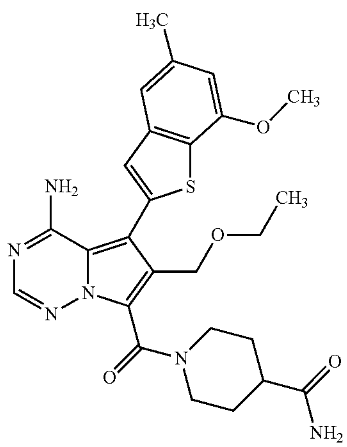 [SMILES: CCOCc1c(-c2cc3cc(C)cc(OC)c3s2)c2c(N)ncnn2c1C(=O)N1CCC(C(N)=O)CC1] | P1, P5 | Method 2:<br>$R_t$ = 0.84 min;<br>MS (ESIpos): m/z = 523 (M + H)$^+$ |
| 114 | 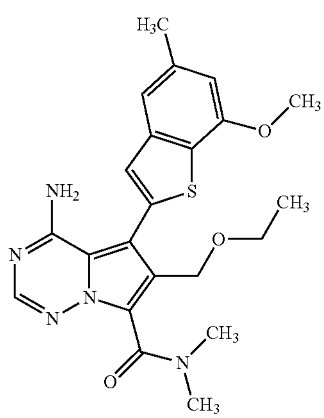 [SMILES: CCOCc1c(-c2cc3cc(C)cc(OC)c3s2)c2c(N)ncnn2c1C(=O)N(C)C] | P1, P5 | Method 2:<br>$R_t$ = 0.96 min;<br>MS (ESIpos): m/z = 440 (M + H)$^+$ |

TABLE II-continued

| Example No. | Structure | Purification method(s) | LC-MS data |
|---|---|---|---|
| 115 | 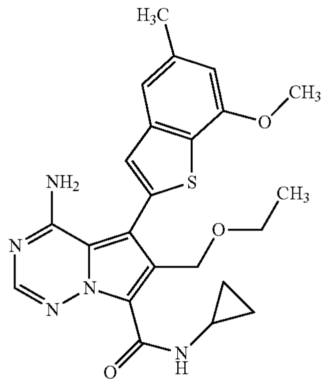 [SMILES: CCOCc1c(-c2cc3cc(C)cc(OC)c3s2)c2c(N)ncnn2c1C(=O)NC1CC1] | P1, P5 | Method 2: $R_t$ = 1.09 min; MS (ESIpos): m/z = 452 (M + H)$^+$ |
| 116 | 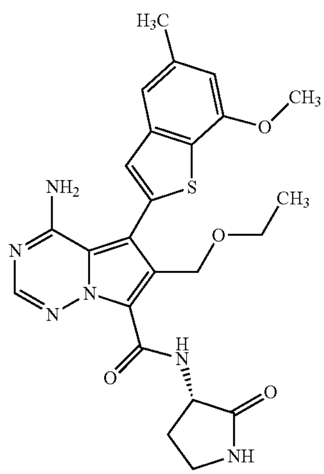 [SMILES: CCOCc1c(-c2cc3cc(C)cc(OC)c3s2)c2c(N)ncnn2c1C(=O)N[C@H]1CCNC1=O] | P1, P5 | Method 4: $R_t$ = 0.95 min; MS (ESIpos): m/z = 495 (M + H)$^+$ |
| 117 | 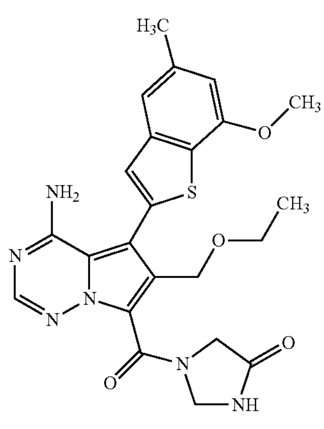 [SMILES: CCOCc1c(-c2cc3cc(C)cc(OC)c3s2)c2c(N)ncnn2c1C(=O)N1CNC(=O)C1] | P1, P5 | Method 4: $R_t$ = 0.93 min; MS (ESIpos): m/z = 481 (M + H)$^+$ |

TABLE II-continued
| Example No. | Structure | Purification method(s) | LC-MS data |
|---|---|---|---|
| 118 | 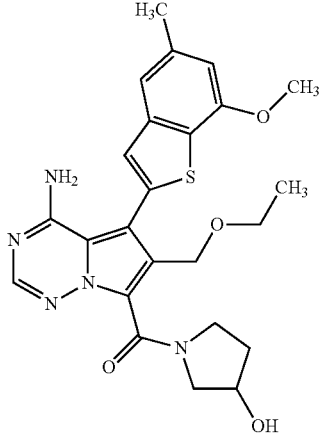 [SMILES: CCOCc1c(-c2cc3cc(C)cc(OC)c3s2)c2c(N)ncnn2c1C(=O)N1CCC(O)C1] | P1, P5 | Method 2:<br>$R_t$ = 0.93 min;<br>MS (ESIpos): m/z = 482 (M + H)$^+$ |
| 119 | 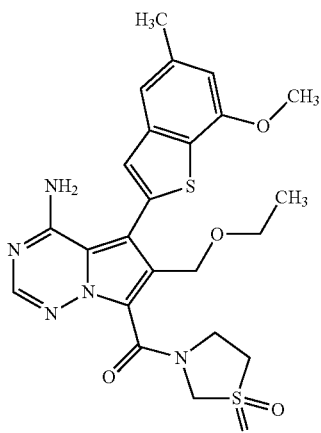 | P1, P5 | Method 2:<br>$R_t$ = 1.04 min;<br>MS (ESIpos): m/z = 516 (M + H)$^+$ |
| 120 | 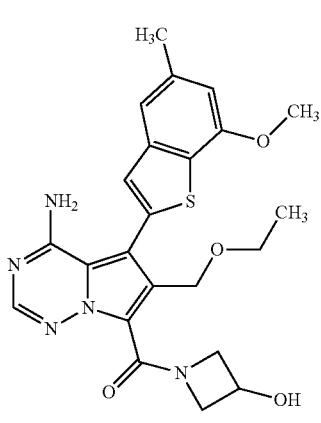 [SMILES: CCOCc1c(-c2cc3cc(C)cc(OC)c3s2)c2c(N)ncnn2c1C(=O)N1CC(O)C1] | P1, P5 | Method 4:<br>$R_t$ = 0.88 min;<br>MS (ESIpos): m/z = 468 (M + H)$^+$ |

TABLE II-continued

| Example No. | Structure | Purification method(s) | LC-MS data |
|---|---|---|---|
| 121 | 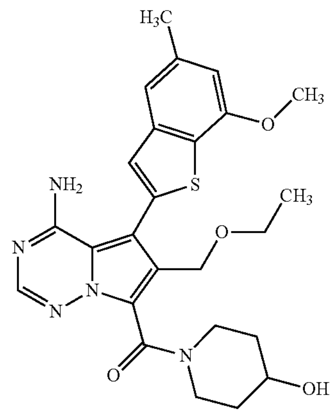 [SMILES: CCOCc1c(-c2cc3cc(C)cc(OC)c3s2)c2c(N)ncnn2c1C(=O)N1CCC(O)CC1] | P1, P5 | Method 4: R$_t$ = 0.91 min; MS (ESIpos): m/z = 496 (M + H)$^+$ |
| 122 | 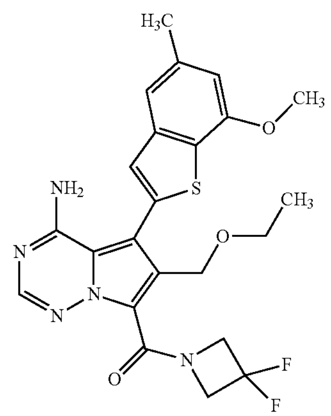 [SMILES: CCOCc1c(-c2cc3cc(C)cc(OC)c3s2)c2c(N)ncnn2c1C(=O)N1CC(F)(F)C1] | P1, P5 | Method 4: R$_t$ = 1.09 min; MS (ESIpos): m/z = 488 (M + H)$^+$ |
| 123 | 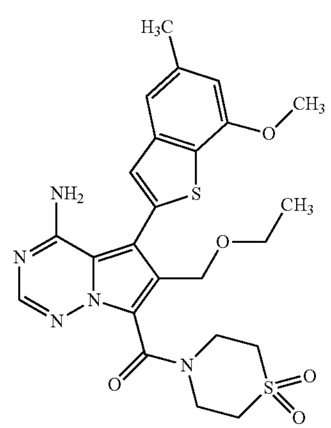 [SMILES: CCOCc1c(-c2cc3cc(C)cc(OC)c3s2)c2c(N)ncnn2c1C(=O)N1CCS(=O)(=O)CC1] | P1, P5 | Method 4: R$_t$ = 0.98 min; MS (ESIpos): m/z = 530 (M + H)$^+$ |

Example 124

4-{[4-Amino-5-(5,7-dimethoxy-1-benzothiophen-2-yl)-6-(methoxymethyl)pyrrolo[2,1-f][1,2,4]-triazin-7-yl]methyl}piperazin-2-one

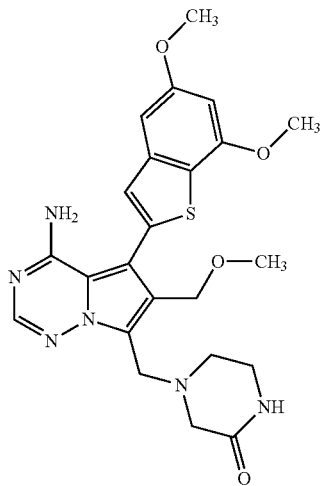 [SMILES: COCc1c(-c2cc3cc(OC)cc(OC)c3s2)c2c(N)ncnn2c1CN1CCNC(=O)C1]

To a solution of Intermediate 62A (100 mg, 271 µmol), Intermediate 66A (77 mg, 325 µmol) and caesium fluoride (206 mg, 1.35 mmol) in degassed THF/water (10:1; 5 ml) under argon was added (2'-aminobiphenyl-2-yl)(chloro)palladium-dicyclohexyl(2',4',6'-triisopropylbiphenyl-2-yl) phosphine (1:1; 42.6 mg, 54 mol; see S. L. Buchwald et al., *J. Am. Chem. Soc.* 132 (40), 14073-14075 (2010)). The resulting mixture was degassed again and stirred under argon at 60° C. for 6 h. Then, another portion of Intermediate 66A (39 mg, 162 µmol) was added, and stirring at 60° C. was continued for 10 h. After this, the reaction mixture was separated by preparative RP-HPLC (Reprosil C18, gradient 30-50% acetonitrile/0.1% aq. TFA). The product fractions were combined and evaporated to dryness. The residue was dissolved in methanol and filtered through an anion exchange cartridge (Stratospheres SPE, PL-HCO$_3$ MP-resin). The cartridge was eluted with methanol, and the filtrate was evaporated affording 40 mg (28% of th.) of the title compound.

LC-MS (method 2): $R_t$=0.78 min; MS (ESIpos): m/z=483 (M+H)$^+$ $^1$H-NMR (500 MHz, DMSO-d$_6$): δ=7.99 (s, 1H), 7.68 (br. s, 1H), 7.49-8.17 (br. s, 1H), 7.37 (s, 1H), 7.05 (d, 1H), 6.63 (d, 1H), 5.5-6.0 (br. s, 1H), 4.42 (s, 2H), 3.97 (s, 2H), 3.94 (s, 3H), 3.84 (s, 3H), 3.20 (s, 3H), 3.09-3.14 (m, 2H), 3.01 (s, 2H), 2.62-2.67 (m, 2H) ppm.

Example 125

4-{[4-Amino-7-(hydroxymethyl)-5-(7-methoxy-5-methyl-1-benzothiophen-2-yl)pyrrolo[2,1-f]-[1,2,4]triazin-6-yl]methyl}piperazin-2-one

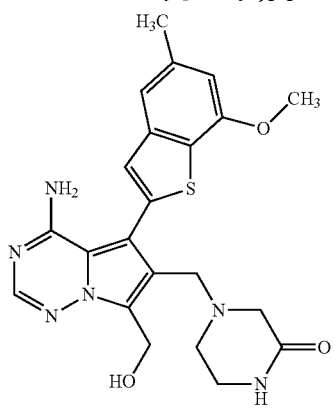

To a suspension of Intermediate 70A (700 mg, 1.49 mmol), Intermediate 5A (497 mg, 2.24 mmol) and caesium fluoride (1.36 g, 8.95 mmol) in degassed THF/water (2:1, 90 ml) under argon was added (2'-aminobiphenyl-2-yl)(chloro)palladium-dicyclohexyl(2',4',6'-triisopropylbiphenyl-2-yl)phosphine (1:1; 117 mg, 0.149 mmol; see S. L. Buchwald et al., *J. Am. Chem. Soc.* 132 (40), 14073-14075 (2010)). The resulting mixture was degassed again and stirred under argon at 60° C. overnight. Another portion of Intermediate 5A (231 mg, 1.04 mmol) and (2'-aminobiphenyl-2-yl)(chloro)palladium-dicyclohexyl(2',4',6'-triisopropylbiphenyl-2-yl)phosphine (1:1; 117 mg, 0.149 mmol) were added, and stirring was continued at 60° C. for 3 h. The precipitate was filtered off, washed with THF and dried in vacuo. The solid was suspended in mixture of DMF and 1 M aq. trifluoroacetic acid and filtered. The filtrate was separated by preparative RP-HPLC (Reprosil C18, gradient 20-40% acetonitrile/0.2% aq. trifluoroacetic acid). The product fractions were combined and then alkalized by addition of sat. aq. sodium bicarbonate solution. The solution was extracted with ethyl acetate, and the organic layer was washed with brine, dried over magnesium sulfate and evaporated to yield 88 mg of the title compound (13% of th.).

LC-MS (method 2): $R_t$=0.70 min; MS (ESIpos): m/z=453 (M+H)$^+$ $^1$H-NMR (400 MHz, DMSO-d$_6$): inter al. δ=7.6-8.0 (br. s, 1H), 7.98 (s, 1H), 7.71 (s, 1H), 7.37 (s, 1H), 7.31 (s, 1H), 6.84 (s, 1H), 5.4-5.8 (br. s, 1H), 5.19 (t, 1H), 4.85 (d, 2H), 3.95 (s, 3H), 3.58 (s, 2H), 3.04 (br. m, 2H), 2.88 (s, 2H), 2.45 (s, 3H) ppm.

Example 126

4-{[4-Amino-7-(methoxymethyl)-5-(7-methoxy-5-methyl-1-benzothiophen-2-yl)pyrrolo[2,1-f]-[1,2,4]triazin-6-yl]methyl}piperazin-2-one

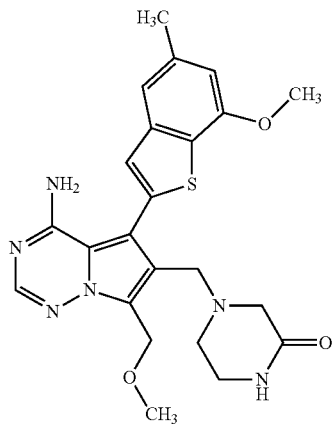 [SMILES: COCc1c(CN2CCNC(=O)C2)c(-c2cc3cc(C)cc(OC)c3s2)c2c(N)ncnn12]

A suspension of Example 125 (88 mg, 194 µmol) in dichloromethane (5 ml) was treated with thionyl chloride (29 µl, 389 µmol), and the mixture was stirred at rt for 65 min. Another portion of thionyl chloride (29 µl, 389 µmol) was added, and stirring was continued for 1.5 h. An excess of methanol was then added, followed by dropwise addition of a 5.4 M solution of sodium methylate in methanol (84 mg, 1.56 mmol) until pH 8 was reached. After stirring for 3 days, the volatiles were evaporated under reduced pressure, and the residue was separated by preparative RP-HPLC (Reprosil C18, gradient 20-40% acetonitrile/0.2% aq. trifluoroacetic acid). The product fractions were evaporated to yield 19 mg of the title compound (21% of th.).

LC-MS (method 2): $R_t$=0.77 min; MS (ESIpos): m/z=466 (M+H)$^+$ $^1$H-NMR (400 MHz, DMSO-d$_6$): δ=7.99 (s, 1H), 7.75-8.11 (br. s, 1H), 7.68 (s, 1H), 7.38 (s, 1H), 7.31 (s, 1H), 6.84 (s, 1H), 5.51-5.82 (m, 1H), 4.77 (s, 2H), 3.95 (s, 3H), 3.55 (s, 2H), 3.31 (s, 3H), 3.04 (br. s, 2H), 2.85 (s, 2H), 2.42-2.48 (m, 5H) ppm.

Example 127

4-{[4-Amino-7-(ethoxymethyl)-5-(7-methoxy-5-methyl-1-benzothiophen-2-yl)pyrrolo[2,1-f]-[1,2,4]triazin-6-yl]methyl}piperazin-2-one

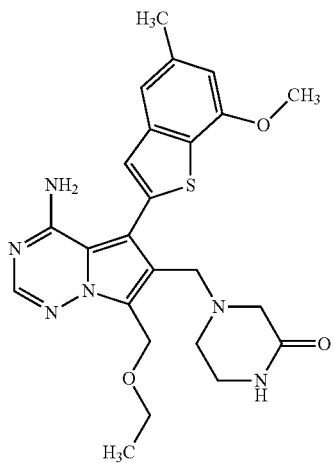 [SMILES: CCOCc1c(CN2CCNC(=O)C2)c(-c2cc3cc(C)cc(OC)c3s2)c2c(N)ncnn12]

A suspension of Example 125 (100 mg, 221 μmol) in dichloromethane (10 ml) was treated with thionyl chloride (161 μl, 2.21 mmol), and the mixture was stirred at rt for 30 min. Ethanol was added, and the volatiles were evaporated under reduced pressure. The residue was dissolved in ethanol (10 ml), sodium ethylate (30 mg, 442 μmol) was added, and the mixture was stirred at rt for 1 h. The mixture was then directly separated by preparative RP-HPLC (Reprosil C18, gradient 20-40% acetonitrile/0.2% aq. trifluoroacetic acid). The product fractions were combined and alkalized by addition of sat. aq. sodium bicarbonate solution. The solution was extracted with ethyl acetate, and the organic layer was washed with brine, dried over magnesium sulfate and evaporated to yield 57 mg of the title compound (54% of th.).

LC-MS (method 2): $R_t$=0.85 min; MS (ESIpos): m/z=480 (M+H)$^+$ $^1$H-NMR (400 MHz, DMSO-d$_6$): δ=7.99 (s, 1H), 7.75-8.09 (br. s, 1H), 7.64-7.71 (m, 1H), 7.38 (s, 1H), 7.31 (s, 1H), 6.84 (s, 1H), 5.38-5.91 (br. s, 1H), 4.81 (s, 2H), 3.95 (s, 3H), 3.49-3.59 (m, 4H), 2.99-3.08 (m, 2H), 2.86 (s, 2H), 1.12 (t, 3H) ppm.

B. EVALUATION OF BIOLOGICAL ACTIVITY

Abbreviations and Acronyms

Ahx 6-aminohexanoic acid
ATP adenosine triphosphate
BSA bovine serum albumin
CREB cAMP-response element-binding protein
DMSO dimethylsulfoxide
EDTA ethylenediaminetetraacetic acid
EGTA ethyleneglycol-bis(2-aminoethylether)-N,N,N',N'-tetraacetic acid
FBS fetal bovine serum
FGF fibroblast growth factor
FGFR fibroblast growth factor receptor
GFP green fluorescent protein
GST glutathione S-transferase
HEPES 4-(2-hydroxyethyl)piperazine-1-ethansulfonic acid
HRTF homogeneous time-resolved fluorescence
MOPS 3-(N-morpholino)propanesulfonic acid
mTOR mammalian target of Rapamycin
PBS phosphate buffered saline
PI3K phosphatidylinositol 3-kinase
RTK receptor tyrosine kinase
SNP single nucleotide polymorphism
TR-FRET time-resolved fluorescence resonance energy transfer
VEGF vascular endothelial growth factor
VEGFR vascular endothelial growth factor receptor Demonstration of the activity of the compounds of the present invention may be accomplished through in vitro, ex vivo, and in vivo assays that are well known in the art. For example, to demonstrate the activity of the compounds of the present invention, the following assays may be used.

B-1. FGFR-1 High ATP Kinase Assay

FGFR-1 inhibitory activity at high ATP concentration of the compounds of the present invention after their pre-incubation with FGFR-1 was quantified employing the TR-FRET based FGFR-1 high ATP assay as described in the following paragraphs:

A recombinant tagged FGFR-1 fusion protein [fusion of glutathione-S-transferase (GST) (N-terminally), His6-tag, thrombin cleavage site, and the intracellular part of human FGFR-1 from amino acids G400 to R800 as in GenBank entry NM_015850], expressed in SF9 insect cells using baculovirus expression system and purified via glutathione-agarose affinity chromatography, was purchased from Proqinase (product no. 0101-0000-1) and used as enzyme. As substrate for the kinase reaction, the biotinylated peptide biotin-Ahx-AAEEEYFFLFAKKK (C-terminus in amide form) was used which can be purchased, e.g., from Biosyntan (Berlin-Buch, Germany).

Usually, test compounds were tested on the same microtiter plate at 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM, and 0.1 nM) in duplicates for each concentration. The dilution series was prepared separately prior to the assay as 100-fold concentrated stock solutions in DMSO; exact concentrations could vary depending on the pipettor used. For the assay, 50 nl of each stock solution of the test compound in DMSO was pipetted into a black, low-volume 384-well microtiter plate (Greiner Bio-One, Frickenhausen, Germany) 2 μl of a solution of the above FGFR-1 fusion protein in aqueous assay buffer [8 mM MOPS pH 7.0, 10 mM magnesium acetate, 1.0 mM dithiothreitol, 0.05% (w/v) bovine serum albumin (BSA), 0.07% (v/v) Tween-20, 0.2 mM EDTA] was added, and the mixture was incubated for 15 min at 22° C. to allow pre-binding of the test compound to the enzyme. Then, the kinase reaction was started by the addition of 3 μl of a solution of adenosine triphosphate (ATP, 3.3 mM; final concentration in the 5 μl assay volume=2 mM) and substrate (0.16 μM; final concentration in the 5 μl assay volume=0.1 μM) in assay buffer, and the resulting mixture was incubated for a reaction time of 15 min at 22° C. The concentration of FGFR-1 fusion protein was adjusted depending on the activity of the enzyme lot and was chosen appropriately to have the assay in the linear range (typical concentrations were in the range of 0.05 μg/ml). The reaction was stopped by the addition of 5 μl of a solution of HTRF detection reagents [25 nM streptavidin-XL665 (C is Biointernational) and 1 nM PT66-Eu-chelate, an europium-chelate labelled anti-phosphotyrosine antibody (Perkin-Elmer; PT66-Tb-cryptate from C is Biointernational may be used instead), in an aqueous EDTA solution (50 mM EDTA, 0.1% (w/v) BSA in 50 mM HEPES/NaOH pH 7.5)].

The resulting mixture was incubated for 1 h at 22° C. to allow formation of the complex between the phosphorylated biotinylated peptide and the detection reagents. Subsequently, the amount of phosphorylated substrate was evaluated by measurement of the resonance energy transfer from the Eu-chelate to the streptavidin-XL665. For this, the fluorescence emissions at 620 nm and 665 nm after excitation at 350 nm were measured in a TR-FRET reader [e.g. Rubystar (BMG Labtechnologies, Offenburg, Germany) or Viewlux (Perkin-Elmer)]. The ratio of the emissions at 665 nm and at 620 nm was taken as the measure for the amount of phosphorylated substrate. Data were normalised (enzyme reaction without inhibitor=0% inhibition, all other assay components but no enzyme=100% inhibition), and $IC_{50}$ values were calculated by a 4-parameter fit using an in-house software.

$IC_{50}$ values for individual compounds of the invention from this assay are listed in Table 1A below:

TABLE 1A

| Example No. | FGFR-1 (high ATP) $IC_{50}$ [nM] |
|---|---|
| 1 | 12.2 |
| 2 | 7.2 |
| 3 | 6.6 |
| 4 | 13.7 |
| 5 | 4.6 |
| 6 | 9.0 |
| 7 | 4.2 |
| 8 | 9.4 |
| 9 | 31.0 |
| 10 | 12.7 |
| 11 | 6.5 |
| 12 | 3.3 |
| 13 | 2.5 |
| 14 | 1.4 |
| 15 | 1.0 |
| 16 | 12.5 |
| 17 | 0.9 |
| 18 | 0.7 |
| 19 | 0.5 |
| 20 | 25.0 |
| 21 | 4.2 |
| 22 | 0.9 |
| 23 | 17.9 |
| 24 | 1.3 |
| 25 | 0.7 |
| 26 | 0.9 |
| 27 | 1.3 |
| 28 | 2.1 |
| 29 | 1.6 |
| 30 | 2.8 |
| 31 | 1.5 |
| 32 | 5.2 |
| 33 | 1.0 |
| 34 | 6.0 |
| 35 | 61.3 |
| 36 | 3.0 |
| 37 | 22.1 |
| 38 | 6.9 |
| 39 | 1.1 |
| 40 | 2.1 |
| 41 | 2.8 |
| 42 | 5.1 |
| 43 | 8.6 |
| 44 | 2.1 |
| 45 | 3.4 |
| 46 | 3.2 |
| 47 | 1.7 |
| 48 | 12.8 |
| 51 | 4.4 |
| 52 | 9.7 |
| 53 | 3.9 |
| 54 | 11.2 |
| 56 | 2.4 |
| 57 | 3.2 |
| 58 | 6.8 |
| 59 | 3.8 |
| 60 | 16.2 |
| 61 | 0.5 |
| 62 | 3.1 |
| 64 | 1.0 |
| 65 | 5.6 |
| 66 | 1.6 |
| 67 | 5.0 |
| 68 | 27.0 |
| 69 | 55.3 |
| 70 | 39.1 |
| 71 | 2.7 |
| 72 | 1.4 |
| 73 | 4.4 |
| 74 | 4.0 |
| 75 | 4.1 |
| 76 | 2.8 |
| 77 | 1.4 |
| 78 | 1.7 |
| 79 | 12.6 |
| 80 | 1.3 |
| 81 | 1.9 |
| 82 | 3.4 |
| 83 | 14.5 |
| 84 | 3.7 |
| 85 | 26.4 |
| 86 | 3.9 |
| 87 | 14.1 |
| 88 | 79.6 |
| 89 | 82.9 |
| 90 | 9.9 |
| 91 | 52.9 |
| 92 | 8.2 |
| 93 | 5.5 |
| 94 | 81.9 |
| 95 | 17.0 |
| 96 | 54.5 |
| 97 | 16.4 |
| 98 | 17.0 |
| 99 | 24.8 |
| 100 | 54.5 |
| 101 | 30.8 |
| 102 | 39.2 |
| 103 | 50.3 |
| 104 | 5.6 |
| 105 | 8.7 |
| 106 | 6.4 |
| 107 | 9.4 |
| 108 | 3.9 |
| 109 | 8.4 |
| 110 | 17.5 |
| 111 | 27.0 |
| 112 | 42.1 |
| 113 | 52.7 |
| 114 | 11.2 |
| 115 | 24.9 |
| 116 | 3.7 |
| 117 | 8.8 |
| 118 | 6.8 |
| 119 | 9.0 |
| 120 | 6.8 |
| 121 | 8.2 |
| 122 | 18.9 |
| 123 | 25.1 |
| 124 | 27.3 |
| 125 | 5.0 |
| 126 | 3.9 |
| 127 | 8.0 |

Selected 8-amino-1-(benzothiophen-2-yl)imidazo[1,5-a] pyrazine derivatives and related compounds which were regarded to be representative of closest prior art (see Int. Pat. Appl. WO 2007/061737-A2 and example compounds described therein) were synthesized following the published procedures and also tested in the FGFR-1 high ATP assay for comparative purposes. IC$_{50}$ values that were obtained for these compounds are listed in Table 1B below:

TABLE 1B

| Structure of comparative compound | Example No. in WO 2007/ 061737 | FGFR-1 (high ATP) IC$_{50}$ [nM] |
|---|---|---|
| | 4 | 12000 |
| | 5 | 500 |
| | 25 | 880 |

TABLE 1B-continued

| Structure of comparative compound | Example No. in WO 2007/ 061737 | FGFR-1 (high ATP) IC$_{50}$ [nM] |
|---|---|---|
| | 120 | 985 |
| | 205 | 20000 |
| | 210 | 456 |
| | 233 | 4600 |

The IC$_{50}$ values specified in Table 1A and 1B demonstrate that the compounds of the present invention are about five to a thousand times more potent in inhibiting FGFR-1 kinase activity than the selected prior art compounds.

B-2. FGFR-3 Kinase Assay

FGFR-3 inhibitory activity of the compounds of the present invention after their pre-incubation with FGFR-3 was quantified employing the TR-FRET based FGFR-3 assay as described in the following paragraphs:

A recombinant tagged FGFR-3 fusion protein [fusion of glutathione-S-transferase (GST) (N-terminally), His6-tag, thrombin cleavage site, and the intracellular part of human FGFR-3 from amino acids R397 to T806 as in NCBI/Protein entry NP_000133.1], expressed in SF9 insect cells using baculovirus expression system and purified via glutathione-S-transferase affinity chromatography, was purchased from Proqinase (product no. 1068-0000-1) and used as enzyme. As substrate for the kinase reaction, the biotinylated peptide biotin-Ahx-AAEEEYFFLFAKKK (C-terminus in amide form) was used which can be purchased, e.g., from Biosyntan (Berlin-Buch, Germany).

Usually, test compounds were tested on the same microtiter plate at 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM, and 0.1 nM) in duplicates for each concentration. The dilution series was prepared separately prior to the assay as 100-fold concentrated stock solutions in DMSO; exact concentrations could vary depending on the pipettor used. For the assay, 50 nl of each stock solution of the test compound in DMSO was pipetted into a black, low-volume 384-well microtiter plate (Greiner Bio-One, Frickenhausen, Germany) 2 µl of a solution of the above FGFR-3 fusion protein in aqueous assay buffer [8 mM MOPS pH 7.0, 10 mM magnesium acetate, 1.0 mM dithiothreitol, 0.05% (w/v) bovine serum albumin (BSA), 0.07% (v/v) Tween-20, 0.2 mM EDTA] was added, and the mixture was incubated for 15 min at 22° C. to allow pre-binding of the test compound to the enzyme. Then, the kinase reaction was started by the addition of 3 µl of a solution of adenosine triphosphate (ATP, 16.7 µM; final concentration in the 5 µl assay volume=10 µM) and substrate (0.8 µM; final concentration in the 5 µl assay volume=0.5 µM) in assay buffer, and the resulting mixture was incubated for a reaction time of 60 min at 22° C. The concentration of FGFR-3 fusion protein was adjusted depending on the activity of the enzyme lot and was chosen appropriately to have the assay in the linear range (typical concentrations were in the range of 0.03 µg/ml). The reaction was stopped by the addition of 5 µl of a solution of HTRF detection reagents [100 nM streptavidin-XL665 (C is Biointernational) and 1 nM PT66-Tb-cryptate, a terbium-cryptate labelled anti-phosphotyrosine antibody (C is Biointernational; PT66-Eu-chelate from Perkin-Elmer may be used instead), in an aqueous EDTA solution (50 mM EDTA, 0.1% (w/v) BSA in 50 mM HEPES/NaOH pH 7.5)].

The resulting mixture was incubated for 1 h at 22° C. to allow formation of the complex between the phosphorylated biotinylated peptide and the detection reagents. Subsequently, the amount of phosphorylated substrate was evaluated by measurement of the resonance energy transfer from the Tb-chelate to the streptavidin-XL665. For this, the fluorescence emissions at 620 nm and 665 nm after excitation at 350 nm were measured in a TR-FRET reader [e.g. Rubystar (BMG Labtechnologies, Offenburg, Germany) or Viewlux (Perkin-Elmer)]. The ratio of the emissions at 665 nm and at 620 nm was taken as the measure for the amount of phosphorylated substrate. Data were normalised (enzyme reaction without inhibitor=0% inhibition, all other assay components but no enzyme=100% inhibition), and $IC_{50}$ values were calculated by a 4-parameter fit using an in-house software.

$IC_{50}$ values for individual compounds of the invention from this assay are listed in Table 2A below:

TABLE 2A

| Example No. | FGFR-3 $IC_{50}$ [nM] |
|---|---|
| 1 | 24.8 |
| 2 | 29.4 |
| 3 | 46.6 |
| 4 | 24.8 |
| 5 | 12.1 |
| 6 | 28.5 |
| 7 | 10.4 |
| 8 | 17.7 |
| 9 | 63.9 |
| 10 | 8.3 |
| 11 | 13.0 |
| 12 | 14.0 |
| 13 | 10.0 |
| 14 | 2.5 |
| 15 | 1.0 |
| 16 | 9.4 |
| 17 | 3.3 |
| 18 | 2.8 |
| 19 | 2.7 |
| 20 | 26.1 |
| 21 | 13.0 |
| 22 | 4.7 |
| 23 | 41.9 |
| 24 | 5.7 |
| 25 | 5.2 |
| 26 | 4.9 |
| 27 | 12.6 |
| 28 | 9.7 |
| 29 | 2.5 |
| 30 | 6.4 |
| 31 | 13.3 |
| 32 | 52.3 |
| 33 | 7.2 |
| 34 | 10.5 |
| 35 | 65.4 |
| 36 | 9.8 |
| 37 | 34.6 |
| 38 | 18.8 |
| 39 | 4.9 |
| 40 | 7.9 |
| 41 | 7.2 |
| 42 | 18.4 |
| 43 | 32.4 |
| 44 | 6.1 |
| 45 | 9.7 |
| 46 | 8.1 |
| 47 | 3.4 |
| 48 | 45.4 |
| 51 | 3.9 |
| 52 | 7.0 |
| 53 | 2.5 |
| 54 | 6.8 |
| 56 | 2.0 |
| 57 | 1.8 |
| 58 | 9.8 |
| 59 | 6.8 |
| 60 | 77.9 |
| 61 | 0.9 |
| 62 | 11.0 |
| 64 | 2.9 |
| 65 | 3.1 |
| 66 | 3.7 |
| 67 | 9.4 |
| 68 | 42.7 |
| 69 | 58.1 |
| 71 | 5.4 |
| 72 | 0.7 |
| 73 | 12.2 |
| 74 | 1.4 |
| 75 | 19.8 |
| 76 | 1.4 |
| 77 | 3.8 |
| 78 | 2.0 |
| 79 | 17.9 |
| 80 | 0.2 |
| 81 | 0.5 |
| 82 | 16.0 |
| 83 | 2.1 |

TABLE 2A-continued

| Example No. | FGFR-3 IC$_{50}$ [nM] |
|---|---|
| 84 | 16.5 |
| 85 | 26.0 |
| 86 | 6.8 |
| 87 | 28.1 |
| 90 | 11.0 |
| 91 | 31.1 |
| 93 | 8.7 |
| 95 | 28.7 |
| 98 | 26.5 |
| 99 | 36.9 |
| 102 | 39.8 |
| 106 | 7.1 |
| 107 | 17.4 |
| 108 | 7.7 |
| 114 | 9.6 |
| 117 | 5.3 |
| 119 | 4.5 |
| 121 | 24.6 |

Selected 8-amino-1-(benzothiophen-2-yl)imidazo[1,5-a]pyrazine derivatives and related compounds which were regarded to be representative of closest prior art (see Int. Pat. Appl. WO 2007/061737-A2 and example compounds described therein) were synthesized following the published procedures and also tested in the FGFR-3 assay for comparative purposes. IC$_{50}$ values that were obtained for these compounds are listed in Table 2B below:

TABLE 2B

| Structure of comparative compound | Example No. in WO 2007/ 061737 | FGFR-3 IC$_{50}$ [nM] |
|---|---|---|
| | 4 | 2400 |
| | 5 | 250 |
| | 25 | 1200 |
| | 120 | 506 |
| | 205 | 20000 |
| | 210 | 554 |

TABLE 2B-continued

| Structure of comparative compound | Example No. in WO 2007/ 061737 | FGFR-3 IC$_{50}$ [nM] |
|---|---|---|
| (structure shown: amino-imidazopyrazine bearing a chlorobenzothiophene and a cyclobutyl substituent) | 233 | 10000 |

The IC$_{50}$ values specified in Table 2A and 2B demonstrate that the compounds of the present invention are about three to a thousand times more potent in inhibiting FGFR-3 kinase activity than the selected prior art compounds.

B-3. FGFR-4 High ATP Kinase Assay

FGFR-4 inhibitory activity at high ATP concentration of the compounds of the present invention after their pre-incubation with FGFR-4 was quantified employing the TR-FRET based FGFR-4 high ATP assay as described in the following paragraphs:

A recombinant tagged FGFR-4 fusion protein [fusion of glutathione-S-transferase (GST) (N-terminally), His6-tag, thrombin cleavage site, and the intracellular part of human FGFR-4 from amino acids R391 to T802 as in GenBank entry NM_002011], expressed in SF9 insect cells using baculovirus expression system and purified via glutathione-agarose affinity chromatography, was purchased from Proqinase (product no. 0127-0000-3) and used as enzyme. As substrate for the kinase reaction, the biotinylated peptide biotin-Ahx-AAEEEYFFLFAKKK (C-terminus in amide form) was used which can be purchased, e.g., from Biosyntan (Berlin-Buch, Germany).

Usually, test compounds were tested on the same microtiter plate at 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM, and 0.1 nM) in duplicates for each concentration. The dilution series was prepared separately prior to the assay as 100-fold concentrated stock solutions in DMSO; exact concentrations could vary depending on the pipettor used. For the assay, 50 nl of each stock solution of the test compound in DMSO was pipetted into a black, low-volume 384-well microtiter plate (Greiner Bio-One, Frickenhausen, Germany) 2 µl of a solution of the above FGFR-4 fusion protein in aqueous assay buffer [8 mM MOPS pH 7.0, 10 mM magnesium acetate, 1.0 mM dithiothreitol, 0.05% (w/v) bovine serum albumin (BSA), 0.07% (v/v) Tween-20, 0.2 mM EDTA] was added, and the mixture was incubated for 15 min at 22° C. to allow pre-binding of the test compound to the enzyme. Then, the kinase reaction was started by the addition of 3 µl of a solution of adenosine triphosphate (ATP, 3.3 mM; final concentration in the 5 µl assay volume=2 mM) and substrate (0.8 µM; final concentration in the 5 µl assay volume=0.5 µM) in assay buffer, and the resulting mixture was incubated for a reaction time of 60 min at 22° C. The concentration of FGFR-4 fusion protein was adjusted depending on the activity of the enzyme lot and was chosen appropriately to have the assay in the linear range (typical concentrations were in the range of 0.03 µg/ml). The reaction was stopped by the addition of 5 µl of a solution of HTRF detection reagents [100 nM streptavidin-XL665 (C is Biointernational) and 1 nM PT66-Tb-cryptate, a terbium-cryptate labelled anti-phosphotyrosine antibody (C is Biointernational; PT66-Eu-chelate from Perkin-Elmer may be used instead), in an aqueous EDTA solution (50 mM EDTA, 0.1% (w/v) BSA in 50 mM HEPES/NaOH pH 7.5)].

The resulting mixture was incubated for 1 h at 22° C. to allow formation of the complex between the phosphorylated biotinylated peptide and the detection reagents. Subsequently, the amount of phosphorylated substrate was evaluated by measurement of the resonance energy transfer from the Tb-chelate to the streptavidin-XL665. For this, the fluorescence emissions at 620 nm and 665 nm after excitation at 350 nm were measured in a TR-FRET reader [e.g. Rubystar (BMG Labtechnologies, Offenburg, Germany) or Viewlux (Perkin-Elmer)]. The ratio of the emissions at 665 nm and at 620 nm was taken as the measure for the amount of phosphorylated substrate. Data were normalised (enzyme reaction without inhibitor=0% inhibition, all other assay components but no enzyme=100% inhibition), and IC$_{50}$ values were calculated by a 4-parameter fit using an in-house software.

B-4. mTOR Kinase Assay (for Comparative Purposes)

mTOR inhibitory activity of the compounds of the present invention was quantified employing the TR-FRET based mTOR assay as described in the following paragraphs:

Recombinant fusion tagged mTOR protein [glutathione-S-transferase (GST) fused to human mTOR amino acids from 1360 to 2549], expressed in insect cells and purified by glutathione-sepharose affinity chromatography, was purchased from Invitrogen (Cat.-No. 4753) and used as enzyme. As substrate for the kinase reaction, a recombinant fusion protein of GFP and 4E-BP1 (purchased from Invitrogen, Cat.-No. PV4759) was used.

Test compounds were dissolved in DMSO to generate 10 mM stock solutions. These solutions were first 10-fold diluted by 100% DMSO to get 1 mM solutions in 100% DMSO, then 100-fold diluted by 50% DMSO to get 10 µM solutions in 50% DMSO.

For the assay, 0.5 µl of a 10 µM solution of the test compound in 50% DMSO was pipetted into a black, low-volume 384-well microtiter plate (Greiner Bio-One, Frickenhausen, Germany). 2 µl of a solution of the above mTOR fusion protein in aqueous assay buffer [50 mM HEPES/NaOH pH 7.5, 5 mM magnesium chloride, 1.0 mM dithiothreitol, 1 mM EGTA, 0.01% (v/v) Triton-X100, 0.01% (w/v) bovine serum albumin (BSA)] was added, and the mixture was incubated for 15 min at 22° C. to allow pre-binding of the test compound to the enzyme. Then, the kinase reaction was started by the addition of 2.5 µl of a solution of adenosine triphosphate (ATP, 80 µM; final concentration in the 5 µl assay volume=40 µM) and substrate (0.6 µM; final concentration in the 5 µl assay volume=0.3 µM) in assay buffer, and the resulting mixture was incubated for a reaction time of 60 min at 22° C. The concentration of mTOR fusion protein was chosen appropriately to have the assay in the linear range (a typical final concentration in the 5 µl assay volume was 1.25 ng/µl). The reaction was stopped by the addition of 5 µl of 30 mM EDTA (final concentration in the 10 µl assay volume=15 mM) and 2 nM Tb-chelate labelled anti-4E-BP1 [pT46] phosphospecific antibody [Invitrogen Cat.-No. PV4755] (final concentration in the 10 µl assay volume=1 nM) in FRET buffer.

The resulting mixture was incubated for 1 h at 22° C. to allow formation of the complex between the phosphorylated substrate and the Tb-chelate labelled antibody. Subsequently, the amount of phosphorylated substrate was evaluated by measurement of the resonance energy transfer from the Tb-chelate to the GFP. For this, the fluorescence emissions at 495 nm and 520 nm after excitation at 340 nm was measured in an Envision 2104 multilabel reader (Perkin-Elmer). The ratio of the emissions at 520 nm and at 495 nm was taken as the measure for the amount of phosphorylated substrate. Data were normalised (enzyme reaction without inhibitor=0% inhibition, all other assay components but no enzyme=100% inhibition), and either mean values (if tested in replicates at a single concentration) or $IC_{50}$ values (by a 4-parameter fit using an in-house software) were calculated.

Mean inhibition values at 1 µM for individual compounds of the present invention are listed in Table 3 below:

TABLE 3

| Example No. | mTOR inhibition @ 1 µM |
|---|---|
| 1 | 8.7 |
| 2 | 7.2 |
| 3 | 8.2 |
| 5 | 9.7 |
| 6 | 0.3 |
| 7 | 3.1 |
| 8 | 7.8 |
| 9 | no inhib. effect detect. |
| 10 | 6.0 |
| 11 | 33.2 |
| 12 | 25.8 |
| 13 | 14.9 |
| 14 | 15.7 |
| 16 | 36.9 |
| 17 | 6.7 |
| 18 | no inhib. effect detect. |
| 19 | 17.6 |
| 20 | 31.3 |
| 21 | 5.0 |
| 22 | 17.6 |
| 23 | 11.6 |
| 24 | 6.3 |
| 25 | 3.5 |
| 26 | 6.8 |
| 27 | 5.9 |
| 28 | no inhib. effect detect. |
| 29 | 28.5 |
| 30 | 21.1 |
| 31 | 16.3 |
| 32 | 1.6 |
| 33 | 0.9 |
| 34 | 25.9 |
| 35 | 1.4 |
| 36 | 14.4 |
| 37 | 8.6 |
| 38 | 20.8 |
| 39 | 11.5 |
| 40 | 0.1 |
| 41 | no inhib. effect detect. |
| 42 | no inhib. effect detect. |
| 43 | 10.1 |
| 44 | 13.3 |
| 45 | 15.5 |
| 46 | 11.0 |
| 47 | 14.7 |
| 48 | 4.1 |
| 51 | 8.4 |
| 52 | 4.2 |
| 53 | 3.3 |
| 54 | 1.7 |
| 56 | 16.1 |
| 57 | 2.0 |
| 58 | 4.0 |
| 59 | 0.8 |
| 60 | 11.1 |
| 61 | 15.9 |
| 62 | 0.2 |
| 64 | 1.1 |
| 65 | 13.9 |
| 66 | 15.8 |
| 67 | 8.4 |
| 68 | 8.0 |
| 69 | 8.7 |
| 70 | 5.8 |
| 71 | 0.1 |
| 72 | 8.2 |
| 73 | 18.5 |
| 74 | 18.6 |
| 75 | 10.2 |
| 76 | 8.5 |
| 77 | 0.7 |
| 78 | 5.8 |
| 79 | 14.7 |
| 80 | 3.9 |
| 81 | 4.1 |
| 82 | 7.1 |
| 83 | 6.3 |
| 84 | 9.1 |
| 85 | 0.9 |
| 87 | 12.7 |
| 88 | 5.3 |
| 89 | no inhib. effect detect. |
| 93 | 12.5 |
| 98 | no inhib. effect detect. |
| 99 | 5.3 |
| 103 | no inhib. effect detect. |
| 107 | no inhib. effect detect. |
| 108 | 8.5 |
| 119 | no inhib. effect detect. |
| 121 | no inhib. effect detect. |

(no inhib. effect detect. = no inhibitory effect detectable at 1 µM).

The data in Table 3 show that the compounds of the present invention only have a weak, if any, inhibitory effect on mTOR kinase which is not considered to contribute to the pharmacological activity observed with these compounds.

B-5. Inhibition of Growth Factor-Mediated Cell Proliferation

Human umbilical vein endothelial cells (HUVEC) were obtained from Cellsystems (FC-0003) and grown in Vasculife VEGF complete medium (Cellsystems, LL-1020) containing 2% fetal bovine serum (FBS) at 37° C. and 5% $CO_2$. The cells were used for proliferation assays up to passage 7.

The HUVEC cells were harvested using accutase (PAA, L11-007) and seeded in columns 2 to 12 of 96-well plates (Falcon MICROTEST tissue culture plate 96-well flat bottom, BD 353075, or µCLEAR-PLATE, black, 96-well, Greiner Bio-One, No. 655090) at a cell density of 2500 cells/well in 100 µl Vasculife VEGF complete medium with column 1 remaining empty as blank. Cells were allowed to incubate at 37° C. and 5% $CO_2$ for at least 6 h. Then, the cells were washed once with PBS and starved overnight in Vasculife basal medium (Cellsystems, LM-0002) containing heparin, ascorbate and L-glutamine (components of the Vasculife Life Factors Kit, Cellsystems, LL-1020) as well as 0.2% FBS.

After about 18 h, the starving medium was discarded, and the cells were exposed for 72 h to 9 consecutive log or half-log concentrations of test compound in the range of 10 µM to 30 µM and to 5, 10 or 20 ng/ml hFGF-2 (recombinant human FGF basic, R&D Systems, 233-FB) in 100 µl starving medium. 10 mM stock solutions of test compounds in DMSO were diluted to 200× final concentration in DMSO resulting in a final DMSO concentration of 0.5% in all wells. Controls consisted of cells grown in starving medium only and of cells grown in hFGF-2 containing starving medium with 0.5% DMSO. To determine cell proliferation, 5 µl Alamar Blue solution (Biosource, DAL1100) was added to each well (1:20 dilution), and the cells were allowed to incubate for further 4 h at 37° C. and 5% $CO_2$ before measuring fluorescence (ex. 535 nm, em. 595 nm) with a Spectrafluor Plus Tecan plate reader (XFLUOR4 version 4.20). In some experiments, an ATP Determination Kit (BIAFFIN GmbH, LBR-T100) was used according to the manufacturer's instructions. In each experiment, samples were assayed in triplicate, and the standard deviations were determined GraphPad Prism 5 software was used to analyze the data and to obtain $IC_{50}$ values. All test compounds were assayed 2 to 10 times in independent experiments and similar results were obtained.

The data listed in Table 4 below represent the $IC_{50}$ values for representative compounds of the invention resulting from the corresponding averaged $pIC_{50}$ values:

TABLE 4

| Example No. | hFGF-2 mediated HUVEC proliferation, $IC_{50}$ [nM] |
|---|---|
| 1 | 16.4 |
| 4 | 17.5 |
| 5 | 5.3 |
| 8 | 9.7 |
| 10 | 16.0 |
| 11 | 150.0 |
| 13 | 17.0 |
| 14 | 25.0 |
| 16 | 117.3 |
| 18 | 10.4 |
| 21 | 3.7 |
| 26 | 56.7 |
| 34 | 37.3 |
| 38 | 213.3 |
| 39 | 365.0 |
| 45 | 171.0 |
| 46 | 84.5 |
| 48 | 360.0 |
| 51 | 1.2 |
| 52 | 4.0 |
| 53 | 3.3 |
| 54 | 2.2 |
| 56 | 18.1 |
| 57 | 3.2 |
| 59 | 51.1 |
| 60 | 250.0 |
| 64 | 4.5 |
| 67 | 12.1 |
| 68 | 14.4 |
| 71 | 5.4 |
| 72 | 1.6 |
| 73 | 5.5 |
| 74 | 0.2 |
| 75 | 1.5 |
| 76 | 1.5 |
| 77 | 3.2 |
| 79 | 3.5 |
| 80 | 1.6 |
| 81 | 1.6 |
| 84 | 46.6 |
| 85 | 126.0 |

Most compounds of the present invention displayed about ten- to hundred-fold reduced inhibitory activity in this proliferation assay when vascular endothelial growth factor (VEGF-A165 isoform) was used as mediating growth factor (instead of FGF-2), indicating a significant selectivity of these compounds for FGFR versus VEGFR kinases.

B-6. Human Xenograft and Syngeneic Tumor Models

Different tumor models have been conducted in order to profile compounds of the present invention in vivo. Human, rat or mouse tumor cells were cultivated in vitro and implanted into either immunodeficient or immunocompetent mice, or immunodeficient rats. Treatment started after tumor establishment, and tumor-bearing animals were treated with substances via different routes (per os, intravenously, intraperitoneally or subcutaneously). Substances were tested as monotherapy or in combination therapy with other pharmacological substances. Treatment of the tumor-bearing animals was conducted until the tumors reached an average size of 120 $mm^2$. Tumors were measured in two dimensions using a caliper, and tumor volume was calculated according to the formula (length×width)/2. Substance efficacy was evaluated at the end of the experiment using the T/C ratio [T=final tumor weight in the treated group; C=final tumor weight in the control group]. Statistical significance of the efficacy between control and treated groups was determined using the ANOVA variance test. All animal studies were conducted according to the German regulatory guidelines.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C. EXAMPLES RELATING TO PHARMACEUTICAL COMPOSITIONS

Pharmaceutical compositions according to the present invention can be illustrated as follows:

Sterile i.v. Solution:

A 5 mg/mL solution of the desired compound of the invention can be made using sterile, injectable water, and the pH is adjusted if necessary. The solution is diluted for administration to 1-2 mg/mL with sterile 5% dextrose and is administered as an i.v. infusion over about 60 minutes.

Lyophilized Powder for i.v. Administration:

A sterile preparation can be prepared with (i) 100-1000 mg of the desired compound of the invention as a lyophilized powder, (ii) 32-327 mg/mL sodium citrate, and (iii) 300-3000 mg Dextran 40. The formulation is reconstituted with sterile, injectable saline or 5% dextrose to a concentration of 10 to 20 mg/mL, which is further diluted with saline or 5% dextrose to 0.2 to 0.4 mg/mL, and is administered either as i.v. bolus or by i.v. infusion over 15-60 minutes.

Intramuscular Suspension:

The following solution or suspension can be prepared for intramuscular injection:

50 mg/mL of the desired, water-insoluble compound of the invention; 5 mg/mL sodium carboxymethylcellulose; 4 mg/mL Tween 80; 9 mg/mL sodium chloride; 9 mg/mL benzyl alcohol.

Hard Shell Capsules:

A large number of unit capsules are prepared by filling standard two-piece hard gelatin capsules each with 100 mg of the desired, powdered compound of the invention, 150 mg of lactose, 50 mg of cellulose and 6 mg of magnesium stearate.

Soft Gelatin Capsules:

A mixture of the desired compound of the invention in a digestible oil, such as soybean oil, cottonseed oil or olive oil, is prepared and injected by means of a positive displacement pump into molten gelatin to form soft gelatin capsules containing 100 mg of the active ingredient. The capsules are washed and dried. The desired compound of the invention can be dissolved in a mixture of polyethylene glycol, glycerin and sorbitol to prepare a water-miscible medicine mix.

Tablets:

A large number of tablets are prepared by conventional procedures so that the dosage unit is 100 mg of the desired compound of the invention, 0.2 mg of colloidal silicon dioxide, 5 mg of magnesium stearate, 275 mg of microcrystalline cellulose, 11 mg of starch, and 98.8 mg of lactose.

Appropriate aqueous and non-aqueous coatings may be applied to increase palatability, improve elegance and stability, or delay absorption.

Solution or Suspension for Topical Application to the Eye (Eye Drops):

A sterile formulation can be prepared with 100 mg of the desired compound of the invention as a lyophilized powder reconstituted in 5 mL of sterile saline. As preservative, benzalkonium chloride, thimerosal, phenylmercuric nitrate, or the like may be used in a range of about 0.001% to 1% by weight.

We claim:

1. The compound 4-{[4-Amino-6-(methoxymethyl)-5-(7-methoxy-5-methyl-1-benzothiophen-2-yl)pyrrolo[2,1-f]-[1,2,4]-triazin-7-yl]methyl}piperazin-2-one or a pharmaceutically acceptable salt, hydrate, or solvate thereof.

2. A pharmaceutical composition comprising the compound according to claim 1 and one or more pharmaceutically acceptable excipients.

3. A compound of formula

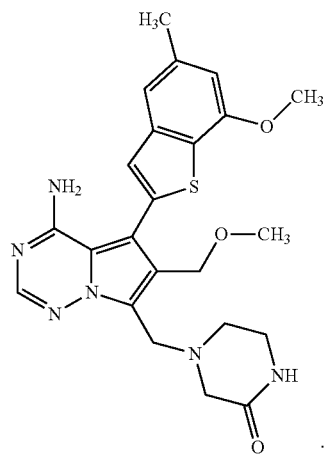 [SMILES: COCc1c(-c2cc3cc(C)cc(OC)c3s2)c2c(N)ncnn2c1CN1CCNC(=O)C1]

4. A pharmaceutical composition comprising the compound according to claim 3 and one or more pharmaceutically acceptable excipients.

* * * * *